US011807899B2

(12) United States Patent
Armes et al.

(10) Patent No.: US 11,807,899 B2
(45) Date of Patent: Nov. 7, 2023

(54) BIOCHEMICAL REACTION METHODS AND REAGENTS COMPRISING INTRINSICALLY DISORDERED REGIONS

(71) Applicant: Biocrucible Limited, Cambridge (GB)

(72) Inventors: Niall Armes, Cambridge (GB); Hannah Williams, Cambridge (GB); Matthew Forrest, Cambridge (GB); Mathew Parker, Cambridge (GB); Sidong Liu, Cambridge (GB); Lauren Parker, Cambridge (GB)

(73) Assignee: Biocrucible Limited

( * ) Notice: Subject to any disclaimer, the term of this patent is extended or adjusted under 35 U.S.C. 154(b) by 0 days.

(21) Appl. No.: 17/531,349

(22) Filed: Nov. 19, 2021

(65) Prior Publication Data

US 2022/0145378 A1     May 12, 2022

Related U.S. Application Data

(63) Continuation of application No. PCT/GB2020/052866, filed on Nov. 11, 2020.

(30) Foreign Application Priority Data

Nov. 11, 2019 (GB) ...................................... 1916379

(51) Int. Cl.
*C12Q 1/6848* (2018.01)
*C07K 1/14* (2006.01)
*C12Q 1/6853* (2018.01)

(52) U.S. Cl.
CPC .............. *C12Q 1/6848* (2013.01); *C07K 1/14* (2013.01); *C12Q 1/6853* (2013.01); *C07K 2319/00* (2013.01)

(58) Field of Classification Search
CPC .......... C07K 14/00; C12N 19/12; C12N 9/00; C12Q 1/6848
See application file for complete search history.

(56) References Cited

U.S. PATENT DOCUMENTS

| 7,270,981 | B2 | 9/2007 | Armes et al. | |
| 7,399,590 | B2 | 7/2008 | Piepenburg et al. | |
| 7,435,561 | B2 | 10/2008 | Piepenburg et al. | |
| 7,666,598 | B2 | 2/2010 | Piepenburg et al. | |
| 8,071,308 | B2 | 12/2011 | Piepenburg et al. | |
| 8,637,253 | B2* | 1/2014 | Piepenburg | C12Y 207/07 435/6.12 |
| 10,093,908 | B2* | 10/2018 | Piepenburg | C12N 9/00 |
| 11,339,382 | B2* | 5/2022 | Piepenburg | C12Q 1/6844 |
| 2005/0112631 | A1 | 5/2005 | Piepenburg et al. | |
| 2009/0029421 | A1 | 1/2009 | Piepenburg et al. | |
| 2009/0079963 | A1 | 3/2009 | Ermantraut et al. | |
| 2009/0297733 | A1 | 12/2009 | Yamazaki et al. | |
| 2009/0326903 | A1 | 12/2009 | Ludwig | |
| 2010/0179068 | A1 | 7/2010 | Kaiser et al. | |
| 2017/0355977 | A1 | 12/2017 | Brangwynne et al. | |
| 2022/0112547 | A1* | 4/2022 | Armes | C12Q 1/6848 |

FOREIGN PATENT DOCUMENTS

WO    2009112594 A2    9/2009
WO    2010141940 A1    12/2010

OTHER PUBLICATIONS

Chong, A. et al., "Liquid-liquid phase separation in cellular signaling systems," Current Opinion in Structural Biology, vol. 41: 180-186 (2016).
Invitation to Pay Additional Fees and where Applicable, Protest Fees, PCT/GB2020/052866, dated Feb. 15, 2021, 14 pages.
Tan, H. et al., "The intrinsically disordered linker of E. coli SSB is critical for the release from single-stranded DNA : SSB IDL is Required for DNA Release," Protein Science, vol. 26(4):700-717 (2017).
Al-Husini N et al., α-Proteobacterial RNA Degradosomes Assemble Liquid-Liquid Phase-Separated RNP Bodies.
Ambadipudi et al., Liquid-liquid phase separation of the microtubule-binding repeats of the Alzheimer-related protein Tau.
Bakthavachalu et al., RNP-Granule Assembly via Ataxin-2 Disordered Domains Is Required for Long-Term Memory and Neurodegeneration.
Biswas, S. et al., Mixed Macromolecular Crowding: A Protein and Solvent Perspective, 2018, ACS Omega, 3(4), pp. 4316-4330.
Boehning et al., RNA polymerase II clustering through carboxy-terminal domain phase separation.
Brady et al., Structural and hydrodynamic properties of an intrinsically disordered region of a germ cell-specific protein on phase separation.
Chen, X., et al. Fusion Protein Linkers: Property, Design and Functionality, 2013, Adv. Drug Deliv. Rev., 15, 65(10), pp. 1357-1369).

(Continued)

*Primary Examiner* — Karen Cochrane Carlson
(74) *Attorney, Agent, or Firm* — Potomac Law Group, PLLC; Reza Mollaaghababa; Joseph F. Murphy

(57) ABSTRACT

The invention relates to processes for performing biochemical reactions, such as in an aqueous in vitro reaction system. The processes involve macromolecules, particularly polypeptides, comprising one or more functional intrinsically disordered regions (IDRs). The invention also relates to IDR-macromolecules, including IDR-polypeptides, including macromolecules or polypeptides comprising a tagged amino acid sequence which comprises or consists of one or more functional IDRs. Such functional IDRs are capable of increasing the efficiency of the biochemical reaction. The invention relates to kits comprising any such macromolecules and polypeptides. The invention further relates to processes for stimulating or enhancing liquid-liquid demixing in a solution using any such macromolecules and polypeptides, including in combination with multivalent metal ions, thereby providing reagents capable of increasing the efficiency of a biochemical reaction.

26 Claims, 52 Drawing Sheets

Specification includes a Sequence Listing.

(56) References Cited

OTHER PUBLICATIONS

Chong et al., "Liquid-liquid phase separation in cellular signalling systems", Current Opinion in Structural Biology, Elsevier Ltd, GB, vol. 41, Aug. 20, 2016 (Aug. 20, 2016), pp. 180-186.
Chong et al., Imaging dynamic and selective low-complexity domain interactions that control gene transcription.
Chong et al., RGG/RG Motif Regions in RNA Binding and Phase Separation.
Chou, W-L., et al., (2015) Recent Advances in Applications of Droplet Microfluidics, Micromachines, 6: 1249-1271.
Cuevas-Velazquez et al., Organization out of disorder: liquid-liquid phase separation in plants.
Cummings et al., Phase Separation Behavior of Supercharged Proteins and Polyelectrolytes.
Cuylen et al., Ki-67 acts as a biological surfactant to disperse mitotic chromosomes.
Dao et al., Ubiquitin Modulates Liquid-Liquid Phase Separation of UBQLN2 via Disruption of Multivalent Interactions.
Darling et al., Intrinsically Disordered Proteome of Human Membrane-Less Organelles.
DeAngelis M. M. et al., (1995) Solid-Phase Reversible Immobilization for the Isolation of PCR Products, Nucleic Acids Research, 23(22): 4742-4743.
Dignon et al., Relation between single-molecule properties and phase behavior of intrinsically disordered proteins.
Dignon et al., Sequence determinants of protein phase behavior from a coarse-grained model.
Drino et al., RNAs, Phase Separation, and Membrane-Less Organelles: Are Post-Transcriptional Modifications Modulating Organelle Dynamics? BioEssays, 2018.
Dzuricky et al., Convergence of Artificial Protein Polymers and Intrinsically Disordered Proteins.
Erdel F & Rippe K. Formation of Chromatin Subcompartments by Phase Separation.
Faltova et al., Multifunctional Protein Materials and Microreactors using Low Complexity Domains as Molecular Adhesives.
Fisher et al., A review of metabolic and enzymatic engineering strategies for designing and optimizing performance of microbial cell factories.
Gaddiel Rodriguez et al., Disordered N-Terminal Domain of Human Uracil DNA Glycosylase (hUNG2) Enhances DNA Translocation.
Harmon et al., Intrinsically disordered linkers determine the interplay between phase separation and gelation in multivalent proteins.
Heinrich BS et al., Phase Transitions Drive the Formation of Vesicular Stomatitis Virus Replication Compartments.
Heyn P et al., Activation of transcription enforces the formation of distinct nuclear bodies in zebrafish embryos.
Hnisz et al., A Phase Separation Model for Transcriptional Control. Cell, Mar. 23, 2017;169(1):13-23.
International Search Report and Written Opinion, PCT/GB2020/052866, dated Apr. 7, 2021, 17 pages.
Invitation to Pay Additional Fees and where Applicable, Protest Fees, PCT/GB2020/052866, dated Feb. 15, 2021, 13 pages.
Mitrea et al., Self-interaction of NPM1 modulates multiple mechanisms of liquid-liquid phase separation.
Itakura et al., It Pays to Be in Phase.
Kazuhiro Maeshima et al., Nucleosomal arrays self-assemble into supramolecular globular structures lacking 30-nm fibers.
Kojima & Takayama., Membraneless Compartmentalization Facilitates Enzymatic Cascade Reactions and Reduces Substrate Inhibition.
Kong et al., Biphasic recruitment of TRF2 to DNA damage sites promotes non-sister chromatid homologous recombination repair. J Cell Sci. 2018;131(23).
Kosuri and Church, Nature Methods, 2014, 11, 499-507.
Kozlowski, L. P., et al., MetaDisorder: a meta-server for the prediction of intrinsic disorder in proteins. BMC Bioinformatics, 2012, 13(1): 111.
Kulkarni et al., Intrinsically Disordered Proteins: The Dark Horse of the Dark Proteome.

Kuznetsova, I., M. et al., (What Macromolecular Crowding Can Do to a Protein, 2014, Int. J. Mol. Sci., 15, pp. 23090-23140.
Lee Cf et al., Spatial organization of the cell cytoplasm by position-dependent phase separation.
Li et al., The physical forces mediating self-association and phase-separation in the C-terminal domain of TDP-43.
Li, J. et al., 2019, Analyst, 144, pp. 31-67.
Lin et al., The intrinsically disordered N-terminal domain of galectin-3 dynamically mediates multisite self-association of the protein through fuzzy interactions.
Milavanovic et al., A liquid phase of synapsin and lipid vesicles.
Lin et al., Theories for Sequence-Dependent Phase Behaviors of Biomolecular Condensates.
Mark C. Leake, Transcription factors in eukaryotic cells can functionally regulate gene expression by acting in oligomeric assemblies formed from an intrinsically disordered protein phase transition enabled by molecular crowding.
Maucuer et al., Microtubules as platforms for probing liquid-liquid phase separation in cells—application to RNA-binding proteins.
Mittag et al., Multiple Modes of Protein-Protein Interactions Promote RNP Granule Assembly.
Monterroso B et al., Microenvironments created by liquid-liquid phase transition control the dynamic distribution of bacterial division FtsZ protein.
Muiznieks et al., Role of Liquid-Liquid Phase Separation in Assembly of Elastin and Other Extracellular Matrix Proteins.
Nikolic J et al., [Rabies virus factories are formed by liquid-liquid phase separation].
Owen et al., CRIB effector disorder: exquisite function from chaos.
Perovic et al., IDPpi: Protein-Protein Interaction Analyses of Human Intrinsically Disordered Proteins.
Phillip Y. et al., Common Crowding Agents Have Only a Small Effect on Protein-Protein Interactions, 2009, Biophysical Journal, 97 pp. 875-885.
Poudyal et al., Physical Principles and Extant Biology Reveal Roles for RNA-Containing Membraneless Compartments in Origins of Life Chemistry.
Protter et al., Intrinsically Disordered Regions Can Contribute Promiscuous Interactions to RNP Granule Assembly.
Qamar et al., FUS Phase Separation Is Modulated by a Molecular Chaperone and Methylation of Arginine Cation-π Interactions.
Rauscher et al., The liquid structure of elastin.
Raut et al., Effect of Excipients on Liquid-Liquid Phase Separation and Aggregation in Dual Variable Domain Immunoglobulin Protein Solutions.
Reuven et al., "Recruitment of DNA repair MRN complex . . . ", Biomolecules (Oct. 2019); vol. 9, Art. No. 584.
Ruff et al., Advances in Understanding Stimulus-Responsive Phase Behavior of Intrinsically Disordered Protein Polymers.
Ryan et al., Mechanistic View of hnRNPA2 Low-Complexity Domain Structure, Interactions, and Phase Separation Altered by Mutation and Arginine Methylation.
Sabari BR, et al., Coactivator condensation at super-enhancers links phase separation and gene control.
Sabari BR, et al., Phase Separation Concentrates Transcription Proteins at Superenhancers.
Sarkar et al., Single-Molecule and Ensemble Methods to Probe Initial Stages of RNP Granule Assembly.
Savitskaya et al., C-terminal intrinsically disordered region-dependent organization of the mycobacterial genome by a histone-like protein.
Schuster et al., Controllable protein phase separation and modular recruitment to form responsive membraneless organelles.
Seydoux G, The P Granules of C. elegans: A Genetic Model for the Study of RNA-Protein Condensates.
Strom AR et al., Phase separation drives heterochromatin domain formation.
Tan et al., "The intrinsically disordered linker of E. coli SSB is critical for the release from single-stranded DNA : SSB IDL is Required for DNA Release", Protein Science, vol. 26, No. 4, Apr. 1, 2017 (Apr. 1, 2017), pp. 700-717.

(56) References Cited

OTHER PUBLICATIONS

Zilman, Aggregation, Phase Separation and Spatial Morphologies of the Assemblies of FG Nucleoporins. Journal of Mol. Bio, vol. 430, Issue 23, Nov. 2, 2018, pp. 4730-4740.

Zhou et al., NEIL3 Repairs Telomere Damage during S Phase to Secure Chromosome Segregation at Mitosis.

Tang, W. et al., 2014, Chem. Soc. Rev.,43, pp. 7013-7039.

Taylor et al., Biophysical characterization of organelle-based RNA/protein liquid phases using microfluidics.

Uebel et al., Distinct regions of the intrinsically disordered protein MUT-16 mediate assembly of a small RNA amplification complex and promote phase separation of Mutator foci. PLOSGenetics, 2018.

Uversky et al., The roles of intrinsic disorder-based liquid-liquid phase transitions in the "Dr. Jekyll-Mr. Hyde" behavior of proteins involved in amyotrophic lateral sclerosis and frontotemporal lobar degeneration.

Uversky., Intrinsic Disorder, Protein-Protein Interactions, and Disease.

Van der Lee et al., Classification of Intrinsically Disordered Regions and Proteins, 2014, Chem. Rev. 114, pp. 6589-6631.

Vernon et al., Pi-Pi contacts are an overlooked protein feature relevant to phase separation.

Vieregg JR et al., Oligonucleotide-Peptide Complexes: Phase Control by Hybridization.

Wang et al., A Molecular Grammar Governing the Driving Forces for Phase Separation of Prion-like RNA Binding Proteins.

Wang L et al., TDP-43 NTD can be induced while CTD is significantly enhanced by ssDNA to undergo liquid-liquid phase separation.

Wegmann et al., Tau protein liquid-liquid phase separation can initiate tau aggregation.

Wei MT et al., Phase behaviour of disordered proteins underlying low density and high permeability of liquid organelles.

Woodruff et al., Assembly of Mitotic Structures through Phase Separation.

Yoonjung Shim et al., Polycistronic co-expression and non-denaturing purification of histone octamers.

Yoshizawa et al., Nuclear Import Receptor Inhibits Phase Separation of FUS through Binding to Multiple Sites.

Zaslavsky et al., In Aqua Veritas: The Indispensable yet Mostly Ignored Role of Water in Phase Separation and Membrane-less Organelles.

Zaslavsky et al., The solvent side of proteinaceous membrane-less organelles in light of aqueous two-phasesystems.

Lin et al., Intrinsically disordered sequences enable modulation of protein phase separation through distributed tyrosine motifs.

Shan Z et al., Basal condensation of Numb and Pon complex via phase transition during *Drosophila* neuroblast asymmetric division.

\* cited by examiner

Image 1 – Bright field on glass cover slip   Image 1 – Fluorescence on glass cover slip Image 2 – Bright field on C-   Image 2 – Fluorescence on C-
Chip haemocytometer   Chip haemocytometer Image 1 – Bright field on glass cover slip  Image 1 – Fluorescence on glass cover slip Image 2 – Bright field on C-Chip  Image 2 – Fluorescence on C-haemocytometer Chip haemocytometer dsDNA Template
(TF1L)

1mg/ml RB69 ligase, 50mM NaCl, 0.4uM FAM-oligo, 2mM Mg2+

1mg/ml RB69 ligase-His2, 50mM NaCl, 0.4uM FAM-oligo, 2mM Mg2+

1mg/ml RB69 ligase, 50mM NaCl, 0.4uM FAM-oligo, 0.02mM Mg2+

1mg/ml RB69 ligase-His2, 50mM NaCl, 0.4uM FAM-oligo, 0.02mM Mg2+

Brightfield            FAM

0nM Cas12a protein, 333ng/µl T4 GP32 HRP1 protein, 5% PEG35K, 30mM NaCl, 10mM Tris Acetate pH8.3, 20mM Mg Acetate, 0.1mg/ml BSA, 33.3nM guide RNA, 50nM dsDNA.

33.3nM Cas12a protein, 0ng/µl T4 GP32 HRP1 protein, 5% PEG35K, 30mM NaCl, 10mM Tris Acetate pH8.3, 20mM Mg Acetate, 0.1mg/ml BSA, 33.3nM guide RNA, 50nM dsDNA.

33.3nM Cas12a protein, 333ng/µl T4 GP32 HRP1 protein, 5% PEG35K, 30mM NaCl, 10mM Tris Acetate pH8.3, 20mM Mg Acetate, 0.1mg/ml BSA, 33.3nM guide RNA, 50nM dsDNA.

SEQUENCE LISTING

<160> NUMBER OF SEQ ID NOS: 137

<210> SEQ ID NO 1
<211> LENGTH: 43
<212> TYPE: PRT
<213> ORGANISM: Homo sapiens

<400> SEQUENCE: 1

Pro Gly Phe Ser Pro Arg Gly Gly Gly Phe Gly Gly Arg Gly Gly Phe
1               5                   10                  15

Gly Asp Arg Gly Gly Arg Gly Gly Arg Gly Gly Phe Gly Gly Gly Arg
            20                  25                  30

Gly Arg Gly Gly Gly Phe Arg Gly Arg Gly Arg
        35                  40

<210> SEQ ID NO 2
<211> LENGTH: 86
<212> TYPE: PRT
<213> ORGANISM: Homo sapiens

<400> SEQUENCE: 2

Pro Gly Phe Ser Pro Arg Gly Gly Gly Phe Gly Gly Arg Gly Gly Phe
1               5                   10                  15

Gly Asp Arg Gly Gly Arg Gly Gly Arg Gly Gly Phe Gly Gly Gly Arg
            20                  25                  30

Gly Arg Gly Gly Gly Phe Arg Gly Arg Gly Arg Pro Gly Phe Ser Pro
        35                  40                  45

Arg Gly Gly Gly Phe Gly Gly Arg Gly Gly Phe Gly Asp Arg Gly Gly
    50                  55                  60

Arg Gly Gly Arg Gly Gly Phe Gly Gly Gly Arg Gly Arg Gly Gly Gly
65                  70                  75                  80

Phe Arg Gly Arg Gly Arg
                85

<210> SEQ ID NO 3
<211> LENGTH: 25
<212> TYPE: PRT
<213> ORGANISM: Homo sapiens

<400> SEQUENCE: 3

Arg Gly Gly Gly Phe Gly Gly Arg Gly Phe Gly Asp Arg Gly Gly
1               5                   10                  15

Arg Gly Gly Arg Gly Gly Phe Gly Gly
            20                  25

<210> SEQ ID NO 4
<211> LENGTH: 36
<212> TYPE: PRT
<213> ORGANISM: Artificial Sequence
<220> FEATURE:
<223> OTHER INFORMATION: fib-2 (clipper1) - 7 amino acid deletion at the
      C-terminus of fib-1

<400> SEQUENCE: 4

Pro Gly Phe Ser Pro Arg Gly Gly Gly Phe Gly Gly Arg Gly Gly Phe
1               5                   10                  15

Gly Asp Arg Gly Gly Arg Gly Arg Gly Gly Phe Gly Gly Arg
            20                  25                  30

Gly Arg Gly Gly
        35

```
<210> SEQ ID NO 5
<211> LENGTH: 27
<212> TYPE: PRT
<213> ORGANISM: Artificial Sequence
<220> FEATURE:
<223> OTHER INFORMATION: fib-3 (clipper2) - 16 amino acids deletion at
      the C-terminus of fib-1

<400> SEQUENCE: 5

Pro Gly Phe Ser Pro Arg Gly Gly Phe Gly Gly Arg Gly Gly Phe
1               5                   10                  15

Gly Asp Arg Gly Gly Arg Gly Gly Arg Gly Gly
            20                  25

<210> SEQ ID NO 6
<211> LENGTH: 15
<212> TYPE: PRT
<213> ORGANISM: Artificial Sequence
<220> FEATURE:
<223> OTHER INFORMATION: fib-4 (clipper3) - 28 amino acids deletion at
      the C-terminus of fib-1

<400> SEQUENCE: 6

Pro Gly Phe Ser Pro Arg Gly Gly Phe Gly Gly Arg Gly Gly
1               5                   10                  15

<210> SEQ ID NO 7
<211> LENGTH: 67
<212> TYPE: PRT
<213> ORGANISM: Saccharomyces cerevisiae

<400> SEQUENCE: 7

Gln Val Gln Met Gln Leu Arg Gln Val Phe Ser Gln Asp Gln Val
1               5                   10                  15

Leu Gln Glu Arg Met Arg Tyr His Glu Leu Gln Gln Gln Gln Gln
            20                  25                  30

Gln Tyr His Glu Thr Lys Asp Met Val Gly Ser Tyr Thr Gln Asn Ser
        35                  40                  45

Asn Ser Ala Ile Pro Leu Phe Gly Asn Asn Ser Asp Thr Thr Asn Gln
    50                  55                  60

Gln Asn Ser
65

<210> SEQ ID NO 8
<211> LENGTH: 59
<212> TYPE: PRT
<213> ORGANISM: Saccharomyces cerevisiae

<400> SEQUENCE: 8

Gln Asn Pro Thr Gly Ile Ser Tyr Ser Gln Pro Gln Gln Gln Gln
1               5                   10                  15

Pro Gln Gln Gln Pro Gln Tyr Met Gln Asn Phe Gln Gln Gln Pro
            20                  25                  30

Gln Tyr Ala Gln Asn Phe Gln Gln Pro Gln Tyr Thr Gln Asn Tyr
        35                  40                  45

Gln Gln Gln Pro Gln Tyr Ile Gln Pro His Gln
    50                  55

<210> SEQ ID NO 9
<211> LENGTH: 58
<212> TYPE: PRT
<213> ORGANISM: Saccharomyces cerevisiae
```

<400> SEQUENCE: 9

Gly Gly Asn Asn Gly Gly Asn Asn Met Asn Arg Arg Gly Gly Asn Phe
1               5                   10                  15

Gly Asn Gln Gly Asp Phe Asn Gln Met Tyr Gln Asn Pro Met Met Gly
            20                  25                  30

Gly Tyr Asn Pro Met Met Asn Pro Gln Ala Met Thr Asp Tyr Tyr Gln
        35                  40                  45

Lys Met Gln Glu Tyr Tyr Gln Gln Met Gln
    50                  55

<210> SEQ ID NO 10
<211> LENGTH: 116
<212> TYPE: PRT
<213> ORGANISM: Saccharomyces cerevisiae

<400> SEQUENCE: 10

Gly Gly Asn Asn Gly Gly Asn Asn Met Asn Arg Arg Gly Gly Asn Phe
1               5                   10                  15

Gly Asn Gln Gly Asp Phe Asn Gln Met Tyr Gln Asn Pro Met Met Gly
            20                  25                  30

Gly Tyr Asn Pro Met Met Asn Pro Gln Ala Met Thr Asp Tyr Tyr Gln
        35                  40                  45

Lys Met Gln Glu Tyr Tyr Gln Gln Met Gln Gly Gly Asn Asn Gly Gly
    50                  55                  60

Asn Asn Met Asn Arg Arg Gly Gly Asn Phe Gly Asn Gln Gly Asp Phe
65                  70                  75                  80

Asn Gln Met Tyr Gln Asn Pro Met Met Gly Gly Tyr Asn Pro Met Met
                85                  90                  95

Asn Pro Gln Ala Met Thr Asp Tyr Tyr Gln Lys Met Gln Glu Tyr Tyr
            100                 105                 110

Gln Gln Met Gln
    115

<210> SEQ ID NO 11
<211> LENGTH: 240
<212> TYPE: PRT
<213> ORGANISM: Homo sapiens

<400> SEQUENCE: 11

Met Gly Asp Glu Asp Trp Glu Ala Glu Ile Asn Pro His Met Ser Ser
1               5                   10                  15

Tyr Val Pro Ile Phe Glu Lys Asp Arg Tyr Ser Gly Glu Asn Gly Asp
            20                  25                  30

Asn Phe Asn Arg Thr Pro Ala Ser Ser Ser Glu Met Asp Asp Gly Pro
        35                  40                  45

Ser Arg Arg Asp His Phe Met Lys Ser Gly Phe Ala Ser Gly Arg Asn
    50                  55                  60

Phe Gly Asn Arg Asp Ala Gly Glu Cys Asn Lys Arg Asp Asn Thr Ser
65                  70                  75                  80

Thr Met Gly Gly Phe Gly Val Gly Lys Ser Phe Gly Asn Arg Gly Phe
                85                  90                  95

Ser Asn Ser Arg Phe Glu Asp Gly Asp Ser Ser Gly Phe Trp Arg Glu
            100                 105                 110

Ser Ser Asn Asp Cys Glu Asp Asn Pro Thr Arg Asn Arg Gly Phe Ser
        115                 120                 125

```
Lys Arg Gly Gly Tyr Arg Asp Gly Asn Asn Ser Glu Ala Ser Gly Pro
130                 135                 140

Tyr Arg Arg Gly Arg Gly Ser Phe Arg Gly Cys Arg Gly Gly Phe
145                 150                 155                 160

Gly Leu Gly Ser Pro Asn Asn Asp Leu Asp Pro Asp Glu Cys Met Gln
                165                 170                 175

Arg Thr Gly Gly Leu Phe Gly Ser Arg Arg Pro Val Leu Ser Gly Thr
                180                 185                 190

Gly Asn Gly Asp Thr Ser Gln Ser Arg Ser Gly Ser Gly Ser Glu Arg
                195                 200                 205

Gly Gly Tyr Lys Gly Leu Asn Glu Glu Val Ile Thr Gly Ser Gly Lys
210                 215                 220

Asn Ser Trp Lys Ser Glu Ala Glu Gly Gly Glu Ser Ser Asp Thr Gln
225                 230                 235                 240

<210> SEQ ID NO 12
<211> LENGTH: 134
<212> TYPE: PRT
<213> ORGANISM: Homo sapiens

<400> SEQUENCE: 12

Ala Ser Ala Ser Ser Gln Arg Gly Arg Ser Gly Ser Gly Asn Phe
1               5                   10                  15

Gly Gly Gly Arg Gly Gly Gly Phe Gly Gly Asn Asp Asn Phe Gly Arg
                20                  25                  30

Gly Gly Asn Phe Ser Gly Arg Gly Gly Phe Gly Gly Ser Arg Gly Gly
                35                  40                  45

Gly Gly Tyr Gly Gly Ser Gly Asp Gly Tyr Asn Gly Phe Gly Asn Asp
                50                  55                  60

Gly Ser Asn Phe Gly Gly Gly Gly Ser Tyr Asn Asp Phe Gly Asn Tyr
65                  70                  75                  80

Asn Asn Gln Ser Ser Asn Phe Gly Pro Met Lys Gly Gly Asn Phe Gly
                85                  90                  95

Gly Arg Ser Ser Gly Pro Tyr Gly Gly Gly Gly Gln Tyr Phe Ala Lys
                100                 105                 110

Pro Gln Asn Gln Gly Gly Tyr Gly Val Ser Ser Ser Ser Ser Ser Tyr
                115                 120                 125

Gly Ser Gly Arg Arg Phe
                130

<210> SEQ ID NO 13
<211> LENGTH: 204
<212> TYPE: PRT
<213> ORGANISM: Saccharomyces cerevisiae

<400> SEQUENCE: 13

Ser Pro Phe Gly Ala Tyr Gly Glu Ala Pro Thr Ser Pro Gly Phe Gly
1               5                   10                  15

Val Ser Ser Pro Gly Phe Ser Pro Thr Ser Thr Tyr Ser Pro Thr
                20                  25                  30

Ser Pro Ala Tyr Ser Pro Thr Ser Pro Ser Tyr Ser Pro Thr Ser Pro
                35                  40                  45

Ser Tyr Ser Pro Thr Ser Pro Ser Tyr Ser Pro Thr Ser Pro Ser Tyr
                50                  55                  60

Ser Pro Thr Ser Pro Ser Tyr Ser Pro Thr Ser Pro Ser Tyr Ser Pro
65                  70                  75                  80
```

```
Thr Ser Pro Ser Tyr Ser Pro Thr Ser Pro Ser Tyr Ser Pro Thr Ser
                85                  90                  95

Pro Ser Tyr Ser Pro Thr Ser Pro Ser Tyr Ser Pro Thr Ser Pro Ser
            100                 105                 110

Tyr Ser Pro Thr Ser Pro Ser Tyr Ser Pro Thr Ser Pro Ser Tyr Ser
        115                 120                 125

Pro Thr Ser Pro Ser Tyr Ser Pro Thr Ser Pro Ala Tyr Ser Pro Thr
    130                 135                 140

Ser Pro Ser Tyr Ser Pro Thr Ser Pro Ser Tyr Ser Pro Thr Ser Pro
145                 150                 155                 160

Ser Tyr Ser Pro Thr Ser Pro Ser Tyr Ser Pro Thr Ser Pro Asn Tyr
                165                 170                 175

Ser Pro Thr Ser Pro Ser Tyr Ser Pro Thr Ser Pro Gly Tyr Ser Pro
            180                 185                 190

Gly Ser Pro Ala Tyr Ser Pro Lys Gln Asp Glu Gln
            195                 200

<210> SEQ ID NO 14
<211> LENGTH: 42
<212> TYPE: PRT
<213> ORGANISM: Saccharomyces cerevisiae

<400> SEQUENCE: 14

Thr Ser Pro Ser Tyr Ser Pro Thr Ser Pro Ser Tyr Ser Pro Thr Ser
1               5                   10                  15

Pro Gly Tyr Ser Pro Thr Ser Pro Ala Tyr Ser Pro Thr Ser Pro Thr
            20                  25                  30

Tyr Ser Pro Thr Ser Pro Thr Tyr Ser Pro
        35                  40

<210> SEQ ID NO 15
<211> LENGTH: 49
<212> TYPE: PRT
<213> ORGANISM: Artificial Sequence
<220> FEATURE:
<223> OTHER INFORMATION: mimic1 - seven repeats of YDPTSPS motifs
      mimiking the c-terminus of RNA polymerase II

<400> SEQUENCE: 15

Tyr Asp Pro Thr Ser Pro Ser Tyr Asp Pro Thr Ser Pro Ser Tyr Asp
1               5                   10                  15

Pro Thr Ser Pro Ser Tyr Asp Pro Thr Ser Pro Ser Tyr Asp Pro Thr
            20                  25                  30

Ser Pro Ser Tyr Asp Pro Thr Ser Pro Ser Tyr Asp Pro Thr Ser Pro
        35                  40                  45

Ser

<210> SEQ ID NO 16
<211> LENGTH: 49
<212> TYPE: PRT
<213> ORGANISM: Artificial Sequence
<220> FEATURE:
<223> OTHER INFORMATION: mimic2 - seven repeats of YSPTDPS motifs
      mimiking the c-terminus of RNA polymerase II

<400> SEQUENCE: 16

Tyr Ser Pro Thr Asp Pro Ser Tyr Ser Pro Thr Asp Pro Ser Tyr Ser
1               5                   10                  15

Pro Thr Asp Pro Ser Tyr Ser Pro Thr Asp Pro Ser Tyr Ser Pro Thr
            20                  25                  30
```

-continued

```
Asp Pro Ser Tyr Ser Pro Thr Asp Pro Ser Tyr Ser Pro Thr Asp Pro
        35                  40                  45
Ser

<210> SEQ ID NO 17
<211> LENGTH: 21
<212> TYPE: PRT
<213> ORGANISM: Saccharomyces cerevisiae

<400> SEQUENCE: 17

Pro Thr Ser Pro Ser Tyr Ser Pro Thr Ser Pro Ser Tyr Ser Pro Tyr
1               5                  10                  15

Ser Pro Ala Tyr Ser
            20

<210> SEQ ID NO 18
<211> LENGTH: 115
<212> TYPE: PRT
<213> ORGANISM: Saccharomyces cerevisiae

<400> SEQUENCE: 18

Met Ser Asp Ser Asn Gln Gly Asn Asn Gln Gln Asn Tyr Gln Gln Tyr
1               5                  10                  15

Ser Gln Asn Gly Asn Gln Gln Gln Gly Asn Asn Arg Tyr Gln Gly Tyr
            20                  25                  30

Gln Ala Tyr Asn Ala Gln Ala Gln Pro Ala Gly Gly Tyr Tyr Gln Asn
        35                  40                  45

Tyr Gln Gly Tyr Ser Gly Tyr Gln Gln Gly Gly Tyr Gln Gln Tyr Gln
    50                  55                  60

Tyr Asn Pro Gln Gly Gly Tyr Gln Gln Tyr Asn Pro Gln Gly Gly Tyr
65                  70                  75                  80

Gln Gln Tyr Asn Pro Gln Gly Gly Tyr Gln Gln Gln Phe Asn Pro Gln
                85                  90                  95

Gly Gly Arg Gly Asn Tyr Lys Asn Phe Asn Tyr Asn Asn Asn Leu Gln
            100                 105                 110

Gly Tyr Gln
        115

<210> SEQ ID NO 19
<211> LENGTH: 9
<212> TYPE: PRT
<213> ORGANISM: Artificial Sequence
<220> FEATURE:
<223> OTHER INFORMATION: Sup1 - single repeat of YNPQGGYQQ

<400> SEQUENCE: 19

Tyr Asn Pro Gln Gly Gly Tyr Gln Gln
1               5

<210> SEQ ID NO 20
<211> LENGTH: 18
<212> TYPE: PRT
<213> ORGANISM: Artificial Sequence
<220> FEATURE:
<223> OTHER INFORMATION: Sup2 - two repeat of YNPQGGYQQ

<400> SEQUENCE: 20

Tyr Asn Pro Gln Gly Gly Tyr Gln Gln Tyr Asn Pro Gln Gly Gly Tyr
1               5                  10                  15

Gln Gln
```

```
<210> SEQ ID NO 21
<211> LENGTH: 27
<212> TYPE: PRT
<213> ORGANISM: Artificial Sequence
<220> FEATURE:
<223> OTHER INFORMATION: Sup3 - three repeat of YNPQGGYQQ

<400> SEQUENCE: 21

Tyr Asn Pro Gln Gly Gly Tyr Gln Gln Tyr Asn Pro Gln Gly Gly Tyr
1               5                   10                  15

Gln Gln Tyr Asn Pro Gln Gly Gly Tyr Gln Gln
            20                  25

<210> SEQ ID NO 22
<211> LENGTH: 36
<212> TYPE: PRT
<213> ORGANISM: Artificial Sequence
<220> FEATURE:
<223> OTHER INFORMATION: Sup4 - four repeat of YNPQGGYQQ

<400> SEQUENCE: 22

Tyr Asn Pro Gln Gly Gly Tyr Gln Gln Tyr Asn Pro Gln Gly Gly Tyr
1               5                   10                  15

Gln Gln Tyr Asn Pro Gln Gly Gly Tyr Gln Gln Tyr Asn Pro Gln Gly
            20                  25                  30

Gly Tyr Gln Gln
        35

<210> SEQ ID NO 23
<211> LENGTH: 31
<212> TYPE: PRT
<213> ORGANISM: Homo sapiens

<400> SEQUENCE: 23

Pro Gln Gln Asn Ala Leu His His His His Gly Asn Ser Ser His His
1               5                   10                  15

His His His His His His His His His Gly Gln Gln Ala
            20                  25                  30

<210> SEQ ID NO 24
<211> LENGTH: 36
<212> TYPE: PRT
<213> ORGANISM: Homo sapiens

<400> SEQUENCE: 24

Ala Gly His His His His His Pro His Ala His Pro Leu Ser Gln
1               5                   10                  15

Ser Ser Gly His His His His His His His His Gln Gly Tyr
            20                  25                  30

Gly Gly Ser Gly
        35

<210> SEQ ID NO 25
<211> LENGTH: 43
<212> TYPE: PRT
<213> ORGANISM: Homo sapiens

<400> SEQUENCE: 25

Ala Gly His His His His His His His Leu Pro His Leu Pro Pro
1               5                   10                  15

Pro His Leu His His His His His Pro Gln His His Leu His Pro Gly
```

```
                    20                  25                  30

Ser Ala Ala Ala Val His Pro Val Gln Gln His
        35                  40

<210> SEQ ID NO 26
<211> LENGTH: 42
<212> TYPE: PRT
<213> ORGANISM: Homo sapiens

<400> SEQUENCE: 26

Asn His His Ala Ser His Gly His His Asn Ser His His Pro Gln His
1               5                   10                  15

His His His His His His His His His Pro Pro Pro Pro Ala Pro
            20                  25                  30

Gln Pro Pro Pro Pro Pro Gln Gln Gln Gln
        35                  40

<210> SEQ ID NO 27
<211> LENGTH: 76
<212> TYPE: PRT
<213> ORGANISM: Homo sapiens

<400> SEQUENCE: 27

Ser Gly His His Gly Ala His His Gly Ala His His Pro Ala Ala Ala
1               5                   10                  15

Ala Ala Tyr Glu Ala Phe Arg Gly Pro Gly Phe Ala Gly Gly Gly Gly
            20                  25                  30

Ala Asp Asp Met Gly Ala Gly His His His Gly Ala His His Ala Ala
        35                  40                  45

His His His His Ala Ala His His His His His His His His His His
    50                  55                  60

Gly Gly Ala Gly His Gly Gly Ala Gly His His
65                  70                  75

<210> SEQ ID NO 28
<211> LENGTH: 27
<212> TYPE: PRT
<213> ORGANISM: Homo sapiens

<400> SEQUENCE: 28

Gly Gly Gly Gly Asp His Gly Gly Gly Gly His Gly His Ala Gly
1               5                   10                  15

His His His His His His His His His His
            20                  25

<210> SEQ ID NO 29
<211> LENGTH: 25
<212> TYPE: PRT
<213> ORGANISM: Homo sapiens

<400> SEQUENCE: 29

Pro Gly Ser Gly Gly Pro His Thr Ser His His His His His His
1               5                   10                  15

His His His His His Gln Ser Arg His
            20                  25

<210> SEQ ID NO 30
<211> LENGTH: 25
<212> TYPE: PRT
<213> ORGANISM: Homo sapiens
```

-continued

```
<400> SEQUENCE: 30

Ala Pro Ser Tyr His His His His His His His His His His
1               5                   10                  15

His His Gln Gln Gln His Gln Gln Pro
            20                  25

<210> SEQ ID NO 31
<211> LENGTH: 24
<212> TYPE: PRT
<213> ORGANISM: Homo sapiens

<400> SEQUENCE: 31

Thr His Pro Pro Ser His His Pro His Pro His Pro His His His
1               5                   10                  15

His His His His His His His His
            20

<210> SEQ ID NO 32
<211> LENGTH: 38
<212> TYPE: PRT
<213> ORGANISM: Homo sapiens

<400> SEQUENCE: 32

Pro Pro Pro His His His His His His His His His His His
1               5                   10                  15

His His Arg Ala Gln Pro Pro Gln Gln Ser His His Pro Pro His His
            20                  25                  30

His Arg Pro Gln Pro His
        35

<210> SEQ ID NO 33
<211> LENGTH: 18
<212> TYPE: PRT
<213> ORGANISM: Homo sapiens

<400> SEQUENCE: 33

Asn His Ala His His His His His Pro Pro Gln His His His His
1               5                   10                  15

His Gln

<210> SEQ ID NO 34
<211> LENGTH: 37
<212> TYPE: PRT
<213> ORGANISM: Artificial Sequence
<220> FEATURE:
<223> OTHER INFORMATION: Synthetic: His12

<400> SEQUENCE: 34

Ala Gly His His His His His His His His His Gly Gly Ala Gly
1               5                   10                  15

Gly Ala Gly Gly Ala Gly Gly Ala His His His His His His His
            20                  25                  30

His His Gly Gly Ala
        35

<210> SEQ ID NO 35
<211> LENGTH: 37
<212> TYPE: PRT
<213> ORGANISM: Artificial Sequence
<220> FEATURE:
<223> OTHER INFORMATION: Synthetic: His13
```

-continued

```
<400> SEQUENCE: 35

Ala Gly His His His His His His His His His Ser Ser Gly Ser
1               5                   10                  15

Gly Ser Ser Gly Ser Gly Ser Ser His His His His His His His
                20                  25                  30

His His Gly Gly Ala
            35

<210> SEQ ID NO 36
<211> LENGTH: 17
<212> TYPE: PRT
<213> ORGANISM: Artificial Sequence
<220> FEATURE:
<223> OTHER INFORMATION: Synthetic: His14

<400> SEQUENCE: 36

Ala Gly His His His His His His His His His His His Gly Gly
1               5                   10                  15

Ala

<210> SEQ ID NO 37
<211> LENGTH: 24
<212> TYPE: PRT
<213> ORGANISM: Artificial Sequence
<220> FEATURE:
<223> OTHER INFORMATION: Synthetic: His15

<400> SEQUENCE: 37

Ala Gly His His His His His His His His His His His His His
1               5                   10                  15

His His His His His Gly Gly Ala
                20

<210> SEQ ID NO 38
<211> LENGTH: 74
<212> TYPE: PRT
<213> ORGANISM: Unknown
<220> FEATURE:
<223> OTHER INFORMATION: Escherichia phage

<400> SEQUENCE: 38

Lys Lys Val Ala Ser Lys Leu Lys Phe Lys Lys Lys Met Glu Ala Phe
1               5                   10                  15

Ser Ser Ala Lys Thr Lys Lys Lys Phe Met Ser Ser Ser Ser Lys
                20                  25                  30

Lys Ser Lys Leu Lys Lys Leu Leu Ala Gly Leu Met Glu Ala Phe Ser
            35                  40                  45

Ser Ala Lys Thr Lys Lys Lys Phe Met Ser Ser Ser Ser Lys Lys
        50                  55                  60

Ser Lys Leu Lys Lys Leu Leu Ala Gly Leu
65                  70

<210> SEQ ID NO 39
<211> LENGTH: 75
<212> TYPE: PRT
<213> ORGANISM: Unknown
<220> FEATURE:
<223> OTHER INFORMATION: Escherichia phage

<400> SEQUENCE: 39

Asp Asp Val Ala Ser Asp Leu Asp Asp Phe Asp Asp Met Glu Ala
1               5                   10                  15
```

```
Phe Ser Ser Ala Asp Thr Glu Asp Phe Met Ser Ser Ser Ser
                20                  25                  30

Asp Asp Ser Asp Leu Asp Leu Leu Ala Gly Leu Met Glu Ala Phe
            35                  40                  45

Ser Ser Ala Asp Thr Glu Asp Asp Phe Met Ser Ser Ser Ser Asp
50                  55                  60

Asp Ser Asp Leu Asp Asp Leu Leu Ala Gly Leu
65                  70                  75
```

<210> SEQ ID NO 40
<211> LENGTH: 90
<212> TYPE: PRT
<213> ORGANISM: Unknown
<220> FEATURE:
<223> OTHER INFORMATION: Escherichia phage

<400> SEQUENCE: 40

```
Arg Ile Val Lys Ala Lys Val Lys Arg Leu Ile Asn Ser Lys Val Lys
1               5                   10                  15

Lys Phe Lys Ser Pro Lys Ser Lys Ser Lys Ser Ala Ala Lys Leu Lys
                20                  25                  30

Thr Lys Leu Lys Gln Leu Ser Lys Met Lys Lys Phe Asn Lys Ile Val
            35                  40                  45

Lys Ala Lys Val Lys Lys Leu Ile Asn Ser Lys Val Arg Lys Phe Lys
50                  55                  60

Ser Pro Lys Ser Lys Ser Lys Ser Ala Ala Lys Leu Lys Thr Lys Leu
65                  70                  75                  80

Lys Gln Leu Ser Lys Met Lys Glu Phe Asn
                85                  90
```

<210> SEQ ID NO 41
<211> LENGTH: 90
<212> TYPE: PRT
<213> ORGANISM: Unknown
<220> FEATURE:
<223> OTHER INFORMATION: Escherichia phage

<400> SEQUENCE: 41

```
Glu Ile Val Glu Ala Glu Val Asp Glu Leu Ile Asn Ser Glu Val Glu
1               5                   10                  15

Glu Phe Asp Ser Pro Glu Ser Asp Ser Asp Glu Ala Ala Asp Leu Glu
                20                  25                  30

Thr Asp Leu Glu Gln Leu Ser Asp Met Glu Glu Phe Asn Glu Ile Val
            35                  40                  45

Glu Ala Glu Val Asp Glu Leu Ile Asn Ser Glu Val Glu Asp Phe Asp
50                  55                  60

Ser Pro Glu Ser Asp Ser Asp Glu Ala Ala Asp Leu Glu Thr Asp Leu
65                  70                  75                  80

Glu Gln Leu Ser Asp Met Glu Glu Phe Asn
                85                  90
```

<210> SEQ ID NO 42
<211> LENGTH: 90
<212> TYPE: PRT
<213> ORGANISM: Unknown
<220> FEATURE:
<223> OTHER INFORMATION: Escherichia phage

<400> SEQUENCE: 42

```
Glu Ile Val Glu Ala Glu Val Asp Glu Leu Ile Asn Ser Lys Val Glu
1               5                   10                  15

Lys Phe Lys Ser Pro Glu Ser Lys Ser Lys Ser Ala Ala Asp Leu Glu
            20                  25                  30

Thr Asp Leu Glu Gln Leu Ser Asp Met Glu Glu Phe Asn Glu Ile Val
        35                  40                  45

Glu Ala Glu Val Asp Glu Leu Ile Asn Ser Lys Val Glu Lys Phe Lys
    50                  55                  60

Ser Pro Glu Ser Lys Ser Lys Ser Ala Ala Asp Leu Glu Thr Asp Leu
65                  70                  75                  80

Glu Gln Leu Ser Asp Met Glu Glu Phe Asn
                85                  90
```

<210> SEQ ID NO 43
<211> LENGTH: 135
<212> TYPE: PRT
<213> ORGANISM: Unknown
<220> FEATURE:
<223> OTHER INFORMATION: Escherichia phage

<400> SEQUENCE: 43

```
Glu Ile Val Glu Ala Glu Val Asp Glu Leu Ile Asn Ser Lys Val Glu
1               5                   10                  15

Lys Phe Lys Ser Pro Glu Ser Lys Ser Lys Ser Ala Ala Asp Leu Glu
            20                  25                  30

Thr Asp Leu Glu Gln Leu Ser Asp Met Glu Glu Phe Asn Glu Ile Val
        35                  40                  45

Glu Ala Glu Val Asp Glu Leu Ile Asn Ser Lys Val Glu Lys Phe Lys
    50                  55                  60

Ser Pro Glu Ser Lys Ser Lys Ser Ala Ala Asp Leu Glu Thr Asp Leu
65                  70                  75                  80

Glu Gln Leu Ser Asp Met Glu Glu Phe Asn Glu Ile Val Glu Ala Glu
                85                  90                  95

Val Asp Glu Leu Ile Asn Ser Lys Val Glu Lys Phe Lys Ser Pro Glu
            100                 105                 110

Ser Lys Ser Lys Ser Ala Ala Asp Leu Glu Thr Asp Leu Glu Gln Leu
        115                 120                 125

Ser Asp Met Glu Glu Phe Asn
    130                 135
```

<210> SEQ ID NO 44
<211> LENGTH: 400
<212> TYPE: PRT
<213> ORGANISM: Artificial Sequence
<220> FEATURE:
<223> OTHER INFORMATION: UvsX (7His)

<400> SEQUENCE: 44

```
Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80
```

```
Asn Lys Tyr Pro Asp Ala Ile Cys Leu Phe Tyr Asp Ser Glu Phe Gly
            85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
            115                 120                 125

Asn Gln Leu Glu Thr Ile Glu Arg Gly Glu Lys Val Ile Val Phe Ile
            130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
            165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
            195                 200                 205

Val Met Thr Gly Gly Thr Gly Val Met Tyr Ser Ala Asp Thr Val Phe
            210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
            245                 250                 255

Lys Phe Phe Ile Asp Val Lys Phe Asp Gly Gly Ile Asp Pro Tyr Ser
            260                 265                 270

Gly Leu Leu Asp Met Ala Leu Glu Leu Gly Phe Val Val Lys Pro Lys
            275                 280                 285

Asn Gly Trp Tyr Ala Arg Glu Phe Leu Asp Glu Glu Thr Gly Glu Met
            290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
            325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
            355                 360                 365

Glu Ser Lys Ser Lys Ser Ala Ala Asp Leu Thr Asp Leu Glu Gln
            370                 375                 380

Leu Ser Asp Met Glu Glu Phe Asn Glu His His His His His His
385                 390                 395                 400
```

<210> SEQ ID NO 45
<211> LENGTH: 443
<212> TYPE: PRT
<213> ORGANISM: Artificial Sequence
<220> FEATURE:
<223> OTHER INFORMATION: UvsX-fib-1

<400> SEQUENCE: 45

```
Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
            35                  40                  45
```

Ile Asp Gly Gly Met Gln Ser Gly Leu Thr Ile Phe Ala Gly Pro Ser
 50                  55                  60

Lys Ser Phe Lys Ser Asn Met Ser Leu Thr Met Val Ala Ala Tyr Leu
 65                  70                  75                  80

Asn Lys Tyr Pro Asp Ala Ile Cys Leu Phe Tyr Asp Ser Glu Phe Gly
                 85                  90                  95

Ile Thr Pro Ala Tyr Leu Lys Ser Met Gly Val Asp Pro Glu Arg Val
                100                 105                 110

Ile His Thr Pro Ile Gln Ser Val Glu Gln Leu Lys Ile Asp Met Val
                115                 120                 125

Asn Gln Leu Glu Thr Ile Glu Arg Gly Glu Lys Val Ile Val Phe Ile
         130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
         180                 185                 190

Val Ala Val Asn His Thr Ile Glu Thr Ile Glu Met Phe Ser Lys Thr
         195                 200                 205

Val Met Thr Gly Gly Thr Gly Val Met Tyr Ser Ala Asp Thr Val Phe
210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
                260                 265                 270

Gly Leu Leu Asp Met Ala Leu Glu Leu Gly Phe Val Val Lys Pro Lys
         275                 280                 285

Asn Gly Trp Tyr Ala Arg Glu Phe Leu Asp Glu Glu Thr Gly Glu Met
         290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
                340                 345                 350

Glu Val Asp Glu Leu Ile Asn Ser Lys Val Glu Lys Phe Lys Ser Pro
         355                 360                 365

Glu Ser Lys Ser Lys Ser Ala Ala Asp Leu Glu Thr Asp Leu Glu Gln
         370                 375                 380

Leu Ser Asp Met Glu Glu Phe Asn Glu Pro Gly Phe Ser Pro Arg Gly
385                 390                 395                 400

Gly Gly Phe Gly Gly Arg Gly Gly Phe Gly Asp Arg Gly Gly Arg Gly
                405                 410                 415

Gly Arg Gly Gly Phe Gly Gly Gly Arg Gly Arg Gly Gly Gly Phe Arg
                420                 425                 430

Gly Arg Gly Arg His His His His His His
         435                 440

<210> SEQ ID NO 46
<211> LENGTH: 437

```
<212> TYPE: PRT
<213> ORGANISM: Artificial Sequence
<220> FEATURE:
<223> OTHER INFORMATION: UvsX-fib-2

<400> SEQUENCE: 46

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Thr Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
    210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Ile Asp Pro Tyr Ser
            260                 265                 270

Gly Leu Leu Asp Met Ala Leu Glu Leu Gly Phe Val Val Lys Pro Lys
        275                 280                 285

Asn Gly Trp Tyr Ala Arg Glu Phe Leu Asp Glu Glu Thr Gly Glu Met
    290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
        355                 360                 365

Glu Ser Lys Ser Lys Ser Ala Ala Asp Leu Glu Thr Asp Leu Glu Gln
    370                 375                 380
```

```
Leu Ser Asp Met Glu Glu Phe Asn Glu Pro Gly Phe Ser Pro Arg Gly
385                 390                 395                 400

Gly Gly Phe Gly Gly Arg Gly Gly Phe Gly Asp Arg Gly Gly Arg Gly
            405                 410                 415

Gly Arg Gly Gly Phe Gly Gly Gly Arg Gly Arg Gly Gly Val Glu His
        420                 425                 430

His His His His His
        435

<210> SEQ ID NO 47
<211> LENGTH: 428
<212> TYPE: PRT
<213> ORGANISM: Artificial Sequence
<220> FEATURE:
<223> OTHER INFORMATION: UvsX-fib-3

<400> SEQUENCE: 47

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
                20                  25                  30

Val Ile Arg Thr Lys Ile Pro Met Leu Asn Ile Ala Ile Ser Gly Ala
            35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
    115                 120                 125

Asn Gln Leu Glu Thr Ile Glu Arg Gly Glu Lys Val Ile Val Phe Ile
130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
    195                 200                 205

Val Met Thr Gly Gly Thr Gly Val Met Tyr Ser Ala Asp Thr Val Phe
210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
            260                 265                 270

Gly Leu Leu Asp Met Ala Leu Glu Leu Gly Phe Val Val Lys Pro Lys
    275                 280                 285

Asn Gly Trp Tyr Ala Arg Glu Phe Leu Asp Glu Glu Thr Gly Glu Met
290                 295                 300
```

-continued

```
Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
            325                 330                 335

Arg Ala Tyr Gln Leu Gly Ala Ile Asp Ser Asn Glu Ile Val Glu Ala
        340                 345                 350

Glu Val Asp Glu Leu Ile Asn Ser Lys Val Glu Lys Phe Lys Ser Pro
    355                 360                 365

Glu Ser Lys Ser Lys Ser Ala Ala Asp Leu Glu Thr Asp Leu Glu Gln
370                 375                 380

Leu Ser Asp Met Glu Glu Phe Asn Glu Pro Gly Phe Ser Pro Arg Gly
385                 390                 395                 400

Gly Gly Phe Gly Gly Arg Gly Gly Phe Gly Asp Arg Gly Gly Arg Gly
            405                 410                 415

Gly Arg Gly Gly Val Glu His His His His His
            420                 425

<210> SEQ ID NO 48
<211> LENGTH: 416
<212> TYPE: PRT
<213> ORGANISM: Artificial Sequence
<220> FEATURE:
<223> OTHER INFORMATION: UvsX-fib-4

<400> SEQUENCE: 48

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Thr Ile Glu Arg Gly Glu Lys Val Ile Val Phe Ile
130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
    210                 215                 220

Ile Ile Gly Lys Arg Gln Ile Lys Asp Gly Ser Asp Leu Gln Gly Tyr
225                 230                 235                 240
```

```
Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
            260                 265                 270

Gly Leu Leu Asp Met Ala Leu Glu Leu Gly Phe Val Val Lys Pro Lys
        275                 280                 285

Asn Gly Trp Tyr Ala Arg Glu Phe Leu Asp Glu Glu Thr Gly Glu Met
    290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
        355                 360                 365

Glu Ser Lys Ser Lys Ser Ala Ala Asp Leu Glu Thr Asp Leu Glu Gln
    370                 375                 380

Leu Ser Asp Met Glu Glu Phe Asn Pro Gly Phe Ser Pro Arg Gly Gly
385                 390                 395                 400

Gly Gly Phe Gly Gly Arg Gly Gly Val Glu His His His His His His
                405                 410                 415

<210> SEQ ID NO 49
<211> LENGTH: 534
<212> TYPE: PRT
<213> ORGANISM: Artificial Sequence
<220> FEATURE:
<223> OTHER INFORMATION: UvsX-HNRNPA1

<400> SEQUENCE: 49

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
                20                  25                  30

Val Ile Arg Thr Lys Ile Pro Met Leu Asn Ile Ala Ile Ser Gly Ala
            35                  40                  45

Ile Asp Gly Gly Met Gln Ser Gly Leu Thr Ile Phe Ala Gly Pro Ser
        50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Thr Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190
```

```
Val Ala Val Asn His Thr Ile Glu Thr Ile Glu Met Phe Ser Lys Thr
            195                 200                 205
Val Met Thr Gly Gly Thr Gly Val Met Tyr Ser Ala Asp Thr Val Phe
    210                 215                 220
Ile Ile Gly Lys Arg Gln Ile Lys Asp Gly Ser Asp Leu Gln Gly Tyr
225                 230                 235                 240
Gln Phe Val Leu Asn Val Glu Lys Ser Arg Thr Val Lys Glu Lys Ser
                245                 250                 255
Lys Phe Phe Ile Asp Val Lys Phe Asp Gly Gly Ile Asp Pro Tyr Ser
            260                 265                 270
Gly Leu Leu Asp Met Ala Leu Glu Leu Gly Phe Val Val Lys Pro Lys
        275                 280                 285
Asn Gly Trp Tyr Ala Arg Glu Phe Leu Asp Glu Glu Thr Gly Glu Met
    290                 295                 300
Ile Arg Glu Glu Lys Ser Trp Arg Ala Lys Asp Thr Asn Cys Thr Thr
305                 310                 315                 320
Phe Trp Gly Pro Leu Phe Lys His Gln Pro Phe Arg Asp Ala Ile Lys
                325                 330                 335
Arg Ala Tyr Gln Leu Gly Ala Ile Asp Ser Asn Glu Ile Val Glu Ala
            340                 345                 350
Glu Val Asp Glu Leu Ile Asn Ser Lys Val Glu Lys Phe Lys Ser Pro
        355                 360                 365
Glu Ser Lys Ser Lys Ser Ala Ala Asp Leu Glu Thr Asp Leu Glu Gln
    370                 375                 380
Leu Ser Asp Met Glu Glu Phe Asn Glu Ala Ser Ala Ser Ser Ser Gln
385                 390                 395                 400
Arg Gly Arg Ser Gly Ser Gly Asn Phe Gly Gly Gly Arg Gly Gly Gly
                405                 410                 415
Phe Gly Gly Asn Asp Asn Phe Gly Arg Gly Gly Asn Phe Ser Gly Arg
            420                 425                 430
Gly Gly Phe Gly Gly Ser Arg Gly Gly Gly Gly Tyr Gly Gly Ser Gly
        435                 440                 445
Asp Gly Tyr Asn Gly Phe Gly Asn Asp Gly Ser Asn Phe Gly Gly Gly
    450                 455                 460
Gly Ser Tyr Asn Asp Phe Gly Asn Tyr Asn Asn Gln Ser Ser Asn Phe
465                 470                 475                 480
Gly Pro Met Lys Gly Gly Asn Phe Gly Gly Arg Ser Ser Gly Pro Tyr
                485                 490                 495
Gly Gly Gly Gly Gln Tyr Phe Ala Lys Pro Gln Asn Gln Gly Gly Tyr
            500                 505                 510
Gly Val Ser Ser Ser Ser Ser Ser Tyr Gly Ser Gly Arg Arg Phe His
        515                 520                 525
His His His His His
    530

<210> SEQ ID NO 50
<211> LENGTH: 640
<212> TYPE: PRT
<213> ORGANISM: Artificial Sequence
<220> FEATURE:
<223> OTHER INFORMATION: UvsX-DDX

<400> SEQUENCE: 50

Met Ser Ile Ala Asp Leu Lys Ser Arg Leu Ile Lys Ala Ser Thr Ser
1               5                   10                  15
```

-continued

```
Lys Met Thr Ala Glu Leu Thr Thr Ser Lys Phe Phe Asn Glu Lys Asp
             20                  25                  30
Val Ile Arg Thr Lys Ile Pro Met Leu Asn Ile Ala Ile Ser Gly Ala
         35                  40                  45
Ile Asp Gly Gly Met Gln Ser Gly Leu Thr Ile Phe Ala Gly Pro Ser
     50                  55                  60
Lys Ser Phe Lys Ser Asn Met Ser Leu Thr Met Val Ala Ala Tyr Leu
 65                  70                  75                  80
Asn Lys Tyr Pro Asp Ala Ile Cys Leu Phe Tyr Asp Ser Glu Phe Gly
                 85                  90                  95
Ile Thr Pro Ala Tyr Leu Lys Ser Met Gly Val Asp Pro Glu Arg Val
            100                 105                 110
Ile His Thr Pro Ile Gln Ser Val Glu Gln Leu Lys Ile Asp Met Val
        115                 120                 125
Asn Gln Leu Glu Thr Ile Glu Arg Gly Glu Lys Val Ile Val Phe Ile
    130                 135                 140
Asp Ser Ile Gly Asn Met Ala Ser Lys Lys Glu Thr Glu Asp Ala Leu
145                 150                 155                 160
Asn Glu Lys Ser Val Ala Asp Met Thr Arg Ala Lys Ser Leu Lys Ser
                165                 170                 175
Leu Phe Arg Ile Val Thr Pro Tyr Phe Ser Ile Lys Asn Ile Pro Cys
            180                 185                 190
Val Ala Val Asn His Thr Ile Glu Thr Ile Glu Met Phe Ser Lys Thr
        195                 200                 205
Val Met Thr Gly Gly Thr Gly Val Met Tyr Ser Ala Asp Thr Val Phe
    210                 215                 220
Ile Ile Gly Lys Arg Gln Ile Lys Asp Gly Ser Asp Leu Gln Gly Tyr
225                 230                 235                 240
Gln Phe Val Leu Asn Val Glu Lys Ser Arg Thr Val Lys Glu Lys Ser
                245                 250                 255
Lys Phe Phe Ile Asp Val Lys Phe Asp Gly Gly Ile Asp Pro Tyr Ser
            260                 265                 270
Gly Leu Leu Asp Met Ala Leu Glu Leu Gly Phe Val Val Lys Pro Lys
        275                 280                 285
Asn Gly Trp Tyr Ala Arg Glu Phe Leu Asp Glu Glu Thr Gly Glu Met
    290                 295                 300
Ile Arg Glu Glu Lys Ser Trp Arg Ala Lys Asp Thr Asn Cys Thr Thr
305                 310                 315                 320
Phe Trp Gly Pro Leu Phe Lys His Gln Pro Phe Arg Asp Ala Ile Lys
                325                 330                 335
Arg Ala Tyr Gln Leu Gly Ala Ile Asp Ser Asn Glu Ile Val Glu Ala
            340                 345                 350
Glu Val Asp Glu Leu Ile Asn Ser Lys Val Glu Lys Phe Lys Ser Pro
        355                 360                 365
Glu Ser Lys Ser Lys Ser Ala Ala Asp Leu Glu Thr Asp Leu Glu Gln
    370                 375                 380
Leu Ser Asp Met Glu Glu Phe Asn Glu Met Gly Asp Glu Asp Trp Glu
385                 390                 395                 400
Ala Glu Ile Asn Pro His Met Ser Ser Tyr Val Pro Ile Phe Glu Lys
                405                 410                 415
Asp Arg Tyr Ser Gly Glu Asn Gly Asp Asn Phe Asn Arg Thr Pro Ala
            420                 425                 430
Ser Ser Ser Glu Met Asp Asp Gly Pro Ser Arg Arg Asp His Phe Met
```

```
                435                 440                 445
Lys Ser Gly Phe Ala Ser Gly Arg Asn Phe Gly Asn Arg Asp Ala Gly
450                 455                 460

Glu Cys Asn Lys Arg Asp Asn Thr Ser Thr Met Gly Gly Phe Gly Val
465                 470                 475                 480

Gly Lys Ser Phe Gly Asn Arg Gly Phe Ser Asn Ser Arg Phe Glu Asp
                485                 490                 495

Gly Asp Ser Ser Gly Phe Trp Arg Glu Ser Ser Asn Asp Cys Glu Asp
                500                 505                 510

Asn Pro Thr Arg Asn Arg Gly Phe Ser Lys Arg Gly Tyr Arg Asp
                515                 520                 525

Gly Asn Asn Ser Glu Ala Ser Gly Pro Tyr Arg Arg Gly Arg Gly
530                 535                 540

Ser Phe Arg Gly Cys Arg Gly Gly Phe Gly Leu Gly Ser Pro Asn Asn
545                 550                 555                 560

Asp Leu Asp Pro Asp Glu Cys Met Gln Arg Thr Gly Gly Leu Phe Gly
                565                 570                 575

Ser Arg Arg Pro Val Leu Ser Gly Thr Gly Asn Gly Asp Thr Ser Gln
                580                 585                 590

Ser Arg Ser Gly Ser Gly Ser Glu Arg Gly Gly Tyr Lys Gly Leu Asn
                595                 600                 605

Glu Glu Val Ile Thr Gly Ser Gly Lys Asn Ser Trp Lys Ser Glu Ala
610                 615                 620

Glu Gly Gly Glu Ser Ser Asp Thr Gln His His His His His His
625                 630                 635                 640

<210> SEQ ID NO 51
<211> LENGTH: 618
<212> TYPE: PRT
<213> ORGANISM: Artificial Sequence
<220> FEATURE:
<223> OTHER INFORMATION: UvsX addPolCTD

<400> SEQUENCE: 51

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
                20                  25                  30

Val Ile Arg Thr Lys Ile Pro Met Leu Asn Ile Ala Ile Ser Gly Ala
            35                  40                  45

Ile Asp Gly Gly Met Gln Ser Gly Leu Thr Ile Phe Ala Gly Pro Ser
        50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Thr Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
```

```
                165                 170                 175
Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
            195                 200                 205

Val Met Thr Gly Gly Thr Gly Val Met Tyr Ser Ala Asp Thr Val Phe
210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
            245                 250                 255

Lys Phe Phe Ile Asp Val Lys Phe Asp Gly Ile Asp Pro Tyr Ser
            260                 265                 270

Gly Leu Leu Asp Met Ala Leu Glu Leu Gly Phe Val Val Lys Pro Lys
            275                 280                 285

Asn Gly Trp Tyr Ala Arg Glu Phe Leu Asp Glu Glu Thr Gly Glu Met
            290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
            325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
            355                 360                 365

Glu Ser Lys Ser Lys Ser Ala Ala Asp Leu Glu Thr Asp Leu Glu Gln
            370                 375                 380

Leu Ser Asp Met Glu Glu Phe Asn Glu His His His His His His
385                 390                 395                 400

Phe Glu Phe Ser Pro Phe Gly Ala Tyr Gly Glu Ala Pro Thr Ser Pro
            405                 410                 415

Gly Phe Gly Val Ser Ser Pro Gly Phe Ser Pro Thr Ser Pro Thr Tyr
            420                 425                 430

Ser Pro Thr Ser Pro Ala Tyr Ser Pro Thr Ser Pro Ser Tyr Ser Pro
            435                 440                 445

Thr Ser Pro Ser Tyr Ser Pro Thr Ser Pro Ser Tyr Ser Pro Thr Ser
            450                 455                 460

Pro Ser Tyr Ser Pro Thr Ser Pro Ser Tyr Ser Pro Thr Ser Pro Ser
465                 470                 475                 480

Tyr Ser Pro Thr Ser Pro Ser Tyr Ser Pro Thr Ser Pro Ser Tyr Ser
            485                 490                 495

Pro Thr Ser Pro Ser Tyr Ser Pro Thr Ser Pro Ser Tyr Ser Pro Thr
            500                 505                 510

Ser Pro Ser Tyr Ser Pro Thr Ser Pro Ser Tyr Ser Pro Thr Ser Pro
            515                 520                 525

Ser Tyr Ser Pro Thr Ser Pro Ser Tyr Ser Pro Thr Ser Pro Ala Tyr
            530                 535                 540

Ser Pro Thr Ser Pro Ser Tyr Ser Pro Thr Ser Pro Ser Tyr Ser Pro
545                 550                 555                 560

Thr Ser Pro Ser Tyr Ser Pro Thr Ser Pro Ser Tyr Ser Pro Thr Ser
            565                 570                 575

Pro Asn Tyr Ser Pro Thr Ser Pro Ser Tyr Ser Pro Thr Ser Pro Gly
            580                 585                 590
```

```
Tyr Ser Pro Gly Ser Pro Ala Tyr Ser Pro Lys Gln Asp Glu Gln Thr
        595                 600                 605

Ala Ala Leu Glu His His His His His His
        610                 615

<210> SEQ ID NO 52
<211> LENGTH: 442
<212> TYPE: PRT
<213> ORGANISM: Artificial Sequence
<220> FEATURE:
<223> OTHER INFORMATION: UvsX-fusPolII

<400> SEQUENCE: 52

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Thr Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
    210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
            260                 265                 270

Gly Leu Leu Asp Met Ala Leu Glu Leu Gly Phe Val Val Lys Pro Lys
        275                 280                 285

Asn Gly Trp Tyr Ala Arg Glu Phe Leu Asp Glu Thr Gly Glu Met
    290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335
```

```
Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
        355                 360                 365

Glu Ser Lys Ser Lys Ser Ala Ala Asp Leu Glu Thr Asp Leu Glu Gln
    370                 375                 380

Leu Ser Asp Met Glu Glu Phe Asn Glu Thr Ser Pro Ser Tyr Ser Pro
385                 390                 395                 400

Thr Ser Pro Ser Tyr Ser Pro Thr Ser Pro Gly Tyr Ser Pro Thr Ser
                405                 410                 415

Pro Ala Tyr Ser Pro Thr Ser Pro Thr Tyr Ser Pro Thr Ser Pro Thr
            420                 425                 430

Tyr Ser Pro His His His His His His
            435                 440

<210> SEQ ID NO 53
<211> LENGTH: 467
<212> TYPE: PRT
<213> ORGANISM: Artificial Sequence
<220> FEATURE:
<223> OTHER INFORMATION: UvsX-PCF11

<400> SEQUENCE: 53

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Thr Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
    210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255
```

```
Lys Phe Phe Ile Asp Val Lys Phe Asp Gly Ile Asp Pro Tyr Ser
            260                 265                 270

Gly Leu Leu Asp Met Ala Leu Glu Leu Gly Phe Val Val Lys Pro Lys
        275                 280                 285

Asn Gly Trp Tyr Ala Arg Glu Phe Leu Asp Glu Thr Gly Glu Met
    290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
        355                 360                 365

Glu Ser Lys Ser Lys Ser Ala Ala Asp Leu Glu Thr Asp Leu Glu Gln
    370                 375                 380

Leu Ser Asp Met Glu Glu Phe Asn Glu Gln Val Gln Met Gln Leu Arg
385                 390                 395                 400

Gln Val Phe Ser Gln Asp Gln Gln Val Leu Gln Glu Arg Met Arg Tyr
                405                 410                 415

His Glu Leu Gln Gln Gln Gln Gln Gln Tyr His Glu Thr Lys Asp
            420                 425                 430

Met Val Gly Ser Tyr Thr Gln Asn Ser Asn Ser Ala Ile Pro Leu Phe
        435                 440                 445

Gly Asn Asn Ser Asp Thr Thr Asn Gln Gln Asn Ser His His His His
    450                 455                 460

His His His
465

<210> SEQ ID NO 54
<211> LENGTH: 515
<212> TYPE: PRT
<213> ORGANISM: Artificial Sequence
<220> FEATURE:
<223> OTHER INFORMATION: UvsX-Sup

<400> SEQUENCE: 54

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Thr Ile Glu Arg Gly Glu Lys Val Ile Val Phe Ile
    130                 135                 140
```

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
            165                 170                 175

Leu Phe Arg Ile Val Thr Pro Tyr Phe Ser Ile Lys Asn Ile Pro Cys
        180                 185                 190

Val Ala Val Asn His Thr Ile Glu Thr Ile Glu Met Phe Ser Lys Thr
    195                 200                 205

Val Met Thr Gly Gly Thr Gly Val Met Tyr Ser Ala Asp Thr Val Phe
210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Ile Asp Pro Tyr Ser
        260                 265                 270

Gly Leu Leu Asp Met Ala Leu Glu Leu Gly Phe Val Val Lys Pro Lys
        275                 280                 285

Asn Gly Trp Tyr Ala Arg Glu Phe Leu Asp Glu Thr Gly Glu Met
290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
            325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
            355                 360                 365

Glu Ser Lys Ser Lys Ser Ala Ala Asp Leu Glu Thr Asp Leu Glu Gln
        370                 375                 380

Leu Ser Asp Met Glu Glu Phe Asn Glu Met Ser Asp Ser Asn Gln Gly
385                 390                 395                 400

Asn Asn Gln Gln Asn Tyr Gln Gln Tyr Ser Gln Asn Gly Asn Gln Gln
                405                 410                 415

Gln Gly Asn Asn Arg Tyr Gln Gly Tyr Gln Ala Tyr Asn Ala Gln Ala
            420                 425                 430

Gln Pro Ala Gly Gly Tyr Tyr Gln Asn Tyr Gln Gly Tyr Ser Gly Tyr
            435                 440                 445

Gln Gln Gly Gly Tyr Gln Gln Tyr Gln Tyr Asn Pro Gln Gly Gly Tyr
            450                 455                 460

Gln Gln Tyr Asn Pro Gln Gly Tyr Gln Gln Tyr Asn Pro Gln Gly
465                 470                 475                 480

Gly Tyr Gln Gln Gln Phe Asn Pro Gln Gly Gly Arg Gly Asn Tyr Lys
                485                 490                 495

Asn Phe Asn Tyr Asn Asn Asn Leu Gln Gly Tyr Gln His His His His
                500                 505                 510

His His His
        515

<210> SEQ ID NO 55
<211> LENGTH: 499
<212> TYPE: PRT
<213> ORGANISM: Artificial Sequence
<220> FEATURE:

<223> OTHER INFORMATION: UvsX-DoubleX

<400> SEQUENCE: 55

```
Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Thr Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
    210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
            260                 265                 270

Gly Leu Leu Asp Met Ala Leu Glu Leu Gly Phe Val Val Lys Pro Lys
        275                 280                 285

Asn Gly Trp Tyr Ala Arg Glu Phe Leu Asp Glu Glu Thr Gly Glu Met
    290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
        355                 360                 365

Glu Ser Lys Ser Lys Ser Ala Ala Asp Leu Glu Thr Asp Leu Glu Gln
    370                 375                 380

Leu Ser Asp Met Glu Glu Phe Asn Glu His His His His His His
385                 390                 395                 400
```

```
Phe Glu Phe Glu Ile Val Glu Ala Glu Val Asp Glu Leu Ile Asn Ser
                405                 410                 415

Lys Val Glu Lys Phe Lys Ser Pro Glu Ser Lys Ser Lys Ser Ala Ala
            420                 425                 430

Asp Leu Glu Thr Asp Leu Glu Gln Leu Ser Asp Met Glu Glu Phe Asn
        435                 440                 445

Glu Ile Val Glu Ala Glu Val Asp Glu Leu Ile Asn Ser Lys Val Glu
    450                 455                 460

Lys Phe Lys Ser Pro Glu Ser Lys Ser Lys Ser Ala Ala Asp Leu Glu
465                 470                 475                 480

Thr Asp Leu Glu Gln Leu Ser Asp Met Glu Glu Phe Asn His His His
                485                 490                 495

His His His

<210> SEQ ID NO 56
<211> LENGTH: 444
<212> TYPE: PRT
<213> ORGANISM: Artificial Sequence
<220> FEATURE:
<223> OTHER INFORMATION: Superpositive

<400> SEQUENCE: 56

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Thr Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
    210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
```

```
                260                 265                 270
Gly Leu Leu Asp Met Ala Leu Glu Leu Gly Phe Val Val Lys Pro Lys
            275                 280                 285

Asn Gly Trp Tyr Ala Arg Glu Phe Leu Asp Glu Thr Gly Glu Met
        290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Arg Ile Val Lys Ala
            340                 345                 350

Lys Val Lys Arg Leu Ile Asn Ser Lys Val Lys Phe Lys Ser Pro
        355                 360                 365

Lys Ser Lys Ser Lys Ser Ala Ala Lys Leu Lys Thr Lys Leu Lys Gln
        370                 375                 380

Leu Ser Lys Met Lys Lys Phe Asn Lys Ile Val Lys Ala Lys Val Lys
385                 390                 395                 400

Lys Leu Ile Asn Ser Lys Val Arg Lys Phe Lys Ser Pro Lys Ser Lys
                405                 410                 415

Ser Lys Ser Ala Ala Lys Leu Lys Thr Lys Leu Lys Gln Leu Ser Lys
            420                 425                 430

Met Lys Glu Phe Asn His His His His His His
        435                 440

<210> SEQ ID NO 57
<211> LENGTH: 444
<212> TYPE: PRT
<213> ORGANISM: Artificial Sequence
<220> FEATURE:
<223> OTHER INFORMATION: Supernegative

<400> SEQUENCE: 57

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Thr Ile Glu Arg Gly Glu Lys Val Ile Val Phe Ile
    130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
```

```
                180                 185                 190
Val Ala Val Asn His Thr Ile Glu Thr Ile Glu Met Phe Ser Lys Thr
            195                 200                 205

Val Met Thr Gly Gly Thr Gly Val Met Tyr Ser Ala Asp Thr Val Phe
        210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
            260                 265                 270

Gly Leu Leu Asp Met Ala Leu Glu Leu Gly Phe Val Val Lys Pro Lys
        275                 280                 285

Asn Gly Trp Tyr Ala Arg Glu Phe Leu Asp Glu Thr Gly Glu Met
    290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Glu Val Glu Phe Asp Ser Pro
        355                 360                 365

Glu Ser Asp Ser Asp Glu Ala Ala Asp Leu Thr Asp Leu Glu Gln
    370                 375                 380

Leu Ser Asp Met Glu Glu Phe Asn Glu Ile Val Ala Glu Val Asp
385                 390                 395                 400

Glu Leu Ile Asn Ser Glu Val Glu Asp Phe Asp Ser Pro Glu Ser Asp
                405                 410                 415

Ser Asp Glu Ala Ala Asp Leu Thr Asp Leu Glu Gln Leu Ser Asp
            420                 425                 430

Met Glu Glu Phe Asn His His His His His His
        435                 440

<210> SEQ ID NO 58
<211> LENGTH: 429
<212> TYPE: PRT
<213> ORGANISM: Artificial Sequence
<220> FEATURE:
<223> OTHER INFORMATION: UvsX His2

<400> SEQUENCE: 58

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Ser Phe Lys Ser Asn Met Ser Leu Thr Met Val Ala Ala Tyr Leu
65                  70                  75                  80

Asn Lys Tyr Pro Asp Ala Ile Cys Leu Phe Tyr Asp Ser Glu Phe Gly
                85                  90                  95

Ile Thr Pro Ala Tyr Leu Lys Ser Met Gly Val Asp Pro Glu Arg Val
```

```
                100             105             110
Ile His Thr Pro Ile Gln Ser Val Glu Gln Leu Lys Ile Asp Met Val
            115             120             125

Asn Gln Leu Glu Thr Ile Glu Arg Gly Glu Lys Val Ile Val Phe Ile
            130             135             140

Asp Ser Ile Gly Asn Met Ala Ser Lys Lys Glu Thr Glu Asp Ala Leu
145             150             155             160

Asn Glu Lys Ser Val Ala Asp Met Thr Arg Ala Lys Ser Leu Lys Ser
                165             170             175

Leu Phe Arg Ile Val Thr Pro Tyr Phe Ser Ile Lys Asn Ile Pro Cys
            180             185             190

Val Ala Val Asn His Thr Ile Glu Thr Ile Glu Met Phe Ser Lys Thr
            195             200             205

Val Met Thr Gly Gly Thr Gly Val Met Tyr Ser Ala Asp Thr Val Phe
            210             215             220

Ile Ile Gly Lys Arg Gln Ile Lys Asp Gly Ser Asp Leu Gln Gly Tyr
225             230             235             240

Gln Phe Val Leu Asn Val Glu Lys Ser Arg Thr Val Lys Glu Lys Ser
            245             250             255

Lys Phe Phe Ile Asp Val Lys Phe Asp Gly Gly Ile Asp Pro Tyr Ser
            260             265             270

Gly Leu Leu Asp Met Ala Leu Glu Leu Gly Phe Val Val Lys Pro Lys
            275             280             285

Asn Gly Trp Tyr Ala Arg Glu Phe Leu Asp Glu Glu Thr Gly Glu Met
            290             295             300

Ile Arg Glu Glu Lys Ser Trp Arg Ala Lys Asp Thr Asn Cys Thr Thr
305             310             315             320

Phe Trp Gly Pro Leu Phe Lys His Gln Pro Phe Arg Asp Ala Ile Lys
            325             330             335

Arg Ala Tyr Gln Leu Gly Ala Ile Asp Ser Asn Glu Ile Val Glu Ala
            340             345             350

Glu Val Asp Glu Leu Ile Asn Ser Lys Val Glu Lys Phe Lys Ser Pro
            355             360             365

Glu Ser Lys Ser Lys Ser Ala Ala Asp Leu Glu Thr Asp Leu Glu Gln
            370             375             380

Leu Ser Asp Met Glu Glu Phe Asn Glu Ala Gly His His His His
385             390             395             400

Pro His Ala His His Pro Leu Ser Gln Ser Ser Gly His His His
            405             410             415

His His His His His Gln Gly Tyr Gly Gly Ser Gly
            420             425
```

<210> SEQ ID NO 59
<211> LENGTH: 496
<212> TYPE: PRT
<213> ORGANISM: Artificial Sequence
<220> FEATURE:
<223> OTHER INFORMATION: UvsX+PCF+His2

<400> SEQUENCE: 59

```
Met Ser Ile Ala Asp Leu Lys Ser Arg Leu Ile Lys Ala Ser Thr Ser
1               5               10              15

Lys Met Thr Ala Glu Leu Thr Thr Ser Lys Phe Phe Asn Glu Lys Asp
            20              25              30

Val Ile Arg Thr Lys Ile Pro Met Leu Asn Ile Ala Ile Ser Gly Ala
```

```
                35                  40                  45
Ile Asp Gly Gly Met Gln Ser Gly Leu Thr Ile Phe Ala Gly Pro Ser
 50                  55                  60

Lys Ser Phe Lys Ser Asn Met Ser Leu Thr Met Val Ala Ala Tyr Leu
 65                  70                  75                  80

Asn Lys Tyr Pro Asp Ala Ile Cys Leu Phe Tyr Asp Ser Glu Phe Gly
                 85                  90                  95

Ile Thr Pro Ala Tyr Leu Lys Ser Met Gly Val Asp Pro Glu Arg Val
                100                 105                 110

Ile His Thr Pro Ile Gln Ser Val Glu Gln Leu Lys Ile Asp Met Val
                115                 120                 125

Asn Gln Leu Glu Thr Ile Glu Arg Gly Glu Lys Val Ile Val Phe Ile
130                 135                 140

Asp Ser Ile Gly Asn Met Ala Ser Lys Lys Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
                180                 185                 190

Val Ala Val Asn His Thr Ile Glu Thr Ile Glu Met Phe Ser Lys Thr
                195                 200                 205

Val Met Thr Gly Thr Gly Val Met Tyr Ser Ala Asp Thr Val Phe
210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
                260                 265                 270

Gly Leu Leu Asp Met Ala Leu Glu Leu Gly Phe Val Val Lys Pro Lys
                275                 280                 285

Asn Gly Trp Tyr Ala Arg Glu Phe Leu Asp Glu Glu Thr Gly Glu Met
                290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
                340                 345                 350

Glu Val Asp Glu Leu Ile Asn Ser Lys Val Glu Lys Phe Lys Ser Pro
                355                 360                 365

Glu Ser Lys Ser Lys Ser Ala Ala Asp Leu Glu Thr Asp Leu Glu Gln
                370                 375                 380

Leu Ser Asp Met Glu Glu Phe Asn Glu Gln Val Gln Met Gln Leu Arg
385                 390                 395                 400

Gln Val Phe Ser Gln Asp Gln Val Leu Gln Glu Arg Met Arg Tyr
                405                 410                 415

His Glu Leu Gln Gln Gln Gln Gln Gln Tyr His Gly Thr Lys Asp
                420                 425                 430

Met Val Gly Ser Tyr Thr Gln Asn Ser Asn Ser Ala Ile Pro Leu Phe
                435                 440                 445

Gly Asn Asn Ser Asp Thr Thr Asn Gln Gln Asn Ser Ala Gly His His
450                 455                 460
```

```
His His His Pro His Ala His His Pro Leu Ser Gln Ser Ser Gly His
465                 470                 475                 480

His His His His His His His His Gln Gly Tyr Gly Gly Ser Gly
                485                 490                 495
```

<210> SEQ ID NO 60
<211> LENGTH: 145
<212> TYPE: PRT
<213> ORGANISM: Artificial Sequence
<220> FEATURE:
<223> OTHER INFORMATION: UvsY [Phage ST0]

<400> SEQUENCE: 60

```
Met His His His His His His Met Lys Leu Glu Asp Leu Gln Glu
1               5                   10                  15

Glu Leu Asp Ala Asp Leu Ala Ile Asp Met Ser Lys Leu Gln Tyr Glu
                20                  25                  30

Thr Ala Asn Asn Val Lys Leu Tyr Ser Lys Trp Leu Arg Lys His Ser
            35                  40                  45

Phe Ile Arg Lys Glu Met Leu Arg Ile Glu Thr Gln Lys Lys Thr Ala
    50                  55                  60

Leu Lys Ala Arg Leu Asp Tyr Tyr Ser Gly Arg Gly Asp Gly Asp Glu
65                  70                  75                  80

Phe Ser Met Asp Arg Tyr Glu Lys Ser Glu Met Lys Thr Val Leu Ala
                85                  90                  95

Ala Asp Lys Asp Val Leu Lys Ile Glu Thr Thr Leu Gln Tyr Trp Gly
            100                 105                 110

Ile Leu Leu Glu Phe Cys Ser Gly Ala Leu Asp Ala Val Lys Ser Arg
        115                 120                 125

Ser Phe Ala Leu Lys His Ile Gln Asp Met Arg Glu Phe Glu Ala Gly
    130                 135                 140

Gln
145
```

<210> SEQ ID NO 61
<211> LENGTH: 172
<212> TYPE: PRT
<213> ORGANISM: Artificial Sequence
<220> FEATURE:
<223> OTHER INFORMATION: UvsY C-Pol CTD

<400> SEQUENCE: 61

```
Met His His His His His His His Lys Leu Glu Asp Leu Gln Glu
1               5                   10                  15

Glu Leu Asp Ala Asp Leu Ala Ile Asp Met Ser Lys Leu Gln Tyr Glu
                20                  25                  30

Thr Ala Asn Asn Val Lys Leu Tyr Ser Lys Trp Leu Arg Lys His Ser
            35                  40                  45

Phe Ile Arg Lys Glu Met Leu Arg Ile Glu Thr Gln Lys Lys Thr Ala
    50                  55                  60

Leu Lys Ala Arg Leu Asp Tyr Tyr Ser Gly Arg Gly Asp Gly Asp Glu
65                  70                  75                  80

Phe Ser Met Asp Arg Tyr Glu Lys Ser Glu Met Lys Thr Val Leu Ala
                85                  90                  95

Ala Asp Lys Asp Val Leu Lys Ile Glu Thr Thr Leu Gln Tyr Trp Gly
            100                 105                 110

Ile Leu Leu Glu Phe Cys Ser Gly Ala Leu Asp Ala Val Lys Ser Arg
```

```
                115                 120                 125
Ser Phe Ala Leu Lys His Ile Gln Asp Met Arg Glu Phe Glu Ala Gly
        130                 135                 140

Gln Ser Gly Ser Gly Ser Gly Pro Thr Ser Pro Ser Tyr Ser Pro Thr
145                 150                 155                 160

Ser Pro Ser Tyr Ser Pro Tyr Ser Pro Ala Tyr Ser
                165                 170

<210> SEQ ID NO 62
<211> LENGTH: 176
<212> TYPE: PRT
<213> ORGANISM: Artificial Sequence
<220> FEATURE:
<223> OTHER INFORMATION: UvsY fib[short]

<400> SEQUENCE: 62

Met His His His His His His His Lys Leu Glu Asp Leu Gln Glu
1               5                  10                  15

Glu Leu Asp Ala Asp Leu Ala Ile Asp Met Ser Lys Leu Gln Tyr Glu
                20                  25                  30

Thr Ala Asn Asn Val Lys Leu Tyr Ser Lys Trp Leu Arg Lys His Ser
            35                  40                  45

Phe Ile Arg Lys Glu Met Leu Arg Ile Glu Thr Gln Lys Lys Thr Ala
    50                  55                  60

Leu Lys Ala Arg Leu Asp Tyr Tyr Ser Gly Arg Gly Asp Gly Asp Glu
65                  70                  75                  80

Phe Ser Met Asp Arg Tyr Glu Lys Ser Glu Met Lys Thr Val Leu Ala
                85                  90                  95

Ala Asp Lys Asp Val Leu Lys Ile Glu Thr Thr Leu Gln Tyr Trp Gly
            100                 105                 110

Ile Leu Leu Glu Phe Cys Ser Gly Ala Leu Asp Ala Val Lys Ser Arg
    115                 120                 125

Ser Phe Ala Leu Lys His Ile Gln Asp Met Arg Glu Phe Glu Ala Gly
        130                 135                 140

Gln Ser Gly Ser Gly Ser Gly Arg Gly Gly Phe Gly Gly Arg Gly
145                 150                 155                 160

Gly Phe Gly Asp Arg Gly Gly Arg Gly Gly Arg Gly Gly Phe Gly Gly
                165                 170                 175

<210> SEQ ID NO 63
<211> LENGTH: 161
<212> TYPE: PRT
<213> ORGANISM: Artificial Sequence
<220> FEATURE:
<223> OTHER INFORMATION: UvsY Sup1

<400> SEQUENCE: 63

Met His His His His His His His Lys Leu Glu Asp Leu Gln Glu
1               5                  10                  15

Glu Leu Asp Ala Asp Leu Ala Ile Asp Met Ser Lys Leu Gln Tyr Glu
                20                  25                  30

Thr Ala Asn Asn Val Lys Leu Tyr Ser Lys Trp Leu Arg Lys His Ser
            35                  40                  45

Phe Ile Arg Lys Glu Met Leu Arg Ile Glu Thr Gln Lys Lys Thr Ala
    50                  55                  60

Leu Lys Ala Arg Leu Asp Tyr Tyr Ser Gly Arg Gly Asp Gly Asp Glu
65                  70                  75                  80
```

-continued

Phe Ser Met Asp Arg Tyr Glu Lys Ser Glu Met Lys Thr Val Leu Ala
                85                  90                  95

Ala Asp Lys Asp Val Leu Lys Ile Glu Thr Thr Leu Gln Tyr Trp Gly
            100                 105                 110

Ile Leu Leu Glu Phe Cys Ser Gly Ala Leu Asp Ala Val Lys Ser Arg
        115                 120                 125

Ser Phe Ala Leu Lys His Ile Gln Asp Met Arg Glu Phe Glu Ala Gly
    130                 135                 140

Gln Ser Gly Ser Gly Tyr Asn Pro Gln Gly Gly Tyr Gln Gln Asn Asn
145                 150                 155                 160

Leu

<210> SEQ ID NO 64
<211> LENGTH: 190
<212> TYPE: PRT
<213> ORGANISM: Artificial Sequence
<220> FEATURE:
<223> OTHER INFORMATION: UvsY Sup1 HIS2

<400> SEQUENCE: 64

Met Ala Gly His His His His His Pro His Ala His His Pro Leu Ser
1               5                   10                  15

Gln Ser Ser Gly His His His His His His His His Gln Gly
            20                  25                  30

Tyr Gly Gly Ser Gly Lys Leu Glu Asp Leu Gln Glu Glu Leu Asp Ala
        35                  40                  45

Asp Leu Ala Ile Asp Met Ser Lys Leu Gln Tyr Glu Thr Ala Asn Asn
    50                  55                  60

Val Lys Leu Tyr Ser Lys Trp Leu Arg Lys His Ser Phe Ile Arg Lys
65                  70                  75                  80

Glu Met Leu Arg Ile Glu Thr Gln Lys Lys Thr Ala Leu Lys Ala Arg
                85                  90                  95

Leu Asp Tyr Tyr Ser Gly Arg Gly Asp Gly Asp Glu Phe Ser Met Asp
            100                 105                 110

Arg Tyr Glu Lys Ser Glu Met Lys Thr Val Leu Ala Ala Asp Lys Asp
        115                 120                 125

Val Leu Lys Ile Glu Thr Thr Leu Gln Tyr Trp Gly Ile Leu Leu Glu
    130                 135                 140

Phe Cys Ser Gly Ala Leu Asp Ala Val Lys Ser Arg Ser Phe Ala Leu
145                 150                 155                 160

Lys His Ile Gln Asp Met Arg Glu Phe Glu Ala Gly Gln Ser Gly Ser
                165                 170                 175

Gly Tyr Asn Pro Gln Gly Gly Tyr Gln Gln Asn Asn Leu Gln
            180                 185                 190

<210> SEQ ID NO 65
<211> LENGTH: 306
<212> TYPE: PRT
<213> ORGANISM: Artificial Sequence
<220> FEATURE:
<223> OTHER INFORMATION: Gp32 (7His) from phage vB

<400> SEQUENCE: 65

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
            35                  40                  45

Pro Ala Lys Thr Asp Asp Ala Leu Pro Phe Thr Ile Leu Val Asn His
        50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
        275                 280                 285

Asp Ser Asp Leu Asp Asp Leu Leu Ala Gly Leu His His His His His
    290                 295                 300

His His
305

<210> SEQ ID NO 66
<211> LENGTH: 336
<212> TYPE: PRT
<213> ORGANISM: Artificial Sequence
<220> FEATURE:
<223> OTHER INFORMATION: Gp32Super +ve

<400> SEQUENCE: 66

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
            115                 120                 125

Asp Asn Glu Gly Lys Val Phe Lys Tyr Arg Phe Gly Lys Lys Ile Trp
130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
            195                 200                 205

Leu Phe Glu Gln Met Val Asp Leu Ser Glu Met Thr Ser Lys Asp Lys
            210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Lys
                245                 250                 255

Lys Val Ala Ser Lys Leu Lys Phe Lys Lys Met Glu Ala Phe Ser
            260                 265                 270

Ser Ala Lys Thr Lys Lys Phe Met Ser Ser Ser Ser Lys Lys
            275                 280                 285

Ser Lys Leu Lys Lys Leu Leu Ala Gly Leu Met Glu Ala Phe Ser Ser
290                 295                 300

Ala Lys Thr Lys Lys Phe Met Ser Ser Ser Ser Lys Lys Ser
305                 310                 315                 320

Lys Leu Lys Lys Leu Leu Ala Gly Leu His His His His His His
                325                 330                 335

<210> SEQ ID NO 67
<211> LENGTH: 337
<212> TYPE: PRT
<213> ORGANISM: Artificial Sequence
<220> FEATURE:
<223> OTHER INFORMATION: Gp32Super -ve

<400> SEQUENCE: 67

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

```
Thr Ser Tyr Trp Ala Asn Ile Leu Val Val Lys Asp Pro Gln Ala Pro
            115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Asp Val Ala Ser Asp Leu Asp Asp Phe Asp Asp Met Glu Ala Phe
                260                 265                 270

Ser Ser Ala Asp Thr Glu Asp Asp Phe Met Ser Ser Ser Ser Asp
                275                 280                 285

Asp Ser Asp Leu Asp Asp Leu Ala Gly Leu Met Glu Ala Phe Ser
        290                 295                 300

Ser Ala Asp Thr Glu Asp Asp Phe Met Ser Ser Ser Ser Asp Asp
305                 310                 315                 320

Ser Asp Leu Asp Asp Leu Ala Gly Leu His His His His His
                325                 330                 335

His

<210> SEQ ID NO 68
<211> LENGTH: 403
<212> TYPE: PRT
<213> ORGANISM: Artificial Sequence
<220> FEATURE:
<223> OTHER INFORMATION: Gp32-TripleXtail

<400> SEQUENCE: 68

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
                100                 105                 110

Thr Ser Tyr Trp Ala Asn Ile Leu Val Val Lys Asp Pro Gln Ala Pro
            115                 120                 125

Asp Asn Glu Gly Lys Val Phe Lys Tyr Arg Phe Gly Lys Lys Ile Trp
```

```
                130                 135                 140
Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Asp Val Ala Ser Glu Phe Glu Ile Val Glu Ala Glu Val Asp Glu Leu
            260                 265                 270

Ile Asn Ser Lys Val Glu Lys Phe Lys Ser Pro Glu Ser Lys Ser Lys
        275                 280                 285

Ser Ala Ala Asp Leu Glu Thr Asp Leu Glu Gln Leu Ser Asp Met Glu
    290                 295                 300

Glu Phe Asn Glu Ile Val Glu Ala Glu Val Asp Glu Leu Ile Asn Ser
305                 310                 315                 320

Lys Val Glu Lys Phe Lys Ser Pro Glu Ser Lys Ser Lys Ser Ala Ala
                325                 330                 335

Asp Leu Glu Thr Asp Leu Glu Gln Leu Ser Asp Met Glu Glu Phe Asn
            340                 345                 350

Glu Ile Val Glu Ala Glu Val Asp Glu Leu Ile Asn Ser Lys Val Glu
        355                 360                 365

Lys Phe Lys Ser Pro Glu Ser Lys Ser Lys Ser Ala Ala Asp Leu Glu
    370                 375                 380

Thr Asp Leu Glu Gln Leu Ser Asp Met Glu Glu Phe Asn His His His
385                 390                 395                 400

His His His

<210> SEQ ID NO 69
<211> LENGTH: 349
<212> TYPE: PRT
<213> ORGANISM: Artificial Sequence
<220> FEATURE:
<223> OTHER INFORMATION: Gp32-fib

<400> SEQUENCE: 69

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95
```

Asp Leu Tyr Asn Thr Asn Lys Thr Glu Tyr Ser Gln Leu Lys Arg Lys
                100                 105                 110

Thr Ser Tyr Trp Ala Asn Ile Leu Val Val Lys Asp Pro Gln Ala Pro
            115                 120                 125

Asp Asn Glu Gly Lys Val Phe Lys Tyr Arg Phe Gly Lys Lys Ile Trp
        130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Asp
        275                 280                 285

Asp Ser Asp Leu Asp Asp Leu Ala Gly Leu Pro Gly Phe Ser Pro
    290                 295                 300

Arg Gly Gly Gly Phe Gly Gly Arg Gly Gly Phe Gly Asp Arg Gly Gly
305                 310                 315                 320

Arg Gly Gly Arg Gly Gly Phe Gly Gly Arg Gly Arg Gly Gly
                325                 330                 335

Phe Arg Gly Arg Gly Arg His His His His His His
            340                 345

<210> SEQ ID NO 70
<211> LENGTH: 375
<212> TYPE: PRT
<213> ORGANISM: Artificial Sequence
<220> FEATURE:
<223> OTHER INFORMATION: Gp32-PCF11

<400> SEQUENCE: 70

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
                100                 105                 110

```
Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
        275                 280                 285

Asp Ser Asp Leu Asp Asp Leu Leu Ala Gly Leu Asn Glu Gln Val Gln
    290                 295                 300

Met Gln Leu Arg Gln Val Phe Ser Gln Asp Gln Val Leu Gln Glu
305                 310                 315                 320

Arg Met Arg Tyr His Glu Leu Gln Gln Gln Gln Gln Gln Tyr His
                325                 330                 335

Glu Thr Lys Asp Met Val Gly Ser Tyr Thr Gln Asn Ser Asn Ser Ala
            340                 345                 350

Ile Pro Leu Phe Gly Asn Asn Ser Asp Thr Thr Asn Gln Gln Asn Ser
        355                 360                 365

His His His His His His
    370                 375

<210> SEQ ID NO 71
<211> LENGTH: 421
<212> TYPE: PRT
<213> ORGANISM: Artificial Sequence
<220> FEATURE:
<223> OTHER INFORMATION: Gp32-Sup

<400> SEQUENCE: 71

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95
```

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Asp
        275                 280                 285

Asp Ser Asp Leu Asp Asp Leu Ala Gly Leu Met Ser Asp Ser Asn
    290                 295                 300

Gln Gly Asn Asn Gln Gln Asn Tyr Gln Gln Tyr Ser Gln Asn Gly Asn
305                 310                 315                 320

Gln Gln Gln Gly Asn Asn Arg Tyr Gln Gly Tyr Gln Ala Tyr Asn Ala
                325                 330                 335

Gln Ala Gln Pro Ala Gly Gly Tyr Tyr Gln Asn Tyr Gln Gly Tyr Ser
            340                 345                 350

Gly Tyr Gln Gln Gly Gly Tyr Gln Gln Tyr Tyr Asn Pro Gln Gly
        355                 360                 365

Gly Tyr Gln Gln Tyr Asn Pro Gln Gly Gly Tyr Gln Gln Tyr Asn Pro
    370                 375                 380

Gln Gly Gly Tyr Gln Gln Gln Phe Asn Pro Gln Gly Gly Arg Gly Asn
385                 390                 395                 400

Tyr Lys Asn Phe Asn Tyr Asn Asn Asn Leu Gln Gly Tyr Gln His His
                405                 410                 415

His His His His His
            420

<210> SEQ ID NO 72
<211> LENGTH: 315
<212> TYPE: PRT
<213> ORGANISM: Artificial Sequence
<220> FEATURE:
<223> OTHER INFORMATION: Gp32-Sup1

<400> SEQUENCE: 72

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

-continued

```
Leu Lys Leu Asp Ala Ser Gly Asn Gly Gln Ala Val Ile Arg Phe Leu
         35                  40                  45

Pro Ala Lys Thr Asp Asp Ala Leu Pro Phe Thr Ile Leu Val Asn His
 50                  55                  60

Gly Phe Lys Lys Asn Gly Lys Trp Tyr Ile Glu Thr Cys Ser Ser Thr
 65                  70                  75                  80

His Gly Asp Tyr Asp Ser Cys Pro Val Cys Gln Tyr Ile Ser Lys Asn
                 85                  90                  95

Asp Leu Tyr Asn Thr Asn Lys Thr Glu Tyr Ser Gln Leu Lys Arg Lys
                100                 105                 110

Thr Ser Tyr Trp Ala Asn Ile Leu Val Val Lys Asp Pro Gln Ala Pro
                115                 120                 125

Asp Asn Glu Gly Lys Val Phe Lys Tyr Arg Phe Gly Lys Lys Ile Trp
            130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
                180                 185                 190

Asn Gln Ser Ala Ile Pro Asn Ile Asp Asp Glu Ser Phe Gln Lys Glu
            195                 200                 205

Leu Phe Glu Gln Met Val Asp Leu Ser Glu Met Thr Ser Lys Asp Lys
210                 215                 220

Phe Lys Ser Phe Glu Glu Leu Asn Thr Lys Phe Asn Gln Val Leu Gly
225                 230                 235                 240

Thr Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
            275                 280                 285

Asp Ser Asp Leu Asp Asp Leu Leu Ala Gly Leu Tyr Asn Pro Gln Gly
            290                 295                 300

Gly Tyr Gln Gln His His His His His His
305                 310                 315

<210> SEQ ID NO 73
<211> LENGTH: 324
<212> TYPE: PRT
<213> ORGANISM: Artificial Sequence
<220> FEATURE:
<223> OTHER INFORMATION: Gp32-Sup2

<400> SEQUENCE: 73

Met Phe Lys Arg Lys Ser Thr Ala Asp Leu Ala Ala Gln Met Ala Lys
 1               5                  10                  15

Leu Asn Gly Asn Lys Gly Phe Ser Ser Glu Asp Lys Gly Glu Trp Lys
             20                  25                  30

Leu Lys Leu Asp Ala Ser Gly Asn Gly Gln Ala Val Ile Arg Phe Leu
         35                  40                  45

Pro Ala Lys Thr Asp Asp Ala Leu Pro Phe Thr Ile Leu Val Asn His
 50                  55                  60

Gly Phe Lys Lys Asn Gly Lys Trp Tyr Ile Glu Thr Cys Ser Ser Thr
 65                  70                  75                  80
```

His Gly Asp Tyr Asp Ser Cys Pro Val Cys Gln Tyr Ile Ser Lys Asn
            85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
            115                 120                 125

Asp Asn Glu Gly Lys Val Phe Lys Tyr Arg Phe Gly Lys Lys Ile Trp
130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
            165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
            195                 200                 205

Leu Phe Glu Gln Met Val Asp Leu Ser Glu Met Thr Ser Lys Asp Lys
210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
            245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
            275                 280                 285

Asp Ser Asp Leu Asp Asp Leu Leu Ala Gly Leu Tyr Asn Pro Gln Gly
            290                 295                 300

Gly Tyr Gln Gln Tyr Asn Pro Gln Gly Gly Tyr Gln Gln His His His
305                 310                 315                 320

His His His His

<210> SEQ ID NO 74
<211> LENGTH: 333
<212> TYPE: PRT
<213> ORGANISM: Artificial Sequence
<220> FEATURE:
<223> OTHER INFORMATION: Gp32-Sup3

<400> SEQUENCE: 74

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
            35                  40                  45

Pro Ala Lys Thr Asp Asp Ala Leu Pro Phe Thr Ile Leu Val Asn His
            50                  55                  60

Gly Phe Lys Lys Asn Gly Lys Trp Tyr Ile Glu Thr Cys Ser Ser Thr
65              70                  75                  80

His Gly Asp Tyr Asp Ser Cys Pro Val Cys Gln Tyr Ile Ser Lys Asn
            85                  90                  95

Asp Leu Tyr Asn Thr Asn Lys Thr Glu Tyr Ser Gln Leu Lys Arg Lys
            100                 105                 110

```
Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
                260                 265                 270

Ser Ser Ala Lys Thr Glu Asp Asp Phe Met Ser Ser Ser Ser Ser Asp
                275                 280                 285

Asp Ser Asp Leu Asp Asp Leu Leu Ala Gly Leu Tyr Asn Pro Gln Gly
        290                 295                 300

Gly Tyr Gln Gln Tyr Asn Pro Gln Gly Gly Tyr Gln Gln Tyr Asn Pro
305                 310                 315                 320

Gln Gly Gly Tyr Gln Gln His His His His His His
                325                 330
```

<210> SEQ ID NO 75
<211> LENGTH: 342
<212> TYPE: PRT
<213> ORGANISM: Artificial Sequence
<220> FEATURE:
<223> OTHER INFORMATION: Gp32-Sup4

<400> SEQUENCE: 75

```
Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
                20                  25                  30

Leu Lys Leu Asp Ala Ser Gly Asn Gly Gln Ala Val Ile Arg Phe Leu
            35                  40                  45

Pro Ala Lys Thr Asp Asp Ala Leu Pro Phe Thr Ile Leu Val Asn His
        50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140
```

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
            165                 170                 175

Val Lys Gln Val Ser Gly Phe Ser Asn Tyr Asp Glu Ser Lys Phe Leu
        180                 185                 190

Asn Gln Ser Ala Ile Pro Asn Ile Asp Asp Glu Ser Phe Gln Lys Glu
    195                 200                 205

Leu Phe Glu Gln Met Val Asp Leu Ser Glu Met Thr Ser Lys Asp Lys
210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Asp
        275                 280                 285

Asp Ser Asp Leu Asp Asp Leu Leu Ala Gly Leu Tyr Asn Pro Gln Gly
    290                 295                 300

Gly Tyr Gln Gln Tyr Asn Pro Gln Gly Gly Tyr Gln Gln Tyr Asn Pro
305                 310                 315                 320

Gln Gly Gly Tyr Gln Gln Tyr Asn Pro Gln Gly Gly Tyr Gln Gln His
                325                 330                 335

His His His His His His
            340

<210> SEQ ID NO 76
<211> LENGTH: 557
<212> TYPE: PRT
<213> ORGANISM: Artificial Sequence
<220> FEATURE:
<223> OTHER INFORMATION: Gp32-DDX

<400> SEQUENCE: 76

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
             165                 170                 175

Val Lys Gln Val Ser Gly Phe Ser Asn Tyr Asp Glu Ser Lys Phe Leu
        180                 185                 190

Asn Gln Ser Ala Ile Pro Asn Ile Asp Asp Glu Ser Phe Gln Lys Glu
            195                 200                 205

Leu Phe Glu Gln Met Val Asp Leu Ser Glu Met Thr Ser Lys Asp Lys
        210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
                260                 265                 270

Ser Ser Ala Lys Thr Glu Asp Asp Phe Met Ser Ser Ser Ser Ser Asp
                275                 280                 285

Asp Ser Asp Leu Asp Asp Leu Leu Ala Gly Leu His His His His
        290                 295                 300

His His Phe Glu Phe Met Gly Asp Glu Asp Trp Glu Ala Glu Ile Asn
305                 310                 315                 320

Pro His Met Ser Ser Tyr Val Pro Ile Phe Glu Lys Asp Arg Tyr Ser
                325                 330                 335

Gly Glu Asn Gly Asp Asn Phe Asn Arg Thr Pro Ala Ser Ser Ser Glu
                340                 345                 350

Met Asp Asp Gly Pro Ser Arg Arg Asp His Phe Met Lys Ser Gly Phe
                355                 360                 365

Ala Ser Gly Arg Asn Phe Gly Asn Arg Asp Ala Gly Glu Cys Asn Lys
        370                 375                 380

Arg Asp Asn Thr Ser Thr Met Gly Gly Phe Gly Val Gly Lys Ser Phe
385                 390                 395                 400

Gly Asn Arg Gly Phe Ser Asn Ser Arg Phe Glu Asp Gly Asp Ser Ser
                405                 410                 415

Gly Phe Trp Arg Glu Ser Ser Asn Asp Cys Glu Asp Asn Pro Thr Arg
                420                 425                 430

Asn Arg Gly Phe Ser Lys Arg Gly Gly Tyr Arg Asp Gly Asn Asn Ser
        435                 440                 445

Glu Ala Ser Gly Pro Tyr Arg Arg Gly Gly Arg Gly Ser Phe Arg Gly
        450                 455                 460

Cys Arg Gly Gly Phe Gly Leu Gly Ser Pro Asn Asn Asp Leu Asp Pro
465                 470                 475                 480

Asp Glu Cys Met Gln Arg Thr Gly Gly Leu Phe Gly Ser Arg Arg Pro
                485                 490                 495

Val Leu Ser Gly Thr Gly Asn Gly Asp Thr Ser Gln Ser Arg Ser Gly
                500                 505                 510

Ser Gly Ser Glu Arg Gly Gly Tyr Lys Gly Leu Asn Glu Glu Val Ile
        515                 520                 525

Thr Gly Ser Gly Lys Asn Ser Trp Lys Ser Glu Ala Glu Gly Gly Glu
        530                 535                 540

Ser Ser Asp Thr Gln Leu Glu His His His His His
545                 550                 555

<210> SEQ ID NO 77
<211> LENGTH: 521
<212> TYPE: PRT

<213> ORGANISM: Artificial Sequence
<220> FEATURE:
<223> OTHER INFORMATION: Gp32 PolCTD

<400> SEQUENCE: 77

```
Met Phe Lys Arg Lys Ser Thr Ala Asp Leu Ala Ala Gln Met Ala Lys
1               5                   10                  15
Leu Asn Gly Asn Lys Gly Phe Ser Ser Glu Asp Lys Gly Glu Trp Lys
            20                  25                  30
Leu Lys Leu Asp Ala Ser Gly Asn Gly Gln Ala Val Ile Arg Phe Leu
        35                  40                  45
Pro Ala Lys Thr Asp Asp Ala Leu Pro Phe Thr Ile Leu Val Asn His
    50                  55                  60
Gly Phe Lys Lys Asn Gly Lys Trp Tyr Ile Glu Thr Cys Ser Ser Thr
65                  70                  75                  80
His Gly Asp Tyr Asp Ser Cys Pro Val Cys Gln Tyr Ile Ser Lys Asn
                85                  90                  95
Asp Leu Tyr Asn Thr Asn Lys Thr Glu Tyr Ser Gln Leu Lys Arg Lys
            100                 105                 110
Thr Ser Tyr Trp Ala Asn Ile Leu Val Val Lys Asp Pro Gln Ala Pro
        115                 120                 125
Asp Asn Glu Gly Lys Val Phe Lys Tyr Arg Phe Gly Lys Lys Ile Trp
    130                 135                 140
Asp Lys Ile Asn Ala Met Ile Ala Val Asp Thr Glu Met Gly Glu Thr
145                 150                 155                 160
Pro Val Asp Val Thr Cys Pro Trp Glu Gly Ala Asn Phe Val Leu Lys
                165                 170                 175
Val Lys Gln Val Ser Gly Phe Ser Asn Tyr Asp Glu Ser Lys Phe Leu
            180                 185                 190
Asn Gln Ser Ala Ile Pro Asn Ile Asp Asp Glu Ser Phe Gln Lys Glu
        195                 200                 205
Leu Phe Glu Gln Met Val Asp Leu Ser Glu Met Thr Ser Lys Asp Lys
    210                 215                 220
Phe Lys Ser Phe Glu Glu Leu Asn Thr Lys Phe Asn Gln Val Leu Gly
225                 230                 235                 240
Thr Ala Ala Leu Gly Gly Ala Ala Ala Ala Ala Ser Val Ala Asp
                245                 250                 255
Lys Val Ala Ser Asp Leu Asp Asp Phe Asp Lys Asp Met Glu Ala Phe
            260                 265                 270
Ser Ser Ala Lys Thr Glu Asp Asp Phe Met Ser Ser Ser Ser Ser Asp
        275                 280                 285
Asp Ser Asp Leu Asp Asp Leu Leu Ala Gly Leu His His His His
    290                 295                 300
His His Phe Glu Phe Ser Pro Phe Gly Ala Tyr Gly Glu Ala Pro Thr
305                 310                 315                 320
Ser Pro Gly Phe Gly Val Ser Ser Pro Gly Phe Ser Pro Thr Ser Pro
                325                 330                 335
Thr Tyr Ser Pro Thr Ser Pro Ala Tyr Ser Pro Thr Ser Pro Ser Tyr
            340                 345                 350
Ser Pro Thr Ser Pro Ser Tyr Ser Pro Thr Ser Pro Ser Tyr Ser Pro
        355                 360                 365
Thr Ser Pro Ser Tyr Ser Pro Thr Ser Pro Ser Tyr Ser Pro Thr Ser
    370                 375                 380
Pro Ser Tyr Ser Pro Thr Ser Pro Ser Tyr Ser Pro Thr Ser Pro Ser
```

```
                385                 390                 395                 400
Tyr Ser Pro Thr Ser Pro Ser Tyr Ser Pro Thr Ser Pro Ser Tyr Ser
                    405                 410                 415
Pro Thr Ser Pro Ser Tyr Ser Pro Thr Ser Pro Ser Tyr Ser Pro Thr
                    420                 425                 430
Ser Pro Ser Tyr Ser Pro Thr Ser Pro Ser Tyr Ser Pro Thr Ser Pro
                    435                 440                 445
Ala Tyr Ser Pro Thr Ser Pro Ser Tyr Ser Pro Thr Ser Pro Ser Tyr
            450                 455                 460
Ser Pro Thr Ser Pro Ser Tyr Ser Pro Thr Ser Pro Ser Tyr Ser Pro
465                 470                 475                 480
Thr Ser Pro Asn Tyr Ser Pro Thr Ser Pro Ser Tyr Ser Pro Thr Ser
                    485                 490                 495
Pro Gly Tyr Ser Pro Gly Ser Pro Ala Tyr Ser Pro Lys Gln Asp Glu
                500                 505                 510
Gln Leu Glu His His His His His His
                515                 520

<210> SEQ ID NO 78
<211> LENGTH: 440
<212> TYPE: PRT
<213> ORGANISM: Artificial Sequence
<220> FEATURE:
<223> OTHER INFORMATION: Gp32 HNRNPA1

<400> SEQUENCE: 78

Met Phe Lys Arg Lys Ser Thr Ala Asp Leu Ala Ala Gln Met Ala Lys
1               5                   10                  15
Leu Asn Gly Asn Lys Gly Phe Ser Ser Glu Asp Lys Gly Glu Trp Lys
                20                  25                  30
Leu Lys Leu Asp Ala Ser Gly Asn Gly Gln Ala Val Ile Arg Phe Leu
            35                  40                  45
Pro Ala Lys Thr Asp Asp Ala Leu Pro Phe Thr Ile Leu Val Asn His
        50                  55                  60
Gly Phe Lys Lys Asn Gly Lys Trp Tyr Ile Glu Thr Cys Ser Ser Thr
65                  70                  75                  80
His Gly Asp Tyr Asp Ser Cys Pro Val Cys Gln Tyr Ile Ser Lys Asn
                85                  90                  95
Asp Leu Tyr Asn Thr Asn Lys Thr Glu Tyr Ser Gln Leu Lys Arg Lys
                100                 105                 110
Thr Ser Tyr Trp Ala Asn Ile Leu Val Val Lys Asp Pro Gln Ala Pro
            115                 120                 125
Asp Asn Glu Gly Lys Val Phe Lys Tyr Arg Phe Gly Lys Lys Ile Trp
        130                 135                 140
Asp Lys Ile Asn Ala Met Ile Ala Val Asp Thr Glu Met Gly Glu Thr
145                 150                 155                 160
Pro Val Asp Val Thr Cys Pro Trp Glu Gly Ala Asn Phe Val Leu Lys
                    165                 170                 175
Val Lys Gln Val Ser Gly Phe Ser Asn Tyr Asp Glu Ser Lys Phe Leu
                180                 185                 190
Asn Gln Ser Ala Ile Pro Asn Ile Asp Asp Glu Ser Phe Gln Lys Glu
            195                 200                 205
Leu Phe Glu Gln Met Val Asp Leu Ser Glu Met Thr Ser Lys Asp Lys
        210                 215                 220
Phe Lys Ser Phe Glu Glu Leu Asn Thr Lys Phe Asn Gln Val Leu Gly
```

```
                225                 230                 235                 240
        Thr Ala Ala Leu Gly Gly Ala Ala Ala Ala Ala Ser Val Ala Asp
                        245                 250                 255
        Lys Val Ala Ser Asp Leu Asp Asp Phe Asp Lys Asp Met Glu Ala Phe
                        260                 265                 270
        Ser Ser Ala Lys Thr Glu Asp Asp Phe Met Ser Ser Ser Ser Asp
                        275                 280                 285
        Asp Ser Asp Leu Asp Asp Leu Leu Ala Gly Leu Ala Ser Ala Ser Ser
                290                 295                 300
        Ser Gln Arg Gly Arg Ser Gly Ser Gly Asn Phe Gly Gly Arg Gly
        305                 310                 315                 320
        Gly Gly Phe Gly Gly Asn Asp Asn Phe Gly Arg Gly Gly Asn Phe Ser
                        325                 330                 335
        Gly Arg Gly Gly Phe Gly Gly Ser Arg Gly Gly Gly Tyr Gly Gly
                        340                 345                 350
        Ser Gly Asp Gly Tyr Asn Gly Phe Gly Asn Asp Gly Ser Asn Phe Gly
                        355                 360                 365
        Gly Gly Gly Ser Tyr Asn Asp Phe Gly Asn Tyr Asn Asn Gln Ser Ser
                370                 375                 380
        Asn Phe Gly Pro Met Lys Gly Gly Asn Phe Gly Gly Arg Ser Ser Gly
        385                 390                 395                 400
        Pro Tyr Gly Gly Gly Gln Tyr Phe Ala Lys Pro Gln Asn Gln Gly
                        405                 410                 415
        Gly Tyr Gly Val Ser Ser Ser Ser Ser Tyr Gly Ser Gly Arg Arg
                        420                 425                 430
        Phe His His His His His His
                        435                 440

<210> SEQ ID NO 79
<211> LENGTH: 364
<212> TYPE: PRT
<213> ORGANISM: Artificial Sequence
<220> FEATURE:
<223> OTHER INFORMATION: Gp32 HRP1

<400> SEQUENCE: 79

Met Phe Lys Arg Lys Ser Thr Ala Asp Leu Ala Ala Gln Met Ala Lys
1               5                   10                  15
Leu Asn Gly Asn Lys Gly Phe Ser Ser Glu Asp Lys Gly Glu Trp Lys
                20                  25                  30
Leu Lys Leu Asp Ala Ser Gly Asn Gly Gln Ala Val Ile Arg Phe Leu
            35                  40                  45
Pro Ala Lys Thr Asp Asp Ala Leu Pro Phe Thr Ile Leu Val Asn His
        50                  55                  60
Gly Phe Lys Lys Asn Gly Lys Trp Tyr Ile Glu Thr Cys Ser Ser Thr
65                  70                  75                  80
His Gly Asp Tyr Asp Ser Cys Pro Val Cys Gln Tyr Ile Ser Lys Asn
                85                  90                  95
Asp Leu Tyr Asn Thr Asn Lys Thr Glu Tyr Ser Gln Leu Lys Arg Lys
                100                 105                 110
Thr Ser Tyr Trp Ala Asn Ile Leu Val Val Lys Asp Pro Gln Ala Pro
            115                 120                 125
Asp Asn Glu Gly Lys Val Phe Lys Tyr Arg Phe Gly Lys Lys Ile Trp
        130                 135                 140
Asp Lys Ile Asn Ala Met Ile Ala Val Asp Thr Glu Met Gly Glu Thr
```

```
                145                 150                 155                 160
Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
                180                 185                 190

Asn Gln Ser Ala Ile Pro Asn Ile Asp Asp Glu Ser Phe Gln Lys Glu
                195                 200                 205

Leu Phe Glu Gln Met Val Asp Leu Ser Glu Met Thr Ser Lys Asp Lys
        210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
                260                 265                 270

Ser Ser Ala Lys Thr Glu Asp Asp Phe Met Ser Ser Ser Ser Asp
                275                 280                 285

Asp Ser Asp Leu Asp Asp Leu Leu Ala Gly Leu Gly Gly Asn Asn Gly
        290                 295                 300

Gly Asn Asn Met Asn Arg Arg Gly Gly Asn Phe Gly Asn Gln Gly Asp
305                 310                 315                 320

Phe Asn Gln Met Tyr Gln Asn Pro Met Met Gly Gly Tyr Asn Pro Met
                325                 330                 335

Met Asn Pro Gln Ala Met Thr Asp Tyr Tyr Gln Lys Met Gln Glu Tyr
                340                 345                 350

Tyr Gln Gln Met Gln His His His His His His
        355                 360

<210> SEQ ID NO 80
<211> LENGTH: 422
<212> TYPE: PRT
<213> ORGANISM: Artificial Sequence
<220> FEATURE:
<223> OTHER INFORMATION: Gp32 HRP2

<400> SEQUENCE: 80

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
                20                  25                  30

Leu Lys Leu Asp Ala Ser Gly Asn Gly Gln Ala Val Ile Arg Phe Leu
            35                  40                  45

Pro Ala Lys Thr Asp Asp Ala Leu Pro Phe Thr Ile Leu Val Asn His
        50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
                100                 105                 110

Thr Ser Tyr Trp Ala Asn Ile Leu Val Val Lys Asp Pro Gln Ala Pro
            115                 120                 125

Asp Asn Glu Gly Lys Val Phe Lys Tyr Arg Phe Gly Lys Lys Ile Trp
        130                 135                 140

Asp Lys Ile Asn Ala Met Ile Ala Val Asp Thr Glu Met Gly Glu Thr
```

-continued

```
                145                 150                 155                 160
Pro Val Asp Val Thr Cys Pro Trp Glu Gly Ala Asn Phe Val Leu Lys
                    165                 170                 175

Val Lys Gln Val Ser Gly Phe Ser Asn Tyr Asp Glu Ser Lys Phe Leu
                    180                 185                 190

Asn Gln Ser Ala Ile Pro Asn Ile Asp Asp Glu Ser Phe Gln Lys Glu
                    195                 200                 205

Leu Phe Glu Gln Met Val Asp Leu Ser Glu Met Thr Ser Lys Asp Lys
                    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                    245                 250                 255

Lys Val Ala Ser Asp Leu Asp Asp Phe Asp Lys Asp Met Glu Ala Phe
                    260                 265                 270

Ser Ser Ala Lys Thr Glu Asp Asp Phe Met Ser Ser Ser Ser Asp
                    275                 280                 285

Asp Ser Asp Leu Asp Asp Leu Leu Ala Gly Leu Gly Gly Asn Asn Gly
                    290                 295                 300

Gly Asn Asn Met Asn Arg Arg Gly Gly Asn Phe Gly Asn Gln Gly Asp
305                 310                 315                 320

Phe Asn Gln Met Tyr Gln Asn Pro Met Met Gly Gly Tyr Asn Pro Met
                    325                 330                 335

Met Asn Pro Gln Ala Met Thr Asp Tyr Tyr Gln Lys Met Gln Glu Tyr
                    340                 345                 350

Tyr Gln Gln Met Gln Gly Gly Asn Asn Gly Gly Asn Asn Met Asn Arg
                    355                 360                 365

Arg Gly Gly Asn Phe Gly Asn Gln Gly Asp Phe Asn Gln Met Tyr Gln
                    370                 375                 380

Asn Pro Met Met Gly Gly Tyr Asn Pro Met Met Asn Pro Gln Ala Met
385                 390                 395                 400

Thr Asp Tyr Tyr Gln Lys Met Gln Glu Tyr Tyr Gln Gln Met Gln His
                    405                 410                 415

His His His His His
            420

<210> SEQ ID NO 81
<211> LENGTH: 330
<212> TYPE: PRT
<213> ORGANISM: Artificial Sequence
<220> FEATURE:
<223> OTHER INFORMATION: Gp32 HIS1

<400> SEQUENCE: 81

Met Phe Lys Arg Lys Ser Thr Ala Asp Leu Ala Ala Gln Met Ala Lys
1               5                   10                  15

Leu Asn Gly Asn Lys Gly Phe Ser Glu Asp Lys Gly Glu Trp Lys
                20                  25                  30

Leu Lys Leu Asp Ala Ser Gly Asn Gly Gln Ala Val Ile Arg Phe Leu
            35                  40                  45

Pro Ala Lys Thr Asp Asp Ala Leu Pro Phe Thr Ile Leu Val Asn His
                50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
```

```
              85                  90                  95
Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
        275                 280                 285

Asp Ser Asp Leu Asp Asp Leu Leu Ala Gly Leu Pro Gln Gln Asn Ala
    290                 295                 300

Leu His His His His Gly Asn Ser Ser His His His His His His
305                 310                 315                 320

His His His His His His Gly Gln Gln Ala
                325                 330
```

<210> SEQ ID NO 82
<211> LENGTH: 335
<212> TYPE: PRT
<213> ORGANISM: Artificial Sequence
<220> FEATURE:
<223> OTHER INFORMATION: GP32 HIS2

<400> SEQUENCE: 82

```
Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
```

```
            115                 120                 125
Asp Asn Glu Gly Lys Val Phe Lys Tyr Arg Phe Gly Lys Lys Ile Trp
        130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Asp
        275                 280                 285

Asp Ser Asp Leu Asp Asp Leu Leu Ala Gly Leu Ala Gly His His His
    290                 295                 300

His His Pro His Ala His His Pro Leu Ser Gln Ser Ser Gly His His
305                 310                 315                 320

His His His His His His His Gln Gly Tyr Gly Gly Ser Gly
                325                 330                 335

<210> SEQ ID NO 83
<211> LENGTH: 342
<212> TYPE: PRT
<213> ORGANISM: Artificial Sequence
<220> FEATURE:
<223> OTHER INFORMATION: GP32 HIS3

<400> SEQUENCE: 83

Met Phe Lys Arg Lys Ser Thr Ala Asp Leu Ala Ala Gln Met Ala Lys
1               5                  10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
```

```
                145                 150                 155                 160
Pro Val Asp Val Thr Cys Pro Trp Glu Gly Ala Asn Phe Val Leu Lys
                    165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Asp
        275                 280                 285

Asp Ser Asp Leu Asp Asp Leu Leu Ala Gly Leu Ala Gly His His His
    290                 295                 300

His His His His His Leu Pro His Leu Pro Pro His Leu His His
305                 310                 315                 320

His His His Pro Gln His His Leu His Pro Gly Ser Ala Ala Ala Val
                325                 330                 335

His Pro Val Gln Gln His
            340

<210> SEQ ID NO 84
<211> LENGTH: 341
<212> TYPE: PRT
<213> ORGANISM: Artificial Sequence
<220> FEATURE:
<223> OTHER INFORMATION: GP32 HIS4

<400> SEQUENCE: 84

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
```

```
                    165                 170                 175
Val Lys Gln Val Ser Gly Phe Ser Asn Tyr Asp Glu Ser Lys Phe Leu
                180                 185                 190

Asn Gln Ser Ala Ile Pro Asn Ile Asp Asp Glu Ser Phe Gln Lys Glu
            195                 200                 205

Leu Phe Glu Gln Met Val Asp Leu Ser Glu Met Thr Ser Lys Asp Lys
        210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ser Val Ala Asp
                245                 250                 255

Lys Val Ala Ser Asp Leu Asp Asp Phe Asp Lys Asp Met Glu Ala Phe
                260                 265                 270

Ser Ser Ala Lys Thr Glu Asp Asp Phe Met Ser Ser Ser Ser Asp
            275                 280                 285

Asp Ser Asp Leu Asp Asp Leu Leu Ala Gly Leu Asn His His Ala Ser
        290                 295                 300

His Gly His His Asn Ser His His Pro Gln His His His His His
305                 310                 315                 320

His His His His His Pro Pro Pro Ala Pro Gln Pro Pro Pro
                325                 330                 335

Pro Gln Gln Gln Gln
            340
```

<210> SEQ ID NO 85
<211> LENGTH: 375
<212> TYPE: PRT
<213> ORGANISM: Artificial Sequence
<220> FEATURE:
<223> OTHER INFORMATION: GP32 HIS5

<400> SEQUENCE: 85

```
Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
```

```
            180             185                 190
Asn Gln Ser Ala Ile Pro Asn Ile Asp Asp Glu Ser Phe Gln Lys Glu
            195                 200             205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Asp
        275                 280                 285

Asp Ser Asp Leu Asp Asp Leu Leu Ala Gly Leu Ser Gly His His Gly
    290                 295                 300

Ala His His Gly Ala His His Pro Ala Ala Ala Ala Tyr Glu Ala
305                 310                 315                 320

Phe Arg Gly Pro Gly Phe Ala Gly Gly Gly Ala Asp Asp Met Gly
                325                 330                 335

Ala Gly His His His Gly Ala His His Ala Ala His His His Ala
            340                 345                 350

Ala His His His His His His His His Gly Gly Ala Gly His
        355                 360                 365

Gly Gly Gly Ala Gly His His
    370             375

<210> SEQ ID NO 86
<211> LENGTH: 355
<212> TYPE: PRT
<213> ORGANISM: Artificial Sequence
<220> FEATURE:
<223> OTHER INFORMATION: Gp32 Mimic1

<400> SEQUENCE: 86

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
```

165                 170                 175
Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
            195                 200                 205

Leu Phe Glu Gln Met Val Asp Leu Ser Glu Met Thr Ser Lys Asp Lys
            210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
                260                 265                 270

Ser Ser Ala Lys Thr Glu Asp Asp Phe Met Ser Ser Ser Ser Ser Asp
                275                 280                 285

Asp Ser Asp Leu Asp Asp Leu Leu Ala Gly Leu Tyr Asp Pro Thr Ser
            290                 295                 300

Pro Ser Tyr Asp Pro Thr Ser Pro Ser Tyr Asp Pro Thr Ser Pro Ser
305                 310                 315                 320

Tyr Asp Pro Thr Ser Pro Ser Tyr Asp Pro Thr Ser Pro Ser Tyr Asp
                325                 330                 335

Pro Thr Ser Pro Ser Tyr Asp Pro Thr Ser Pro Ser His His His
                340                 345                 350

His His His
        355

<210> SEQ ID NO 87
<211> LENGTH: 355
<212> TYPE: PRT
<213> ORGANISM: Artificial Sequence
<220> FEATURE:
<223> OTHER INFORMATION: Gp32 Mimic2

<400> SEQUENCE: 87

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys 165                 170                 175
Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
            195                 200                 205

Leu Phe Glu Gln Met Val Asp Leu Ser Glu Met Thr Ser Lys Asp Lys
            210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
            245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
            275                 280                 285

Asp Ser Asp Leu Asp Asp Leu Leu Ala Gly Leu Tyr Ser Pro Thr Asp
            290                 295                 300

Pro Ser Tyr Ser Pro Thr Asp Pro Ser Tyr Ser Pro Thr Asp Pro Ser
305                 310                 315                 320

Tyr Ser Pro Thr Asp Pro Ser Tyr Ser Pro Thr Asp Pro Ser Tyr Ser
            325                 330                 335

Pro Thr Asp Pro Ser Tyr Ser Pro Thr Asp Pro Ser His His His His
            340                 345                 350

His His His
        355

<210> SEQ ID NO 88
<211> LENGTH: 348
<212> TYPE: PRT
<213> ORGANISM: Artificial Sequence
<220> FEATURE:
<223> OTHER INFORMATION: Gp32 short pol ctd

<400> SEQUENCE: 88

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Thr Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
            85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys

```
            165                 170                 175
Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
        275                 280                 285

Asp Ser Asp Leu Asp Asp Leu Leu Ala Gly Leu Thr Ser Pro Ser Tyr
    290                 295                 300

Ser Pro Thr Ser Pro Ser Tyr Ser Pro Thr Ser Pro Gly Tyr Ser Pro
305                 310                 315                 320

Thr Ser Pro Ala Tyr Ser Pro Thr Ser Pro Thr Tyr Ser Pro Thr Ser
                325                 330                 335

Pro Thr Tyr Ser Pro His His His His His His
            340                 345

<210> SEQ ID NO 89
<211> LENGTH: 6
<212> TYPE: PRT
<213> ORGANISM: Artificial Sequence
<220> FEATURE:
<223> OTHER INFORMATION: 6-histidine

<400> SEQUENCE: 89

His His His His His His
1               5

<210> SEQ ID NO 90
<211> LENGTH: 10
<212> TYPE: PRT
<213> ORGANISM: Artificial Sequence
<220> FEATURE:
<223> OTHER INFORMATION: C-myc epitope

<400> SEQUENCE: 90

Glu Gln Lys Leu Ile Ser Glu Glu Asp Leu
1               5                   10

<210> SEQ ID NO 91
<211> LENGTH: 8
<212> TYPE: PRT
<213> ORGANISM: Artificial Sequence
<220> FEATURE:
<223> OTHER INFORMATION: FLAG octapeptide

<400> SEQUENCE: 91

Asp Tyr Lys Asp Asp Asp Asp Lys
1               5

<210> SEQ ID NO 92
<211> LENGTH: 12
<212> TYPE: PRT
<213> ORGANISM: Artificial Sequence
```

```
<220> FEATURE:
<223> OTHER INFORMATION: Protein C

<400> SEQUENCE: 92

Glu Asp Gln Val Asp Pro Arg Leu Ile Asp Gly Lys
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Tag-100

<400> SEQUENCE: 93

Glu Glu Thr Ala Arg Phe Gln Pro Gly Tyr Arg Ser
1               5                   10

<210> SEQ ID NO 94
<211> LENGTH: 14
<212> TYPE: PRT
<213> ORGANISM: Artificial Sequence
<220> FEATURE:
<223> OTHER INFORMATION: V5 epitope

<400> SEQUENCE: 94

Gly Lys Pro Ile Pro Asn Pro Leu Leu Gly Leu Asp Ser Thr
1               5                   10

<210> SEQ ID NO 95
<211> LENGTH: 11
<212> TYPE: PRT
<213> ORGANISM: Artificial Sequence
<220> FEATURE:
<223> OTHER INFORMATION: VSV-G

<400> SEQUENCE: 95

Tyr Thr Asp Ile Glu Met Asn Arg Leu Gly Lys
1               5                   10

<210> SEQ ID NO 96
<211> LENGTH: 8
<212> TYPE: PRT
<213> ORGANISM: Artificial Sequence
<220> FEATURE:
<223> OTHER INFORMATION: Xpress

<400> SEQUENCE: 96

Asp Leu Tyr Asp Asp Asp Asp Lys
1               5

<210> SEQ ID NO 97
<211> LENGTH: 9
<212> TYPE: PRT
<213> ORGANISM: Artificial Sequence
<220> FEATURE:
<223> OTHER INFORMATION: Hemagglutinin

<400> SEQUENCE: 97

Tyr Pro Tyr Asp Val Pro Asp Tyr Ala
1               5

<210> SEQ ID NO 98
<211> LENGTH: 36
<212> TYPE: DNA
<213> ORGANISM: Artificial Sequence
<220> FEATURE:
```

```
<223> OTHER INFORMATION: Example 1 - Forward primer

<400> SEQUENCE: 98
cgcctgcaag tcctaagacg ccaatcgaaa agaaac                                  36

<210> SEQ ID NO 99
<211> LENGTH: 35
<212> TYPE: DNA
<213> ORGANISM: Artificial Sequence
<220> FEATURE:
<223> OTHER INFORMATION: Example 1 - Reverse primer

<400> SEQUENCE: 99
ctgcatctcc gtggtatact aatacattgt tttta                                   35

<210> SEQ ID NO 100
<211> LENGTH: 45
<212> TYPE: DNA
<213> ORGANISM: Artificial Sequence
<220> FEATURE:
<223> OTHER INFORMATION: Example 1 - Probe
<220> FEATURE:
<221> NAME/KEY: modified_base
<222> LOCATION: (31)..(31)
<223> OTHER INFORMATION: Modified with FAM - fluorescein, THF -
      tetrahydrofuran and BHQ - Black Hole Quencher

<400> SEQUENCE: 100
cgaaaagaaa cacgcggatg aaatcgataa gatacaagga ttgga                        45

<210> SEQ ID NO 101
<211> LENGTH: 32
<212> TYPE: DNA
<213> ORGANISM: Artificial Sequence
<220> FEATURE:
<223> OTHER INFORMATION: Example 5 - Forward primer

<400> SEQUENCE: 101
gcagctgtat agcaaattcc tgttgaaagc ag                                      32

<210> SEQ ID NO 102
<211> LENGTH: 30
<212> TYPE: DNA
<213> ORGANISM: Artificial Sequence
<220> FEATURE:
<223> OTHER INFORMATION: Example 5 - Reverse primer

<400> SEQUENCE: 102
tcctggctgt attcattgtt gttaaattgg                                         30

<210> SEQ ID NO 103
<211> LENGTH: 47
<212> TYPE: DNA
<213> ORGANISM: Artificial Sequence
<220> FEATURE:
<223> OTHER INFORMATION: Example 5 - probe
<220> FEATURE:
<221> NAME/KEY: modified_base
<222> LOCATION: (30)..(30)
<223> OTHER INFORMATION: FAM - fluorescein
<220> FEATURE:
<221> NAME/KEY: modified_base
<222> LOCATION: (31)..(31)
<223> OTHER INFORMATION: THF - tetrahydrofuran
<220> FEATURE:
<221> NAME/KEY: modified_base
<222> LOCATION: (33)..(33)
<223> OTHER INFORMATION: BHQ - Black Hole Quencher
```

<400> SEQUENCE: 103
cactgatgct tttcctagac acgagatgat gcttgtggag cctttgt            47

<210> SEQ ID NO 104
<211> LENGTH: 37
<212> TYPE: DNA
<213> ORGANISM: Artificial Sequence
<220> FEATURE:
<223> OTHER INFORMATION: Example 12 - Probe
<220> FEATURE:
<221> NAME/KEY: FAM - Fluorescein
<222> LOCATION: (1)..(37)

<400> SEQUENCE: 104
ccgcaatggt gcactctcag tacaatctgc tctgatg                       37

<210> SEQ ID NO 105
<211> LENGTH: 30
<212> TYPE: DNA
<213> ORGANISM: Artificial Sequence
<220> FEATURE:
<223> OTHER INFORMATION: Example 18 - PA30 forward primer

<400> SEQUENCE: 105
ccatctcatc cctgcgtgtc tccgactcag                               30

<210> SEQ ID NO 106
<211> LENGTH: 30
<212> TYPE: DNA
<213> ORGANISM: Artificial Sequence
<220> FEATURE:
<223> OTHER INFORMATION: Example 18 - PB30 reverse primer

<400> SEQUENCE: 106
cctatcccct gtgtgccttg gcagtctcag                               30

<210> SEQ ID NO 107
<211> LENGTH: 46
<212> TYPE: DNA
<213> ORGANISM: Artificial Sequence
<220> FEATURE:
<223> OTHER INFORMATION: Example 18 - Probe
<220> FEATURE:
<221> NAME/KEY: modified_base
<222> LOCATION: (29)..(29)
<223> OTHER INFORMATION: FAM - fluorescein
<220> FEATURE:
<221> NAME/KEY: modified_base
<222> LOCATION: (30)..(30)
<223> OTHER INFORMATION: THF - tetrahydrofuran
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: modified_base
<222> LOCATION: (32)..(32)
<223> OTHER INFORMATION: Quencher - Black Hole Quencher

<400> SEQUENCE: 107
agcagaagca ataccgccag caatagcatg ngtagagcga gctgcc             46

<210> SEQ ID NO 108
<211> LENGTH: 188
<212> TYPE: DNA
<213> ORGANISM: Artificial Sequence
<220> FEATURE:
<223> OTHER INFORMATION: Example 18 - TF1L template sequence -continued

```
<400> SEQUENCE: 108
ccatctcatc cctgcgtgtc tccgactcag tgttttaggg tccccggggt taaaaggttt      60
cgaactcaac agctgtctgg cagctcgctc tacgcatgct attgctggcg gtattgcttc     120
tgctcttgct ggtggcgcca tgtctaaatt gtttggagct gagactgcca aggcacacag     180
gggatagg                                                              188

<210> SEQ ID NO 109
<211> LENGTH: 30
<212> TYPE: DNA
<213> ORGANISM: Artificial Sequence
<220> FEATURE:
<223> OTHER INFORMATION: Example 18 - PB30' probe
<220> FEATURE:
<221> NAME/KEY: 5' - ROX (carboxyrhodamine)
<222> LOCATION: (1)..(30)

<400> SEQUENCE: 109
ctgagactgc caaggcacac agggataggg                                       30

<210> SEQ ID NO 110
<211> LENGTH: 20
<212> TYPE: DNA
<213> ORGANISM: Artificial Sequence
<220> FEATURE:
<223> OTHER INFORMATION: Example 18 - TF1L probe
<220> FEATURE:
<221> NAME/KEY: 5' FAM (fluorescein)
<222> LOCATION: (1)..(20)

<400> SEQUENCE: 110
ggtttcgaac tcaacagctg                                                  20

<210> SEQ ID NO 111
<211> LENGTH: 504
<212> TYPE: PRT
<213> ORGANISM: Artificial Sequence
<220> FEATURE:
<223> OTHER INFORMATION: Example 20 - RB69 ligase

<400> SEQUENCE: 111

Met Ile Leu Asp Ile Leu Asn Gln Ile Ala Ala Ile Gly Ser Thr Lys
1               5                   10                  15

Thr Lys Gln Glu Ile Leu Lys Lys Asn Lys Asp Asn Lys Leu Leu Glu
            20                  25                  30

Arg Val Tyr Arg Leu Thr Tyr Ala Arg Gly Ile Gln Tyr Tyr Ile Lys
        35                  40                  45

Lys Trp Pro Gly Pro Gly Glu Arg Ser Gln Ala Tyr Gly Leu Leu Glu
    50                  55                  60

Leu Asp Asp Met Leu Asp Phe Ile Glu Phe Thr Leu Ala Thr Arg Lys
65                  70                  75                  80

Leu Thr Gly Asn Ala Ala Ile Lys Glu Leu Met Gly Tyr Ile Ala Asp
                85                  90                  95

Gly Lys Pro Asp Asp Val Glu Val Leu Arg Arg Val Met Met Arg Asp
            100                 105                 110

Leu Glu Val Gly Ala Ser Val Ser Ile Ala Asn Lys Val Trp Pro Gly
        115                 120                 125

Leu Ile Gln Leu Gln Pro Gln Met Leu Ala Ser Ala Tyr Asp Glu Lys
    130                 135                 140

Leu Ile Thr Lys Asn Ile Lys Trp Pro Ala Phe Ala Gln Leu Lys Ala
145                 150                 155                 160
```

```
Asp Gly Ala Arg Cys Phe Ala Glu Val Arg Asp Asp Gly Val Gln Phe
                165                 170                 175

Phe Ser Arg Ala Gly Asn Glu Tyr His Gly Leu Thr Leu Leu Ala Asp
            180                 185                 190

Glu Leu Met Glu Met Thr Lys Glu Ala Arg Glu Arg His Pro Asn Gly
        195                 200                 205

Val Leu Ile Asp Gly Glu Leu Val Tyr His Ser Phe Asp Ile Lys Lys
    210                 215                 220

Ala Val Ser Ser Gly Asn Asp Leu Ser Phe Leu Phe Gly Asp Asn Glu
225                 230                 235                 240

Glu Ser Glu Glu Val Gln Val Ala Asp Arg Ser Thr Ser Asn Gly Leu
                245                 250                 255

Ala Asn Lys Ser Leu Gln Gly Thr Ile Ser Pro Lys Glu Ala Glu Gly
            260                 265                 270

Met Val Leu Gln Ala Trp Asp Tyr Val Pro Leu Asp Glu Val Tyr Ser
        275                 280                 285

Asp Gly Lys Ile Lys Gly Gln Lys Tyr Asp Val Arg Phe Ala Ala Leu
    290                 295                 300

Glu Asn Met Ala Glu Gly Phe Lys Arg Ile Glu Pro Ile Glu Asn Gln
305                 310                 315                 320

Leu Val Arg Asn Leu Asp Glu Ala Lys Val Val Tyr Lys Lys Tyr Val
                325                 330                 335

Asp Gln Gly Leu Glu Gly Ile Ile Leu Lys Asn Arg Asp Ser Tyr Trp
            340                 345                 350

Glu Asn Lys Arg Ser Lys Asn Leu Ile Lys Phe Lys Glu Val Ile Asp
        355                 360                 365

Ile Ala Leu Glu Val Val Gly Tyr Tyr Glu His Ser Lys Asp Pro Asn
    370                 375                 380

Lys Leu Gly Gly Val Glu Leu Val Ser Arg Cys Arg Arg Ile Thr Thr
385                 390                 395                 400

Asp Cys Gly Ser Gly Phe Lys Asp Thr Thr His Lys Thr Val Asp Gly
                405                 410                 415

Val Lys Val Leu Ile Pro Leu Asp Glu Arg His Asp Leu Asp Arg Glu
            420                 425                 430

Arg Leu Met Ser Glu Ala Arg Glu Gly Lys Leu Ile Gly Arg Ile Ala
        435                 440                 445

Asp Cys Glu Cys Asn Gly Trp Val His Ser Lys Gly Arg Glu Gly Thr
    450                 455                 460

Val Gly Ile Phe Leu Pro Ile Ile Lys Gly Phe Arg Phe Asp Lys Thr
465                 470                 475                 480

Glu Ala Asp Ser Phe Glu Asp Val Phe Gly Ser Trp Asp Gln Thr Gly
                485                 490                 495

Val Ser Gly His His His His His
            500

<210> SEQ ID NO 112
<211> LENGTH: 533
<212> TYPE: PRT
<213> ORGANISM: Artificial Sequence
<220> FEATURE:
<223> OTHER INFORMATION: Example 20 - RB69 ligase-His2

<400> SEQUENCE: 112

Met Ile Leu Asp Ile Leu Asn Gln Ile Ala Ala Ile Gly Ser Thr Lys
1               5                   10                  15
```

```
Thr Lys Gln Glu Ile Leu Lys Lys Asn Lys Asp Asn Lys Leu Leu Glu
             20                  25                  30

Arg Val Tyr Arg Leu Thr Tyr Ala Arg Gly Ile Gln Tyr Tyr Ile Lys
             35                  40                  45

Lys Trp Pro Gly Pro Gly Glu Arg Ser Gln Ala Tyr Gly Leu Leu Glu
 50                  55                  60

Leu Asp Asp Met Leu Asp Phe Ile Glu Phe Thr Leu Ala Thr Arg Lys
 65                  70                  75                  80

Leu Thr Gly Asn Ala Ala Ile Lys Glu Leu Met Gly Tyr Ile Ala Asp
                 85                  90                  95

Gly Lys Pro Asp Asp Val Glu Val Leu Arg Arg Val Met Met Arg Asp
             100                 105                 110

Leu Glu Val Gly Ala Ser Val Ser Ile Ala Asn Lys Val Trp Pro Gly
             115                 120                 125

Leu Ile Gln Leu Gln Pro Gln Met Leu Ala Ser Ala Tyr Asp Glu Lys
         130                 135                 140

Leu Ile Thr Lys Asn Ile Lys Trp Pro Ala Phe Ala Gln Leu Lys Ala
145                 150                 155                 160

Asp Gly Ala Arg Cys Phe Ala Glu Val Arg Asp Asp Gly Val Gln Phe
                 165                 170                 175

Phe Ser Arg Ala Gly Asn Glu Tyr His Gly Leu Thr Leu Leu Ala Asp
             180                 185                 190

Glu Leu Met Glu Met Thr Lys Glu Ala Arg Glu Arg His Pro Asn Gly
             195                 200                 205

Val Leu Ile Asp Gly Glu Leu Val Tyr His Ser Phe Asp Ile Lys Lys
         210                 215                 220

Ala Val Ser Ser Gly Asn Asp Leu Ser Phe Leu Phe Gly Asp Asn Glu
225                 230                 235                 240

Glu Ser Glu Glu Val Gln Val Ala Asp Arg Ser Thr Ser Asn Gly Leu
                 245                 250                 255

Ala Asn Lys Ser Leu Gln Gly Thr Ile Ser Pro Lys Glu Ala Glu Gly
             260                 265                 270

Met Val Leu Gln Ala Trp Asp Tyr Val Pro Leu Asp Glu Val Tyr Ser
             275                 280                 285

Asp Gly Lys Ile Lys Gly Gln Lys Tyr Asp Val Arg Phe Ala Ala Leu
         290                 295                 300

Glu Asn Met Ala Glu Gly Phe Lys Arg Ile Glu Pro Ile Glu Asn Gln
305                 310                 315                 320

Leu Val Arg Asn Leu Asp Glu Ala Lys Val Val Tyr Lys Lys Tyr Val
                 325                 330                 335

Asp Gln Gly Leu Glu Gly Ile Ile Leu Lys Asn Arg Asp Ser Tyr Trp
             340                 345                 350

Glu Asn Lys Arg Ser Lys Asn Leu Ile Lys Phe Lys Glu Val Ile Asp
             355                 360                 365

Ile Ala Leu Glu Val Val Gly Tyr Tyr Glu His Ser Lys Asp Pro Asn
         370                 375                 380

Lys Leu Gly Gly Val Glu Leu Val Ser Arg Cys Arg Arg Ile Thr Thr
385                 390                 395                 400

Asp Cys Gly Ser Gly Phe Lys Asp Thr Thr His Lys Thr Val Asp Gly
                 405                 410                 415

Val Lys Val Leu Ile Pro Leu Asp Glu Arg His Asp Leu Asp Arg Glu
             420                 425                 430
```

```
Arg Leu Met Ser Glu Ala Arg Glu Gly Lys Leu Ile Gly Arg Ile Ala
        435                 440                 445

Asp Cys Glu Cys Asn Gly Trp Val His Ser Lys Gly Arg Glu Gly Thr
    450                 455                 460

Val Gly Ile Phe Leu Pro Ile Ile Lys Gly Phe Arg Phe Asp Lys Thr
465                 470                 475                 480

Glu Ala Asp Ser Phe Glu Asp Val Phe Gly Ser Trp Asp Gln Thr Gly
                485                 490                 495

Val Ser Gly His His His His Pro His Ala His His Pro Leu Ser
                500                 505                 510

Gln Ser Ser Gly His His His His His His His His Gln Gly
            515                 520                 525

Tyr Gly Gly Ser Gly
    530
```

<210> SEQ ID NO 113
<211> LENGTH: 17
<212> TYPE: DNA
<213> ORGANISM: Artificial Sequence
<220> FEATURE:
<223> OTHER INFORMATION: Example 21 - Lig170 Forward primer

<400> SEQUENCE: 113
gagcgcaacg caattaa                                                17

<210> SEQ ID NO 114
<211> LENGTH: 20
<212> TYPE: DNA
<213> ORGANISM: Artificial Sequence
<220> FEATURE:
<223> OTHER INFORMATION: Example 21 - Lig170_Reverse primer

<400> SEQUENCE: 114
atccgctcac aattccacac                                             20

<210> SEQ ID NO 115
<211> LENGTH: 100
<212> TYPE: DNA
<213> ORGANISM: Artificial Sequence
<220> FEATURE:
<223> OTHER INFORMATION: Example 21 - Lig170 template

<400> SEQUENCE: 115
gagcgcaacg caattaatgt gagttagctc actcattagg cacccaggc tttacacttt    60 atgcttccgg ctcgtatgtt gtgtggaatt gtgagcggat                       100

<210> SEQ ID NO 116
<211> LENGTH: 58
<212> TYPE: DNA
<213> ORGANISM: Artificial Sequence
<220> FEATURE:
<223> OTHER INFORMATION: Example 21 - ILMN_AD_P5

<400> SEQUENCE: 116
aatgatacgg cgaccaccga gatctacact ctttccctac acgacgctct tccgatct     58

<210> SEQ ID NO 117
<211> LENGTH: 63
<212> TYPE: DNA
<213> ORGANISM: Artificial Sequence
<220> FEATURE:
<223> OTHER INFORMATION: Example 21 - ILMN_AD_P7rc_IDX01
<220> FEATURE:

```
<221> NAME/KEY: 5'-PO4
<222> LOCATION: (1)..(63)

<400> SEQUENCE: 117
gatcggaaga gcacacgtct gaactccagt cacatcacga tctcgtatgc cgtcttctgc    60
ttg                                                                  63

<210> SEQ ID NO 118
<211> LENGTH: 20
<212> TYPE: DNA
<213> ORGANISM: Artificial Sequence
<220> FEATURE:
<223> OTHER INFORMATION: Example 22 - ILMN_P5

<400> SEQUENCE: 118
aatgatacgg cgaccaccga                                                20

<210> SEQ ID NO 119
<211> LENGTH: 20
<212> TYPE: DNA
<213> ORGANISM: Artificial Sequence
<220> FEATURE:
<223> OTHER INFORMATION: Example 22 - ILMN_P7

<400> SEQUENCE: 119
caagcagaag acggcatacg                                                20

<210> SEQ ID NO 120
<211> LENGTH: 366
<212> TYPE: PRT
<213> ORGANISM: Artificial Sequence
<220> FEATURE:
<223> OTHER INFORMATION: Example 24 - T4-Gp32-HRP1

<400> SEQUENCE: 120
```

Met Phe Lys Arg Lys Ser Thr Ala Glu Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Asn Ala Gly Asn Gly Gln Ala Val Ile Arg Phe Leu
        35                  40                  45

Pro Ser Lys Asn Asp Glu Gln Ala Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asp Asn Lys Glu Tyr Ser Leu Val Lys Arg Lys
            100                 105                 110

Thr Ser Tyr Trp Ala Asn Ile Leu Val Val Lys Asp Pro Ala Ala Pro
        115                 120                 125

Glu Asn Glu Gly Lys Val Phe Lys Tyr Arg Phe Gly Lys Lys Ile Trp
    130                 135                 140

Asp Lys Ile Asn Ala Met Ile Ala Val Asp Val Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
            195                 200                 205

Leu Phe Glu Gln Met Val Asp Leu Ser Glu Met Thr Ser Lys Asp Lys
210                 215                 220

Phe Lys Ser Phe Glu Glu Leu Asn Thr Lys Phe Gly Gln Val Met Gly
225                 230                 235                 240

Thr Ala Val Met Gly Gly Ala Ala Thr Ala Ala Lys Lys Ala Asp
            245                 250                 255

Lys Val Ala Asp Asp Leu Asp Ala Phe Asn Val Asp Asp Phe Asn Thr
            260                 265                 270

Lys Thr Glu Asp Asp Phe Met Ser Ser Ser Gly Ser Ser Ser
            275                 280                 285

Ala Asp Asp Thr Asp Leu Asp Asp Leu Leu Asn Asp Leu Gly Gly Asn
290                 295                 300

Asn Gly Gly Asn Asn Met Asn Arg Arg Gly Gly Asn Phe Gly Asn Gln
305                 310                 315                 320

Gly Asp Phe Asn Gln Met Tyr Gln Asn Pro Met Met Gly Gly Tyr Asn
            325                 330                 335

Pro Met Met Asn Pro Gln Ala Met Thr Asp Tyr Tyr Gln Lys Met Gln
            340                 345                 350

Glu Tyr Tyr Gln Gln Met Gln His His His His His His
            355                 360                 365

<210> SEQ ID NO 121
<211> LENGTH: 182
<212> TYPE: DNA
<213> ORGANISM: Artificial Sequence
<220> FEATURE:
<223> OTHER INFORMATION: Example 24 - UP1-UP2'_TF1L template sequence

<400> SEQUENCE: 121
aatgatacgg cgaccaccgt gatctacact gttttacaac ctcagcatgg aaaaaggttt        60
cgaactcaac agctgtctgg cagctcgctc tacgcatgct attgctggcg gtattgcttc       120
tgctcttgct ggtggcgcca tgtctaaatt gtcgatacat ctcgtatgcc gtcttctgct       180
tg                                                                      182

<210> SEQ ID NO 122
<211> LENGTH: 29
<212> TYPE: DNA
<213> ORGANISM: Artificial Sequence
<220> FEATURE:
<223> OTHER INFORMATION: Example 24 - UP1 forward primer

<400> SEQUENCE: 122
aatgatacgg cgaccaccga gatctacac                                          29

<210> SEQ ID NO 123
<211> LENGTH: 18
<212> TYPE: DNA
<213> ORGANISM: Artificial Sequence
<220> FEATURE:
<223> OTHER INFORMATION: Example 24 - UP2-18 reverse primer

<400> SEQUENCE: 123
caagcagaag acggcata                                                      18

<210> SEQ ID NO 124
<211> LENGTH: 7
<212> TYPE: PRT

```
<213> ORGANISM: Artificial Sequence
<220> FEATURE:
<223> OTHER INFORMATION: Amino acid sequence comprised in functional
      IDRs

<400> SEQUENCE: 124

Tyr Ser Pro Thr Ser Pro Ser
1               5

<210> SEQ ID NO 125
<211> LENGTH: 7
<212> TYPE: PRT
<213> ORGANISM: Artificial Sequence
<220> FEATURE:
<223> OTHER INFORMATION: Amino acid sequence comprised in functional
      IDRs

<400> SEQUENCE: 125

Phe Ser Pro Thr Ser Pro Thr
1               5

<210> SEQ ID NO 126
<211> LENGTH: 7
<212> TYPE: PRT
<213> ORGANISM: Artificial Sequence
<220> FEATURE:
<223> OTHER INFORMATION: Amino acid sequence comprised in functional
      IDRs
<220> FEATURE:
<221> NAME/KEY: Xaa
<222> LOCATION: (7)..(7)
<223> OTHER INFORMATION: Xaa is A, N or G

<400> SEQUENCE: 126

Tyr Ser Pro Thr Ser Pro Xaa
1               5

<210> SEQ ID NO 127
<211> LENGTH: 7
<212> TYPE: PRT
<213> ORGANISM: Artificial Sequence
<220> FEATURE:
<223> OTHER INFORMATION: Amino acid sequence comprised in functional
      IDRs

<400> SEQUENCE: 127

Tyr Ser Pro Gly Ser Pro Ala
1               5

<210> SEQ ID NO 128
<211> LENGTH: 6
<212> TYPE: PRT
<213> ORGANISM: Artificial Sequence
<220> FEATURE:
<223> OTHER INFORMATION: Amino acid sequence comprised in functional
      IDRs

<400> SEQUENCE: 128

Gln Gln Gln Pro Gln Tyr
1               5

<210> SEQ ID NO 129
<211> LENGTH: 7
<212> TYPE: PRT
<213> ORGANISM: Artificial Sequence
<220> FEATURE:
<223> OTHER INFORMATION: YDPTSPS motif

<400> SEQUENCE: 129
```

```
<210> SEQ ID NO 130
<211> LENGTH: 7
<212> TYPE: PRT
<213> ORGANISM: Artificial Sequence
<220> FEATURE:
<223> OTHER INFORMATION: YSPTDPS motif

<400> SEQUENCE: 130

Tyr Ser Pro Thr Asp Pro Ser
1               5

<210> SEQ ID NO 131
<211> LENGTH: 31
<212> TYPE: PRT
<213> ORGANISM: Artificial Sequence
<220> FEATURE:
<223> OTHER INFORMATION: Self-designed double sequence of
      MEAFSSAKTEDDFMSSSSSDDSDLDDLLAGL

<400> SEQUENCE: 131

Met Glu Ala Phe Ser Ser Ala Lys Thr Glu Asp Asp Phe Met Ser Ser
1               5                   10                  15

Ser Ser Ser Asp Asp Ser Asp Leu Asp Asp Leu Leu Ala Gly Leu
            20                  25                  30

<210> SEQ ID NO 132
<211> LENGTH: 45
<212> TYPE: PRT
<213> ORGANISM: Artificial Sequence
<220> FEATURE:
<223> OTHER INFORMATION: Self-designed double sequence of
      EIVEAEVDELINSKVEKFKSPESKSKSAADLETDLEQLSDMEEFN

<400> SEQUENCE: 132

Glu Ile Val Glu Ala Glu Val Asp Glu Leu Ile Asn Ser Lys Val Glu
1               5                   10                  15

Lys Phe Lys Ser Pro Glu Ser Lys Ser Lys Ser Ala Ala Asp Leu Glu
            20                  25                  30

Thr Asp Leu Glu Gln Leu Ser Asp Met Glu Glu Phe Asn
        35                  40                  45

<210> SEQ ID NO 133
<211> LENGTH: 7
<212> TYPE: PRT
<213> ORGANISM: Artificial Sequence
<220> FEATURE:
<223> OTHER INFORMATION: Self designed linker of DDVASEF

<400> SEQUENCE: 133

Asp Asp Val Ala Ser Glu Phe
1               5

<210> SEQ ID NO 134
<211> LENGTH: 43
<212> TYPE: RNA
<213> ORGANISM: Artificial Sequence
<220> FEATURE:
<223> OTHER INFORMATION: Example 26 - guide-RNA sequence

<400> SEQUENCE: 134
uaauuucuac uguuguagau aaagugcuca ucauuggaaa acg                    43
```

```
<210> SEQ ID NO 135
<211> LENGTH: 59
<212> TYPE: DNA
<213> ORGANISM: Artificial Sequence
<220> FEATURE:
<223> OTHER INFORMATION: Example 26 - top oligo
<220> FEATURE:
<221> NAME/KEY: 5' FAM (fluorescein)
<222> LOCATION: (1)..(59)

<400> SEQUENCE: 135
gaacgttttc caatgatgag cacttttaaa gttctatgta tcaaagcggc catttgcgg          59

<210> SEQ ID NO 136
<211> LENGTH: 35
<212> TYPE: DNA
<213> ORGANISM: Artificial Sequence
<220> FEATURE:
<223> OTHER INFORMATION: Example 26 - bottom oligo
<220> FEATURE:
<221> NAME/KEY: 3' - BHQ-1 (quencher)
<222> LOCATION: (1)..(35)

<400> SEQUENCE: 136
agaactttaa aagtgctcat cattggaaaa cgttc                                   35

<210> SEQ ID NO 137
<211> LENGTH: 6
<212> TYPE: PRT
<213> ORGANISM: Artificial Sequence
<220> FEATURE:
<223> OTHER INFORMATION: Hemagglutinin C terminus

<400> SEQUENCE: 137

Asp Val Pro Asp Tyr Ala
1               5
```

BIOCHEMICAL REACTION METHODS AND REAGENTS COMPRISING INTRINSICALLY DISORDERED REGIONS

RELATED APPLICATIONS

This application is a continuation of International Patent Application No. PCT/GB2020/052866 filed on Nov. 11, 2020, which claims priority to United Kingdom application 1916379.9 filed on Nov. 11, 2019. The contents of the aforementioned applications are hereby incorporated by reference in their entireties.

REFERENCE TO SEQUENCE LISTING

The instant application contains a Sequence Listing which has been submitted electronically in ASCII format and is hereby incorporated by reference in its entirety. Said ASCII copy, created on Dec. 23, 2021, is named BOM_001PCCNB_SL.txt and is 203119 bytes in size.

FIELD OF THE INVENTION

The invention relates to processes for performing biochemical reactions, such as in an aqueous in vitro reaction system. The processes involve macromolecules, particularly polypeptides, comprising one or more functional intrinsically disordered regions (IDRs). The invention also relates to IDR-macromolecules, including IDR-polypeptides, including macromolecules or polypeptides comprising a tagged amino acid sequence which comprises or consists of one or more functional IDRs. Such functional IDRs are capable of increasing the efficiency of the biochemical reaction. The invention relates to kits comprising any such macromolecules and polypeptides. The invention further relates to processes for stimulating or enhancing liquid-liquid demixing in a solution using any such macromolecules and polypeptides, including in combination with multivalent metal ions, thereby providing reagents capable of increasing the efficiency of a biochemical reaction.

BACKGROUND TO THE INVENTION

The performance of biochemical reactions, and in particular in vitro biochemical reactions, is of fundamental importance in the biological sciences. Many biochemical reactions may need to be performed outside of the laboratory, such as at the point of care or in the field. In these settings it may not be possible to control biochemical reactions in the precise manner afforded by the laboratory environment. Improving the efficiency of biochemical reactions performed in these settings would be of value. Indeed, it may be desirable to increase the efficiency of biochemical reactions, regardless of the exact setting, including in vitro and in vivo biochemical reactions. The present invention addresses these issues.

Many biochemical reactions require the use of co-factors to aid in driving performance efficiency. One particular example of such a co-factor is a macromolecular crowding agent. Crowding agents are essential for the performance of many biochemical reactions. A notable example is the recombinase polymerase amplification (RPA) system for the amplification of nucleic acids. The use of a crowding agent has been considered essential in driving RPA performance efficiency. However, crowding agents may have drawbacks. Accordingly, alternative means for driving performance efficiency of biochemical reactions, including RPA, and that obviate the need for added/exogenous crowding agents would be of use. In addition, reagents that add to or synergise with the functional effects of crowding agents in increasing the performance efficiency of biochemical reactions would be of use. The present invention also addresses these issues.

SUMMARY OF THE INVENTION

The present invention provides a process of performing a biochemical reaction in an aqueous in vitro reaction system, wherein the biochemical reaction is dependent on the function of at least one reaction macromolecule, optionally at least one reaction polypeptide, the process comprising: introducing at least one IDR-macromolecule into the in vitro reaction system under conditions suitable for performing the reaction, wherein the at least one IDR-macromolecule comprises one or more functional intrinsically disordered regions (IDRs), wherein upon introduction of the at least one IDR-macromolecule into the in vitro reaction system the efficiency of the biochemical reaction is increased by the at least one IDR-macromolecule; preferably wherein the at least one IDR-macromolecule is at least one IDR-polypeptide.

In the above-described process, the biochemical reaction may be dependent on the function of the at least one IDR-macromolecule, optionally the at least one IDR-polypeptide, wherein upon its introduction into the in vitro reaction system the at least one IDR-macromolecule or the at least one IDR-polypeptide performs its reaction function in the biochemical reaction and increases the efficiency of the reaction.

Any of the herein-described processes may further comprise maintaining the IDR-macromolecule or the IDR-polypeptide in the system to cause liquid-liquid demixing and the formation of a plurality of phase-separated aqueous compartments within the system by the IDR-macromolecule or the IDR-polypeptide, thereby increasing the efficiency of the biochemical reaction in the system.

Any of the herein-described processes may further comprise maintaining the IDR-macromolecule or the IDR-polypeptide in the system to cause molecules necessary for the performance of the reaction to co-localise with the IDR-macromolecule or the IDR-polypeptide within the plurality of phase-separated aqueous compartments, or to further stimulate or enhance co-localisation of molecules necessary for the performance of the reaction with the IDR-macromolecule or the IDR-polypeptide within the plurality of phase-separated aqueous compartments, thereby increasing the efficiency of the biochemical reaction in the system.

In any of the herein-described processes the plurality of phase-separated aqueous compartments may be a plurality of detectable phase-separated aqueous particles.

In an additional aspect the invention provides a process of performing a biochemical reaction in an aqueous in vitro reaction system, wherein the biochemical reaction is dependent on the function of at least one reaction macromolecule, optionally at least one reaction polypeptide, the process comprising: introducing at least one polypeptide tagged with an amino acid sequence comprising or consisting of one or more functional intrinsically disordered regions (IDRs) (IDR-polypeptide) into the in vitro reaction system under conditions suitable for performing the reaction, and maintaining the IDR-polypeptide in the system to cause liquid-liquid demixing and the formation of a plurality of phase-separated aqueous compartments, preferably detectable phase-separated aqueous particles, within the system by the IDR-polypeptide and to cause molecules necessary for the performance of the reaction to co-localise with the IDR-polypeptide within the compartments thereby increasing the efficiency of the biochemical reaction in the system.

Optionally, in a process according to this additional aspect, the biochemical reaction is dependent on the function of at least one reaction polypeptide, wherein the reaction polypeptide is the at least one IDR-polypeptide, wherein upon introduction into the system the at least one IDR-polypeptide performs its reaction function in the biochemical reaction and increases the efficiency of the reaction in the system.

In any of the processes according to this additional aspect, the conditions suitable for performing the reaction may further comprise providing multivalent metal ions to the IDR-polypeptide thereby further stimulating or enhancing the liquid-liquid demixing and the formation of the plurality of phase-separated aqueous compartments caused by the IDR-polypeptide and thereby further increasing the efficiency of the biochemical reaction in the system; optionally wherein the multivalent metal ions are provided at a concentration of about 22 mM or more, preferably wherein the multivalent metal ions are provided at a concentration of between about 22 mM to 50 mM. The multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$.

In any of the processes according to this additional aspect, the conditions suitable for performing the reaction may further comprise providing ATP to the IDR-polypeptide in the in vitro reaction system, thereby further simulating or enhancing the liquid-liquid demixing and the formation of the plurality of phase-separated aqueous compartments caused by the IDR-polypeptide and thereby further increasing the efficiency of the biochemical reaction in the system, wherein ATP is provided in the system at a concentration of 1 mM to 3.5 mM, optionally 1 mM to 2 mM, preferably 1 mM.

In any of the processes according to this additional aspect, the conditions suitable for performing the reaction may further comprise providing multivalent metal ions to the IDR-polypeptide thereby further stimulating or enhancing molecules necessary for the performance of the reaction to co-localise with the IDR-polypeptide within the plurality of phase-separated aqueous compartments thereby further increasing the efficiency of the biochemical reaction in the system; optionally wherein the multivalent metal ions are provided at a concentration of about 22 mM or more, preferably wherein the multivalent metal ions are provided at a concentration of between about 22 mM to 50 mM. The multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$.

In any of the processes according to this additional aspect, the conditions suitable for performing the reaction may further comprise providing ATP to the IDR-polypeptide in the in vitro reaction system, thereby further stimulating or enhancing molecules necessary for the performance of the reaction to co-localise with the IDR-polypeptide within the plurality of phase-separated aqueous compartments and thereby further increasing the efficiency of the biochemical reaction in the system, wherein ATP is provided in the system at a concentration of 1 mM to 3.5 mM, optionally 1 mM to 2 mM, preferably 1 mM.

In any of the processes according to this additional aspect, the efficiency of the reaction in the system may be increased by the IDR-polypeptide compared to the efficiency of the reaction in the system following introduction of the at least one polypeptide under the same reaction conditions except that the at least one polypeptide has not been tagged with the amino acid sequence comprising or consisting of the one or more functional IDRs.

The invention also provides a process of performing a biochemical reaction in an aqueous in vitro reaction system, wherein the biochemical reaction is dependent on the function of at least one reaction macromolecule, optionally at least one reaction polypeptide, the process comprising:

i. introducing molecules comprising at least one IDR-macromolecule into the system under conditions suitable for performing the reaction, wherein the at least one IDR-macromolecule comprises one or more functional intrinsically disordered regions (IDRs), preferably wherein the at least one IDR-macromolecule is at least one IDR-polypeptide;

ii. maintaining the IDR-macromolecule or the IDR-polypeptide in the system to cause liquid-liquid demixing in the system, wherein the liquid-liquid demixing is caused by the IDR-macromolecule or the IDR-polypeptide and forms a plurality of phase-separated aqueous compartments within the system;

iii. maintaining the IDR-macromolecule or the IDR-polypeptide in the system to cause molecules necessary for the performance of the reaction to co-localise with the IDR-macromolecule or the IDR-polypeptide within the compartments; and iv. allowing the biochemical reaction to proceed within the compartments; wherein the efficiency of the biochemical reaction in the system is increased by the presence of the at least one IDR-macromolecule.

In the above-described process, the biochemical reaction may be dependent on the function of the at least one IDR-macromolecule, optionally the at least one IDR-polypeptide, wherein upon its introduction into the in vitro reaction system the at least one IDR-macromolecule or the at least one IDR-polypeptide performs its reaction function in the biochemical reaction and increases the efficiency of the reaction. The plurality of phase-separated aqueous compartments may be a plurality of detectable phase-separated aqueous particles.

In a further aspect the invention provides a process of performing a biochemical reaction in an aqueous in vitro reaction system, wherein the biochemical reaction is dependent on the function of at least one reaction macromolecule, optionally at least one reaction polypeptide, the process comprising:

i. introducing molecules comprising at least one polypeptide tagged with an amino acid sequence comprising or consisting of one or more functional intrinsically disordered regions (IDRs) (IDR-polypeptide) into the system under conditions suitable for performing the reaction;

ii. maintaining the IDR-polypeptide in the system to cause liquid-liquid demixing and the formation of a plurality of phase-separated aqueous compartments, preferably detectible phase-separated aqueous particles, within the system, wherein the liquid-liquid demixing is caused by the IDR-polypeptide;

iii. maintaining the IDR-polypeptide in the system to cause molecules necessary for the performance of the reaction to co-localise with the IDR-polypeptide within the compartments; and iv. allowing the biochemical reaction to proceed within the compartments; wherein the efficiency of the biochemical reaction in the system is increased by the presence of the at least one IDR-polypeptide.

Optionally, in a process according to this further aspect, the biochemical reaction is dependent on the function of at least one reaction polypeptide, wherein the reaction polypeptide is the at least one IDR-polypeptide, wherein upon introduction into the system the at least one IDR-polypeptide performs its reaction function in the biochemical reaction and increases the efficiency of the reaction in the system.

In any of the processes according to this further aspect, the conditions suitable for performing the reaction may further comprise providing multivalent metal ions to the IDR-polypeptide thereby further stimulating or enhancing the liquid-liquid demixing and the formation of the plurality of phase-separated aqueous compartments caused by the IDR-polypeptide and thereby further increasing the efficiency of the biochemical reaction in the system; optionally wherein the multivalent metal ions are provided at a concentration of about 22 mM or more, preferably wherein the multivalent metal ions are provided at a concentration of between about 22 mM to 50 mM. The multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$.

In any of the processes according to this further aspect, the conditions suitable for performing the reaction may further comprise providing ATP to the IDR-polypeptide in the in vitro reaction system, thereby further simulating or enhancing the liquid-liquid demixing and the formation of the plurality of phase-separated aqueous compartments caused by the IDR-polypeptide and thereby further increasing the efficiency of the biochemical reaction in the system, wherein ATP is provided in the system at a concentration of 1 mM to 3.5 mM, optionally 1 mM to 2 mM, preferably 1 mM.

In any of the processes according to this further aspect, the conditions suitable for performing the reaction may further comprise providing multivalent metal ions to the IDR-polypeptide thereby further stimulating or enhancing molecules necessary for the performance of the reaction to co-localise with the IDR-polypeptide within the plurality of phase-separated aqueous compartments thereby further increasing the efficiency of the biochemical reaction in the system; optionally wherein the multivalent metal ions are provided at a concentration of about 22 mM or more, preferably wherein the multivalent metal ions are provided at a concentration of between about 22 mM to 50 mM. The multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$.

In any of the processes according to this further aspect, the conditions suitable for performing the reaction may further comprise providing ATP to the IDR-macromolecule or IDR-polypeptide in the in vitro reaction system, thereby further stimulating or enhancing molecules necessary for the performance of the reaction to co-localise with the IDR-polypeptide within the plurality of phase-separated aqueous compartments and thereby further increasing the efficiency of the biochemical reaction in the system, wherein ATP is provided in the system at a concentration of 1 mM to 3.5 mM, optionally 1 mM to 2 mM, preferably 1 mM.

In any of the processes according to this further aspect, the conditions suitable for performing the reaction may further comprise providing multivalent metal ions to the IDR-polypeptide thereby further stimulating or enhancing molecules necessary for the performance of the reaction to co-localise with the IDR-macromolecule or the IDR-polypeptide within the plurality of phase-separated aqueous compartments thereby further increasing the efficiency of the biochemical reaction in the system; optionally wherein the multivalent metal ions are provided at a concentration of about 22 mM or more, preferably wherein the multivalent metal ions are provided at a concentration of between about 22 mM to 50 mM. The multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$.

In any of the processes according to this further aspect, the efficiency of the reaction in the system may be increased by the IDR-polypeptide compared to the efficiency of the reaction in the system following introduction of the at least one polypeptide under the same reaction conditions except that the at least one polypeptide has not been tagged with the amino acid sequence comprising or consisting of the one or more functional IDRs.

In any of the above-described processes, the process may be a biochemical reaction for synthesizing a nucleic acid molecule in an in vitro reaction system comprising:
(a) providing at least one nucleic acid primer;
(b) providing a target nucleic acid molecule comprising at least one target strand, and contacting the at least one nucleic acid primer with the target strand, thereby forming a double stranded structure;
(c) providing the IDR-macromolecule as an IDR-polypeptide, wherein the IDR-polypeptide is polymerase or one or more polypeptide co-factors; and
(d) allowing the reaction to proceed, thereby extending the 3' end of the at least one nucleic acid primer with polymerase and dNTPs, optionally in the presence of one or more polypeptide co-factors, to generate a double stranded nucleic acid, wherein the first strand comprises a sequence of the target strand and the second strand comprises a sequence which is complementary thereto.

Alternatively, in any of the above-described processes, the process may be a biochemical for amplifying a single stranded target nucleic acid molecule or a double stranded target nucleic acid molecule in an in vitro reaction system, preferably wherein the target nucleic acid molecule is a DNA molecule.

The process may be a biochemical reaction for amplifying a double stranded target nucleic acid molecule in an in vitro reaction system comprising:
(a) providing first and second nucleic acid primers;
(b) providing a double stranded target nucleic acid molecule comprising a first strand and a second strand, and contacting the first and second nucleic acid primers with the target nucleic acid molecule thereby forming a first double stranded structure with the first strand and a second double stranded structure with the second strand;
(c) providing the IDR-macromolecule as an IDR-polypeptide, wherein the IDR-polypeptide is polymerase or one or more protein co-factors;
(d) allowing the reaction to proceed, thereby extending the 3' ends of the first and second nucleic acid primers with polymerase and dNTPs, optionally in the presence of one or more protein co-factors, to generate first and second double stranded nucleic acids; and
(e) repeating steps (b) to (d) until a desired degree of amplification is reached.

In the above-described process for amplifying a double stranded target nucleic acid molecule in an in vitro reaction system, the process may be a recombinase polymerase amplification (RPA) process of amplifying the double stranded target nucleic acid molecule in the in vitro reaction system comprising:

(a) providing a recombinase agent, optionally a recombinase loading protein, a single strand stabilizing agent, polymerase, first and a second nucleic acid primers, double stranded target nucleic acid comprising a first strand and a second strand, and optionally an exonuclease such as Exonuclease III;

(b) contacting the recombinase agent with the first and second nucleic acid primers and optionally with the recombinase loading protein to form first and second nucleoprotein primers which comprise a single stranded region at their 3' ends;

(c) contacting the first and second nucleoprotein primers with the target nucleic acid molecule thereby forming a first double stranded structure with the first strand and a second double stranded structure with the second strand;

(d) allowing the reaction to proceed, thereby extending the 3' end of the first and second nucleoprotein primers with polymerase and dNTPs to generate first and second double stranded nucleic acids and first and a second displaced nucleic acid strands, wherein the single strand stabilizing agent stabilizes the first and second displaced strands; and (e) continuing the reaction by repeating steps (b) to (d) until a desired degree of amplification is reached;

wherein the recombinase agent, and/or the recombinase loading protein, and/or the single strand stabilizing agent, and/or the polymerase is provided as the IDR-polypeptide.

In the above-described RPA process of amplifying a double stranded target nucleic acid molecule in the in vitro reaction system, the recombinase agent may be selected from the group consisting of UvsX, T4 UvsX, T6 UvsX, RB18 UvsX, *E. coli* phage wV7 UvsX, *Shigella* phage CB8 UvsX, *Shigella* phage Shfl2 UvsX, *E. coli* phage AR1 UvsX, phage vB_EcoM_G4507 UvsX, *Shigella* phage SHFML-11 UvsX, *Escherichia* phage vB_EcoM_DalCa UvsX, *E. coli* RecA, *E. coli* RadA, *E. coli* RadB, *E. coli* Rad 51 or any functional analog, homolog or derivative thereof, and any combination thereof, preferably wherein the recombinase agent is UvsX, more preferably *Escherichia* phage vB_EcoM_DalCa UvsX.

In any one of the above-described RPA processes of amplifying a double stranded target nucleic acid molecule in the in vitro reaction system, the process may include a recombinase loading protein and wherein the recombinase loading protein is selected from the group consisting of UvsY, *E. coli* RecO, *E. coli* RecR or any functional analog, homolog or derivative thereof, and any combination thereof, preferably wherein the recombinase loading protein is UvsY, more preferably *Escherichia* phage STO UvsY.

In any one of the above-described RPA processes of amplifying a double stranded target nucleic acid molecule in the in vitro reaction system, the polymerase may be a eukaryotic polymerase selected from the group consisting of pol-α, pol-β, pol-δ, pol-ε or any functional analog, homolog or derivative thereof, and any combination thereof. The polymerase may be a prokaryotic polymerase selected from the group consisting of *Bacillus stearothermophilus* polymerase I large fragment, *Bacillus subtilis* Pol I large fragment (Bsu polymerase), *Listeria monocytogenes* DNA polymerase I, *S. aureus* DNA polymerase I (Sau polymerase), *E. coli* DNA polymerase I Klenow fragment, *E. coli* DNA polymerase I, *E. coli* DNA polymerase II, *E. coli* DNA polymerase III, *E. coli* DNA polymerase IV, *E. coli* DNA polymerase V, or any functional analog, homolog or derivative thereof, and any combination thereof, preferably wherein the polymerase is *S. aureus* DNA polymerase I (Sau polymerase) or *Bacillus subtilis* Pol I large fragment (Bsu polymerase). The polymerase may be a bacteriophage polymerase selected from the group consisting of bacteriophage T4 gp43 DNA polymerase, T7 DNA polymerase and Phi-29 DNA polymerase, or any functional analog, homolog or derivative thereof, and any combination thereof.

In any one of the above-described RPA processes of amplifying a double stranded target nucleic acid molecule in the in vitro reaction system, the single strand stabilizing agent may be selected from the group consisting of Gp32, *E. coli* SSB protein, phage T4 Gp32 protein, phage Rb69 Gp32, phage vB_EcoM_NBG1 Gp32, or any functional analog, homolog or derivative thereof, and any combination thereof, preferably the single strand stabilizing agent is Gp32 or phage vB_EcoM_NBG1 Gp32.

In any one of the above-described RPA processes of amplifying a double stranded target nucleic acid molecule in the in vitro reaction system, only the recombinase agent may be provided as the IDR-polypeptide, or only the recombinase loading protein may be provided as the IDR-polypeptide, or only the single strand stabilizing agent may be provided as the IDR-polypeptide, or only the polymerase may be provided as the IDR-polypeptide, or only the exonuclease may be provided as the IDR-polypeptide.

In any one of the above-described RPA processes of amplifying a double stranded target nucleic acid molecule in the in vitro reaction system, the one or more functional IDRs of the IDR-polypeptide may be tagged to the IDR-polypeptide as an amino acid sequence comprising or consisting of the one or more IDRs such that the IDR-polypeptide is a genetically engineered fusion protein, wherein the one or more functional IDRs are located at the C-terminus of the IDR-polypeptide, at the N-terminus of the IDR-polypeptide, or at both the C-terminus of the IDR-polypeptide and the N-terminus of the IDR-polypeptide, or at any amino acid position along the length of the polypeptide.

In any one of the above-described processes, the one or more functional IDRs of the IDR-macromolecule or the IDR-polypeptide may be characterised as a sequence of amino acids which scores greater than 0.5 when analysed by the algorithm MetaDisorder.

In any one of the above-described processes, the one or more functional IDRs of the IDR-macromolecule or the IDR-polypeptide may comprise or consist of an amino acid sequence which includes one or more repeats of the tripeptide sequence RGG. In any such process, the one or more functional IDRs of the IDR-macromolecule or the IDR-polypeptide may comprise or consist of an amino acid sequence which further includes one or more repeats of the di-peptide sequence FG. In any such process, the one or more functional IDRs of the IDR-macromolecule or the IDR-polypeptide may comprise or consist of an amino acid sequence which further includes at least one aromatic amino acid residue consisting of tyrosine or phenylalanine.

In any one of the above-described processes, the one or more functional IDRs of the IDR-macromolecule or the IDR-polypeptide may comprise or consist of the amino acid sequence of i. $(YNPQGGYQQ)_n$ (SEQ ID NO: 19), wherein n is a positive integer between 1 and 10, optionally wherein n=1, 2, or 3; or ii. (YSPTSPS)$_n$ (SEQ ID NO: 124), wherein n is a positive integer between 1 and 10, optionally wherein n=1, 2, or 3; or iii. (FSPTSPT)$_n$ (SEQ ID NO: 125), wherein n is a positive integer between 1 and 10, optionally wherein n=1, 2, or 3; or iv. (YSPTSP-A/N/G)$_n$ (SEQ ID NO: 126), wherein n is a positive integer between 1 and 10, optionally wherein n=1, 2, or 3; or v. (YSPGSPA)$_n$ (SEQ ID NO: 127), wherein n is a positive integer between 1 and 10, optionally wherein n=1, 2, or 3.

In any one of the above-described processes, the one or more functional IDRs of the IDR-macromolecule or the IDR-polypeptide may comprise or consist of an amino acid sequence which is glutamine rich, optionally wherein the amino acid sequence comprises at least 4, at least 5, at least 6, at least 7, at least 8, at least 9, or at least 10 consecutive glutamine residues. In any such process, the one or more functional IDRs of the IDR-macromolecule or the IDR-polypeptide may comprise or consist of an amino acid sequence comprising one or more repeats of the tri-peptide sequence QQQ. In any such process, the one or more functional IDRs of the IDR-macromolecule or the IDR-polypeptide comprises or consists of the amino acid sequence of (QQQPQY)$_n$ (SEQ ID NO: 128), wherein n is a positive integer between 1 and 10, optionally wherein n=1, 2, or 3.

In any one of the above-described processes, the one or more functional IDRs of the IDR-macromolecule or the IDR-polypeptide may comprise or consist of a sequence of at least 5 consecutive amino acids of SEQ ID NO:1.

In any one of the above-described processes, the one or more functional IDRs of the IDR-macromolecule or the IDR-polypeptide may comprise or consist of an amino acid sequence of at least 5 consecutive amino acids of SEQ ID NO:9.

In any one of the above-described processes, the one or more functional IDRs of the IDR-macromolecule or the IDR-polypeptide may comprise an amino acid sequence containing one or more aromatic tyrosine residues and one or more phenylalanine residues which can engage in aromatic cation-pi interactions with multivalent metal ions, preferably divalent metal ions.

In any one of the above-described processes, the one or more functional IDRs of the IDR-macromolecule or the IDR-polypeptide may comprise an amino acid sequence containing one or more arginine residues which can engage in guanidine-metal interactions with multivalent metal ions, preferably divalent metal ions.

In any one of the above-described processes, the IDR-macromolecule or the IDR-polypeptide may comprise or consist of the macromolecule or polypeptide tagged with an amino acid sequence which comprises or consists of the amino acid sequence of any one of SEQ ID NOs 1 to 43, or which comprises or consists of a functional variant amino acid sequence of SEQ ID NOs 1 to 43, e.g. which has 80% or more identity to any one of SEQ ID NOs 1 to 43.

In any one of the above-described RPA processes of amplifying a double stranded target nucleic acid molecule in the in vitro reaction system, the IDR-polypeptide may be a single strand stabilizing agent which is Gp32 and which has the amino acid sequence of any one of SEQ ID NOs 65 to 88, or wherein the IDR-polypeptide is a functional variant thereof, e.g. an IDR-polypeptide having an amino acid sequence which has 80% or more identity to any one of SEQ ID NOs 65 to 88.

In any one of the above-described RPA processes of amplifying a double stranded target nucleic acid molecule in the in vitro reaction system, the IDR-polypeptide may be a recombinase agent which is UvsX and which has the amino acid sequence of any one of SEQ ID NOs 44 to 59, or wherein the IDR-polypeptide is a functional variant thereof, e.g. an IDR-polypeptide having an amino acid sequence which has 80% or more identity to any one of SEQ ID NOs 44 to 59.

In any one of the above-described RPA processes of amplifying a double stranded target nucleic acid molecule in the in vitro reaction system, the IDR-polypeptide may be a recombinase loading protein which is UvsY and which has the amino acid sequence of any one of SEQ ID NOs 60 to 64, or wherein the IDR-polypeptide is a functional variant thereof, e.g. an IDR-polypeptide having an amino acid sequence which has 80% or more identity to any one of SEQ ID NOs 60 to 64.

In any one of the above-described processes, the process may further comprise providing multivalent metal ions to the IDR-macromolecule or IDR-polypeptide in the in vitro reaction system, thereby further simulating or enhancing the liquid-liquid demixing in the in vitro reaction system, thereby further increasing the efficiency of the biochemical reaction in the system, wherein the multivalent metal ions further stimulate or enhance the formation of the plurality of phase-separated aqueous compartments within the system thereby further increasing the efficiency of the biochemical reaction in the system, preferably wherein the multivalent metal ions further stimulate or enhance the formation of a plurality of detectable phase-separated aqueous particles; optionally wherein the multivalent metal ions are provided at a concentration of; optionally wherein the multivalent metal ions are provided at a concentration of about 22 mM or more, preferably wherein the multivalent metal ions are provided at a concentration of between about 22 mM to 50 mM. In any such process, the multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$.

In any one of the above-described processes, the conditions suitable for performing the reaction may further comprise providing ATP to the IDR-macromolecule or the IDR-polypeptide in the in vitro reaction system, thereby further simulating or enhancing the liquid-liquid demixing and the formation of the plurality of phase-separated aqueous compartments caused by the IDR-macromolecule or the IDR-polypeptide and thereby further increasing the efficiency of the biochemical reaction in the system, wherein ATP is provided in the system at a concentration of 1 mM to 3.5 mM, optionally 1 mM to 2 mM, preferably 1 mM.

In any one of the above-described processes, the conditions suitable for performing the reaction may further comprise providing multivalent metal ions to the IDR-polypeptide thereby further stimulating or enhancing molecules necessary for the performance of the reaction to co-localise with the IDR-macromolecule or the IDR-polypeptide within the plurality of phase-separated aqueous compartments thereby further increasing the efficiency of the biochemical reaction in the system; optionally wherein the multivalent metal ions are provided at a concentration of about 22 mM or more, preferably wherein the multivalent metal ions are provided at a concentration of between about 22 mM to 50 mM. The multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$.

In any one of the above-described processes, the conditions suitable for performing the reaction may further comprise providing ATP to the IDR-macromolecule or IDR-polypeptide in the in vitro reaction system, thereby further stimulating or enhancing molecules necessary for the performance of the reaction to co-localise with the IDR-polypeptide within the plurality of phase-separated aqueous compartments and thereby further increasing the efficiency of the biochemical reaction in the system, wherein ATP is provided in the system at a concentration of 1 mM to 3.5 mM, optionally 1 mM to 2 mM, preferably 1 mM.

In any one of the above-described processes, the biochemical reaction may be performed in a solid phase reaction system which comprises a surface. In any such process the biochemical reaction may be a process of amplifying a single stranded target nucleic acid molecule or a double stranded target nucleic acid molecule in the in vitro reaction system as described above, wherein the at least one nucleic acid primer and/or the IDR-macromolecule and/or the one or more polypeptide co-factors are attached to the surface.

In any one of the above-described RPA processes of amplifying a double stranded target nucleic acid molecule in the in vitro reaction system, the reaction may be performed in a solid phase reaction system which comprises a surface, and wherein the recombinase agent and/or the recombinase loading protein and/or the single strand stabilizing agent and/or the polymerase and/or the exonuclease and/or the first nucleic acid primer and/or the second nucleic acid primer is attached to the surface, preferably wherein: (i) the first nucleic acid primer or the second nucleic acid primer is attached to the surface; or (ii) both the first and second nucleic acid primers are attached to the surface.

In any of the above described process performed in a solid phase reaction system which comprises a surface, the surface may be planar or may be a microbead, preferably the surface comprises silicon, glass, a gel-based material and/or a polymeric material such as polystyrene, more preferably the surface is a microbead comprising a polymeric material such as polystyrene. In any such process, the surface may be bound to a substrate, preferably the surface is planar and/or the substrate comprises glass. The surface, e.g. a planar surface and/or the substrate may be provided as a flow-cell.

The invention provides a processes for performing a biochemical reaction within a cell in culture by introducing at least one of any of the above-described IDR-macromolecules or at least one of any of the above-described IDR-polypeptides into a cultured host cell, or by expressing at least one of any of the above-described IDR-polypeptides in the cultured host cell, to increase the efficiency of the biochemical reaction within the cultured host cell.

Any of the above-described processes for performing an in vitro biochemical reaction may comprise a biochemical reaction performed within a cell in culture, such as by introducing the at least one IDR-macromolecule or the at least one IDR-polypeptide into a cultured host cell, or by expressing the at least one IDR-polypeptide in the cultured host cell, to increase the efficiency of the biochemical reaction within the cultured host cell.

The biochemical reaction may be any reaction which leads to the manipulation of a nucleic acid molecule within the cultured host cell, or which leads to the alteration of a nucleic acid molecule within the cultured host cell, such as a change in the structure of a nucleic acid molecule, such as a change in the nucleotide sequence of a nucleic acid molecule. The biochemical reaction may be any reaction which leads to the synthesis of a nucleic acid molecule in the cultured host cell. The biochemical reaction may be any reaction which leads to the expression of a polypeptide from a nucleic acid molecule. The biochemical reaction may be any reaction which leads to the editing of a nucleic acid sequence within the cultured host cell, e.g. wherein the IDR-polypeptide is a CRISPR polypeptide, such as a Cas polypeptide, including a Cas9 polypeptide). The biochemical reaction may be any reaction which leads to the cleavage of a nucleic acid within the cultured host cell. The biochemical reaction may be any reaction which leads to the homologous recombination of nucleic acids within the cultured host cell. The biochemical reaction may be a metabolic reaction within the cultured host cell to produce one or more biological products of interest within the cultured host cell, or to produce one or more biological products of interest which are secreted from the cultured host cell or otherwise released from the cultured host cell into the culture media.

In any one of the above-described processes, increasing the efficiency of the biochemical reaction may comprise increasing the efficiency of the reaction using the at least one IDR-macromolecule or the at least one IDR-polypeptide compared to the efficiency of the reaction obtained by performing the reaction under the same conditions but wherein the relevant at least one macromolecule or the at least one polypeptide does not comprise or has not been tagged with one or more functional intrinsically disordered region polypeptide sequences, optionally wherein the reaction is performed in the absence of an exogenously added crowding agent.

In any one of the above-described RPA processes, increasing or enhancing the efficiency or performance of an RPA biochemical reaction may comprise increasing the amount of amplified product obtained in the RPA reaction using the at least one IDR-polypeptide compared to the amount of amplified product obtained by performing the reaction under the same conditions but wherein the relevant at least one polypeptide has not been tagged with one or more functional intrinsically disordered region polypeptide sequences, optionally wherein the reaction is performed in the absence of an exogenously added crowding agent.

In any one of the above-described processes involving introducing at least one IDR-macromolecule or IDR-polypeptide into the in vitro reaction system, the efficiency of the reaction in the system is increased by the IDR-macromolecule or the IDR-polypeptide compared to the efficiency of the reaction in the system following the introduction of the at least one macromolecule or polypeptide under the same reaction conditions except that the at least one macromolecule or polypeptide does not comprise one or more functional intrinsically disordered regions (IDRs).

In any one of the above-described processes involving introducing at least at least one polypeptide tagged with an amino acid sequence comprising or consisting of one or more functional intrinsically disordered regions (IDRs) (IDR-polypeptide) into the in vitro reaction system the efficiency of the reaction in the system is increased by the IDR-polypeptide compared to the efficiency of the reaction in the system following the introduction of the at least one polypeptide under the same reaction conditions except that the at least one polypeptide has not been tagged with the amino acid sequence comprising or consisting of the one or more functional IDRs.

The invention also provides a non-naturally occurring IDR-macromolecule comprising a macromolecule and a tag amino acid sequence, wherein the tag amino acid sequence comprises or consists of one or more functional intrinsically disordered regions (IDRs), wherein the IDR-macromolecule is capable of causing liquid-liquid demixing in an aqueous in vitro reaction system. Any such IDR-macromolecule may be capable of causing liquid-liquid demixing and the formation of a plurality of phase-separated aqueous compartments in the system, preferably a plurality of detectable phase-separated aqueous particles. Any such liquid-liquid demixing caused by any such non-naturally occurring IDR-macromolecule in the in vitro reaction system may thereby increase the efficiency of the biochemical reaction.

Any one of the above-described IDR-macromolecules may be a non-naturally occurring, artificial or genetically engineered IDR-macromolecule or IDR-polypeptide comprising a macromolecule or polypeptide and the tag amino acid sequence. In the case of an IDR-polypeptide, the tag amino acid sequence may be located at the C-terminus of the polypeptide, at the N-terminus of the polypeptide or at both the C-terminus of the polypeptide and the N-terminus of the polypeptide, or at any amino acid position along the length of the polypeptide.

In any one of the above-described IDR-macromolecules or IDR-polypeptides, the one or more functional IDRs of the tag amino acid sequence are functional IDRs as defined in any one of the above-described processes.

In any one of the above-described IDR-macromolecules or IDR-polypeptides the tag sequence comprises amino acid residues which are capable of engaging in aromatic cation-pi interactions with multivalent metal cations, preferably divalent metal cations, more preferably $Mg^{2+}$, $Mn^{2+}$, $Ca^{2+}$, $Co^{2+}$ or $Ni^{2+}$ ions, yet more preferably $Mg^{2+}$, $Mn^{2+}$ or $Ca^{2+}$, even more preferably $Mg^{2+}$.

In any one of the above-described IDR-macromolecules or IDR-polypeptides the IDR-macromolecule or the IDR-polypeptide comprises or consists of the macromolecule or polypeptide tagged with an amino acid sequence which comprises or consists of the amino acid sequence of any one of SEQ ID NOs 1 to 43, or which comprises or consists of a functional variant amino acid sequence of SEQ ID NOs 1 to 43, e.g. which has 80% or more identity to any one of SEQ ID NOs 1 to 43.

In any one of the above-described IDR-polypeptides, the polypeptide to which the sequence comprising or consisting of the one or more functional IDRs is tagged may be an enzyme, such as a helicase, a gyrase, a recombinase, e.g. an RPA recombinase agent, a nuclease, e.g. an exonuclease and an endonuclease, a ligase, a glycolyase, a methylase, a methyltransferase, a glucosyltransferase, a polymerase, a kinase, a phosphatase, a gene editing enzyme such as a CRISPR enzyme, e.g. a Cas9 enzyme; a co-factor, e.g. as an RPA recombinase loading protein and an RPA single strand stabilizing agent. The polypeptide to which the sequence comprising or consisting of the one or more functional IDRs is tagged may be a ligase, optionally an RB69 ligase, such as RB69 ligase-His2 (SEQ ID NO:112). The polypeptide to which the sequence comprising or consisting of the one or more functional IDRs is tagged may be an RPA single strand stabilizing agent, preferably Gp32; optionally wherein the IDR-polypeptide has the amino acid sequence of any one of SEQ ID NOs 65 to 88 and SEQ ID NO:120, or wherein the IDR-polypeptide is a functional variant thereof, e.g. an IDR-polypeptide having an amino acid sequence which has 80% or more identity to any one of SEQ ID NOs 65 to 88 and SEQ ID NO:120. The polypeptide to which the sequence comprising or consisting of the one or more functional IDRs is tagged may be an RPA recombinase agent, preferably UvsX; optionally wherein the IDR-polypeptide has the amino acid sequence of any one of SEQ ID NOs 44 to 59, or wherein the IDR-polypeptide is a functional variant thereof, e.g. an IDR-polypeptide having an amino acid sequence which has 80% or more identity to any one of SEQ ID NOs 44 to 59. The polypeptide to which the sequence comprising or consisting of the one or more functional IDRs is tagged may be an RPA recombinase loading protein, preferably UvsY; optionally wherein the IDR-polypeptide has the amino acid sequence of any one of SEQ ID NOs 60 to 64, or wherein the IDR-polypeptide is a functional variant thereof, e.g. an IDR-polypeptide having an amino acid sequence which has 80% or more identity to any one of SEQ ID NOs 60 to 64.

The invention also provides an isolated nucleic acid molecule comprising a first nucleic acid sequence encoding any of the above-described IDR-polypeptides; optionally including a second nucleic acid sequence encoding a promoter, wherein the first nucleic acid sequence is operably linked to the second nucleic acid sequence. The invention also provides a recombinant polynucleotide expression vector comprising any such nucleic acid molecule. The invention also provides a host cell comprising any such nucleic acid molecule, or any such recombinant polynucleotide expression vector. The invention also provides a cell culture comprising a growth medium and a population of any such host cells.

The invention also provides a kit comprising any of the above-described non-naturally occurring IDR-macromolecules or IDR-polypeptides. Any such kit may further comprising additional RPA components comprising an RPA recombinase agent, and/or an RPA recombinase loading protein, and/or polymerase, and/or first and second nucleic acid primers, and/or an exonuclease, and/or a buffer, and/or a source of multivalent metal ions, preferably divalent metal cations. In any such kit, all components may be provided in lyophilized form.

The invention also provides a process of stimulating or enhancing liquid-liquid demixing in a solution, the process comprising providing a solution comprising any of the above-described IDR-macromolecules or any of the above-described IDR-polypeptides, and contacting the IDR-macromolecule or IDR-polypeptide in solution with multivalent metal ions whereupon liquid-liquid demixing in the solution is stimulated or enhanced. The invention also provides a further process of stimulating or enhancing in an aqueous in vitro reaction system liquid-liquid demixing caused by an IDR-macromolecule or an IDR-polypeptide, the process comprising providing any one of the above-described IDR-macromolecules or any one of the above-described IDR-polypeptides into the system, providing multivalent metal ions into the system and allowing the IDR-macromolecule or IDR-polypeptide to contact the multivalent metal ions whereupon liquid-liquid demixing caused by the IDR-macromolecule or the IDR-polypeptide in the solution is stimulated or enhanced. In any such processes the liquid-liquid demixing may result in the formation of a plurality of phase-separated aqueous compartments, preferably a plurality of detectable phase-separated aqueous particles in the solution. In any such process the multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$. In any such further process, the multivalent metal ions may engage in aromatic cation-pi interactions with amino acid residues in the one or more functional IDR amino acid sequences, thereby promoting liquid-liquid demixing.

In any such further process, the conditions suitable for performing the reaction may further comprise providing ATP to the IDR-macromolecule or the IDR-polypeptide in the in vitro reaction system, thereby further simulating or enhancing the liquid-liquid demixing and the formation of the plurality of phase-separated aqueous compartments caused by the IDR-macromolecule or the IDR-polypeptide and thereby further increasing the efficiency of the biochemical reaction in the system, wherein ATP is provided in the system at a concentration of 1 mM to 3.5 mM, optionally 1 mM to 2 mM, preferably 1 mM.

In any such further process, the conditions suitable for performing the reaction may further comprise providing multivalent metal ions to the IDR-polypeptide thereby further stimulating or enhancing molecules necessary for the performance of the reaction to co-localise with the IDR-macromolecule or the IDR-polypeptide within the plurality of phase-separated aqueous compartments thereby further increasing the efficiency of the biochemical reaction in the system; optionally wherein the multivalent metal ions are provided at a concentration of about 22 mM or more, preferably wherein the multivalent metal ions are provided at a concentration of between about 22 mM to 50 mM. The multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$.

In any such further process, the conditions suitable for performing the reaction may further comprise providing ATP to the IDR-macromolecule or IDR-polypeptide in the in vitro reaction system, thereby further stimulating or enhancing molecules necessary for the performance of the reaction to co-localise with the IDR-polypeptide within the plurality of phase-separated aqueous compartments and thereby further increasing the efficiency of the biochemical reaction in the system, wherein ATP is provided in the system at a concentration of 1 mM to 3.5 mM, optionally 1 mM to 2 mM, preferably 1 mM.

The invention also provides the use of multivalent metal ions in stimulating or enhancing liquid-liquid demixing in a solution, said demixing being mediated by any one of the above-described IDR-macromolecules or any one of the above-described IDR-polypeptides. The invention also provides the use of multivalent metal ions in stimulating or enhancing in an aqueous in vitro reaction system liquid-liquid demixing caused by an IDR-macromolecule or an IDR-polypeptide which has been introduced into the system, wherein said IDR-macromolecule or IDR-polypeptide is any one of the above-described IDR-macromolecules or any one of the above-described IDR-polypeptides. In any such use, said liquid-liquid demixing may result in the formation of a plurality of phase-separated aqueous compartments caused by the IDR-macromolecule or IDR-polypeptide, preferably a plurality of detectable phase-separated aqueous particles in the solution. In any such use, the multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$. In any such use, the multivalent metal ions may engage in aromatic cation-pi interactions with amino acid residues in the one or more functional IDR amino acid sequences, thereby promoting liquid-liquid demixing.

In any such use, the conditions suitable for performing the reaction may further comprise providing ATP to the IDR-macromolecule or the IDR-polypeptide in the in vitro reaction system, thereby further simulating or enhancing the liquid-liquid demixing and the formation of the plurality of phase-separated aqueous compartments caused by the IDR-macromolecule or the IDR-polypeptide and thereby further increasing the efficiency of the biochemical reaction in the system, wherein ATP is provided in the system at a concentration of 1 mM to 3.5 mM, optionally 1 mM to 2 mM, preferably 1 mM.

In any such use, the conditions suitable for performing the reaction may further comprise providing multivalent metal ions to the IDR-polypeptide thereby further stimulating or enhancing molecules necessary for the performance of the reaction to co-localise with the IDR-macromolecule or the IDR-polypeptide within the plurality of phase-separated aqueous compartments thereby further increasing the efficiency of the biochemical reaction in the system; optionally wherein the multivalent metal ions are provided at a concentration of about 22 mM or more, preferably wherein the multivalent metal ions are provided at a concentration of between about 22 mM to 50 mM. The multivalent metal ions may be divalent metal ions, optionally $Mg^{2+}$, $Mn^{2+}$, $Ca^{2+}$, $Co^{2+}$ or $Ni^{2+}$, preferably $Mg^{2+}$, $Mn^{2+}$ or $Ca^{2+}$, more preferably $Mg^{2+}$.

In any such use, the conditions suitable for performing the reaction may further comprise providing ATP to the IDR-macromolecule or IDR-polypeptide in the in vitro reaction system, thereby further stimulating or enhancing molecules necessary for the performance of the reaction to co-localise with the IDR-polypeptide within the plurality of phase-separated aqueous compartments and thereby further increasing the efficiency of the biochemical reaction in the system, wherein ATP is provided in the system at a concentration of 1 mM to 3.5 mM, optionally 1 mM to 2 mM, preferably 1 mM.

The invention also provides any one of the above-described non-naturally occurring IDR-macromolecules or any one of the above-described IDR-polypeptides for use in therapy, for use as a medicament, for use as a pharmaceutical, for use in a diagnostic method or for use as a diagnostic agent.

The invention also provides a process for making any one of the above-described non-naturally occurring IDR-macromolecules or any one of the above-described IDR-polypeptides, the process comprising providing a macromolecule, optionally a polypeptide, and tagging the macromolecule or polypeptide with one or more functional intrinsically disordered region polypeptide sequences. Said tagging may be performed by any means described and defined herein. Said one or more functional intrinsically disordered region polypeptide sequences may be any of the same as described and defined herein. Said macromolecule or polypeptide may be any suitable macromolecule or polypeptide, including any macromolecule or polypeptide described and defined herein.

Any one of the above-described IDR-macromolecules or IDR-polypeptides may increase the efficiency of the biochemical reaction. Increasing the efficiency of the biochemical reaction may comprise increasing the efficiency of the reaction using the IDR-macromolecule or the IDR-polypeptide compared to the efficiency of the reaction obtained by performing the reaction under the same conditions but wherein the relevant macromolecule or the relevant polypeptide does not comprise or has not been tagged with one or more functional intrinsically disordered region polypeptide sequences, optionally wherein the reaction is performed in the absence of an exogenously added crowding agent.

Any one of the above-described IDR-macromolecules or IDR-polypeptides may increase the efficiency of a biochemical reaction, wherein the reaction in a recombinase polymerase amplification (RPA) reaction. Increasing the efficiency or performance of an RPA biochemical reaction may comprise increasing the amount of amplified product obtained in the RPA reaction using the IDR-polypeptide compared to the amount of amplified product obtained by performing the reaction under the same conditions but wherein the relevant polypeptide does not comprise or has not been tagged with one or more functional intrinsically disordered region polypeptide sequences, optionally wherein the RPA reaction is performed in the absence of an exogenously added crowding agent.

The invention also provides a method for determining the nucleotide sequence of one or more target polynucleotide molecules, said method comprising the steps of:
(i) performing an above-described process to amplify the one or more target polynucleotide molecules thereby obtaining a population comprising a plurality of copies of the one or more target polynucleotide molecules; and
(ii) performing one or more nucleic acid sequencing reactions on the population comprising the plurality of copies of the target polynucleotide molecules,
preferably wherein the method is performed in a solid phase reaction system which comprises a surface.

The invention also provides the use of any one of the above-described IDR-macromolecules or any one of the above-described IDR-polypeptides in a method for determining the nucleotide sequence of one or more target polynucleotide molecules, preferably wherein the method is as described above.

The invention also provides a polypeptide or an isolated polypeptide which comprises or consists of the amino acid sequence of any one of SEQ ID NOs 1 to 43, or which comprises or consists of a functional variant amino acid sequence of any one of SEQ ID NOs 1 to 43, e.g. which has 80% or more identity to any one of SEQ ID NOs 1 to 43. Any such polypeptide can be attached to/tagged to a macromolecule or a polypeptide to form an IDR-tagged macromolecule or an IDR-tagged polypeptide as described further herein. The macromolecule or polypeptide which is tagged may be a macromolecule or polypeptide required for the performance of a biochemical reaction in an aqueous reaction system. When maintained within the aqueous reaction system under conditions for performing the biochemcical reaction, any such IDR-tagged macromolecule or IDR-tagged polypeptide can cause liquid-liquid demixing caused by the amino acid sequence of any one of SEQ ID NOs 1 to 43 or any functional variant thereof and the formation of a plurality of phase-separated aqueous compartments, preferably a plurality of detectable phase-separated aqueous particles, in the system thereby increasing the efficiency of the biochemical reaction in the system. When maintained within the aqueous reaction system under conditions for performing the biochemcical reaction, any such IDR-tagged macromolecule or IDR-tagged polypeptide causes molecules necessary for the performance of the reaction to co-localise with the IDR-macromolecule or the IDR-polypeptide within the plurality of phase-separated aqueous compartments, thereby increasing the efficiency of the biochemical reaction in the system.

The aqueous reaction system may be an aqueous in vitro reaction system.

The invention also provides an isolated nucleic acid molecule comprising a nucleic acid sequence encoding a polypeptide which comprises or consists of the amino acid sequence of any one of SEQ ID NOs 1 to 43, or which comprises or consists of a functional variant amino acid sequence of SEQ ID NOs 1 to 43, e.g. which has 80% or more identity to any one of SEQ ID NOs 1 to 43.

The invention also provides the use of an IDR moiety, which is a polypeptide which comprises or consists of one or more functional intrinsically disordered regions (IDRs), in producing an IDR-tagged macromolecule or IDR-tagged polypeptide wherein the IDR moiety is attached to/tagged to a macromolecule or a polypeptide; wherein the macromolecule or polypeptide which is tagged is a macromolecule or polypeptide required for the performance of a biochemical reaction in an aqueous reaction system, and wherein when maintained within the aqueous reaction system under conditions for performing the biochemcical reaction, the IDR-tagged macromolecule or IDR-tagged polypeptide causes liquid-liquid demixing caused by the IDR moiety and causes the formation of a plurality of phase-separated aqueous compartments, preferably a plurality of detectable phase-separated aqueous particles, in the system thereby increasing the efficiency of the biochemical reaction in the system. When maintained within the aqueous reaction system under conditions for performing the biochemcical reaction, any such IDR-tagged macromolecule or IDR-tagged polypeptide causes molecules necessary for the performance of the reaction to co-localise with the IDR-tagged macromolecule or the IDR-tagged polypeptide within the plurality of phase-separated aqueous compartments, thereby increasing the efficiency of the biochemical reaction in the system.

Preferably, the IDR moiety is attached to/tagged to a polypeptide, thereby producing an IDR-tagged polypeptide, preferably produced as a recombinant genetic fusion protein.

Preferably, the IDR moiety is a polypeptide which comprises or consists of the amino acid sequence of any one of SEQ ID NOs 1 to 43, or a polypeptide which comprises or consists of a functional variant amino acid sequence of any one of SEQ ID NOs 1 to 43, e.g. which has 80% or more identity to any one of SEQ ID NOs 1 to 43.

Any of the above-described IDR-tagged macromolecules or IDR-tagged polypeptides may be defined as non-naturally occurring, artificial or genetically engineered macromolecules or polypeptides.

Any of the above-described IDR-tagged macromolecules or IDR-tagged polypeptides may further possess the characteristic features of any one or more of the IDR-macromolecules or IDR-polypeptides described and defined herein.

The aqueous reaction system may be an aqueous in vitro reaction system.

The invention further provides an IDR-tagged macromolecule or an IDR-tagged polypeptide obtained in accordance with any of the above-described uses.

The invention also provides a method for producing an IDR-tagged macromolecule or an IDR-tagged polypeptide comprising providing a macromolecule or a polypeptide and attaching/tagging an IDR moiety thereto, wherein the IDR moiety is a polypeptide which comprises or consists of one or more functional intrinsically disordered regions (IDRs); wherein the macromolecule or polypeptide which is tagged is a macromolecule or polypeptide required for the performance of a biochemical reaction in an aqueous reaction system, and wherein when maintained within the aqueous reaction system under conditions for performing the biochemcical reaction, the IDR-tagged macromolecule or IDR-tagged polypeptide causes liquid-liquid demixing caused by the IDR moiety and causes the formation of a plurality of phase-separated aqueous compartments, preferably a plurality of detectable phase-separated aqueous particles, in the system thereby increasing the efficiency of the biochemical reaction in the system. When maintained within the aqueous reaction system under conditions for performing the biochemcical reaction, any such IDR-tagged macromolecule or IDR-tagged polypeptide causes molecules necessary for the performance of the reaction to co-localise with the IDR-tagged macromolecule or the IDR-tagged polypeptide within the plurality of phase-separated aqueous compartments, thereby increasing the efficiency of the biochemical reaction in the system.

Preferably, the method comprises providing a polypeptide and attaching/tagging an IDR moiety thereto to produce an IDR-tagged polypeptide, preferably produced as a recombinant genetic fusion protein.

Preferably, the IDR moiety is a polypeptide which comprises or consists of the amino acid sequence of any one of SEQ ID NOs 1 to 43, or a polypeptide which comprises or consists of a functional variant amino acid sequence of any one of SEQ ID NOs 1 to 43, e.g. which has 80% or more identity to any one of SEQ ID NOs 1 to 43.

Any of the above-described IDR-tagged macromolecules or IDR-tagged polypeptides may be defined as non-naturally occurring, artificial or genetically engineered macromolecules or polypeptides.

Any of the above-described IDR-tagged macromolecules or IDR-tagged polypeptides may further possess the characteristic features of any one or more of the IDR-macromolecules or IDR-polypeptides described and defined herein.

The aqueous reaction system may be an aqueous in vitro reaction system.

The invention further provides an IDR-tagged macromolecule or an IDR-tagged polypeptide obtained by any of the above-described methods.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
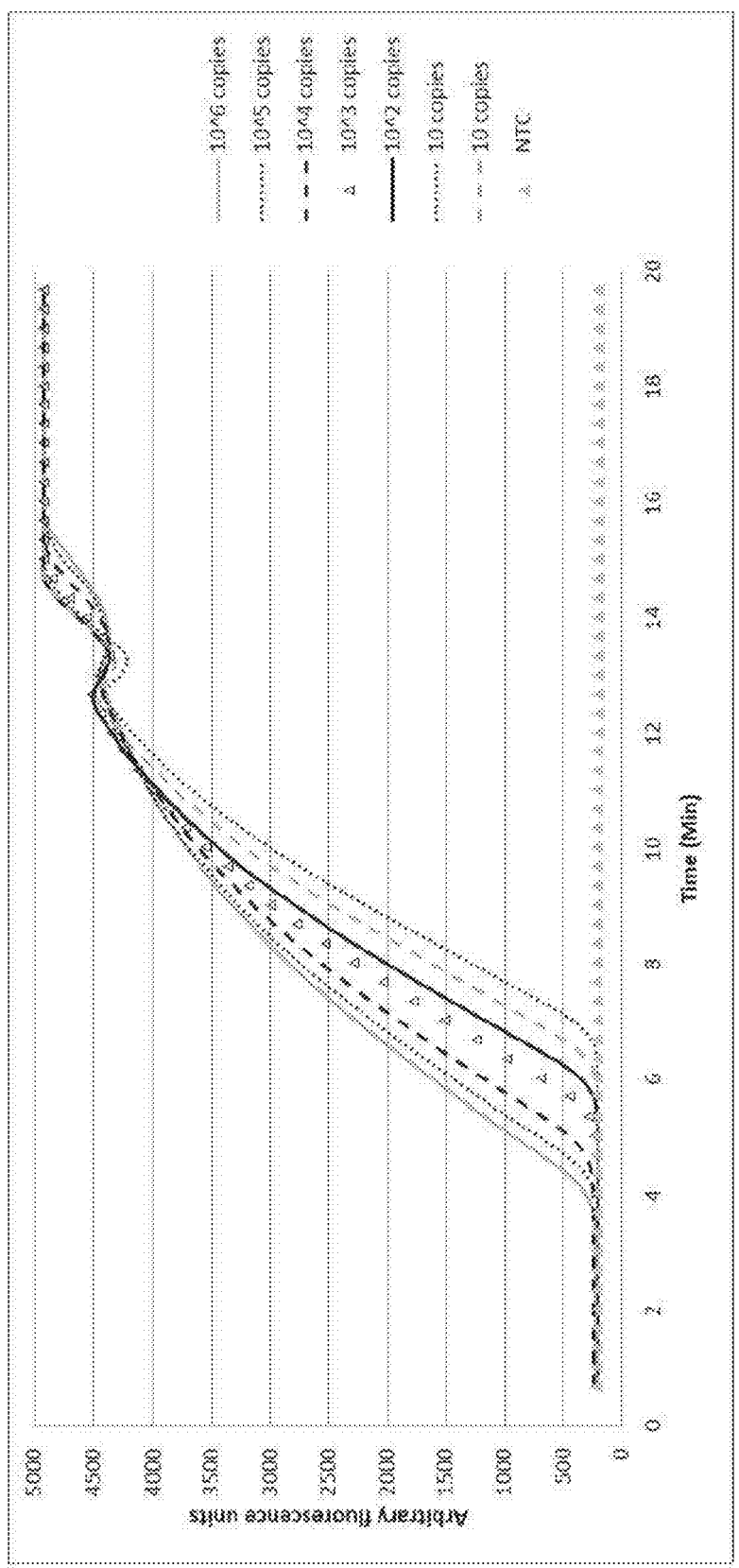
FIG. 1 shows real-time recombinase polymerase amplification traces using an IDR-tagged Gp32 fusion protein (Gp32-HIS2) at varying template nucleic acid concentrations.

Recombinase polymerase amplification is a technique for amplifying nucleic acid molecules. The system utilises, inter alia, a recombinase enzyme and preferably a recombinase loading protein. These protein components form a complex with amplification primers. Following binding to the target nucleic acid molecule to be amplified, the complex "scans" the target nucleic acid molecule and "searches" for regions of complementarity between the target and primer sequences. Once a complementary region is found the complex facilitates the binding of the primer to the target sequence. A polymerase enzyme can then extend the primer to generate a copy of the target sequence. The use of the recombinase complex provides a key difference over other nucleic acid amplification methods such as PCR. In RPA there is no requirement for melting and annealing steps driven by thermal cycling, as the recombinase complex provides an entirely enzymatic-based solution to the issue of primer binding. RPA is thus an isothermal technique. The absence of a requirement for extreme thermal cycling means that RPA has many obvious advantages over techniques such as PCR.

A well-documented requirement in RPA methods is the presence of a "crowding agent", also commonly referred to in the technical field as a "macromolecular crowding agent". These agents are well known in the technical field and have an art-understood meaning. Crowding agents are discussed in more detail herein. One of the most commonly used crowding agents in RPA methods is polyethylene glycol (PEG), although other crowding agents can be used. Prior to the present invention the use of a crowding agent was considered to be an essential requirement in RPA methods.

The present inventors have surprisingly discovered that it is possible to bypass the hitherto-perceived critical requirement for a crowding agent in RPA methods. The present invention is founded on this discovery.

The inventors have surprisingly discovered that by "tagging" a macromolecule, such as a protein component required in RPA methods, with amino acid sequences which comprise or consist of one or more functional "intrinsically disordered regions" (IDRs), the IDR amino acid sequence tag is capable of facilitating efficient RPA in the complete absence of a crowding agent. As such, efficient amplification can be achieved in an RPA system without reliance on a crowding agent, thus reducing the complexity of RPA reactions.

The inventors have also surprisingly discovered that the efficiency of amplification in RPA methods involving an IDR-tagged macromolecular component in the absence of a crowding agent can be correlated with the functional capability of the IDR amino acid tag sequence to promote liquid-liquid demixing leading to phase separation in the biochemical reaction system. Phase separation may be assessed by the formation in the biochemical reaction milieu of phase-separated aqueous compartments, particularly spherical-like aqueous globular foci or phase-separated aqueous particles which are amenable to detection by standard methods, including by microscopic observation, as described further herein.

Furthermore, the inventors have also surprisingly discovered that the provision of an IDR-tagged macromolecular component and a crowding agent can provide additive and even synergistic effects with respect to the efficiency of amplification in RPA methods.

Yet further, the inventors have surprisingly discovered that the efficiency of amplification in RPA methods involving an IDR amino acid-tagged macromolecular component in the absence of a crowding agent can be correlated with the concentration of multivalent metal cations introduced into the biochemical reaction milieu. Thus multivalent metal cations can further stimulate or enhance liquid-liquid demixing caused by IDR-macromolecules or IDR-polypeptides and thereby further increase reaction efficiency.

The inventors have also surprisingly discovered that certain concentrations of ATP, as described further herein, can further stimulate or enhance liquid-liquid demixing caused by IDR-macromolecules or IDR-polypeptides and thereby further increase reaction efficiency.

Based on these surprising discoveries the invention provides methods and reagents which increase the efficiency of enzymatic-based in vitro biochemical reactions, including RPA reactions, as further described herein.

The IDR amino acid sequences and IDR reagents described and defined herein have broad applicability as useful reagents to be applied to any suitable macromolecular component of a biochemical reaction, such as a polypeptide, thereby promoting liquid-liquid demixing and including promoting phase separation in the biochemical reaction milieu without reliance on macromolecular crowding agents, particularly when the IDR amino acid sequences are used in concert with a multivalent metal cation. The invention further embraces the use of a multivalent metal cation, such as a divalent metal cation, or any functional equivalent thereof, in promoting IDR amino acid sequence-mediated phase separation in the biochemical reaction milieu, without reliance on macromolecular crowding agents.

The invention thus provides IDR-based processes, macromolecules, polypeptides, nucleic acids, vectors, host cells and uses, as described and defined further herein.

Elements of the invention are described in turn below.

Biochemical Reactions

As explained above, the inventors have surprisingly discovered that it is possible to bypass the requirement for a crowding agent, a previously-considered essential component of RPA and other reactions. As described in detail herein, this may be achieved by attaching/tethering/tagging an amino acid sequence comprising one or more functional intrinsically disordered regions (JDRs) to a protein component required in the RPA reaction. The inventors have also surprisingly shown that a functional intrinsically disordered region attached to a ligase enzyme is capable of increasing the efficiency of a ligase reaction. The inventors have shown that the degree of phase separation induced by the IDR amino acid sequence can be correlated with the efficiency of the reaction, e.g. amplification, in the absence of a crowding agent, and can be enhanced with a multivalent metal cation. Based on these surprising observations it is plausibly expected that such IDR amino acid sequences associated with a macromolecule or protein component of a biochemical reaction will improve the efficiency of the reaction in the in vitro or in vivo biochemical reaction environment, particularly in the absence of an added/exogenous crowding agent.

Accordingly, the invention embraces the use of any of the IDR amino acid sequences described and defined herein to be applied to any suitable macromolecular or polypeptide component of an in vitro or in vivo biochemical reaction, thus providing IDR reagents capable of promoting liquid-liquid demixing in the biochemical reaction milieu and increasing the efficiency of the biochemical reaction. Such liquid-liquid demixing in the biochemical reaction milieu may result in phase separation the biochemical reaction milieu. Such liquid-liquid demixing in the biochemical reaction milieu may result in phase separation leading to, causing or promoting the formation of phase-separated aqueous compartments, including detectable phase-separated aqueous particles in the biochemical reaction milieu, as described further herein. Such IDR reagents, or IDR-based reagents, as described and defined further herein may be referred to interchangeably to describe any one or more of an IDR-macromolecule or IDR-tagged macromolecule, or an IDR-polypeptide or IDR-tagged polypeptide.

In any one of the methods, processes and uses, or in any one of the non-naturally occurring IDR-macromolecules, IDR-fusion macromolecules or isolated nucleic acid molecules encoding the same, recombinant polynucleotide expression vectors or host cells described and defined herein, increasing or enhancing the efficiency or performance of a biochemical reaction may comprise increasing the efficiency of the reaction using any one or more of the IDR-based macromolecules or polypeptides described herein compared to the efficiency obtained by performing the reaction under the same conditions but wherein the relevant macromolecule or polypeptide does not comprise or has not been tagged with one or more functional intrinsically disordered region polypeptide sequences, optionally wherein the reaction is performed in the absence of an exogenously added crowding agent.

Increasing or enhancing the efficiency or performance of a biochemical reaction is to be understood according to generally accepted concepts. For example, reaction efficiency in an RPA reaction, or in any other nucleic acid amplification reaction, may be understood as providing an equivalent total population of amplicons using comparatively less starting target nucleic acid, or providing a comparatively faster time to detection or a comparatively faster rate of amplification using the same amount of starting target nucleic acid.

Increasing or enhancing the efficiency or performance of an RPA biochemical reaction may comprise increasing the amount of amplified product obtained in the RPA reaction using any one or more of the IDR-based macromolecules or polypeptides described herein compared to the amount of amplified product obtained by performing the reaction under the same conditions but wherein the relevant macromolecule or polypeptide does not comprise or has not been tagged with one or more functional intrinsically disordered region polypeptide sequences, and optionally wherein the reaction is performed in the absence of an exogenously added crowding agent.

Increasing the efficiency of a biochemical reaction in a reaction system, such as an in vitro reaction system, may comprise increasing any measurable parameter of the reaction in the system over a specified time period, such as the rate of the reaction over a time period, the amount of a substrate consumed over a time period, the amount of a product produced over a time period etc.

Increasing the efficiency of a biochemical reaction in a reaction system, such as an in vitro reaction system, may comprise increasing the parameter of the reaction within detectable phase-separated compartments, such as detectable phase-separated aqueous particles. This can, for example, be inferred indirectly by measuring the parameter of the reaction and correlating the increase with formation of detectable phase-separated aqueous particles and/or the detectable co-localisation of reaction molecules into detectable phase-separated aqueous particles.

Described herein are straightforward bioinformatics methods and phase separation assays which can be used to establish whether any IDR amino acid sequence is capable of functioning in the required manner of promoting liquid-liquid demixing and phase separation in the desired biochemical reaction milieu when used with a given a macromolecule or protein and included in the desired in vitro biochemical reaction environment. Moreover the suitability of any given co-factor, in particular a multivalent, e.g. divalent, metal cation, may be established in these assays in a very straightforward way.

Accordingly, the invention provides IDR reagents as described and defined herein that may usefully be applied in any given desired in vitro or in vivo biochemical reaction environment.

Any of the IDR amino acid sequences as described and defined herein may be used with any macromolecular or protein component required for the performance of an in vitro or in vivo biochemical reaction, such as any of the reactions described herein.

Any of the IDR amino acid sequences as described and defined herein may be used with any macromolecular or protein component required for the performance of a nucleic acid synthesis reaction.

Any of the IDR amino acid sequences as described and defined herein may be used with any macromolecular or protein component required for the performance of a nucleic acid synthesis reaction wherein a polymerase is used to synthesize a new nucleic acid molecule by extending a primer nucleic acid molecule.

Any of the IDR amino acid sequences as described and defined herein may be used with any macromolecular or protein component required for the performance of a nucleic acid amplification reaction. The nucleic acid amplification reaction may be a reaction which involves thermal cycling. The nucleic acid amplification reaction may be an isothermal amplification reaction. The nucleic acid amplification reaction may be polymerase chain reaction (PCR), polymerase spiral reaction (PSR), loop mediated isothermal amplification (LAMP), nucleic acid sequence based amplification (NASBA), self-sustained sequence replication (3SR), rolling circle amplification (RCA), strand displacement amplification (SDA), multiple displacement amplification (MDA), ligase chain reaction (LCR), helicase dependent amplification (HDA), ramification amplification method (RAM), recombinase polymerase amplification (RPA), transcription-mediated amplification (TMA) or nicking enzyme amplification reaction (NEAR).

Any of the IDR amino acid sequences as described and defined herein may be used with any macromolecular or protein component required for the performance of a gene editing reaction.

Any of the IDR amino acid sequences as described and defined herein may be used with any macromolecular or protein component required for the performance of a CRISPR reaction.

Any of the IDR amino acid sequences as described and defined herein may be used with any macromolecular or protein component required for the performance of a prime editing gene editing reaction, wherein a CRISPR enzyme, such as a Cas enzyme, e.g. Cas9, is provided in a complex with at least a reverse transcriptase enzyme, optionally further with a prime editing guide RNA (pegRNA), and wherein any component of the prime editing complex may be provided tagged with one or more functional intrinsically disordered region (IDR) polypeptide sequences, e.g. wherein the CRISPR enzyme is tagged with the one or more functional IDR polypeptide sequences or wherein the reverse transcriptase enzyme is tagged with the one or more functional IDR polypeptide sequences.

Any of the IDR amino acid sequences as described and defined herein may be used with any macromolecular or protein component required for the performance of a ligation reaction.

Any of the IDR amino acid sequences as described and defined herein may be used with any macromolecular or protein component required for the performance of an exonuclease reaction.

Any of the IDR amino acid sequences as described and defined herein may be used with any macromolecular or protein component required for the performance of an endonuclease reaction, a transcription reaction, a DNA methylation reaction, a DNA glycosylation reaction, an antibody-antigen reaction, a drug-target reaction.

Any of the IDR amino acid sequences as described and defined herein may be used with any macromolecular or protein component required for the performance of a reaction involving protein:protein interactions.

A process for performing an in vitro biochemical reaction as used herein is intended to embrace biochemical reactions performed directly in solution in a reaction vessel, such as an RPA reaction as described further herein.

A process for performing an in vitro biochemical reaction as used herein also includes biochemical reactions performed within cells in culture, such as by expressing an IDR reagent as defined herein in a cultured host cell to increase the efficiency of a biochemical reaction within the cultured host cell.

A process for performing an in vitro biochemical reaction as used herein includes a biochemical reaction performed within a host cell in culture by introducing an IDR reagent as defined herein into a cultured host cell or expressing an IDR reagent as defined herein in a cultured host cell to increase the efficiency of a biochemical reaction within the cultured host cell, wherein the biochemical reaction is any reaction which leads to the manipulation of a nucleic acid molecule within the cultured host cell, or which leads to the alteration of a nucleic acid molecule within the cultured host cell, such as a change in the structure of a nucleic acid molecule, such as a change in the nucleotide sequence of a nucleic acid molecule.

A process for performing an in vitro biochemical reaction as used herein includes a biochemical reaction performed within cells in culture by introducing an IDR reagent as defined herein into a cultured host cell or expressing an IDR reagent as defined herein in a cultured host cell to increase the efficiency of a biochemical reaction within the cultured host cell, wherein the biochemical reaction is any reaction which leads to the synthesis of a nucleic acid molecule in the cultured host cell.

A process for performing an in vitro biochemical reaction as used herein includes biochemical reactions performed within cells in culture by introducing an IDR reagent as defined herein into a cultured host cell or expressing an IDR reagent as defined herein in a cultured host cell to increase the efficiency of a biochemical reaction within the cultured host cell, wherein the biochemical reaction is any reaction which leads to the expression of a polypeptide from a nucleic acid molecule.

A process for performing an in vitro biochemical reaction as used herein includes biochemical reactions performed within cells in culture by introducing an IDR reagent as defined herein into a cultured host cell or expressing an IDR reagent as defined herein in a cultured host cell to increase the efficiency of a biochemical reaction within the cultured host cell, wherein the biochemical reaction is any reaction which leads to the editing of a nucleic acid sequence within the cultured host cell (e.g. wherein the IDR-polypeptide is a CRISPR polypeptide, such as a Cas polypeptide, including a Cas9 polypeptide, or wherein the IDR-polypeptide is a polypeptide in complex with a CRISPR polypeptide, such as wherein the IDR-polypeptide is a reverse transcriptase enzyme), the cleavage of a nucleic acid within the cultured host cell and homologous recombination of nucleic acids within the cultured host cell.

A process for performing an in vitro biochemical reaction as used herein includes biochemical reactions performed within cells in culture by introducing an IDR reagent as defined herein into a cultured host cell or expressing an IDR reagent as defined herein in a cultured host cell to increase the efficiency of a biochemical reaction within the cultured host cell, wherein the biochemical reaction is a metabolic reaction within the cultured host cell to produce one or more biological products of interest within the cultured host cell, or to produce one or more biological products of interest which are secreted from the cultured host cell or otherwise released from the cultured host cell into the culture media.

The invention is also intended to embrace biochemical reactions performed ex vivo, for example by expressing the IDR reagents defined herein in cells of e.g. a tissue culture or any other suitable complex biological system developed external to the body. Accordingly, any reference to a process for performing a biochemical reaction in an aqueous in vitro reaction system as used herein using any of the IDR reagents as defined herein may alternatively be defined as a process for performing a biochemical reaction in an aqueous ex vivo reaction system using any of the IDR reagents as defined herein.

The invention also provides processes, reagents and methods for increasing the efficiency of a biochemical reaction in vivo. Accordingly, any reference to a process for performing a biochemical reaction in an aqueous in vitro reaction system as used herein using any of the IDR reagents as defined herein may alternatively be defined as a process for performing a biochemical reaction in an aqueous in vivo reaction system using any of the IDR reagents as defined herein.

The invention provides any non-naturally occurring IDR-macromolecule or IDR-polypeptide described or defined herein for use in therapy, for use as a therapeutic, for use as a medicament, for use as a pharmaceutical agent or for use as a diagnostic agent.

The invention provides any non-naturally occurring IDR-macromolecule or IDR-polypeptide described or defined herein for use in a method for the treatment of the human or animal body by therapy.

The invention provides any non-naturally occurring IDR-macromolecule or IDR-polypeptide described or defined herein for use in a diagnostic method practised on the human or animal body.

The invention provides any non-naturally occurring IDR-macromolecule or IDR-polypeptide described or defined herein for use in the manufacture of a medicament for the treatment of the human or animal body by therapy.

The invention provides any non-naturally occurring IDR-macromolecule or IDR-polypeptide described or defined herein for use in the manufacture of a diagnostic agent for a diagnostic method practised on the human or animal body.

The invention provides a method of treatment of a human or animal comprising administering a therapeutically effective amount of any non-naturally occurring IDR-macromolecule or IDR-polypeptide described or defined herein to a human or animal in need thereof.

In any one of the above-described processes, reagents and methods for increasing the efficiency of a biochemical reaction, the non-naturally occurring IDR-macromolecule or IDR-polypeptide is capable of promoting liquid-liquid demixing. Said liquid-liquid demixing may be capable of promoting the formation of phase-separated aqueous compartments in solution, including detectable phase-separated aqueous particles in solution. Said liquid-liquid demixing or said formation of detectable phase-separated compartments or particles thereby increases the efficiency of the biochemical reaction caused by the IDR-macromolecule or the IDR-polypeptide.

A process for performing an in vitro biochemical reaction as used herein includes any biochemical reaction performed in vitro in solution in a reaction vessel or within a host cell in culture by introducing an IDR reagent as defined herein into the solution or introducing or expressing an IDR reagent in a cultured host cell to promote liquid-liquid demixing in the solution or in the cultured host cell. In any such biochemical reaction, the liquid-liquid demixing in the solution or in the cultured host cell promotes phase separation in the solution or in the cultured host cell, as described and defined herein.

Any such biochemical reaction may be performed in order to assess the efficacy of any IDR amino acid sequence as described and defined herein in promoting liquid-liquid demixing in the solution or in the cultured host cell and/or in promoting phase separation in the solution or in the cultured host cell.

Any such biochemical reaction may be performed in order to assess the efficacy of a test agent, such as a drug, a polypeptide or any other molecule, in stimulating or enhancing liquid-liquid demixing mediated by the IDR amino acid sequence in the solution or in the cultured host cell and/or in stimulating or enhancing phase separation mediated by the IDR amino acid sequence in the solution or in the cultured host cell, preferably wherein the test agent interacts with the IDR amino acid sequence.

Any such biochemical reaction may be performed in order to assess the efficacy of a test agent, such as a drug, a polypeptide or any other molecule, in inhibiting liquid-liquid demixing mediated by the IDR amino acid sequence in the solution or in the cultured host cell and/or in inhibiting phase separation mediated by the IDR amino acid sequence in the solution or in the cultured host cell, preferably wherein the test agent interacts with the IDR amino acid sequence.

Any of the processes described herein for performing an in vitro, in vivo or ex vivo biochemical reaction may exclude a process for cloning a human being.

Any of the processes described herein for performing an in vitro, in vivo or ex vivo biochemical reaction may exclude a process for modifying the germ line genetic identity of a human being.

Any of the processes described herein for performing an in vitro, in vivo or ex vivo biochemical reaction may exclude a process involving the use of a human embryo, or the use of a totipotent human cell.

Any host cell described herein may exclude a human embryo, or a totipotent human cell, or a human germ line cell.

Whilst embracing in vivo use in some aspects, the invention embraces the exclusion of in vivo use in some aspects. Accordingly, any of the processes, uses or methods etc. described herein for performing a biochemical reaction in an aqueous reaction system may exclude an in vivo aqueous reaction system.

Whilst embracing ex vivo use in some aspects, the invention embraces the exclusion of ex vivo use in some aspects. Accordingly, any of the processes, uses or methods etc. described herein for performing a biochemical reaction in an aqueous reaction system may exclude an ex vivo aqueous reaction system.

In any of the methods, processes, uses or IDR reagents described herein, the efficiency of the reaction in the system may be increased by the IDR-macromolecule or the IDR-polypeptide compared to the efficiency of the reaction in the system following the introduction of the at least one macromolecule or polypeptide under the same reaction conditions except that the at least one macromolecule or polypeptide does not comprise one or more functional intrinsically disordered regions (IDRs).

In any of the methods, processes, uses or IDR reagents described herein involving at least one macromolecule or at least one polypeptide tagged with an amino acid sequence comprising or consisting of one or more functional intrinsically disordered regions (IDRs) (IDR-tagged macromolecule or IDR-tagged polypeptide) the efficiency of the reaction in the system may be increased by the IDR-tagged macromolecule or IDR-tagged polypeptide compared to the efficiency of the reaction in the system following the introduction of the at least one macromolecule or polypeptide under the same reaction conditions except that the at least one macromolecule or polypeptide has not been tagged with the amino acid sequence comprising or consisting of the one or more functional IDRs.

Accordingly, whether an IDR-macromolecule or IDR-polypeptide, or an IDR-tagged macromolecule or IDR-tagged polypeptide, is capable of increasing the efficiency of the reaction in the system can be established very simply by comparing the reaction efficiency of the macromolecule or polypeptide with or without the one or more functional IDRs. The skilled person is able to carry out simple comparative tests to establish the relevant functional capability. Exemplary test assays are described further herein.

Similarly, whether an IDR-macromolecule or IDR-polypeptide, or an IDR-tagged macromolecule or IDR-tagged polypeptide, is capable of causing molecules necessary for the performance of the reaction to co-localise with the IDR-macromolecule or the IDR-polypeptide, or with the IDR-tagged macromolecule or IDR-tagged polypeptide, within the plurality of phase-separated aqueous compartments, or to further stimulate or enhance co-localisation of molecules necessary for the performance of the reaction within the plurality of phase-separated aqueous compartments, thereby increasing the efficiency of the biochemical reaction in the system, can also be established very simply by comparing co-localisation with or without the one or more functional IDRs. Again, the skilled person is able to carry out simple comparative tests to establish the relevant functional capability. Exemplary test assays are described further herein.

Similarly whether providing multivalent metal ions to an IDR-macromolecule or an IDR-polypeptide, or to an IDR-tagged macromolecule or IDR-tagged polypeptide thereby further stimulating or enhancing liquid-liquid demixing and the formation of the plurality of phase-separated aqueous compartments and thereby further increasing the efficiency of the biochemical reaction in the system can also be established very simply by comparing liquid-liquid demixing with or without providing multivalent metal ions. Again, the skilled person is able to carry out simple comparative tests to establish the relevant functional capability. Exemplary test assays are described further herein.

Similarly whether providing ATP to an IDR-macromolecule or an IDR-polypeptide, or to an IDR-tagged macromolecule or IDR-tagged polypeptide may further simulate or enhance liquid-liquid demixing and the formation of the plurality of phase-separated aqueous compartments and thereby further increase the efficiency of the biochemical reaction in the system can also be established very simply by comparing liquid-liquid demixing with or without providing ATP. Whether providing ATP to an IDR-macromolecule or an IDR-polypeptide, or to an IDR-tagged macromolecule or IDR-tagged polypeptide to further stimulate or enhance co-localisation of molecules necessary for the performance of the reaction within the plurality of phase-separated aqueous compartments, thereby increasing the efficiency of the biochemical reaction in the system, can also be established very simply by comparing co-localisation with or without providing ATP. Again, the skilled person is able to carry out simple comparative tests to establish the relevant functional capability. Exemplary test assays are described further herein.

Assays are described herein to establish the capability to cause liquid-liquid demixing by reference to the capability to cause the formation of phase-separated aqueous particles (see e.g. "phase separation assay method" as described herein). The same assay can be used to establish the capability to cause co-localisation of molecules necessary for the performance of the reaction within the phase-separated aqueous compartments (particles). Assays are described herein to establish the capability to increase the efficiency of a reaction by reference to the capability to increase the efficiency of an RPA method (see e.g. "RPA assay method" as described herein). Such an assay can be used to evaluate the capability of an amino acid sequence consisting of or comprising one or more functional intrinsically disordered regions (IDRs) to increase the efficiency of a reaction, and/or to evaluate the capability of divalent metal ions to further increase the efficiency of a reaction and/or to evaluate the capability of ATP to further increase the efficiency of a reaction.

Using simple assays as described herein the skilled person is able to determine an increase in the efficiency of a reaction of 5% or more, the increase in the efficiency of the reaction may be 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more or 100% or more.

Crowding Agent

A crowding agent is typically a high molecular weight macromolecule, such as a protein or a synthetic block polymer. A crowding agent is considered to be essentially biochemically inert, i.e. it does not contribute to a specific interaction or catalysis.

It is widely postulated that a crowding agent exerts an influence on a biological/biochemical system, be it an in vitro or an in vivo system, through the effects of its physical occupation of volume in a solution thus causing steric obstruction and a reduction in available open solvent space.

By this excluded volume mechanism crowding agents appear to increase the effective concentration of other macromolecules, with particular influence on altering dissociation constants and favouring the association of interacting macromolecules such as multiple proteins which come together into specific organised complexes. The size of the crowding effect depends in particular on the molecular mass of the molecules involved, being generally much stronger with larger molecules. Thus, as a general rule, macromolecular crowding is an effect exerted by large molecules on the properties of other large molecules.

Furthermore, crowding agents have been widely described as being capable of facilitating the formation of biological/biochemical systems with preferred phases in which reactants segregate themselves into micron-sized phase-separated particles. This effect arises substantially from the effects of volume exclusion on the dissociation constant of macromolecular complexes which become relatively "confined" due to the inability to readily diffuse into the largely volume-occupied bulk solvent. Additionally and/or alternatively, some crowding agents such as block chain polymers like polyethylene glycol may exhibit kosmotropic character which leads them to exert an overall alteration in the structure of bulk water, typically lowering water density. Such changes in bulk solvent characteristics may also exert complex effects on other macromolecules and their assemblies whose surfaces must interact with water. This in turn may also promote segregation of those other macromolecules into an alternate phase, significantly enriched in the biological components and concomitantly depleted in the crowding agent which principally occupies the bulk solvent phase.

In either scenario, either by simple volume occupation or solvent modification, the effects individually or in combination of crowding agents in stimulating the condensation of macromolecules into phase-distinct condensates appears to operate by a "repulsive" rather than by an "attractive" mechanism from the perspective of the condensate components. In other words, from the perspective of the components that are highly enriched in the condensate the crowding agent acts to create a bulk phase environment that cannot be readily penetrated by diffusion, and/or whose bulk solvent character is modified in a manner that it presents a net enthalpic disadvantage to disperse into. It is in this manner that the effects of high concentrations of crowding agents, typically greater than 1% w/v, are referred to herein in stimulating phase separation by functioning through an "obstructive" or "repulsive" mechanism insofar as the phenomenon arises due to the condensate components being unable to readily disperse as they would in the absence of the crowding agent. However, at the same time, in view of its generally inert properties, the crowding agent has little or no direct debilitating effects on other specific molecules in the system, for example because the crowding agent does not significantly interact with or exert effects on specific molecular side-chains in a direct fashion.

In standard RPA reactions polyethylene glycols (PEGs) can have profound effects on recombination/DNA synthesis. PEGs can influence the number of multiple invasion/extension cycles that occur, for example, when RecA is combined with Gp32. PEGs can stimulate amplification reactions configured in several different ways. PEGs and other similar crowding agents may affect the cooperativity of Gp32 and recombinases, they may affect polymerase processivity and they may affect the hybridisation rate and behaviour of oligonucleotides in solution. The chain length of the polyethylene glycol can influence results. PEGs may also increase the stability of recombinase-loaded filaments and the increased persistence may increase RPA efficacy.

To exert its effects in an in vitro biochemical reaction milieu an added crowding agent is typically present at concentrations at which steric exclusion/confinement effects are predicted to occur, typically above approximately 1% by volume of the reaction, or by weight of the reaction.

In standard RPA reactions a crowding agent is present at concentrations of approximately 1% to 12% by volume of the reaction or by weight of the reaction.

The terms "macromolecular crowding agent" or more simply "crowding agent" are very well recognised and art-understood terms. This is apparent from the literature in which the terms are used extensively. For example Kuznetsova, I., M. et al., (What Macromolecular Crowding Can Do to a Protein, 2014, Int. J. Mol. Sci., 15, pp 23090-23140) provide a review which purports to cover more than 320 papers and is suggested to represent one of the most comprehensive compendia of the current knowledge in the field. The term "crowding agent" is used extensively throughout the text highlighting its ubiquitous use (see also Mixed Macromolecular Crowding: A Protein and Solvent Perspective, Biswas, S. et al., 2018, ACS Omega, 3(4), pp 4316-4330 and Common Crowding Agents Have Only a Small Effect on Protein-Protein Interactions, Phillip Y. et al., 2009, Biophysical Journal, 97 pp 875-885 875).

A compound or macromolecule can be identified as a crowding agent by means known in the art. For example a crowding agent can be identified as such via its experimentally determined and calculated hydrodynamic radius (Kuznetsova et al., supra). A crowding agent can be identified as such via sol-gel glass encapsulation analysis (Kuznetsova et al., supra).

The following compounds are examples of known crowding agents. A synthetic block polymer, a polyethylene glycol (PEG), PEG 1450, PEG 2050, PEG3000, PEG 4600, PEG 6000, PEG 8000, PEG 10000, PEG 20000, PEG 35000, PEG compound molecular weight 15,000 to 20,000 (also known as Carbowax 20M), a dextran, Dextran 6, Dextran 40, Dextran 70, Dextran 670, Dextran sulfate 10, Dextran sulfate 500, a ficoll, Ficoll 70, Ficoll 400, Poly(sodium 4-styrene sulfonate) (PSS), Bovine pancreatic trypsin inhibitor (BPTI), Ribonuclease A, Lysozyme, β-Lactoglobulin, Hemoglobin, Bovine serum albumin (BSA).

In any one of the methods, processes and uses of the present invention, including in any one of the RPA methods, processes and uses of the present invention, the methods, processes and uses may be performed in the absence of a crowding agent.

In any one of the methods, processes and uses of the present invention, including in any one of the RPA methods, processes and uses of the present invention, the methods, processes and uses may be performed in the presence of a crowding agent.

In any one of the methods, processes and uses of the present invention, including in any one of the RPA methods, processes and uses of the present invention, the methods, processes and uses may be performed in the presence of a crowding agent, wherein the crowding agent is provided at a concentration which provides an enhancement of the increase in the efficiency of the biochemical reaction which is provided by the IDR-macromolecule or the IDR-polypeptide.

In any one of the methods, processes and uses of the present invention, including in RPA methods, processes and uses of the present invention, the methods, processes and uses may be performed in the presence of a crowding agent, wherein the crowding agent is provided at a concentration which provides an additive effect on the efficiency of the biochemical reaction which is provided by the IDR-macromolecule or the IDR-polypeptide.

In any one of the methods, processes and uses of the present invention, including in any one of the RPA methods, processes and uses of the present invention, the methods, processes and uses may be performed in the presence of a crowding agent, wherein the crowding agent is provided at a concentration which provides a synergistic effect on the efficiency of the biochemical reaction which is provided by the IDR-macromolecule or the IDR-polypeptide.

In any one of the methods, processes and uses of the present invention, including in any one of the RPA methods, processes and uses of the present invention, the methods, processes and uses may be performed in the presence of a crowding agent, wherein the introduction of the IDR-macromolecule or the IDR-polypeptide into the biochemical reaction system lowers the concentration of crowding agent which would be required to achieve the same increase in the efficiency of the biochemical reaction in the absence of the introduction of the IDR-macromolecule or the IDR-polypeptide into the biochemical reaction system.

In any one of the above-described methods, processes and uses which may be performed in the presence of a crowding agent, the crowding agent may be present at a concentration below that at which its normal biological effects (steric exclusion/confinement effects) occur.

In any one of the above-described methods, processes and uses which may be performed in the presence of a crowding agent, the crowding agent may be present at concentrations below approximately 3% by volume of the reaction or by weight of the reaction, approximately 2% by volume of the reaction or by weight of the reaction, approximately 1% by volume of the reaction or by weight of the reaction or approximately 0.9%, 0.8%, 0.7%, 0.6%, 0.5%, 0.4%, 0.3%, 0.2% or 0.1% by volume of the reaction or by weight of the reaction.

If used in any one of the methods, processes and uses of the invention, including RPA reaction methods, any suitable crowding agent may be used. Examples of suitable crowding agents are provided herein.

Macromolecule or Polypeptide Comprising an Intrinsically Disordered Region (IDR)

The methods, processes and reagents of the present invention involve "IDR-macromolecules", including "IDR-tagged macromolecules", as described herein. The methods, processes and reagents of the present invention involve "IDR-polypeptides", including "IDR-tagged polypeptides", as described herein. Any such IDR-macromolecules, IDR-tagged macromolecules, IDR-polypeptides or IDR-tagged polypeptides may be referred to interchangeably herein as IDR reagents or IDR-based reagents.

An IDR-macromolecule or IDR-polypeptide or an IDR-tagged macromolecule or IDR-tagged polypeptide as used herein is any macromolecule, or polypeptide or protein, which comprises one or more functional intrinsically disordered regions (JDRs).

An IDR-macromolecule or IDR-polypeptide or an IDR-tagged macromolecule or IDR-tagged polypeptide as used herein is any macromolecule, or polypeptide or protein, which comprises an amino acid sequence consisting of or comprising one or more functional intrinsically disordered regions (JDRs).

Accordingly, an IDR-macromolecule or IDR-polypeptide, as referred to herein, may thus refer to: a macromolecule or polypeptide which comprises an amino acid sequence consisting of one or more functional intrinsically disordered regions; or a macromolecule or polypeptide which comprises an amino acid sequence comprising one or more functional intrinsically disordered regions.

In addition, an IDR-macromolecule comprising one or more functional intrinsically disordered regions (JDRs), as referred to herein may be a macromolecule of interest tagged with an amino acid sequence consisting of or comprising one or more functional intrinsically disordered regions (JDRs). Such an IDR-tagged macromolecule is also an IDR reagent as defined herein. An IDR-tagged polypeptide comprising one or more functional intrinsically disordered regions (JDRs), as referred to herein, may be a polypeptide of interest tagged with an amino acid sequence consisting of or comprising one or more functional intrinsically disordered regions (JDRs). Such an IDR-tagged polypeptide is also an IDR reagent as defined herein.

An IDR-tagged macromolecule or IDR-tagged polypeptide, as used herein, is any macromolecule, or polypeptide or protein, which is "tagged" with an amino acid sequence consisting of or comprising one or more functional intrinsically disordered regions (IDRs).

Accordingly, an IDR-tagged macromolecule or IDR-tagged polypeptide, as referred to herein, may thus refer to: a macromolecule or polypeptide which is tagged with an amino acid sequence consisting of one or more functional intrinsically disordered regions; or a macromolecule or polypeptide which is tagged with an amino acid sequence comprising one or more functional intrinsically disordered regions.

A tagged amino acid sequence consisting of or comprising one or more functional intrinsically disordered regions (IDRs) is not found naturally or ordinarily in the macromolecule or polypeptide or protein to which it is tagged at the tagged position. Accordingly, a tagged amino acid sequence consisting of or comprising one or more functional intrinsically disordered regions (IDRs) can be considered to be an exogenous amino acid sequence compared to the macromolecule or polypeptide or protein to which it is tagged. The tagged macromolecule or polypeptide or protein can therefore be considered to be a non-naturally occurring, artificial or genetically engineered macromolecule, polypeptide or protein.

Mechanisms by which amino acid sequences may be "tagged" to polypeptides and other macromolecules are explained further herein.

Any one or more functional intrinsically disordered regions (IDRs) may be tagged to a macromolecule or polypeptide or protein, including any one or more of the specific IDR amino acid tag sequences disclosed herein, or any one or more functional variants, analogs, homologs or derivatives thereof.

For use in the present invention both an intrinsically disordered region polypeptide sequence and a domain thereof should be "functional". The term "functional" means that any IDR amino acid sequence must possess one of the functional properties outlined further herein.

The term "intrinsically disordered region" is an art-understood term used commonly in the technical field. For a comprehensive review see: Classification of Intrinsically Disordered Regions and Proteins, van der Lee et al., 2014, Chem. Rev. 114, pp 6589-6631.

The invention provides, inter alia, a process of performing a biochemical reaction in an aqueous in vitro reaction system, wherein the biochemical reaction is dependent on the function of at least one reaction macromolecule, optionally at least one reaction polypeptide, the process comprising: introducing at least one IDR-macromolecule into the in vitro reaction system under conditions suitable for performing the reaction, wherein the at least one IDR-macromolecule comprises one or more functional intrinsically disordered regions (IDRs), wherein upon introduction of the at least one IDR-macromolecule into the in vitro reaction system the efficiency of the biochemical reaction is increased by the at least one IDR-macromolecule. The efficiency of the biochemical reaction is increased by the one or more functional IDRs of the IDR-macromolecule. In any such process the at least one IDR-macromolecule may be at least one IDR-polypeptide. In any such process, the IDR-macromolecule or IDR-polypeptide comprising one or more functional intrinsically disordered regions (IDRs) may not be the "reaction macromolecule" or "reaction polypeptide" upon whose function the biochemical reaction depends. Thus in any such process the IDR-macromolecule or IDR-polypeptide may have no intrinsic biochemical role in the biochemical reaction per se. Nevertheless, its introduction into the reaction system leads to an increase in the efficiency of the biochemical reaction.

The process of performing a biochemical reaction in an in vitro reaction system may be a process wherein the biochemical reaction is dependent on the function of the at least one IDR-macromolecule, wherein upon its introduction into the in vitro reaction system the at least one IDR-macromolecule performs its reaction function in the biochemical reaction and increases the efficiency of the reaction. In any such process the at least one IDR-macromolecule may be at least one IDR-polypeptide. In any such process, the IDR-macromolecule or IDR-polypeptide does have an intrinsic biochemical role in the biochemical reaction per se. Thus the at least one IDR-macromolecule or IDR-polypeptide comprising one or more functional intrinsically disordered regions (IDRs) is the "reaction macromolecule" or "reaction polypeptide" upon whose function the biochemical reaction depends.

The at least one IDR-macromolecule or IDR-polypeptide comprises an amino acid sequence comprising or consisting of one or more functional intrinsically disordered regions. The IDR-macromolecule or IDR-polypeptide is introduced into the biochemical reaction system under conditions suitable for performing the biochemical reaction. Because of the presence of the one or more functional intrinsically disordered regions, the IDR-macromolecule or IDR-polypeptide increases the efficiency of the reaction.

By increasing the efficiency of the reaction it is meant that the efficiency of the reaction is improved compared to the efficiency of the reaction which would be observed if the IDR-macromolecule or IDR-polypeptide was provided without an amino acid sequence comprising or consisting of the one or more functional intrinsically disordered regions. Such an improvement can readily be established by comparative testing of the reaction macromolecule or polypeptide with and without the IDR amino acid sequence.

In any one of the methods of the invention the one or more functional intrinsically disordered regions of the IDR-macromolecule or IDR-polypeptide promotes/causes liquid-liquid demixing in the reaction system leading to phase separation. The functional capability of promoting liquid-liquid demixing leading to phase separation in a reaction system can readily be established, for example by performing a phase separation assay as described herein. Such liquid-liquid demixing promotes phase separation and this may lead to the formation of phase separated compartments in the reaction system, such as particles which are detectable, e.g. under microscopic observation, as detailed further herein.

An IDR-macromolecule or IDR-polypeptide may or may not possess catalytic activity. For example, an IDR-polypeptide may have catalytic activity, such as a polymerase enzyme used in a recombinase polymerase amplification reaction, as described further herein. An IDR-polypeptide may not have catalytic activity, such as a single strand stabilizing agent used in a recombinase polymerase amplification reaction, e.g. Gp32 as described further herein.

As discussed further herein, whether an IDR-macromolecule or IDR-polypeptide has catalytic activity or not, the IDR-macromolecule or IDR-polypeptide may possess a function which is required for or influences the biochemical reaction, such that in the absence of the IDR-macromolecule or IDR-polypeptide in the biochemical reaction system the biochemical reaction cannot proceed or proceeds with reduced efficiency. Alternatively, as discussed further herein, the IDR-macromolecule or IDR-polypeptide may not possess any function which is required for or which influences the biochemical reaction per se. Nevertheless, because of the IDR amino acid sequences, the introduction of the IDR-macromolecule or IDR-polypeptide into the biochemical reaction system leads to an increase in the efficiency of the biochemical reaction compared to the efficiency observed in the absence of the IDR-macromolecule or IDR-polypeptide, or in the presence of the same macromolecule or polypeptide without the IDR amino acid sequences.

Structural Properties of an IDR Polypeptide

The presence of IDRs in amino acid sequences may readily be determined by structural analysis. A large number of bioinformatics-based platforms are available for the prediction of the presence of IDRs within polypeptides and proteins. These include ELM, MiniMotif, SLiMPrints, phylo-HMM, DiliMot, SLiMFinder, Phospho.ELM, PhosphoSite, PHOSIDA, ScanSite, NetPhorest, NetworKIN, PhosphoNET, IDEAL, MoRFpred, ANCHOR, Pfam, FFPred, DisProt, $D^2P^2$, and MetaDisorder. Any of these methods may be used to identify IDR amino acid sequences. If necessary, such IDR amino acid sequences can be tested to assess their functional properties, as described further herein.

A preferred bioinformatics-based platform for IDR amino acid sequence identification is the MetaDisorder software program (MetaDisorder: a meta-server for the prediction of intrinsic disorder in proteins. Kozlowski, L. P., et al., BMC Bioinformatics, 2012, 13(1): 111).

The MetaDisorder program is available freely online (genesilico.pl). Using this program an amino acid sequence of interest is simply pasted into an internet browser window and the program is initiated. As the online documentation explains, any amino acid region which scores >0.5 in the software package is considered to comprise an intrinsically disordered region.

Using the MetaDisorder software platform the inventors have identified a number of amino acid sequences which comprise one or more intrinsically disordered regions. These are set out in Table 1.

Accordingly, in any one of the methods, processes and uses, or in any one of the non-naturally occurring IDR-macromolecules, IDR-fusion macromolecules or isolated nucleic acid molecules encoding the same, recombinant polynucleotide expression vectors or host cells, the one or more functional IDRs of the IDR-macromolecule or the IDR-polypeptide may be characterised as a sequence of amino acids which scores greater than 0.5 when analysed by the algorithm MetaDisorder. The sequence of amino acids may be a sequence of amino acids which scores greater than 0.5 when analysed by the algorithm MetaDisorder according to the methods of Kozlowski, L. P., et al., BMC Bioinformatics, 2012, 13(1): 111.

The invention provides and relates to preferred IDR amino acid sequences which comprise or consist of the amino acid sequence of any one of SEQ ID NOs 1 to 43 (Table 1) and variants thereof. In all cases a variant of an amino acid sequence of any one of SEQ ID NOs 1 to 43 is a functional variant which retains the IDR functional properties, as described further herein.

Furthermore, as described further herein, the IDR-macromolecule or IDR-polypeptide may comprise or consist of a macromolecule or polypeptide tagged with an amino acid sequence which comprises or consists of the amino acid sequence of any one of SEQ ID NOs 1 to 43, or which comprises or consists of a functional variant amino acid sequence of SEQ ID NOs 1 to 43.

The functional variant may have at least 80% sequence identity compared to the herein-described IDR amino acid sequence (Table 1). The functional variant may have at least 81% sequence identity compared to the herein-described IDR amino acid sequence (Table 1), or 82% sequence identity, or 83%, 84%, 85%, 86%, 87%, 88%, 89%, 90%, 91%, 92%, 93%, 94%, 95%, 96%, 97%, 98% or 99% sequence identity.

For the purpose of this invention, in order to determine the percent identity e.g. between an amino acid sequence of any one of SEQ ID NOs 1 to 43 and a functional variant of an amino acid sequence of any one of SEQ ID NOs 1 to 43 the two respective amino acid sequences are aligned for optimal comparison purposes (e.g., gaps can be introduced in a first sequence for optimal alignment with a second sequence). The nucleotide residues at nucleotide positions are then compared. When a position in the first sequence is occupied by the same nucleotide residue as the corresponding position in the second sequence, then the nucleotides are identical at that position. The percent identity between the two sequences is a function of the number of identical positions shared by the sequences (i.e., % identity=number of identical positions/total number of positions in the reference sequence×100).

Typically the sequence comparison is carried out over the full length of the reference sequence. For example, if the skilled person wished to determine whether a given ("variant") sequence is 80% identical to SEQ ID NO. 2, SEQ ID NO. 2 would be the reference sequence. For example, to assess whether a variant sequence is at least 80% identical to SEQ ID NO. 2 (an example of a reference sequence), the skilled person would carry out an alignment over the length of SEQ ID NO. 2, and identify how many positions in the test sequence were identical to those of SEQ ID NO. 2. If at least 80% of the positions are identical, the test sequence is at least 80% identical to SEQ ID NO. 2. If the sequence is shorter than SEQ ID NO. 2, the gaps or missing positions should be considered to be non-identical positions.

The skilled person is aware of different computer programs that are available to determine the homology or identity between two sequences. For instance, a comparison of sequences and determination of percent identity between two sequences can be accomplished using a mathematical algorithm. The percent identity between two amino acid or nucleic acid sequences may be determined, for example, using the Needleman and Wunsch (1970) algorithm which has been incorporated into the GAP program in the Accelrys GCG software package (available at accelrys.com), using either a Blosum 62 matrix or a PAM250 matrix, and a gap weight of 16, 14, 12, 10, 8, 6, or 4 and a length weight of 1, 2, 3, 4, 5, or 6.

A functional variant of an amino acid sequence of any one of SEQ ID NOs 1 to 43 may be an amino acid sequence that differs by having a number of amino acids less compared to the amino acid sequence of any one of SEQ ID NOs 1 to 43 respectively (i.e. the functional variant is shorter), or that differs by having a number of amino acids more compared to the amino acid sequence of any one of SEQ ID NOs 1 to 43 respectively (i.e. the functional variant is longer). The functional variant may thus contain one or more amino acid deletions and/or one or more insertions compared to the reference amino acid sequence. The number of amino acids in the functional variant amino acid sequence by which the variant differs from the reference sequence can be 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more or 20 or more.

A functional variant of an amino acid sequence of any one of SEQ ID NOs 1 to 43 may for example comprise conservative amino acid substitutions of amino acid residues indicated in the sequences listed in Table 1. Conservative substitutions may be made, for example according to the table below which describes a generally accepted grouping of amino acids. The functional variant may thus contain conservative amino acid substitutions compared to the reference amino acid sequence. The number of amino acids in the functional variant amino acid sequence which are conservative amino acid substitutions compared to the reference sequence can be 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more or 20 or more.

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

Whether a given variant retains the IDR functional properties may readily be established, for example by methods described further herein.

TABLE 1 amino acid sequences comprising intrinsically disordered regions

| Tag | Original protein | Accession ID | Organism | Position | Length | Comment | Sequence | SEQ ID NO |
|---|---|---|---|---|---|---|---|---|
| fib (or fib-1) | rRNA 2'-O-methyl transferase fibrillarin | Uniprot: P22087 | Homo sapiens | 3-45 | 43 | N/A | ProGlyPheSerProArgGlyGlyGlyPheGlyGlyArgGlyGlyPheGlyAspArgGlyGlyArgGlyGlyArgGlyGlyPheGlyGlyGlyArgGlyArgGlyGlyGlyPheArgGlyArgGlyArg | 1 |
| fib2 | rRNA 2'-O-methyl transferase fibrillarin | Uniprot: P22087 | Homo sapiens | 3-45 | 86 | Double of fib tag | ProGlyPheSerProArgGlyGlyGlyPheGlyGlyArgGlyGlyPheGlyAspArgGlyGlyArgGlyGlyArgGlyGlyPheGlyGlyGlyArgGlyArgGlyGlyGlyPheArgGlyArgGlyArgProGlyPheSerProArgGlyGlyGlyPheGlyGlyArgGlyGlyPheGlyAspArgGlyGlyArgGlyGlyArgGlyGlyPheGlyGlyGlyArgGlyArgGlyGlyGlyPheArgGlyArgGlyArg | 2 |
| Fib [short] | rRNA 2'-O-methyl transferase fibrillarin | Uniprot: P22087 | Homo sapiens | 8-32 | 25 | N/A | ArgGlyGlyGlyPheGlyGlyArgGlyGlyPheGlyAspArgGlyGlyArgGlyGlyArgGlyGlyPheGlyGly | 3 |
| fib-2 (clipper1) | N/A | N/A | N/A | N/A | 36 | self-designed: 7 amino acids deletion at the C-terminus of fib (fib-1) | ProGlyPheSerProArgGlyGlyGlyPheGlyGlyArgGlyGlyPheGlyAspArgGlyGlyArgGlyGlyArgGlyGlyPheGlyGlyGlyArgGlyArgGlyGly | 4 |
| fib-3 (clipper2) | N/A | N/A | N/A | N/A | 27 | self-designed: 16 amino acids deletion at the C-terminus of fib (fib-1) | ProGlyPheSerProArgGlyGlyGlyPheGlyGlyArgGlyGlyPheGlyAspArgGlyGlyArgGlyGlyArgGlyGly | 5 |
| fib-4 (clipper3) | N/A | N/A | N/A | N/A | 15 | self-designed: 28 amino acids deletion at the C-terminus of fib (fib-1) | ProGlyPheSerProArgGlyGlyGlyPheGlyGlyArgGlyGly | 6 |

TABLE 1-continued amino acid sequences comprising intrinsically disordered regions

| Tag | Original protein | Accession ID | Organism | Position | Length | Comment | Sequence | SEQ ID NO |
|---|---|---|---|---|---|---|---|---|
| PCF | Protein PCF11 | Uniprot: P39081 | Saccharomyces cerevisiae | 208-287 | 67 | Modification: amino acids deletion from originial positions 234-246 | GlnValGlnMet GlnLeuArgGln ValPheSerGln AspGlnGlnVal LeuGlnGluArg MetArgTyrHis GluLeuGlnGln GlnGlnGlnGln GlnTyrHisGlu ThrLysAspMet ValGlySerTyr ThrGlnAsnSer AsnSerAlaIle ProLeuPheGly AsnAsnSerAsp ThrThrAsnGln GlnAsnSer | 7 |
| ENT 1 | Ent2p | Uniprot: C7GIT6 | Saccharomyces cerevisiae | 530-588 | 59 | N/A | GlnAsnProThr GlyIleSerTyr SerGlnProGln GlnGlnGlnGln ProGlnGlnGln ProGlnTyrMet GlnAsnPheGln GlnGlnGlnPro GlnTyrAlaGln AsnPheGlnGln GlnProGlnTyr ThrGlnAsnTyr GlnGlnGlnPro GlnTyrIleGln ProHisGln | 8 |
| HRP1 | Nuclear polyadenylated RNA-binding protein 4 | Uniprot: Q99383 | Saccharomyces cerevisiae | 331-388 | 58 | N/A | GlyGlyAsnAsn GlyGlyAsnAsn MetAsnArgArg GlyGlyAsnPhe GlyAsnGlnGly AspPheAsnGln MetTyrGlnAsn ProMetMetGly GlyTyrAsnPro MetMetAsnPro GlnAlaMetThr AspTyrTyrGln LysMetGlnGlu TyrTyrGlnGln MetGln | 9 |
| HRP2 | Nuclear polyadenylated RNA-binding protein 4 | Uniprot: Q99383 | Saccharomyces cerevisiae | 331-388 | 116 | double of HRP1 tag | GlyGlyAsnAsn GlyGlyAsnAsn MetAsnArgArg GlyGlyAsnPhe GlyAsnGlnGly AspPheAsnGln MetTyrGlnAsn ProMetMetGly GlyTyrAsnPro MetMetAsnPro GlnAlaMetThr AspTyrTyrGln LysMetGlnGlu TyrTyrGlnGln MetGlnGlyGly AsnAsnGlyGly AsnAsnMetAsn ArgArgGlyGly AsnPheGlyAsn GlnGlyAspPhe AsnGlnMetTyr GlnAsnProMet MetGlyGlyTyr | 10 |

TABLE 1-continued amino acid sequences comprising intrinsically disordered regions

| Tag | Original protein | Accession ID | Organism | Position | Length | Comment | Sequence | SEQ ID NO |
|---|---|---|---|---|---|---|---|---|
| | | | | | | | AsnProMetMet AsnProGlnAla MetThrAspTyr TyrGlnLysMet GlnGluTyrTyr GlnGlnMetGln | |
| DDX | Probable ATP-dependent RNA helicase DDX4 | Uniprot: Q9NQI0 | Homo sapiens | 4-240 | 240 | N/A | MetGlyAspGlu AspTrpGluAla GluIleAsnPro HisMetSerSer TyrValProIle PheGluLysAsp ArgTyrSerGly GluAsnGlyAsp AsnPheAsnArg ThrProAlaSer SerSerGluMet AspAspGlyPro SerArgArgAsp HisPbeMetLys SerGlyPheAla SerGlyArgAsn PheGlyAsnArg AspAlaGlyGlu CysAsnLysArg AspAsnThrSer ThrMetGlyGly PheGlyValGly LysSerPheGly AsnArgGlyPhe SerAsnSerArg PheGluAspGly AspSerSerGly PheTrpArgGlu SerSerAsnAsp CysGluAspAsn ProThrArgAsn ArgGlyPheSer LysArgGlyGly TyrArgAspGly AsnAsnSerGlu AlaSerGlyPro TyrArgArgGly GlyArgGlySer PheArgGlyCys ArgGlyGlyPhe GlyLeuGlySer ProAsnAsnAsp LeuAspProAsp GluCysMetGln ArgThrGlyGly LeuPheGlySer ArgArgProVal LeuSerGlyThr GlyAsnGlyAsp ThrSerGlnSer ArgSerGlySer GlySerGluArg GlyGlyTyrLys GlyLeuAsnGlu GluValIleThr GlySerGlyLys AsnSerTrpLys SerGluAlaGlu GlyGlyGluSer SerAspThrGln | 11 |
| HNRNPA1 | Heterogeneous nuclear ribonucleo-protein A1 | Uniprot: Q0VAC0 | Homo sapiens | 187-320 | 134 | N/A | AlaSerAlaSer SerSerGlnArg GlyArgSerGly SerGlyAsnPhe GlyGlyGlyArg GlyGlyGlyPhe | 12 |

TABLE 1-continued amino acid sequences comprising intrinsically disordered regions

| Tag | Original protein | Accession ID | Organism | Position | Length | Comment | Sequence | SEQ ID NO |
|---|---|---|---|---|---|---|---|---|
| | | | | | | | GlyGlyAsnAsp AsnPheGlYArg GlyGlyAsnPhe SerGlyArgGly GlyPheGlyGly SerArgGlyGly GlyGlyTyrGly GlySerGlyAsp GlyTyrAsnGly PheGlyAsnAsp GlySerAsnPhe GlyGlyGlyGly SerTyrAsnAsp PheGlyAsnTyr AsnAsnGlnSer SerAsnPheGly ProMetLysGly GlyAsnPheGly GlyArgSerSer GlyProTyrGly GlyGlyGlyGln TyrPheAlalys ProGlnAsnGln GlyGlyTyrGly ValSerSerSer SerSerSerTyr GlySerGlyArg ArgPhe | |
| PolIICTD | DNA-directed RNA polymerase II subunit RPB1 | Uniprot: P04050 | Saccharomyces cerevisiae | 1521-1724 | 204 | N/A | SerProPheGly AlaTyrGlyGlu AlaProThrSer ProGlyPheGly ValSerSerPro GlyPheSerPro ThrSerProThr TyrSerProThr SerProAlaTyr SerProThrSer ProSerTyrSer ProThrSerPro SerTyrSerPro ThrSerProSer TyrSerProThr SerProSerTyr SerProThrSer ProSerTyrSer ProThrSerPro SerTyrSerPro ThrSerProSer TyrSerProThr SerProSerTyr SerProThrSer ProSerTyrSer ProThrSerPro SerTyrSerPro ThrSerProSer TyrSerProThr SerProSerTyr SerProThrSer ProSerTyrSer ProThrSerPro SerTyrSerPro ThrSerProAla TyrSerProThr SerProSerTyr SerProThrSer ProSerTyrSer ProThrSerPro SerTyrSerPro ThrSerProSer TyrSerProThr SerProAsnTyr SerProThrSer | 13 |

TABLE 1-continued amino acid sequences comprising intrinsically disordered regions

| Tag | Original protein | Accession ID | Organism | Position | Length | Comment | Sequence | SEQ ID NO |
|---|---|---|---|---|---|---|---|---|
| | | | | | | | ProSerTyrSer ProThrSerPro GlyTyrSerPro GlySerProAla TyrSerProLys GlnAspGluGln | |
| shortPolCTD | DNA-directed RNA polymerase II subunit RPB1 | Uniprot: P04050 | Saccharomyces cerevisiae | 1636-1677 | 42 | modifications: S1653G\| S1667T\| S1674T | ThrSerProSer TyrSerProThr SerProSerTyr SerProThrSer ProGlyTyrSer ProThrSerPro AlaTyrSerPro ThrSerProThr TyrSerProThr SerProThrTyr SerPro | 14 |
| Mimic1 | N/A | N/A | N/A | N/A | 49 | self-designed: seven repeats of YDPTSPS (SEQ ID NO: 129) motifs mimiking the c-terminus of RNA polymerase II | TyrAspProThr SerProSerTyr AspProThrSer ProSerTyrAsp ProThrSerPro SerTyrAspPro ThrSerProSer TyrAspProThr SerProSerTyr AspProThrSer ProSerTyrAsp ProThrSerPro Ser | 15 |
| mimic2 | N/A | N/A | N/A | N/A | 49 | self-designed: seven repeats of YSPTDPS (SEQ ID NO: 130) motifs mimiking the c-terminus of RNA polymerase II | TyrSerProThr AspProSerTyr SerProThrAsp ProSerTyrSer ProThrAspPro SerTyrSerPro ThrAspProSer TyrSerProThr AspProSerTyr SerProThrAsp ProSerTyrSer ProThrAspPro Ser | 16 |
| C-PolCTD | DNA-directed RNA Polymerase II subunit RPB1 | Uniprot: P04050 | Saccharomyces cerevisiae | 1642-1662 | 21 | N/A | ProThrSerPro SerTyrSerPro ThrSerProSer TyrSerProTyr SerProAlaTyr Ser | 17 |
| Sup | Eukaryotic peptide chain release factor GTP-binding subunit | Uniprot: P05453 | Saccharomyces cerevisiae | 1-114 | 115 | insertion of QY between 61 and 62; mutation: D66QIA67G f deletion of Q70 | MetSerAspSer AsnGlnGlyAsn AsnGlnGlnAsn TyrGlnGlnTyr SerGlnAsnGly AsnGlnGlnGln GlyAsnAsnArg TyrGlnGlyTyr GlnAlaTyrAsn AlaGlnAlaGln ProAlaGlyGly TyrTyrGlnAsn TyrGlnGlyTyr SerGlyTyrGln GlnGlyGlyTyr GlnGlnTyrGln | 18 |

TABLE 1-continued amino acid sequences comprising intrinsically disordered regions

| Tag | Original protein | Accession ID | Organism | Position | Length | Comment | Sequence | SEQ ID NO |
|---|---|---|---|---|---|---|---|---|
| | | | | | | | TyrAsnProGln GlyGlyTyrGln GlnTyrAsnPro GlnGlyGlyTyr GlnGlnTyrAsn ProGlnGlyGly TyrGlnGlnGln PheAsnProGln GlyGlyArgGly AsnTyrLysAsn PheAsnTyrAsn AsnAsnLeuGln GlyTyrGln | |
| Sup1 | N/A | N/A | N/A | N/A | 9 | self-designed: single repeat of YNPQGGYQQ (SEQ ID NO: 19) | TyrAsnProGln GlyGlyTyrGln Gln | 19 |
| Sup2 | N/A | N/A | N/A | N/A | 18 | self-designed: two repeat of YNPQGGYQQ (SEQ ID NO: 19) | TyrAsnProGln GlyGlyTyrGln GlnTyrAsnPro GlnGlyGlyTyr GlnGln | 20 |
| Sup3 | N/A | N/A | N/A | N/A | 27 | self-designed: three repeat of YNPQGGYQQ (SEQ ID NO: 19) | TyrAsnProGln GlyGlyTyrGln GlnTyrAsnPro GlnGlyGlyTyr GlnGlnTyrAsn ProGlnGlyGly TyrGlnGln | 21 |
| Sup4 | N/A | N/A | N/A | N/A | 36 | self-designed: four repeat of YNPQGGYQQ (SEQ ID NO: 19) | TyrAsnProGln GlyGlyTyrGln GlnTyrAsnPro GlnGlyGlyTyr GlnGlnTyrAsn ProGlnGlyGly TyrGlnGlnTyr AsnProGlnGly GlyTyrGlnGln | 22 |
| His1 | Dual specificity tyrosine-phosphorylation-regulated kinase 1A isoform 1 | Uniprot: Q13627 | Homo sapiens | 593-623 | 31 | N/A | ProGlnGlnAsn AlaLeuHisHis HisHisGlyAsn SerSerHisHis HisHisHisHis HisHisHisHis HisHisHisGly GlnGlnAla | 23 |
| His2 | Homeobox protein OTX1 | Uniprot: P32242 | Homo sapiens | 273-308 | 36 | N/A | AlaGlyHisHis HisHisHisPro HisAlaHisHis ProLeuSerGln SerSerGlyHis HisHisHisHis HisHisHisHis HisGlnGlyTyr GlyGlySerGly | 24 |
| His3 | Serine/threonine-protein | Uniprot: Q9UBE8 | Homo sapiens | 25-67 | 43 | N/A | AlaGlyHisHis HisHisHisHis HisHisLeuPro | 25 |

TABLE 1-continued amino acid sequences comprising intrinsically disordered regions

| Tag | Original protein | Accession ID | Organism | Position | Length | Comment | Sequence | SEQ ID NO |
|---|---|---|---|---|---|---|---|---|
| | kinase NLK | | | | | | HisLeuProPro ProHisLeuHis HisHisLeuHis ProGlnHisHis LeuHisProGly SerAlaAlaAla ValHisProVal GlnGlnHis | |
| His4 | Forkhead box protein G1 | Uniprot: P55316 | Homo sapiens | 32-73 | 42 | N/A | AsnHisHisAla SerHisGlyHis HisAsnSerHis HisProGlnHis HisHisHisHis HisHisHisHis HisHisProPro ProProAlaPro GlnProProPro ProProGlnGln GlnGln | 26 |
| His5 | Transcription factor MafA | Uniprot: Q8NHW3 | Homo sapiens | 145-220 | 76 | N/A | SerGlyHisHis GlyAlaHisHis GlyAlaHisHis ProAlaAlaAla AlaAlaTyrGlu AlaPheArgGly ProGlyPheAla GlyGlyGlyGly AlaAspAspMet GlyAlaGlyHis HisHisGlyAla HisHisAlaAla HisHisHisHis AlaAlaHisHis HisHisHisHis HisHisHisHis GlyGlyAlaGly HisGlyGlyGly AlaGlyHisHis | 27 |
| His6 | Transcriptional repressor protein YY1 | Uniprot: P25490 | Homo sapiens | 54-80 | 27 | N/A | GlyGlyGlyGly AspHisGlyGly GlyGlyGlyHis GlyHisAlaGly HisHisHisHis HisHisHisHis HisHisHis | 28 |
| His7 | Disks large-associated protein 3 | Uniprot: O95886 | Homo sapiens | 214-238 | 25 | N/A | ProGlySerGly GlyProHisThr SerHisHisHis HisHisHisHis HisHisHisHis HisGlnSerArg His | 29 |
| His8 | Nuclear receptor subfamily 4 group A member 3 | Uniprot: Q92570 | Homo sapiens | 91-115 | 25 | N/A | AlaProSerTyr HisHisHisHis HisHisHisHis HisHisHisHis HisHisGlnGln GlnHisGlnGln Pro | 30 |
| His9 | E3 SUMO-protein ligase CBX4 | Uniprot: O00257 | Homo sapiens | 377-400 | 24 | N/A | ThrHisProPro SerHisHisPro HisProHisPro HisHisHisHis HisHisHisHis HisHisHisHis | 31 |
| His10 | SKI/DACH domain- | Uniprot: Q1XH10 | Homo sapiens | 334-371 | 38 | N/A | ProProProHis HisHisHisHis | 32 |

TABLE 1-continued amino acid sequences comprising intrinsically disordered regions

| Tag | Original protein | Accession ID | Organism | Position | Length | Comment | Sequence | SEQ ID NO |
|---|---|---|---|---|---|---|---|---|
| | containing protein 1 | | | | | | HisHisHisHisHisHisHisHisHisHisArgAlaGlnProProGlnGlnSerHisHisProProHisHisHisArgProGlnProHis | |
| His11 | GS homeobox 2 | Uniprot: Q9BZM3 | Homo sapiens | 123-140 | 18 | N/A | AsnHisAlaHisHisHisHisHisProProGlnHisHisHisHisHisHisGln | 33 |
| His12 | N/A | N/A | N/A | N/A | 37 | self-designed | AlaGlyHisHisHisHisHisHisHisHisHisHisGlyGlyAlaGlyGlyAlaGlyGlyAlaGlyGlyAlaHisHisHisHisHisHisHisHisHisHisGlyGlyAla | 34 |
| His13 | N/A | N/A | N/A | N/A | 37 | self-designed | AlaGlyHisHisHisHisHisHisHisHisHisHisSerSerGlySerGlySerSerGlySerGlySerSerHisHisHisHisHisHisHisHisHisHisGlyGlyAla | 35 |
| His14 | N/A | N/A | N/A | N/A | 17 | self-designed | AlaGlyHisHisHisHisHisHisHisHisHisHisGlyGlyAla | 36 |
| His15 | N/A | N/A | N/A | N/A | 24 | self-designed | AlaGlyHisHisHisHisHisHisHisHisHisHisHisHisHisHisHisHisHisHisHisGlyGlyAla | 37 |
| super+ve | single stranded DNA-binding protein | GenBank: AWM11745.1 | Escherichia phage vB_EcoM_NBG1 | 256-299 | 74 | self-designed: double sequence of MEAFSSAKTEDDFMSSSSSDDSDLDDLLAGL (SEQ ID NO: 131) and change amino acids D/E to K | LysLysValAlaSerLysLeuLysPheLysLysLysMetGluAlaPheSerSerAlaLysThrLysLysLysPheMetSerSerSerSerSerLysLysSerLysLeuLysLysLeuLeuAlaGlyLeuMetGluAlaPheSerSerAlaLysThrLysLysLysPheMetSerSerSerSerSerLysLysSerLysLeuLysLysLeuLeuAlaGlyLeu | 38 |
| super-ve | single stranded DNA- | GenBank: AWM11745.1 | Escherichia phage vB_EcoM_ | 256-299 | 75 | self-designed: double | AspAspValAlaSerAspLeuAspAspPheAspAsp | 39 |

TABLE 1-continued amino acid sequences comprising intrinsically disordered regions

| Tag | Original protein | Accession ID | Organism | Position | Length | Comment | Sequence | SEQ ID NO |
|---|---|---|---|---|---|---|---|---|
| | binding protein | | NBG1 | | | sequence of MEAFSSAKT EDDFMSSSS SDDSDLDDL LAGL (SEQ ID NO: 131) and change amino acid K to D/E | AspMetGluAla PheSerSerAla AspThrGluAsp AspPheMetSer SerSerSerSer AspAspSerAsp LeuAspAspLeu LeuAlaGlyLeu MetGluAlaPhe SerSerAlaAsp ThrGluAspAsp PheMetSerSer SerSerSerAsp AspSerAspLeu AspAspLeuLeu AlaGlyLeu | |
| super-positive | RecA-like recombination protein | GenBank: AYP69747.1 | Escherichia phage vB_EcoM_DalCa | 348-392 | 90 | self-designed: double sequence of EIVEAEVDE LINSKVEKF KSPESKSKS AADLETDLE QLSDMEEFN SEQ ID NO: 132) and change amino acids D/E to R/K | ArgIleValLys AlaLysValLys ArgLeuIleAsn SerLysValLys LysPheLysSer ProLysSerLys SerLysSerAla AlaLysLeuLys ThrLysLeuLys GlnLeuSerLys MetLysLysPhe AsnLysIleVal LysAlaLysVal LysLysLeuIle AsnSerLysVal ArgLysPheLys SerProLysSer LysSerLysSer AlaAlaLysLeu LysThrLysLeu LysGlnLeuSer LysMetLysGlu PheAsn | 40 |
| super-negative | RecA-like recombination protein | GenBank: AYP69747.1 | Escherichia phage vB_EcoM_Dal Ca | 348-392 | 90 | self-designed: double sequence of EIVEAEVDE LINSKVEKF KSPESKSKS AADLETDLE QLSDMEEFN SEQ ID NO: 132) and change amino acids R/K to D/E | GluIleValGlu AlaGluValAsp GluLeuIleAsn SerGluValGlu GluPheAspSer ProGluSerAsp SerAspGluAla AlaAspLeuGlu ThrAspLeuGlu GlnLeuSerAsp MetGluGluPhe AsnGluIleVal GluAlaGluVal AspGluLeuIle AsnSerGluVal GluAspPheAsp SerProGluSer AspSerAspGlu AlaAlaAspLeu GluThrAspLeu GluGlnLeuSer AspMetGluGlu PheAsn | 41 |
| DoubleX | RecA-like recombination protein | GenBank: AYP69747.1 | Escherichia phage vB_EcoM_Dal Ca | 348-392 | 90 | self-designed: a linker of FEF and double sequence of EIVEAEVDE | GluIleValGlu AlaGluValAsp GluLeuIleAsn SerLysValGlu LysPheLysSer ProGluSerLys SerLysSerAla AlaAspLeuGlu ThrAspLeuGlu | 42 |

TABLE 1-continued amino acid sequences comprising intrinsically disordered regions

| Tag | Original protein | Accession ID | Organism | Position | Length | Comment | Sequence | SEQ ID NO |
|---|---|---|---|---|---|---|---|---|
| | | | | | | LINSKVEKF KSPESKSKS AADLETDLE QLSDMEEFN SEQ ID NO: 132) | GlnLeuSerAsp MetGluGluPhe AsnGluIleVal GluAlaGluVal AspGluLeuIle AsnSerLysVal GluLysPheLys SerProGluSer LysSerLysSer AlaAlaAspLeu GluThrAspLeu GluGlnLeuSer AspMetGluGlu PheAsn | |
| TripleX tail | RecA-like recombination protein | GenBank: AYP69747.1 | *Escherichia phage* vB_EcoM_DalCa | 348-392 | 135 | self-designed: a linker of DDVASEF (SEQ ID NO: 133) and triple sequence of EIVEAEVDE LINSKVEKF KSPESKSKS AADLETDLE QLSDMEEFN (SEQ ID NO: 132) | GluIleValGlu AlaGluValAsp GluLeuIleAsn SerLysValGlu LysPheLysSer ProGluSerLys SerLysSerAla AlaAspLeuGlu ThrAspLeuGlu GlnLeuSerAsp MetGluGluPhe AsnGluIleVal GluAlaGluVal AspGluLeuIle AsnSerLysVal GluLysPheLys SerProGluSer LysSerLysSer AlaAlaAspLeu GluThrAspLeu GluGlnLeuSer AspMetGluGlu PheAsnGluIle ValGluAlaGlu ValAspGluLeu IleAsnSerLys ValGluLysPhe LysSerProGlu SerLysSerLys SerAlaAlaAsp LeuGluThrAsp LeuGluGlnLeu SerAspMetGlu GluPheAsn | 43 |

Like-for-like substitutions may be made, in the case of amino acids such as basic for basic, acidic for acidic, polar for polar, etc. Non-homologous substitution may also occur, i.e. from one class of residue to another, or alternatively involving the inclusion of unnatural amino acids such as ornithine, diaminobutyric acid ornithine, norleucine ornithine, pyriylalanine, thienylalanine, naphthylalanine and phenylglycine.

The specific IDR amino acid sequences disclosed herein (see Table 1) can broadly be classified into four groups. Some IDR sequences can be classified into more than one group. The RGG/RG group includes IDR sequences which are FG/YG rich. This group includes fib, hnrpnA1, DDX, HRP1 and Sup. The Poly Q group includes IDR sequences which are Q/N rich. This group includes PCF11, Ent-1, HRP1, Sup, His4, His8 and His10. The Poly P group includes sequences which are P rich. This group includes His4, His9 and His10. The Poly H group includes sequences which are H rich. This group includes His1-11. Some key features of the IDR amino acid sequences are that they demonstrate cation-pi interactions and pi-pi interactions, and are capable of forming amide bridges and salt bridges. Key features and key inter/intra molecular interactions of preferred IDR amino acid sequences are presented in Tables 2 to 20 below.

TABLE 2

| IDR | fib |
|---|---|
| Sequence | PGFSPRGGGFGGRGGFGD RGGRGGRGGFGGGRGRGG GFRGRGR (SEQ ID NO: 1) |
| Key feature | RGG/RG, FG |

TABLE 2-continued

| IDR | fib |
|---|---|
| Key inter/intra molecular interactions | R-F/H (cation-pi interaction)<br>F/H-F/H (pi-pi interaction)<br>R-D (salt bridge) |

TABLE 3

| IDR | HNRPNA1 |
|---|---|
| Sequence | ASASSSQRGRSGSGNFGGG<br>RGGGFGGNDNFGRGGNFSG<br>RGGFGGSRGGGGYGGSGDG<br>YNGFGNDGSNFGGGGSYND<br>FGNYNNQSSNFGPMKGGN<br>FGGRSSGPYGGGGQYFAKP<br>QNQGGYGVSSSSSSYGSGR<br>RF<br>(SEQ ID NO: 12) |
| Key feature | RGG/RG, FG/YG |
| Key inter/intra molecular interactions | R/K-Y/F/H (cation-pi interaction)<br>Y/F/H-Y/F/H (pi-pi interaction)<br>R/K-D (salt bridge)<br>Q/N-Q/N (amide interaction) |

TABLE 4

| IDR | DDX |
|---|---|
| Sequence | MGDEDWEAEINPHMSSY<br>VPIFEKDRYSGENGDNF<br>NRTPASSSEMDDGPSRR<br>DHFMKSGFASGRNFGNR<br>DAGECNKRDNTSTMGG<br>FGVGKSFGNRGFSNSR<br>FEDGDSSGFWRESSND<br>CEDNPTRNRGFSKRGG<br>YRDGNNSEASGPYRRG<br>GRGSFRGCRGGFGLGS<br>PNNDLDPDECMORTGG<br>LFGSRRPVLSGTGNGD<br>TSQSRSGSGSERGGYK<br>GLNEEVITGSGKNSWK<br>SEAEGGESSDTQ<br>(SEQ ID NO: 11) |
| Key feature | RGG/RG, FG |
| Key inter/intra molecular interactions | R/K-Y/F/H (cation-pi interaction)<br>Y/F/H-Y/F/H (pi-pi interaction)<br>R/K-D/E (salt bridge)<br>Q/N-Q/N (amide interaction) |

TABLE 5

| IDR | HRP1 |
|---|---|
| Sequence | GGNNGGNNMNRRGGNFGN<br>QGDFNQMYQNPMMGGYNP<br>MMNPQAMTDYYQKMQE<br>YYQQMQ<br>(SEQ ID NO: 9) |
| Key feature | RGG/FG, Q/N rich,<br>YYQ-K/Q-MQ repeat |
| Key inter/intra molecular interactions | Q/N-Q/N (amide bridge)<br>R/K-Y/F/H (cation-pi interaction)<br>Y/F/H-Y/F/H (pi-pi interaction)<br>R/K-D/E (salt bridge) |

TABLE 6

| IDR | Sup |
|---|---|
| Sequence | MSDSNQGNNQQNYQQY<br>SQNGNQQQGNNRYQGY<br>QAYNAQAQPAGGYYQN<br>YQGYSGYQQGGYQQYQ<br>YNPQGGYQQYNPQGGY<br>QQYNPQGGYQQQFNPQ<br>GGRGNYKNFNYNNNLQ<br>GYQ<br>(SEQ ID NO: 18) |
| Key feature | YNPQGGYQQ<br>(SEQ ID NO: 19)<br>repeats, RG, Q/N rich |
| Key inter/intra molecular interactions | Q/N-Q/N (amide bridge)<br>R/K-Y/F/H (cation-pi interaction)<br>Y/F/H-Y/F/H (pi-pi interaction)<br>R/K-D (salt bridge) |

TABLE 7

| IDR | PolCTD |
|---|---|
| Sequence | SPFGAYGEAPTSPGFGVSSPGFSPTSPTYSPTSPAYSPTSPYSPTSPSY<br>SPTSPSYSPTSPSYSPTSPSYSPTSPSYSPTSPSYSPTSPSYSPT |

TABLE 7-continued

| IDR | PolCTD |
|---|---|
| | SPSYSPTSPSYSPTSPSYSPTSPSYSPTSPSYSPTSPS<br>YSPTSPSYSPTSPSYSPTSPAYSPTSPSYSPTSPS<br>YSPTSPSYSPTSPSYSPTSPNYSPTSPSYSPTSPGYSPGSPAYSPKQDEQ<br>(SEQ ID NO: 13) |
| Key feature | repeats of YSPTSPS (SEQ ID NO: 124) and its variants (FSPTSPT (SEQ ID NO: 125), YSPTSP-A/N/G (SEQ ID NO: 126), YSPGSPA (SEQ ID NO: 127)) |
| Key inter/intra molecular interactions | Q/N-Q/N(amide bridge)<br>K-Y/F/H (cation-pi interaction)<br>Y/F/H-Y/F/H (pi-pi interaction)<br>K-D/E (salt bridge) |

TABLE 8

| IDR | PCF11 |
|---|---|
| Sequence | QVQMQLRQVFSQDQQVLQERMRYHEL<br>QQQQQQQYHETKDMVGS<br>YTQNSNSAIPLFGNNSDTTNQQNS<br>(SEQ ID NO: 7) |
| Key feature | Poly Q |
| Key inter/intra molecular interactions | Q/N-Q/N(amide bridge)<br>R/K-Y/F/H (cation-pi interaction)<br>Y/F/H-Y/F/H (pi-pi interaction)<br>R/K-D/E (salt bridge) |

TABLE 9

| IDR | ENT1 |
|---|---|
| Sequence | QNPTGISYSQPQQQQQPQQQPQYMQNFQQQQPQYAQNF<br>QQQPQYTQNYQQQPQYIQPHQ (SEQ ID NO: 8) |
| Key feature | Poly Q, QQQPQY repeat (SEQ ID NO: 128) |
| Key inter/intra molecular interactions | Q/N-Q/N (amide bridge)<br>Y/F/H-Y/F/H (pi-pi interaction) |

TABLE 10

| IDR | HIS1 |
|---|---|
| Sequence | PQQNALHHHHGNSSHHHHHHHHHHHHHGQQA<br>(SEQ ID NO: 23) |
| Key feature | Poly H |
| Key inter/intra molecular interactions | Q/N-Q/N (amide bridge)<br>H-H (pi-pi interaction) |

TABLE 11

| IDR | HIS2 |
|---|---|
| Sequence | AGHHHHHPHAHHPLSQSSGHHHHHHHHHHQGYGGS<br>(SEQ ID NO: 24) |
| Key feature | Poly H |

TABLE 11-continued

| IDR | HIS2 |
|---|---|
| Key inter/intra molecular interactions | Q-Q (amide bridge)<br>Y/H-Y/H (pi-pi interaction) |

TABLE 12

| IDR | HIS3 |
|---|---|
| Sequence | AGHHHHHHHHLPHLPPPHLHHHHHPQHHLHPGSAAA<br>VHPVQQH (SEQ ID NO: 25) |
| Key feature | Poly H |
| Key inter/intra molecular interactions | Q-Q (amide bridge)<br>H-H (pi-pi interaction) |

TABLE 13

| IDR | HIS4 |
|---|---|
| Sequence | NHHASHGHHNSHHPQHHHHHHHHHHHPPPPAPQPPPP<br>PQQQQ (SEQ ID NO: 26) |
| Key feature | Poly H, poly Q, poly proline |
| Key inter/intra molecular interactions | Q/N-Q/N (amide bridge)<br>H-H (pi-pi interaction) |

TABLE 14

| IDR | HIS5 |
|---|---|
| Sequence | SGHHGAHHGAHHPAAAAAYEAFRGPGFAGGGGADDM<br>GAGHHHGAHHAAHHHHAAHHHHHHHHHGGAGHGGG<br>AGHH (SEQ ID NO: 27) |
| Key feature | Poly H |
| Key inter/intra molecular interactions | R-Y/F/H(cation-pi interaction)<br>Y/F/H-Y/F/H (pi-pi interaction)<br>R-D/E (salt bridge) |

TABLE 15

| IDR | HIS6 |
|---|---|
| Sequence | GGGGDHGGGGGHGHAGHHHHHHHHHH (SEQ ID NO: 28) |
| Key feature | Poly H |
| Key inter/intra molecular interactions | H-H (pi-pi interaction) |

TABLE 16

| IDR | HIS7 |
|---|---|
| Sequence | PGSGGPHTSHHHHHHHHHHHHQSR (SEQ ID NO: 29) |
| Key feature | Poly H |
| Key inter/intra molecular interactions | H-H (pi-pi interaction)<br>R-H (cation-pi interaction)<br>Q-Q (amide bridge)<br>R-D/E (salt bridge) |

TABLE 17

| IDR | HIS8 |
|---|---|
| Sequence | APSYHHHHHHHHHHHHHHQQQHQQP (SEQ ID NO: 30) |
| Key feature | Poly H, poly Q |
| Key inter/intra molecular interactions | Y/H-Y/H (pi-pi interaction)<br>Q-Q (amide bridge) |

TABLE 18

| IDR | HIS9 |
|---|---|
| Sequence | THPPSHHPHPHPHHHHHHHHHHHH (SEQ ID NO: 31) |
| Key feature | Poly H, P rich |
| Key inter/intra molecular interactions | H-H (pi-pi interaction) |

TABLE 19

| IDR | HIS10 |
|---|---|
| Sequence | PPPHHHHHHHHHHHHHHHHRAQPPQQSHHPPHHHRPQPH (SEQ ID NO: 32) |
| Key feature | Poly H, P and Q rich |
| Key inter/intra molecular interactions | H-H (pi-pi interaction)<br>Q-Q (amide bridge)<br>R-H (cation-pi interaction) |

TABLE 19-continued

| IDR | HIS10 |
|---|---|
| interactions | |

TABLE 20

| IDR | HIS11 |
|---|---|
| Sequence | NHAHHHHHPPQHHHHHHQ (SEQ ID NO: 33) |
| Key feature | Poly H |
| Key inter/intra molecular interactions | H-H (pi-pi interaction)<br>Q/N-Q/N (amide bridge) |

Functional Properties of an IDR-Macromolecule or IDR-Polypeptide

An IDR-tagged macromolecule or polypeptide, or IDR-macromolecule or IDR-polypeptide, as defined herein, must possess an amino acid sequence consisting of or comprising one or more functional IDRs to be of use in the processes of the invention. Whether or not such an IDR amino acid sequence or domain is functional can be established by routine methods, such as those described herein.

Particle Formation

The inventors have surprisingly discovered that IDR-tagged polypeptides or IDR-polypeptides are capable of forming particles in an appropriate solution. This is believed to occur by liquid-liquid demixing leading to phase separation of fluids within the solution mixture mediated by the IDR amino acid sequence.

The formation of particles mediated by IDR amino acid sequences is described further in the examples below. The particles demonstrate a spheroidal appearance and can be described as "globules", "globular foci" or "particles".

The terms "particle", "globules" or "globular foci" as referred to herein are intended to be synonymous and can be used interchangeably. Conditions and methods which permit the observation and detection of particles are set out herein including in the examples below.

In the examples described herein, particle formation was observed to occur in a simple system comprising merely a solution of IDR-tagged polypeptide and divalent metal cation. Particle formation was also found to occur in more complex mixtures including those comprising components required for RPA where one of the RPA protein components (Gp32) was IDR-tagged. In these situations, reaction components were seen to strongly co-localise with the particles, for example particles were seen to be dense in oligonucleotide as detected by the fluorescent labelled probe attached thereto, as well comprising all other RPA reaction protein components.

Detection and monitoring of the particles can be performed using any suitable method, as well as the methods set out in the examples below. Exemplary methods include microscopy, light scattering, flow cytometry, and microfluidic methods.

The particles can be detected using microscopy, e.g., differential interference contrast or fluorescence microscopy, to directly observe the particles at high magnification. With the aid of a computer, microscope images can be automatically obtained and analyzed. Additionally, microscopy can allow for continual or frequent monitoring of at least a portion of a mixture containing particles.

The particles can be detected using flow cytometry. In flow cytometry, one or more beams of light, e.g., each of a single wavelength, are directed onto a hydrodynamically-focused stream of fluid. Suspended particles passing through the beams scatter the light, and fluorescent chemicals found in the particles or attached to the particles may be excited. The scattered and/or fluorescent light is analysed by detectors within the device, from which information about particle size and fluorescence can be determined. Modern flow cytometers can analyze several thousand particles every second, in "real time", and can actively separate and isolate particles having specified properties.

The particles can be detected using cytometry methods, devices, and systems as disclosed e.g. in US patent application publication nos. US2009/0079963 and US2010/0179068, and international patent application publication no. WO2009/112594.

The particles can be detected using microfluidic methods, devices, and systems. For example, the particles can be detected using a lab-on-a-chip device or system, or the like (see, e.g., US patent application publication nos. US2009/0326903 and US2009/0297733).

Particles may be about 0.5-20 µm in size, e.g., between about any two sizes selected from 0.5, 1, 1.5, 2, 2.5, 3, 4, 5, 6, 7, 8, 9, 10, 12, 15, 18, and 20 µm (e.g., about 1-10 µm in size).

The concentration of particles may be approximately 10 to 5000 particles/nl, e.g., between any two numbers of particles selected from 10, 20, 50, 100, 200, 500, 1000, 2000, and 5000 particles per nl, may be detected (e.g. about 100-500 particles per nl). The concentration of particles may be approximately 200-400 particles per nanolitre.

Such phase-separated particles may be smaller than about 0.5 µm in size. Phase-separated particles, including those that are smaller than about 0.5 µm in size, may be detected by changes in the turbidity of the solution. Changes in the turbidity of solutions can be measured by standard means and can be quantified typically according to the Formazin Turbidity Unit (FTU) or Formazin Nephelometric Unit (FNU). Other methods include size exclusion chromatography, including multiangle light scattering (SEC-MALS).

Experimental Determination of IDR Function

An IDR-macromolecule or IDR-polypeptide, or an IDR-tagged macromolecule or IDR-tagged polypeptide, as defined herein, can be determined to possess a functional intrinsically disordered region (IDR) amino acid sequence and/or domain thereof, and thus to be of use in the processes and reagents of the invention, by using e.g. a phase separation assay method or a RPA assay method as described below.

Accordingly, an IDR-macromolecule, IDR-polypeptide or an IDR-tagged macromolecule or IDR-tagged polypeptide is a macromolecule or polypeptide which comprises, or which is tagged with, an amino acid sequence consisting of one or more functional intrinsically disordered regions; or a macromolecule or polypeptide which is tagged with an amino acid sequence comprising one or more functional intrinsically disordered regions. In all cases the functional intrinsically disordered region is one which may be determined to be functional in the phase separation assay method described below and/or in the RPA assay method as described below.

Phase Separation Assay Method

The phase separation assay method is a method comprising:
1. tagging the one or more intrinsically disordered region amino acid sequences to a polypeptide to create an IDR-polypeptide fusion protein, preferably tagged to the recombinant phage vB EcoM NBG1 Gp32 protein to create a Gp32-IDR fusion protein, and providing purified IDR-polypeptide fusion protein;
2. adding the IDR-polypeptide fusion protein to a volume of water to a final concentration of 1000 ng/µl, wherein the final volume of the mixture is 50 µl, and preferably adding a divalent metal cation to a final concentration of 2 mM or more, more preferably wherein the divalent metal cation is $Mg^{2+}$, $Mn^{2+}$, $Ca^{2+}$, $Co^{2+}$ or $Ni^{2+}$;
3. vortexing the mixture followed by pulse centrifuging the mixture;
4. transferring a 10 µl sample of the mixture supernatant to a haemocytometer slide;
5. viewing the haemocytometer slide under a microscope at ×400 magnification;
6. observing the formation of particles in the mixture;
7. in the absence of particles in the mixture, repeating steps 1 to 6 and incrementally increasing the concentration of the divalent metal cation until the formation of particles in the mixture is observed;
8. counting the number of particles which form in a magnification area of 218 µm×175 µm at ×400 magnification; and
9. (i) establishing that the amino acid sequence consisting of or comprising one or more intrinsically disordered regions (IDRs) is functional when 10 or more particles are counted in the magnification area, preferably when 50 or more particles are counted in the magnification area, more preferably when 100 or more particles are counted in the magnification area; or
   (ii) establishing that the amino acid sequence consisting of or comprising one or more intrinsically disordered regions (IDRs) is non-functional if the concentration of the divalent metal cation is increased to 100 mM or more and no particles are observed to form in the magnification area, or less than 10 particles are counted in the magnification area.

In the above method, should it be desirable to examine the effect of providing a divalent metal cation on particle formation, step 2 may comprise adding a divalent metal cation to any desired final concentration. The effects of different concentrations of divalent metal cations may thus be examined.

In the above method, should it be desirable to examine the effect of providing ATP on particle formation, step 2 may comprise adding ATP to any desired final concentration. The effects of different concentrations of ATP may thus be examined. ATP may be provided for example at a concentration of 1 mM to 3.5 mM, e.g. 1 mM to 2 mM.

Step 2 may comprise adding a detectable nucleic acid molecule and wherein step 8 comprises counting the number of particles by the detection means. For example, step 2 may comprise adding a probe having the nucleic acid sequence set for the in SEQ ID NO:104, which is labelled with FAM (fluorescein) and step 8 may comprise detecting particles by fluorescence. The detectable nucleic acid molecule may be added to any suitable final concentration, such as 0.5 µM.

Accordingly, the above assay may be used to examine reaction efficiency, the capability of causing liquid-liquid demixing and the capability of causing molecules to co-localise within a plurality of phase-separated aqueous compartments (particles).

In the above method, if the divalent metal cation is $Mg^{2+}$ the source of the cation is preferably MgOAc. If the divalent metal cation is $Ca^{2+}$, the source of the cation is preferably $CaCl_2$). If the divalent metal cation is $Mn^{2+}$, the source of the cation is preferably $MnCl_2$.

RPA Assay Method

The RPA assay method is a method comprising:
1. tagging the one or more intrinsically disordered region polypeptide sequences to a Gp32 protein, preferably the recombinant phage vB EcoM NBG1 Gp32 protein, to create a Gp32-IDR fusion protein and providing purified Gp32-IDR fusion protein;
2. creating a reaction mixture comprising
    a. Tris HCl pH 8.3, 25 mM;
    b. KOAc, 7.5 mM;
    c. DTT, 1 mM;
    d. ATP, 2.5 mM;
    e. phosphocreatine, 20 mM;
    f. creatine kinase, 1 µM;
    g. dNTPs, 1 mM;
    h. purified Gp32-IDR fusion protein, 20 µM;
    i. purified UvsX, 4.8 µM
    j. purified UvsY, 8.6 µM
    k. *S. aureus* DNA polymerase 1 (Sau), 0.135 µM
    l. Exonuclease III, 0.27 µM
    m. forward primer, 0.4 µM
    n. reverse primer, 0.4 µM
    o. probe, 0.12 µM
3. initiating a recombinase polymerase amplification reaction by adding to the reaction mixture 33 mM MgOAc and 10 copies of template nucleic acid;
4. incubating the reaction mixture at 39° C. in a fluorometer with magnetic mixing using a bearing ball;
5. (i) establishing that the one or more intrinsically disordered region polypeptide sequence is functional when a 2-fold or more increase in amplified product is detectable within 15 minutes by a measurable increase in fluorescence compared to baseline in a template-dependent fashion; or
    (ii) establishing that the one or more intrinsically disordered region polypeptide sequence is non-functional when no amplified product is detected by fluorescence after 15 minutes.

In the above method, the forward primer sequence is: CGCCTGCAAGTCCTAAGACGC-CAATCGAAAAGAAAC (SEQ ID NO:98); the reverse primer sequence is: CTGCATCTCCGTGGTATACTAATA-CATTGTTTTTA (SEQ ID NO:99); the probe sequence is: CGAAAAGAAACACGCGGATGAAATCGATAAG [FAM][THF][BHQ-1]ATACAAGGATTGGA (SEQ ID NO:100), where FAM is fluorescein, THF is tetrahydrofuran and BHQ is Black Hole Quencher; and the template is *Listeria monocytogenes* genomic DNA.

Step 5 of the above RPA assay method may alternatively comprise establishing that the one or more intrinsically disordered region polypeptide sequence is functional when a 5-fold or more increase in amplified product is detectable within 15 minutes by a measurable increase in fluorescence compared to baseline in a template-dependent fashion, or when a 10-fold or more increase is detectable, or a 20-fold or more increase, or a 30-fold or more increase, or a 40-fold or more increase, or a 50-fold or more increase, or a 100-fold or more increase, or a 150-fold or more increase, or a 200-fold or more increase, or a 250-fold or more increase, or a 300-fold or more increase, or a 350-fold or more increase, or a 400-fold or more increase, or a 450-fold or more increase, or a 500-fold or more, 1000-fold or more, 2000-fold or more, 3000-fold or more, 4000-fold or more or 5000-fold or more increase. By an increase in amplified product over baseline it is meant the increase in amplified product compared to the amount of amplified product obtained by performing the reaction under the same conditions except wherein the Gp32 protein has not been tagged with the one or more intrinsically disordered region polypeptide sequences.

In the above method, should it be desirable to examine the effect of providing a divalent metal cation on reaction efficiency, step 3 may comprise adding a divalent metal cation to any desired final concentration. The effects of different concentrations of divalent metal cations may thus be examined.

In the above method, should it be desirable to examine the effect of providing ATP on reaction efficiency, step 2 may comprise adding ATP to any desired final concentration. The effects of different concentrations of ATP may thus be examined. ATP may be provided for example at a concentration of 1 mM to 3.5 mM, e.g. 1 mM to 2 mM.

Tagging of IDR Amino Acid Sequences to Macromolecule and Polypeptides

The methods, processes and reagents of the present invention involve, inter alia, IDR-tagged macromolecules and IDR-tagged polypeptides, wherein an IDR-tagged macromolecule or an IDR-tagged polypeptide is a macromolecule or polypeptide of interest tagged with an amino acid sequence consisting of or comprising one or more intrinsically disordered regions (IDRs) (which may be referred to herein as an IDR moiety).

The term "tag" or "tagging" is to be understood in its broadest sense. The terms are to be understood to mean that an IDR moiety, i.e. an amino acid sequence which consists of or comprises one or more functional IDRs, is attached to, tethered to, bound to or otherwise associated with a macromolecule or a polypeptide of interest in any suitable way.

The most preferred means by which an IDR moiety is tagged to a polypeptide of interest is by creating a recombinant genetic fusion protein, wherein the polypeptide of interest is genetically engineered at the nucleotide level such that when transcribed and translated the expressed protein comprises the polypeptide of interest together with the IDR moiety.

If desired, linkers may be placed between the polypeptide of interest and the IDR moiety. For example, flexible, rigid and cleavable linkers are well known in the art and are widely used in the manufacture of fusion proteins (see, e.g.: Fusion Protein Linkers: Property, Design and Functionality, Chen, X., et al. 2013, Adv. Drug Deliv. Rev., 15, 65(10), pp 1357-1369).

Standard methods for genetic engineering are well known in the art (see for example, Sambrook et al., 2001, Molecular Cloning: a Laboratory Manual, 3rd edition, Cold Spring Harbour Laboratory Press; and Current Protocols in Molecular Biology, Greene Publishing and Wiley-Interscience, New York (1995)), as are methods for protein expression and purification.

Other means by which an IDR moiety may be tagged to a macromolecule or polypeptide of interest is by one or more covalent bonds or by an affinity interaction.

The IDR moiety can be tagged to a polypeptide in any suitable orientation, such as at the N-terminus of the polypeptide of interest, at the C-terminus of the polypeptide of interest, or the polypeptide of interest may comprise an IDR moiety at both its N-terminus and C-terminus, or at any amino acid position along the length of the polypeptide.

Peptides/oligopeptides/polypeptides/proteins may be attached/tethered conjugated to other macromolecules, including other peptides/oligopeptides/polypeptides/proteins, by the use of methods very known in this technical field.

One such method is "click chemistry". The term "click chemistry" is typically used to describe the reaction of an azide with an alkyne resulting in a 1,5-disubstituted 1,2,3-triazole in the presence of a copper catalyst. Click chemistry allows peptides/oligopeptides/polypeptides/proteins to be conjugated to a vast range of other macromolecules including other peptides/oligopeptides/polypeptides/proteins, as well as e.g. carbohydrates, nucleic acids, polymers, drugs, aptamers, hydrogels etc. The method is also referred to as "CuAAC" (Cu catalyzed alkyne azide cycloaddition) (see e.g. "Click" reactions: a versatile toolbox for the synthesis of peptide-conjugates. Tang, W. et al., 2014, Chem. Soc. Rev., 43, pp 7013-7039).

Many other linker/crosslinker chemistries are available to conjugate peptides/oligopeptides/polypeptides/proteins to other macromolecules, such as crosslinkers which contain maleimide, sulfhydryl reactive groups or succinimidyl esters (often referred to as NHS esters), which react with amines. For example, succinimides can be used to form covalent bonds between proteins or peptides and plastics materials.

Standard chemistries can be used which are commonly employed to create conjugates between polypeptides and non-polypeptide molecules, such as chemistries to create antibody-drug conjugates. Many such techniques are well known in this technical field.

Affinity-based interactions can also be employed. For example, an amino acid sequence consisting of or comprising one or more functional intrinsically disordered regions may be attached/tethered to a macromolecule or polypeptide of interest by an affinity-based interaction, such as streptavidin-biotin, receptor-ligand interaction etc.

Multivalent Metal Cations for IDR Amino Acid Sequence Function

When IDR-macromolecules or IDR-polypeptides, as described and defined herein, are used in in vitro biochemical reactions, the in vitro biochemical reaction buffer preferably contains multivalent metal cations, preferably divalent metal cations.

The presence of multivalent/divalent metal cations in the reaction buffer helps to facilitate and enhance liquid-liquid demixing leading to phase separation in the in vitro biochemical reaction milieu mediated/caused by an IDR-macromolecule or an IDR-polypeptide.

The functional capability of a divalent metal cation to enhance phase separation in an in vitro biochemical reaction milieu mediated/caused by an IDR-macromolecule or IDR-polypeptide can readily be established, such as by techniques disclosed and defined herein. In particular, such functional capability can be established by the ability of the multivalent/divalent metal cation to induce the formation of globular foci or particles, as further described and defined herein, in the in vitro biochemical reaction milieu in an IDR-dependent manner, for example as determined by assays described herein.

The use of a divalent metal cation in promoting/enhancing IDR-dependent liquid-liquid demixing leading to phase separation is preferred. However, functional equivalents of any multivalent or any divalent metal cation are envisaged. A functional equivalent of a multivalent/divalent metal cation as described herein is any agent that may substitute for a divalent metal cation in promoting IDR-dependent liquid-liquid demixing leading to phase separation in an in vitro biochemical reaction milieu, for example as determined by assays described herein.

Any suitable multivalent/divalent metal cation may be used, either as a single agent or combination of agents and optionally in the presence of a chelating agent such as ethylenediaminetetraacetic acid (EDTA), ethylene glycol-bis(O-aminoethyl ether)-N,N,N',N'-tetraacetic acid (EGTA) or nitriloacetic acid (NTA).

The divalent metal cation may be $Mg^{2+}$, $Mn^{2+}$, $Ca^{2+}$, $Co^{2+}$, $Ni^{2+}$ or $Cu^{2+}$. Any of these cations may be used as a single agent, or any combination of cations may be used. Preferably they are used as single agents. Preferred divalent metal cations are $Mg^{2+}$ $Mn^{2+}$ and $Ca^{2+}$.

The specific multivalent/divalent metal cation which achieves optimal results in promoting IDR-mediated phase separation in an in vitro biochemical reaction milieu, as well as the specific concentration of the multivalent/divalent metal cation used may depend upon the specific intrinsically disordered region amino acid sequence which is used to tag the macromolecule or polypeptide of interest. The optimal multivalent/divalent metal cation and optimal concentration can be established empirically using routine tests. Phase separation assays as described further herein may be used for this purpose.

Preferred concentrations ranges of the multivalent/divalent metal cations are from about 300 μM to about 100 mM, from about 300 μM to about 50 mM, from about 400 μM to about 50 mM, from about 400 μM to about 20 mM, from about 400 μM to about 30 mM, from about 500 μM to about 10 mM, from about 500 μM to about 25 mM and from about 1 mM to about 35 mM.

An in vitro biochemical reaction buffer may contain $Mg^{2+}$ ions. A preferred concentration range is from about 300 μM to about 100 mM, more preferably from about 400 μM to about 50 mM, yet more preferably from about 500 μM to about 40 mM, even more preferably from about 25 mM to about 35 mM, such as 33 mM. Preferably the buffer contains MgOAc at the indicated concentrations.

An in vitro biochemical reaction buffer may contain $Ca^{2+}$ ions. A preferred concentration range is from about 300 μM to about 100 mM, more preferably from about 400 μM to about 50 mM, yet more preferably from about 1 mM to about 40 mM, even more preferably from about 25 mM to about 35 mM, such as 33 mM. Preferably the buffer contains $CaCl_2$ at the indicated concentrations.

An in vitro biochemical reaction buffer may contain $Mn^{2+}$ ions. A preferred concentration range is from about 300 μM to about 50 mM, more preferably from about 400 μM to about 50 mM, yet more preferably from about 500 μM to about 40 mM, even more preferably from about 25 mM to about 35 mM, such as 33 mM. Preferably the buffer contains $MnCl_2$ at the indicated concentrations.

Recombinase Polymerase Amplification (RPA)

Recombinase polymerase amplification (RPA) is a method for isothermal amplification of nucleic acids. In general, in a first step of RPA, a recombinase agent is contacted with first and second nucleic acid primers and a recombinase loading protein to form first and second nucleoprotein primers. In general, in a second step, the first and second nucleoprotein primers are contacted with a double stranded template nucleic acid to form a first double stranded structure at a first portion of the first strand of the template nucleic acid, and a second double stranded structure at a second portion of the second strand of the template nucleic acid such that the 3' ends of the first nucleic acid primer and the second nucleic acid primer are orientated towards each other on a given nucleic acid molecule. In general, in a third step, the 3' end of the first and the second nucleoprotein primers are extended by polymerase to generate first and second double stranded nucleic acids, and first and second displaced single strands of nucleic acid. A single stranded stabilizing agent is employed to stabilize the first and second displaced single strands of nucleic acid. Generally, the second and third steps can be repeated until a desired degree of amplification is reached.

RPA methods are disclosed extensively, e.g., in U.S. Pat. Nos. 7,270,981; 7,399,590; 7,666,598; 7,435,561 and International Patent Application Publication No. WO2010/141940. In addition, for a comprehensive recent review see: Review: a comprehensive summary of a decade development of the recombinase polymerase amplification, Li, J. et al., 2019, Analyst, 144, pp 31-67).

Recombinase Agent

RPA methods, including those of the present invention, use a recombinase agent.

Any of the one or more IDR-polypeptides of the present invention may be attached/tethered/tagged to any recombinase agent.

A recombinase agent is a molecule, typically an enzyme, that can coat a single stranded nucleic acid, typically DNA (ssDNA) to form a nucleoprotein filament. Such filaments can then "scan" a double stranded nucleic acid molecule, typically DNA (dsDNA) for regions of sequence homology/complementarity. When complementary sequences are located, the nucleoprotein filament (comprising the recombinase agent) strand invades the double stranded nucleic acid molecule creating a short hybrid and a displaced strand bubble known as a D-loop.

Any suitable recombinase agent may be used in the RPA methods described herein, and may be tagged with any of the IDR amino acid sequences as described herein.

The recombinase agent may originate from a prokaryotic, eukaryotic or viral organism.

The recombinase agent may be RecA, UvsX, RadA, RadB, Rad 51 or any functional variant, analoge, homologe or derivative of any of these proteins.

Any combination of these proteins may be used.

Suitable recombinase agents include the E. coli RecA protein, the T4 UvsX protein, or any homologous protein or protein complex from any phyla.

Eukaryotic RecA homologues are generally named Rad51 after the first member of this group to be identified. Other non-homologous recombinase agents may be utilized in place of RecA, for example RecT or RecO.

Exemplary recombinase agents include RecA and UvsX, and fragments or mutants thereof and combinations thereof. The RecA and UvsX proteins can be obtained from any species. RecA and UvsX fragments or mutant proteins can also be produced using the available RecA and UvsS protein and nucleic acids sequences, and molecular biology techniques. Exemplary UvsX proteins include those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.81, Rb49, phage Rb3, and phage LZ2. Additional exemplary recombinase agents include archaebacterial RADA and RADB proteins and eukaryotic (e.g., plant, mammal, and fungal) Rad51 proteins (e.g., RAD51, RAD51B, RAD51C, RAD51D, DMC1, XRCC2, XRCC3, and recA).

The recombinase agent is preferably UvsX, T4 UvsX, T6 UvsX, RB18 UvsX, *E. coli* phage wV7 UvsX, *Shigella* phage CB8 UvsX, *Shigella* phage Shfl2 UvsX, *E. coli* phage AR1 UvsX, phage vB_EcoM_G4507 UvsX, *Shigella* phage SHFML-II UvsX, *Escherichia* phage vB_EcoM_DalCa UvsX, *E. coli* RecA, *E. coli* RadA, *E. coli* RadB, *E. coli* Rad 51 or any functional variant, analog, homolog or derivative thereof or any combination thereof. A particularly preferred recombinase agent is *Escherichia* phage vB_EcoM_DalCa UvsX.

The recombinase agent may also comprise a C-terminal deletion of acidic residues to improve its activity.

Any functional variants, analogs, homologs or derivatives of the recombinase agent above may also function itself as a recombinase agent and these functional variants, analogs, homologs or derivatives are also contemplated as a recombinase agent to be used in the processes described and defined herein.

For example, a small peptide from RecA, has been shown to retain some aspects of the recombination properties of RecA. This peptide comprises residues 193 to 212 of *E. coli* RecA and can mediate pairing of single stranded oligonucleotides.

The recombinase agent (e.g., UvsX) may be a mutant or hybrid recombinase agent. Mutant forms of UvsX are described in U.S. Pat. No. 8,071,308. The mutant UvsX may be an Rb69 UvsX that includes at least one mutation in the Rb69 UvsX amino acid sequence, wherein the mutation is selected from the group consisting of (a) an amino acid which is not histidine at position 64, a serine at position 64, the addition of one or more glutamic acid residues at the C-terminus, the addition of one or more aspartic acid residues at the C-terminus, and a combination thereof.

The mutant UvsX may be a T6 UvsX having at least one mutation in the T6 UvsX amino acid sequence, wherein the mutation is selected from the group consisting of (a) an amino acid which is not histidine at position 66; (b) a serine at position 66; (c) the addition of one or more glutamic acid residues at the C-terminus; (d) the addition of one or more aspartic acid residues at the C-terminus; and (e) a combination thereof. Where a hybrid recombinase agent is used, the hybrid protein may, for example, be a UvsX protein that includes at least one region that includes an amino acid sequence derived from a different UvsX species. The region may be, for example, the DNA-binding loop-2 region of UvsX.

If desired, the recombinase agent may be a temperature-sensitive (referred to herein as "ts") recombinase agent. If a ts recombinase agent is used, the RPA reaction may be started at one temperature (the permissive temperature) and terminated at another temperature (the non-permissive temperature). Combinations of permissive temperatures may be, for example 25° C./30° C., 30° C./37° C., 37° C./42° C. and the like. The ts protein may be reversible. A reversible ts protein's activity is restored when it is shifted from the non-permissive temperature to the permissive temperature.

While any recombinase agent concentration may be used, preferred recombinase concentrations may be, for example, in the range of 0.2-12 µM, 6-12 µM, 4-12 µM and 4-6 µM, preferably about 5 µM, more preferably about 4.8 µM.

Recombinase agents generally require the presence of ATP, ATPγS, or other nucleoside triphosphates or their analogs. It is preferred that recombinase agents are used in a reaction environment in which regeneration of targeting sites can occur shortly following a round of D-loop stimulated synthesis. Completed recombination events involving recombinase disassembly will avoid a stalling of amplification or very inefficient linear amplification of ssDNA caused by oscillating single sided synthesis from one end to the other.

Exemplary UvsX recombinase agents tagged with amino acid tag sequences comprising intrinsically disordered regions are set out in Table 21 below.

TABLE 21

| Name of protein | SEQ ID NO. | Amino acid sequence |
|---|---|---|
| UvsX (7His) | 44 | MSIADLKSRLIKASTSKMTAELTTSKFFNEKDVIRTKIPMLNIAISGAIDGGMQSGLTIFAGPSKSFKSNMSLTMVAAYLNKYPDAICLFYDSEFGITPAYLKSMGVDPERVIHTPIQSVEQLKIDMVNQLETIERGEKVIVFIDSIGNMASKKETEDALNEKSVADMTRAKSLKSLFRIVTPYFSIKNIPCVAVNHTIETIEMFSKTVMTGGTGVMYSADTVFIIGKRQIKDGSDLQGYQFVLNVEKSRTVKEKSKFFIDVKFDGGIDPYSGLLDMALELGFVVKPKNGWYAREFLDEETGEMIREEKSWRAKDTNCTTFWGPLFKHQPFRDAIKRAYQLGAIDSNEIVEAEVDELINSKVEKFKSPESKSKSAADLETDLEQLSDMEEFNEHHHHHHH |
| UvsX-fib-1 | 45 | MSIADLKSRLIKASTSKMTAELTTSKFFNEKDVIRTKIPMLNIAISGAIDGGMQSGLTIFAGPSKSFKSNMSLTMVAAYLNKYPDAICLFYDSEFGITPAYLKSMGVDPERVIHTPIQSVEQLKIDMVNQLETIERGEKVIVFIDSIGNMASKKETEDALNEKSVADMTRAKSLKSLFRIVTPYFSIKNIPCVAVNHTIETIEMFSKTVMTGGTGVMYSADTVFIIGKRQIKDGSDLQGYQFVLNVEKSRTVKEKSKFFIDVKFDGGIDPYSGLLDMALELGFVVKPKNGWYAREFLDEETGEMIREEKSWRAKDTNCTTFWGPLFKHQPFRDAIKRAYQLGAIDSNEIVEAEVDELINSKVEKFKSPESKSKSAADLETDLEQLSDMEEFNEPGFSPRGGGFGGRGGFGDRGGRGGRGGFGGGRGRGGGFRGRGRHHHHHHH |
| UvsX-fib-2 | 46 | MSIADLKSRLIKASTSKMTAELTTSKFFNEKDVIRTKIPMLNIAISGAIDGGMQSGLTIFAGPSKSFKSNMSLTMVAAYLNKYPDAICLFYDSEFGITPAYLKSMGVDPERVIHTPIQSVEQLKIDMVNQLETIERGEKVIVFIDSIGNMASKKETEDALNEKSVADMTRAKSLKSLFRIVTPYFSIKNIPCVAVNHTIETIEMFSKTVMTGGTGVMYSADTVFIIGKRQIKDGSDLQGYQFVLNVEKSRTVKEKSKFFIDVKFDGGIDPYSGLLDMALELGFVVKPKNGWYAREFLDEETGEMIREEKSWRAKDTNCTTFWGPLFKHQPFRDAIKRAYQLGAIDSNEIVEAEVDELINSKVEKFKSPESKSKSAADLETDLEQLSDMEEFNEPGFSPRGGGFGGRGGFGDRGGRGGRGGFGGGRGRGGVEHHHHHH |
| UvsX-fib-3 | 47 | MSIADLKSRLIKASTSKMTAELTTSKFFNEKDVIRTKIPMLNIAISGAIDGGMQSGLTIFAGPSKSFKSNMSLTMVAAYLNKYPDAICLFYDSEFGITPAYLKSMGVDPERVIHTPIQSVEQLKIDMVNQLETIERGEKVIVFIDSIGNMASKKETEDALNEKSVADMTRAKSLKSLFRIVTPYFSIKNIPCVAVNHTIETIEMFSKTVMTGGTGVMYSADTVFIIGKRQIKDGSDLQGYQFVLNVEKSRTVKEKSKFFIDVKFDGGIDPYSGLLDMALELGFVVKPKNGWYAREFLDEETGEMIREEKSWRAKDTNCTTFWGPLFKHQPFRDAIKRAYQLGAIDSNEIVEAEVDELINSKVEKFKSPESKSKSAADLETDLEQLSDMEEFNEPGFSPRGGGFGGRGGFGDRGGRGGRGGVEHHHHHH |
| UvsX-fib-4 | 48 | MSIADLKSRLIKASTSKMTAELTTSKFFNEKDVIRTKIPMLNIAISGAIDGGMQSGLTIFAGPSKSFKSNMSLTMVAAYLNKYPDAICLFYDSEFGITPAYLKSMGVDPERVIHTPIQSVEQLKIDMVNQLETIERGEKVIVFIDSIGNMASKKETEDALNEKSVADMTRAKSLKSLFRIVTPYFSIKNIPCVAVNHTIETIEMFSKTVMTGGTGVMYSADTVFIIGKRQIKDGSDLQGYQFVLNVEKSRTVKEKSKFFIDVKFDGGIDPYSGLLDMALELGFVVKPKNGWYAREFLDEETGEMIREEKSWRAKDTNCTTFWGPLFKHQPFRDAIKRAYQLGAIDSNEIVEAEVDELINSKVEKFKSPESKSKSAADLETDLEQLSDMEEFNEPGFSPRGGGFGGRGGVEHHHHHH |
| UvsX-HNRNPA1 | 49 | MSIADLKSRLIKASTSKMTAELTTSKFFNEKDVIRTKIPMLNIAISGAIDGGMQSGLTIFAGPSKSFKSNMSLTMVAAYLNKYPDAICLFYDSEFGITPAYLKSMGVDPERVIHTPIQSVEQLKIDMVNQLETIERGEKVIVFIDSIGNMASKKETEDALNEKSVADMTRAKSLKSLFRIVTPYFSIKNIPCVAVNHTIETIEMFSKTVMTGGTGVMYSADTVFIIGKRQIKDGSDLQGYQFVLNVEKSRTVKEKSKFFIDVKFDGGIDPYSGLLDMALELGFVVKPKNGWYAREFLDEE |

TABLE 21-continued

| Name of protein | SEQ ID NO. | Amino acid sequence |
|---|---|---|
| | | TGEMIREEKSWRAKDTNCTTFWGPLFKHQPFRDAIKR AYQLGAIDSNEIVEAEVDELINSKVEKFKSPESKSKSA ADLETDLEQLSDMEEFNEASASSSQRGRSGSGNFGGG RGGGFGGNDNFGRGGNFSGRGGFGGSRGGGGYGGS GDGYNGFGNDGSNFGGGGSYNDFGNYNNQSSNFGP MKGGNFGGRSSGPYGGGGQYFAKPQNQGGYGVSSSS SSYGSGRRFHHHHHHH |
| UvsX-DDX | 50 | MSIADLKSRLIKASTSKMTAELTTSKFFNEKDVIRTKIP MLNIAISGAIDGGMQSGLTIFAGPSKSFKSNMSLTMV AAYLNKYPDAICLFYDSEFGITPAYLKSMGVDPERVI HTPIQSVEQLKIDMVNQLETIERGEKVIVFIDSIGNMAS KKETEDALNEKSVADMTRAKSLKSLFRIVTPYFSIKNI PCVAVNHTIETIEMFSKTVMTGGTGVMYSADTVFIIG KRQIKDGSDLQGYQFVLNVEKSRTVKEKSKFFIDVKF DGGIDPYSGLLDMALELGFVVKPKNGWYAREFLDEE TGEMIREEKSWRAKDTNCTTFWGPLFKHQPFRDAIKR AYQLGAIDSNEIVEAEVDELINSKVEKFKSPESKSKSA ADLETDLEQLSDMEEFNEMGDEDWEAEINPHMSSYV PIFEKDRYSGENGDNFNRTPASSSEMDDGPSRRDHFM KSGFASGRNFGNRDAGECNKRDNTSTMGGFGVGKSF GNRGFSNSRFEDGDSSGFWRESSNDCEDNPTRNRGFS KRGGYRDGNNSEASGPYRRGGRGSFRGCRGGFGLGS PNNDLDPDECMQRTGGLFGSRRPVLSGTGNGDTSQS RSGSGSERGGYKGLNEEVITGSGKNSWKSEAEGGESS DTQHHHHHHH |
| UvsX addPolCTD | 51 | MSIADLKSRLIKASTSKMTAELTTSKFFNEKDVIRTKIP MLNIAISGAIDGGMQSGLTIFAGPSKSFKSNMSLTMV AAYLNKYPDAICLFYDSEFGITPAYLKSMGVDPERVI HTPIQSVEQLKIDMVNQLETIERGEKVIVFIDSIGNMAS KKETEDALNEKSVADMTRAKSLKSLFRIVTPYFSIKNI PCVAVNHTIETIEMFSKTVMTGGTGVMYSADTVFIIG KRQIKDGSDLQGYQFVLNVEKSRTVKEKSKFFIDVKF DGGIDPYSGLLDMALELGFVVKPKNGWYAREFLDEE TGEMIREEKSWRAKDTNCTTFWGPLFKHQPFRDAIKR AYQLGAIDSNEIVEAEVDELINSKVEKFKSPESKSKSA ADLETDLEQLSDMEEFNEHHHHHHHFEFSPFGAYGE APTSPGFGVSSPGFSPTSPTYSPTSPAYSPTSPSYPTSP SYSPTSPSYSPTSPSYSPTSPSYSPTSPSYSPTSPSYPTS PSYSPTSPSYSPTSPSYSPTSPSYSPTSPSYSPTSPSYSPT SPSYSPTSPAYSPTSPSYSPTSPSYSPTSPSYSPTSPSYSP TSPNYSPTSPSYSPTSPGYSPGSPAYSPKQDEQTAALE HHHHHH |
| UvsX-fusPolII | 52 | MSIADLKSRLIKASTSKMTAELTTSKFFNEKDVIRTKIP MLNIAISGAIDGGMQSGLTIFAGPSKSFKSNMSLTMV AAYLNKYPDAICLFYDSEFGITPAYLKSMGVDPERVI HTPIQSVEQLKIDMVNQLETIERGEKVIVFIDSIGNMAS KKETEDALNEKSVADMTRAKSLKSLFRIVTPYFSIKNI PCVAVNHTIETIEMFSKTVMTGGTGVMYSADTVFIIG KRQIKDGSDLQGYQFVLNVEKSRTVKEKSKFFIDVKF DGGIDPYSGLLDMALELGFVVKPKNGWYAREFLDEE TGEMIREEKSWRAKDTNCTTFWGPLFKHQPFRDAIKR AYQLGAIDSNEIVEAEVDELINSKVEKFKSPESKSKSA ADLETDLEQLSDMEEFNETSPSYSPTSPSYSPTSPGYSP TSPAYSPTSPTYSPTSPTYSPHHHHHHH |
| UvsX-PCF11 | 53 | MSIADLKSRLIKASTSKMTAELTTSKFFNEKDVIRTKIP MLNIAISGAIDGGMQSGLTIFAGPSKSFKSNMSLTMV AAYLNKYPDAICLFYDSEFGITPAYLKSMGVDPERVI HTPIQSVEQLKIDMVNQLETIERGEKVIVFIDSIGNMAS KKETEDALNEKSVADMTRAKSLKSLFRIVTPYFSIKNI PCVAVNHTIETIEMFSKTVMTGGTGVMYSADTVFIIG KRQIKDGSDLQGYQFVLNVEKSRTVKEKSKFFIDVKF DGGIDPYSGLLDMALELGFVVKPKNGWYAREFLDEE TGEMIREEKSWRAKDTNCTTFWGPLFKHQPFRDAIKR AYQLGAIDSNEIVEAEVDELINSKVEKFKSPESKSKSA ADLETDLEQLSDMEEFNEQVQMQLRQVFSQDQQVLQ ERMRYHELQQQQQQQYHETKDMVGSYTQNSNSAIPL FGNNSDTTNQQNSHHHHHHH |
| UvsX-Sup | 54 | MSIADLKSRLIKASTSKMTAELTTSKFFNEKDVIRTKIP MLNIAISGAIDGGMQSGLTIFAGPSKSFKSNMSLTMV AAYLNKYPDAICLFYDSEFGITPAYLKSMGVDPERVI HTPIQSVEQLKIDMVNQLETIERGEKVIVFIDSIGNMAS KKETEDALNEKSVADMTRAKSLKSLFRIVTPYFSIKNI |

TABLE 21-continued

| Name of protein | SEQ ID NO. | Amino acid sequence |
|---|---|---|
| | | PCVAVNHTIETIEMFSKTVMTGGTGVMYSADTVFIIG KRQIKDGSDLQGYQFVLNVEKSRTVKEKSKFFIDVKF DGGIDPYSGLLDMALELGFVVKPKNGWYAREFLDEE TGEMIREEKSWRAKDTNCTTFWGPLFKHQPFRDAIKR AYQLGAIDSNEIVEAEVDELINSKVEKFKSPESKSKSA ADLETDLEQLSDMEEFNEMSDSNQGNNQQNYQQYSQ NGNQQQGNNRYQGYQAYNAQAQPAGGYYQNYQGY SGYQQGGYQQYQYNPQGGYQQYNPQGGYQQYNPQ GGYQQQFNPQGGRGNYKNFNYNNNLQGYQHHHHH HH |
| UvsX-DoubleX | 55 | MSIADLKSRLIKASTSKMTAELTTSKFFNEKDVIRTKIP MLNIAISGAIDGGMQSGLTIFAGPSKSFKSNMSLTMV AAYLNKYPDAICLFYDSEFGITPAYLKSMGVDPERVI HTPIQSVEQLKIDMVNQLETIERGEKVIVFIDSIGNMAS KKETEDALNEKSVADMTRAKSLKSLFRIVTPYFSIKNI PCVAVNHTIETIEMFSKTVMTGGTGVMYSADTVFIIG KRQIKDGSDLQGYQFVLNVEKSRTVKEKSKFFIDVKF DGGIDPYSGLLDMALELGFVVKPKNGWYAREFLDEE TGEMIREEKSWRAKDTNCTTFWGPLFKHQPFRDAIKR AYQLGAIDSNEIVEAEVDELINSKVEKFKSPESKSKSA ADLETDLEQLSDMEEFNE HHHHHHHFEFEIVEAEVDELINSKVEKFKSPESKSKSA ADLETDLEQLSDMEEFNEIVEAEVDELINSKVEKFKSP ESKSKSAADLETDLEQLSDMEEFNHHHHHH |
| Superpositive | 56 | MSIADLKSRLIKASTSKMTAELTTSKFFNEKDVIRTKIP MLNIAISGAIDGGMQSGLTIFAGPSKSFKSNMSLTMV AAYLNKYPDAICLFYDSEFGITPAYLKSMGVDPERVI HTPIQSVEQLKIDMVNQLETIERGEKVIVFIDSIGNMAS KKETEDALNEKSVADMTRAKSLKSLFRIVTPYFSIKNI PCVAVNHTIETIEMFSKTVMTGGTGVMYSADTVFIIG KRQIKDGSDLQGYQFVLNVEKSRTVKEKSKFFIDVKF DGGIDPYSGLLDMALELGFVVKPKNGWYAREFLDEE TGEMIREEKSWRAKDTNCTTFWGPLFKHQPFRDAIKR AYQLGAIDSNRIVKAKVKRLINSKVKKFKSPKSKSKS AAKLKTKLKQLSKMKKFNKIVKAKVKKLINSKVRKF KSPKSKSKSAAKLKTKLKQLSKMKEFNHHHHHH |
| Supernegative | 57 | MSIADLKSRLIKASTSKMTAELTTSKFFNEKDVIRTKIP MLNIAISGAIDGGMQSGLTIFAGPSKSFKSNMSLTMV AAYLNKYPDAICLFYDSEFGITPAYLKSMGVDPERVI HTPIQSVEQLKIDMVNQLETIERGEKVIVFIDSIGNMAS KKETEDALNEKSVADMTRAKSLKSLFRIVTPYFSIKNI PCVAVNHTIETIEMFSKTVMTGGTGVMYSADTVFIIG KRQIKDGSDLQGYQFVLNVEKSRTVKEKSKFFIDVKF DGGIDPYSGLLDMALELGFVVKPKNGWYAREFLDEE TGEMIREEKSWRAKDTNCTTFWGPLFKHQPFRDAIKR AYQLGAIDSNEIVEAEVDELINSEVEEFDSPESDSDEA ADLETDLEQLSDMEEFNEIVEAEVDELINSEVEDFDSP ESDSDEAADLETDLEQLSDMEEFNHHHHHH |
| UvsX His2 | 58 | MSIADLKSRLIKASTSKMTAELTTSKFFNEKDVIRTKIP MLNIAISGAIDGGMQSGLTIFAGPSKSFKSNMSLTMV AAYLNKYPDAICLFYDSEFGITPAYLKSMGVDPERVI HTPIQSVEQLKIDMVNQLETIERGEKVIVFIDSIGNMAS KKETEDALNEKSVADMTRAKSLKSLFRIVTPYFSIKNI PCVAVNHTIETIEMFSKTVMTGGTGVMYSADTVFIIG KRQIKDGSDLQGYQFVLNVEKSRTVKEKSKFFIDVKF DGGIDPYSGLLDMALELGFVVKPKNGWYAREFLDEE TGEMIREEKSWRAKDTNCTTFWGPLFKHQPFRDAIKR AYQLGAIDSNEIVEAEVDELINSKVEKFKSPESKSKSA ADLETDLEQLSDMEEFNEAGHHHHHPAHHPLSQSS GHHHHHHHHHQGYGGSG |
| UvsX + PCF + His2 | 59 | MSIADLKSRLIKASTSKMTAELTTSKFFNEKDVIRTKIP MLNIAISGAIDGGMQSGLTIFAGPSKSFKSNMSLTMV AAYLNKYPDAICLFYDSEFGITPAYLKSMGVDPERVI HTPIQSVEQLKIDMVNQLETIERGEKVIVFIDSIGNMAS KKETEDALNEKSVADMTRAKSLKSLFRIVTPYFSIKNI PCVAVNHTIETIEMFSKTVMTGGTGVMYSADTVFIIG KRQIKDGSDLQGYQFVLNVEKSRTVKEKSKFFIDVKF DGGIDPYSGLLDMALELGFVVKPKNGWYAREFLDEE TGEMIREEKSWRAKDTNCTTFWGPLFKHQPFRDAIKR AYQLGAIDSNEIVEAEVDELINSKVEKFKSPESKSKSA ADLETDLEQLSDMEEFNEQVQMQLRQVFSQDQQVLQ ERMRYHELQQQQQQQYHETKDMVGSYTQNSNSAIPL |

TABLE 21-continued

| Name of protein | SEQ ID NO. | Amino acid sequence |
|---|---|---|
| | | FGNNSDTTNQQNSAGHHHHHPHAHHPLSQSSGHHHH HHHHHHQGYGGSG |

Recombinase Loading Protein

RPA methods, including those of the present invention, may additionally include/use a recombinase loading protein.

Any suitable recombinase loading protein may be used in the RPA methods described herein.

Any of the one or more IDR-polypeptides of the present invention may be attached/tethered/tagged to any recombinase loading protein.

The recombinase loading protein may originate from a prokaryotic, viral or eukaryotic organism. Exemplary recombinase loading proteins include *E. coli* RecO, *E. coli* RecR, UvsY, and mutants or fragments thereof, or combinations thereof. Exemplary UvsY proteins include those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2.

Preferred recombinase loading proteins are UvsY, *E. coli* RecO, *E. coli* RecR or any functional variant, analoge, homologe or derivative of any of these proteins. A particularly preferred UvsY recombinase loading protein is *Escherichia* phage STO UvsY.

Any combination of any of these proteins may be used.

Preferred concentrations of these proteins is between 0.1-24 µM, 6-24 µM, 4-24 µM and 4-12 µM, preferably about 10 µM, more preferably about 8.6 µM. The recombinase loading protein may be present at between about 0.5 to about 2 times the micromolar concentration of the recombinase agent.

Exemplary UvsY recombinase loading proteins tagged with amino acid tag sequences comprising intrinsically disordered regions are set out in Table 22 below.

TABLE 22

| Name of protein | SEQ ID NO. | Amino acid sequence |
|---|---|---|
| UvsY [Phage ST0] | 60 | MHHHHHHHMKLEDLQEELDADLAIDMSKLQYETAN NVKLYSKWLRKHSFIRKEMLRIETQKKTALKARLDY YSGRGDGDEFSMDRYEKSEMKTVLAADKDVLKIETT LQYWGILLEFCSGALDAVKSRSFALKHIQDMREFEAG Q |
| UvsY C-Pol CTD | 61 | MHHHHHHHHKLEDLQEELDADLAIDMSKLQYETAN NVKLYSKWLRKHSFIRKEMLRIETQKKTALKARLDY YSGRGDGDEFSMDRYEKSEMKTVLAADKDVLKIETT LQYWGILLEFCSGALDAVKSRSFALKHIQDMREFEAG QSGSGSGPTSPSYSPTSPSYSPYSPAYS |
| UvsY fib[short] | 62 | MHHHHHHHHKLEDLQEELDADLAIDMSKLQYETAN NVKLYSKWLRKHSFIRKEMLRIETQKKTALKARLDY YSGRGDGDEFSMDRYEKSEMKTVLAADKDVLKIETT LQYWGILLEFCSGALDAVKSRSFALKHIQDMREFEAG QSGSGSGRGGGFGGRGGFGDRGGRGGRGGFGG |
| UvsY Sup1 | 63 | MHHHHHHHHKLEDLQEELDADLAIDMSKLQYETAN NVKLYSKWLRKHSFIRKEMLRIETQKKTALKARLDY YSGRGDGDEFSMDRYEKSEMKTVLAADKDVLKIETT LQYWGILLEFCSGALDAVKSRSFALKHIQDMREFEAG QSGSGYNPQGGYQQNNL |
| UvsY Sup1 HIS2 | 64 | MAGHHHHHPHAHHPLSQSSGHHHHHHHHHQGYG GSGKLEDLQEELDADLAIDMSKLQYETANNVKLYSK WLRKHSFIRKEMLRIETQKKTALKARLDYYSGRGDG DEFSMDRYEKSEMKTVLAADKDVLKIETTLQYWGIL LEFCSGALDAVKSRSFALKHIQDMREFEAGQSGSGYN PQGGYQQNNLQ |

Single Strand Stabilizing Agent

RPA methods, including those of the present invention, use a single strand stabilizing agent.

Any suitable single strand stabilizing agent (single stranded DNA binding protein) may be used in the RPA methods described herein.

Any of the one or more IDR-polypeptides thereof of the present invention may be attached/tethered/tagged to any single strand stabilizing agent.

A single strand stabilizing agent is used to stabilize nucleic acids during the various exchange reactions that occur during the RPA reaction. In particular a single strand stabilizing agent is used to stabilize recombinase/ssDNA nucleoprotein filaments.

A single strand stabilizing agent can be derived or obtained from any species, e.g., from a prokaryotic, viral or eukaryotic species.

Single strand stabilizing agents include single stranded DNA binding proteins from *E. coli* and those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.81, Rb49, phage Rb3, and phage LZ2. Additional examples of single strand stabilizing agents include *A. denitrificans* Alide_2047, *Burkholderia thailandensis* BthaB_33951, *Prevotella pollens* HMPREF9144_0124, and eukaryotic single stranded DNA binding protein replication protein A.

Preferred single strand stabilizing agents are selected from the group consisting of Gp32, *E. coli* SSB protein, phage T4 Gp32 protein, phage Rb69 Gp32, phage vB_EcoM_NBG1 Gp32, and derivatives thereof and any combination thereof. Particularly preferred single strand stabilizing agents are Gp32 and in particular phage vB_EcoM_NBG1 Gp32.

Any combination of any of these proteins may be used.

One preferred concentration of the single strand stabilizing agent is between approximately 5-30 µM, such as approximately 8.6 µM, preferably between approximately 15-25 µM, more preferably approximately 20 µM.

Exemplary Gp32 single strand stabilizing agents tagged with amino acid tag sequences comprising intrinsically disordered regions are set out in Table 23 below.

TABLE 23

| Name of protein | SEQ ID NO. | Amino acid sequence |
| --- | --- | --- |
| Gp32 (7His) from phage vB | 65 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLHHHHHHH |
| Gp32Super +ve | 66 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVAKKVASKLKFKKKMEAFSSAKTKKKFMSS SSSKKSKLKKLLAGLMEAFSSAKTKKKFMSSSSSKK SKLKKLLAGLHHHHHHH |
| Gp32Super -ve | 67 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADDVASDLDDFDDDMEAFSSADTEDDFMS SSSSDDSDLDDLLAGLMEAFSSADTEDDFMSSSSSD DSDLDDLLAGLHHHHHHH |
| Gp32-TripleXtail | 68 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADDVASEFEIVEAEVDELINSKVEKFKSPES KSKSAADLETDLEQLSDMEEFNEIVEAEVDELINSKV EKFKSPESKSKSAADLETDLEQLSDMEEFNEIVEAEV DELINSKVEKFKSPESKSKSAADLETDLEQLSDMEEF NHHHHHH |
| Gp32-fib | 69 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLPGFSPRGGGFGGRGGFGDRG GRGGRGGFGGGRGRGGGFRGRGRHHHHHHH |
| Gp32-PCF11 | 70 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK |

TABLE 23-continued

| Name of protein | SEQ ID NO. | Amino acid sequence |
|---|---|---|
| | | KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLNEQVQMQLRQVFSQDQQVL QERMRYHELQQQQQQQYHETKDMVGSYTQNSNSA IPLFGNNSDTTNQQNSHHHHHH |
| Gp32-Sup | 71 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLMSDSNQGNNQQNYQQYSQN GNQQQGNNRYQGYQAYNAQAQPAGGYYQNYQGY SGYQQGGYQQYQYNPQGGYQQYNPQGGYQQYNPQ GGYQQQFNPQGGRGNYKNFNYNNNLQGYQHHHHH HH |
| Gp32-Sup1 | 72 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLYNPQGGYQQHHHHHHH |
| Gp32-Sup2 | 73 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLYNPQGGYQQYNPQGGYQQH HHHHHH |
| Gp32-Sup3 | 74 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLYNPQGGYQQYNPQGGYQQY NPQGGYQQHHHHHHH |
| Gp32-Sup4 | 75 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLYNPQGGYQQYNPQGGYQQY NPQGGYQQYNPQGGYQQHHHHHHH |
| Gp32-DDX | 76 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLHHHHHHHFEFMGDEDWEAE INPHMSSYVPIFEKDRYSGENGDNFNRTPASSSEMDD GPSRRDHFMKSGFASGRNFGNRDAGECNKRDNTST MGGFGVGKSFGNRGFSNSRFEDGDSSGFWRESSND |

TABLE 23-continued

| Name of protein | SEQ ID NO. | Amino acid sequence |
| --- | --- | --- |
| | | CEDNPTRNRGFSKRGGYRDGNNSEASGPYRRGGRG SFRGCRGGFGLGSPNNDLDPDECMQRTGGLFGSRRP VLSGTGNGDTSQSRSGSGSERGGYKGLNEEVITGSG KNSWKSEAEGGESSDTQLEHHHHHH |
| Gp32 PolCTD | 77 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLHHHHHHHFEFSPFGAYGEAP TSPGFGVSSPGFSPTSPTYSPTSPAYSPTSPSYSPTSPS YSPTSPSYSPTSPSYSPTSPSYSPTSPSYSPTSPSYSPTS PSYSPTSPSYSPTSPSYSPTSPSYSPTSPSYSPTSPSYSP TSPSYSPTSPAYSPTSPSYSPTSPSYSPTSPSYSPTSPSY SPTSPNYSPTSPSYSPTSPGYSPGSPAYSPKQDEQLEH HHHHH |
| Gp32 HNRNPA1 | 78 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLASASSSQRGRSGSGNFGGGR GGGFGGNDNFGRGGNFSGRGGFGGSRGGGGYGGS GDGYNGFGNDGSNFGGGGSYNDFGNYNNQSSNFGP MKGGNFGGRSSGPYGGGGQYFAKPQNQGGYGVSSS SSSYGSGRRFHHHHHHH |
| Gp32 HRP1 | 79 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLGGNNGGNNMNRRGGNFGNQ GDFNQMYQNPMMGGYNPMMNPQAMTDYYQKMQ EYYQQMQHHHHHHH |
| Gp32 HRP2 | 80 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLGGNNGGNNMNRRGGNFGNQ GDFNQMYQNPMMGGYNPMMNPQAMTDYYQKMQ EYYQQMQGGNNGGNNMNRRGGNFGNQGDFNQMY QNPMMGGYNPMMNPQAMTDYYQKMQEYYQQMQ HHHHHHH |
| Gp32 HIS1 | 81 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLPQQNALHHHHGNSSHHHHH HHHHHHHGQQA |
| GP32 HIS2 | 82 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK |

TABLE 23-continued

| Name of protein | SEQ ID NO. | Amino acid sequence |
|---|---|---|
| | | VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLAGHHHHHPAHHPLSQSSGH HHHHHHHHHQGYGGSG |
| GP32 HIS3 | 83 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLAGHHHHHHHHLPHLPPPHLH HHHHPQHHLHPGSAAAVHPVQQH |
| GP32 HIS4 | 84 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLNHHASHGHHNSHHPQHHHH HHHHHHHPPPPAPQPPPPPQQQQ |
| GP32 HIS5 | 85 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLSGHHGAHHGAHHPAAAAAY EAFRGPGFAGGGGADDMGAGHHHGAHHAAHHHH AAHHHHHHHHHGGAGHGGGAGHH |
| Gp32 Mimic1 | 86 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLYDPTSPSYDPTSPSYDPTSPSY DPTSPSYDPTSPSYDPTSPSYDPTSPSHHHHHHH |
| Gp32 Mimic2 | 87 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLYSPTDPSYSPTDPSYSPTDPSY SPTDPSYSPTDPSYSPTDPSYSPTDPSHHHHHHH |
| Gp32 short pol ctd | 88 | MFKRKSTADLAAQMAKLNGNKGFSSEDKGEWKLK LDASGNGQAVIRFLPAKTDDALPFTILVNHGFKKNG KWYIETCSSTHGDYDSCPVCQYISKNDLYNTNKTEY SQLKRKTSYWANILVVKDPQAPDNEGKVFKYRFGK KIWDKINAMIAVDTEMGETPVDVTCPWEGANFVLK VKQVSGFSNYDESKFLNQSAIPNIDDESFQKELFEQM VDLSEMTSKDKFKSFEELNTKFNQVLGTAALGGAA AAAASVADKVASDLDDFDKDMEAFSSAKTEDDFMS SSSSDDSDLDDLLAGLTSPSYSPTSPSYSPTSPGYSPT SPAYSPTSPTYSPTSPTYSPHHHHHHH |

Polymerase

RPA methods, including those of the present invention, use a polymerase.

Any suitable polymerase may be used in the methods described herein.

Any of the one or more IDR-polypeptides of the present invention may be attached/tethered/tagged to any suitable polymerase.

For the synthesis or amplification of DNA, DNA polymerase are preferably used.

One advantage of the RPA reaction is that there is no limit on the type of polymerase that can be used. For example, eukaryotic, prokaryotic and bacteriophage polymerases can be used.

The DNA polymerase may be a eukaryotic polymerase. Examples of eukaryotic polymerases that may be used include pol-α, pol-β, pol-δ, pol-ε or any functional variant, analoge, homologe or derivative thereof and any combination thereof.

The DNA polymerase may be a prokaryotic polymerase. Examples of prokaryotic polymerases that may be used include *E. coli* DNA, polymerase I Klenow fragment, *E. coli* DNA polymerase I, *E. coli* DNA polymerase II, *E. coli* DNA polymerase III, *E. coli* DNA polymerase IV, *E. coli* DNA polymerase V, *Bacillus stearothennophilus* polymerase I large fragment, *Bacillus subtilis* Pol I large fragment (Bsu polymerase), *Listeria monocytogenes* DNA polymerase I, *Staphylococcus aureus* DNA polymerase 1 (Sau) or any functional variant, analoge, homologe or derivative thereof and any combination thereof.

The DNA polymerase may be a bacteriophage polymerase. Examples of bacteriophage polymerases that may be used in the methods described herein include Phi-29 DNA polymerase, T7 DNA polymerase, bacteriophage T4 gp43 DNA polymerase, or any functional variant, analoge, homologe or derivative thereof and any combination thereof.

The DNA polymerase typically contains strand displacing properties.

DNA polymerases can use the free 3'-hydroxyl of the invading strand to catalyze DNA synthesis by incorporation of new nucleotides. A number of polymerases can use the 3'-hydroxyl of the invading strand to catalyze synthesis and simultaneously displace the other strand as synthesis occurs. For example *E. coli* polymerase II or III can be used to extend invaded D-loops. In addition, *E. coli* polymerase V normally used in SOS-lesion-targeted mutations in *E. coli* can be used. All of these polymerases can be rendered highly processive through their interactions and co-operation with the R-dimer clamp, as well as single stranded DNA binding protein (SSB) and other components. Other polymerases from prokaryotes, viruses, and eukaryotes can also be used to extend the invading strand.

Many DNA polymerases possess 3'-5' exonuclease activity, and some also possess 5'-3' exonuclease activity, which is undesirable in RPA reactions as it results in digestion of one DNA strand progressively as the polymerase moves forward, rather than displacement.

The 3'-5' exonuclease has potential advantages as well as its obvious disadvantages. On the one hand 3'-5' exonuclease activity increases the fidelity of the replication reaction, and can also prevent stalling of polymerases at points of misincorporation. High fidelity amplification is desirable for many DNA applications. The 3'-5' exonuclease activity may also be appropriate for amplification of larger DNA fragments where stalling due to misincorporation could inhibit effective amplification.

Despite these clear advantages of 3'-5' exonuclease activity there are some disadvantages. The free oligonucleotides can be subject to end-dependent degradation when polymerases possessing 3'-5' exonuclease are employed.

Reaction noise can be reduced by utilising polymerases lacking 3'-5' exonuclease activity. This suggests mispriming may result from oligonucleotides that have been shortened by the 3'-5' exonuclease activity of polymerases. Consequently 3'-5' exonuclease editing activity, pyrophosphorylysis, or any other similar editing activity can be a source of noise. This can be suppressed to a large extent by using saturating amounts of relatively cooperative Gp32 protein with some polymerases such as the Klenow fragment. Nevertheless, polymerases for use in the methods described herein might be provided which lack 3'-5' exonuclease activity.

The DNA polymerase may be present at a concentration of between 10,000 units/ml to 10 units/ml, such as between 5000 units/ml to 500 units/ml.

Accessory Agents

RPA reactions, including those of the present invention, may further utilize accessory agents.

Any of the one or more IDR-polypeptides of the present invention may be attached/tethered/tagged to any accessory agent.

These accessory agents include a single strand binding protein, a helicase, a topoisomerase, a resolvase and any combination thereof. Such agents may possess unwinding, relaxing, and resolving activities respectively on nucleic acids.

The accessory agents may also include RuvA, RuvB, RuvC, RecG, PriA, PriB, PriC, DnaT, DnaB, DnaC, DnaG, DnaX clamp loader, polymerase core complex, DNA ligase and a sliding clamp and any combination thereof. The sliding clamp may be *E. coli* β-dimer sliding clamp, the eukaryotic PCNA sliding clamp, or the T4 sliding clamp gp45 and a combination thereof. The accessory agents may include, in addition, DNA Polymerase III holoenzyme complex consisting of β-Clamp, DnaX Clamp Loader, and the Polymerase Core Complex. These latter accessory agents would allow the performance of leading and lagging RPA.

RPA reactions may be performed with one or more additional enzymes that can promote efficient disassembly of recombinase agent/dsDNA complexes after initiation of DNA synthesis. These enzymes include those that are capable of stimulating 3' to 5' disassembly and those capable of supporting 5' to 3' disassembly.

Such additional enzymes include several polymerases that can displace RecA in the 3' to 5' direction and can stimulate 3' to 5' disassembly of recombinase agent/dsDNA complexes. These DNA polymerases include *E. coli* PolV and homologous polymerase of other species. Inclusion of *E. coli* PolV or any functional variant, analoge, homologe or derivative thereof may improve the amplification efficiency.

Other enzymes include a class of enzymes called helicases that can be used to promote the disassembly of RecA from dsDNA. These promote disassembly in both the 5' to 3' and 3' to 5' directions. An ideal helicase complex for stimulating disassembly of RecA from intermediates consists of the *E. coli* proteins RuvA and RuvB. The RuvAB complex promotes branch migration, and dissociates the RecA protein, allowing RecA to be recycled. Incorporation of RuvAB into the RPA mixture can promote the dissociation of RecA from dsDNA following strand exchange and displacement, allowing renewed synthesis of the duplicated template from the same site. Additionally, the RuvAB complex can act in concert with RuvC, which finally cuts and resolves Holliday junctions. With RuvC added to the RPA reaction mixture, complicated structures such as Holliday junctions formed at invasion sites, can be resolved.

Still other enzymes include the *E. coli* RecG protein. RecG can stimulate disassembly of branch structures.

Other enzymes useful in an RPA reaction mixture are those that allow continual generation of RecA nucleoprotein filaments in the presence of ATP and the single strand stabilizing agent. Accordingly, RecO and RecR, and optionally RecF proteins may be used.

Exonuclease enzymes are often included in RPA reaction mixtures. These are included for the efficient operation of cleavable probes. One example of an exonuclease enzyme commonly used is Exonuclease III. Any of the IDR polypeptides of the present invention may be attached/tethered/tagged to any exonuclease.

Primers

RPA methods employ polymerases to generate copies of template nucleic acid molecules. RPA methods, including those of the present invention, therefore use primers to initiate extension by polymerases.

It is a necessity of most nucleic acid polymerases that incorporation requires a free 3'-hydroxyl moiety on the terminal sugar of a short stretch of double stranded nucleic acid adjacent to the site of new synthesis. This stretch of double stranded nucleic acid is typically formed on a template by a short oligonucleotide typically having a complementary sequence, called a primer, which serves as an initiation site for the polymerase synthesis reaction. In some cases a 3' modification, such as a sulfydryl, may be utilized to prime the synthesis reaction. The primer nucleic acid, which is base-paired with the template and extended by the polymerase, can be RNA or DNA. Typically, for in vitro reactions the primer is supplied as a short, often chemically synthesized, single stranded DNA (or modified DNA or RNA), and is usually referred to as an oligonucleotide primer. The primer is often of a specific sequence, although random primers can also be used. The primer is targeted to complementary sequences by virtue of its specific base-pairing capacity. Formation of hybrids between the oligonucleotide primer and target nucleic acid are typically formed by incubation of the two in solution under conditions of salt, pH, and temperature that allow spontaneous annealing.

The primers used in RPA may have a single stranded region for hybridization to the target DNA in the presence of a recombinase agent. The single stranded region may be, for example, about 10 bases, about 15 bases, about 20 bases, about 25 bases, about 30 bases, about 40 bases, and about 50 bases. Even longer regions such as about 75 bases, about 100 bases, about 150 bases or more may in theory be used. The choice of single stranded regions will depend on the complexity of the starting nucleic acid so that for example, a human genome may require a longer primer while a plasmid may require a much shorter primer.

A preferred primer length is between about 30 to about 50 bases. For example, between 30 to 45 bases, between 30 to 40 bases, between 30 to 35 bases, between 35 to 40 bases, between 40 to 45 bases, and between 45 to 50 bases. While the above-referenced primer lengths are indicated, a recombinase and/or single stranded binding protein with an optimum primer length of less than 30 bases is also possible and envisioned.

The primers used in RPA are preferably DNA although PNA, and RNA are also suitable for use as primers. It is noted that in fact, in natural DNA replication, DNA polymerases elongate genomic DNA by extension from RNA primers.

Primers may be synthesized according to standard techniques. Modified bases and/or linker backbone chemistries may be desirable and functional in some cases. Additionally oligonucleotides may be modified at their ends, either 5' or 3', with groups that serve various purposes e.g. fluorescent groups, quenchers, protecting (blocking) groups (reversible or not), magnetic tags, proteins etc. In some cases single stranded oligonucleotides may be used for strand invasion, in others only partly single stranded nucleic acids may be used, the 5' stretch of sequence of an invading nucleic acid being already hybridized to an oligonucleotide.

The primers may comprise a 5' region that is not homologous to the target nucleic acid. It should be noted that amplification may be achieved even if the primers are not completely complementary to the target nucleic acid. The primers may be non-complementary by having additional sequences at their 5' ends. These additional sequences may be, for example, the sequence for a restriction endonuclease recognition site or the sequence that is complementary to a sequencing primer. The restriction endonuclease recognition site may be useful for subsequent cleavage of the amplified sequence. The use of restriction endonuclease that cleaves nucleic acid outside the restriction endonuclease recognition site is also contemplated. The sequence that is complementary for a sequencing primer may allow rapid DNA sequencing of the amplified product using commercially available primers or commercially available sequencing apparatus.

Software to design oligonucleotides for use in in vitro DNA synthesis reactions is well established, particularly for use in PCR. The considerations for the RPA method are similar and include the optimisation of the melting temperature of the oligonucleotide, avoidance of hairpin formation within an oligonucleotide and selection against complementarity with other oligonucleotides present in a given reaction. It is therefore important to design oligonucleotide primer pairs to avoid undesirable side reactions.

Besides optimising oligonucleotide sequence design there are additional approaches to reduce or eliminate primer dimer formation. As noted elsewhere herein, reaction noise can be reduced by utilising polymerases lacking 3'-5' exonuclease activity. This suggests mispriming may result from oligonucleotides that have been shortened by the 3'-5' exonuclease activity of polymerases. Consequently 3'-5' exonuclease editing activity, pyrophosphorylysis, or any other similar editing activity can be a source of noise. In addition to using polymerases lacking exonuclease activity and the removal of pyrophosphate with pyrophosphatase, use of synthetic oligonucleotides with a non-hydrolysable backbone at the ultimate and/or penultimate link may be beneficial to reduce reaction noise. Alternative backbones could be selected from the considerable range of chemistries available such as phosphorothiorate, morpholino, locked nucleic acid, or peptide nucleic acid.

Reagents for Use in RPA Reactions

Reagents for use in RPA methods, including those of the present invention, are outlined below.

dNTPs dNTPs, for example dATP, dGTP, dCTP, and dTTP, and derivatives and analogs thereof, may be added to an RPA reaction. In leading and lagging strand RPA, ATP, GTP, CTP, and UTP may also be included for synthesis of RNA primers. In addition, ddNTPs (ddATP, ddTTP, ddGTP and ddGTP and derivatives and analogs thereof) may be used to generate fragment ladders.

The dNTP may be used at a concentration of between 1 mM to 200 mM of each NTP species.

A mixture of dNTP and ddNTP may be used with ddNTP concentrations at 1/100 to 1/1000 of that of the dNTP (1 mM to 200 mM).

The RPA may be performed in the presence of ATP, a hydrolysable ATP analog, or another nucleoside triphosphate. The ATP analog may be, for example, dATP, ddATP, or another nucleoside triphosphate analog such as UTP.

Reducing Agents

Reducing agents which may be used in the RPA reaction include DTT. The DTT concentration may be between 1 mM and 10 mM, preferably 1 mM.

ATP

ATP or an ATP analog may be used in the RPA reaction. The ATP or ATP analog may be any of ATP, ATP-γ-S, ATP-β-S, ddATP or a combination thereof. A preferred ATP or ATP analog concentration is between 1 mM and 10 mM, preferably 2.5 mM.

System for ATP Regeneration

Other components of the RPA reaction may include a system for ATP regeneration (i.e. a system to convert ADP to ATP). Such a system may be, for example, phosphocreatine and creatine kinase.

An ATP regeneration system permits persistent recombination reactions, as recombinases have an extremely high rate of ATP hydrolysis when bound to nucleic acids. In particular, the UvsX protein has a hydrolysis rate 10-20 times higher than RecA and can consume 200 molecules of ATP per minute per monomer. A number of systems are available. The creatine kinase/phosphocreatine system is preferred. When UvsX is employed the AMP that is produced may be converted into ATP. Chicken myokinase may additionally be used, which converts a molecule of AMP and one of ATP to two molecules of ADP. ADP can then be converted to ATP using the creatine kinase/phosphocreatine system. Poor regeneration of ATP can reduce the reaction rate.

In the RPA methods described herein phosphocreatine is preferably used at a concentration of between 15-25 mM, more preferably 20 mM. Creatine kinase is preferably used at a concentration of between about 0.25-5.0 µM, more preferably 1 µM.

Multivalent Metal Cations

The buffer solution in an RPA reaction preferably contains multivalent metal cations. The buffer may contain a functional equivalent of a multivalent metal cation.

The buffer solution in an RPA reaction more preferably contains divalent metal cations. The buffer may contain a functional equivalent of a divalent metal cation.

Any suitable multivalent or divalent metal cation or functional equivalent thereof may be used, either as a single agent or combination of agents.

The specific multivalent or divalent metal cation or functional equivalent thereof which achieves optimal results in promoting/enhancing IDR-mediated phase separation in an RPA reaction, as well as the specific concentration of the multivalent/divalent metal cation used may depend upon the specific IDR polypeptide which is used. The optimal multivalent/divalent metal cation or functional equivalent thereof, and the optimal concentration thereof, can be established empirically using routine tests, including RPA reactions themselves and/or the phase separation assays which are described further herein.

The divalent metal cation may be $Mg^{2+}$, $Mn^{2+}$, $Ca^{2+}$, $Co^{2+}$, $Ni^{2+}$ or $Cu^{2+}$. Any of these cations may be used as a single agent, or any combination of cations may be used. Preferably they are used as single agents. Preferred divalent metal cations are $Mg^{2+}$, $Mn^{2+}$ and $Ca^{2+}$. A particularly preferred divalent metal cation is $Mg^{2+}$.

A preferred concentration range is from 30 to 40 mM, more preferably from 33 to 39 mM.

The buffer may contain $Mg^{2+}$ ions, preferably at the indicated concentrations. More preferably the buffer contains MgOAc at the indicated concentrations.

The buffer may contain $Ca^{2+}$ ions, preferably at the indicated concentrations. More preferably the buffer contains $CaCl_2$ at the indicated concentrations.

The buffer may contain $Mn^{2+}$ ions, preferably at the indicated concentrations. More preferably the buffer contains $MnCl_2$ at the indicated concentrations.

Buffers

The buffer solution in an RPA reaction may be a Tris-HCl buffer, a Tris-Acetate buffer, or a combination thereof. The buffers may be present at a concentration of between about 10 mM to about 100 mM. A preferred buffer is a Tris-HCl buffer used at a concentration of between about 20 mM to about 30 mM, most preferably 25 mM. The buffered pH may be between 6.5 to 9.0, preferably pH 8.3.

The buffer may contain potassium acetate between about 5 mM to about 50 mM, preferably between about 10 mM to about 40 mM.

Reaction Components

A preferred but non-limiting set of reaction components for an RPA reaction is as follows below.

| | |
|---|---|
| Tris HCl pH 8.3 | 25 mM |
| KOAc | 7.5 mM |
| DTT | 1 mM |
| ATP | 2.5 mM |
| Phosphocreatine | 20 mM |
| Creatine kinase | 1 µM |
| dNTPs | 1 mM |
| Gp32 | 20 µM |
| UvsX | 4.8 µM |
| UvsY | 8.6 µM |
| S. aureus DNA polymerase 1 (Sau) Or B. subtilis DNA polymerase 1 (Bsu) | 0.135 µM |
| Exonuclease III | 0.27 µM |
| MgOAc | 33 mM |
| Forward primer | 0.4 µM |
| Reverse primer | 0.4 µM |
| Exo probe | 0.12 µM |

RPA Reaction Conditions

RPA reactions, including those of the present invention, may incubated for any suitable length of time.

Any of the RPA reactions may be incubated for between 5 minutes and 16 hours or more, such as between 15 minutes and 3 hours or between 30 minutes and 2 hours.

The incubation may be performed until a desired degree of amplification is achieved. The desired degree of amplification may be 10 fold, 100 fold, 1000 fold, 10,000 fold, 100,000 fold or 1,000,000 fold amplification.

One benefit of RPA is that the reaction may be performed at reduced temperatures compared to techniques which require thermal cycling, such as PCR. A further advantage of RPA is that the temperature is not critical and precise control, while preferred, is not absolutely necessary. For example, in a field environment, it is sufficient to incubate the RPA reaction at room temperature, or close to body temperature (35° C. to 38° C.), for example by placing the sample in a body crevice. Furthermore, the RPA reaction may be performed without temperature induced melting of the template nucleic acid.

Thus any of the RPA reactions may be performed at any suitable temperature.

The RPA reactions may be performed at less than 45° C. The RPA reactions may be performed at less than 40° C. The RPA reactions may be performed at less than 35° C. The RPA reactions may be performed at less than 30° C.

The RPA reactions may be performed at between 20° C. and 50° C., between 20° C. and 40° C., such as between 20° C. and 30° C.

Freeze Drying of RPA Reaction Components

One advantage of RPA reactions is that the reagents, with the possible exception of the crowding agent (if used) and buffer, may be freeze dried (i.e., lyophilized) before use. Freeze dried reagents offer the advantage of not requiring refrigeration to maintain activity. For example, a tube of RPA reagents may be stored at room temperature. This advantage is especially useful in field conditions where access to refrigeration is limited.

RPA reagents may be freeze dried onto the bottom of a tube, or on a bead or any other suitable type of solid support. To perform an RPA reaction the freeze dried reagents are reconstituted in a buffer solution and with a crowding agent (if used), or simply a buffered solution or water, depending on the composition of the freeze-dried reagents. Then a target nucleic acid, or a sample suspected to contain a target nucleic acid is added. The reconstitution liquid may also contain the sample nucleic acid. The reconstituted reaction is incubated for a period of time and the amplified nucleic acid, if present, is detected.

In any one of the RPA methods described herein, the reagents that can be freeze dried before use include, at least, the recombinase agent, the recombinase loading protein, the single strand stabilizing agent, the DNA polymerase, the dNTPs or the mixture of dNTPs and ddNTPs, the reducing agent, the ATP or ATP analog, primers and probe.

Stabilizing agents such as trehalose sugar may be included in the freeze dried mixture, for example at 20 mM to 200 mM and most optimally 40 mM to 80 mM in the reconstituted reaction, in order to improve freeze-drying performance and shelf life. If desired, the freeze dried reagents may be stored for 1 day, 1 week, 1 month or 1 year or more before use.

Biochemical reaction reagents, such as RPA reagents, may be freeze dried together with a crowding agent. However, complex inter-related issues may exist which may justify the omission of a crowding agent in a lyophilized mixture. For example, the user may experience difficulty in the effective rehydration of the freeze dried crowding agent, or the user may experience other detrimental effects, including the need for larger lyophilized pellets. Accordingly, there may be advantages in being able to exclude some or all of a crowding agent from freeze dried materials which include among other things reduction of pellet size, shorter cycle times, and easier rehydration. However this has the consequential disadvantage that a crowding agent, if used, would need to be added fresh prior to use after the biochemical reaction mixture was rehydrated and prepared for use. This could be problematic in certain situations, such as for point-of-care use or field use. An advantage of the IDR-based reagents of the present invention is that they would not be expected to exhibit the same drawbacks as crowding agents in a lyophilized setting, and could therefore readily be freeze dried with other biochemical reaction components, thus obviating the need to add fresh additional reagents prior to use.

Detection of RPA Reaction Products Detection of RPA reaction products may be performed using any suitable method.

For example, detection may be performed using electrophoresis on an agarose or PAGE gel followed by ethidium bromide staining.

Monitoring a RPA reaction may involve, for example, removing a fraction of an RPA, reaction, isolating the unincorporated fraction, and detecting the unincorporated primer. Since the size of an unincorporated primer may be less than 50 bp, less than 40 bp, less than 30 bp or less than 25 bp, and the size of the amplified product may be greater than 1 Kb, greater than 2 Kb, greater than 5 Kb, or greater than 10 Kb, there is a great size difference between the incorporated and unincorporated primer. The isolation of the unincorporated primer may be performed rapidly using size exclusion chromatography such as, for example, a spin column. If a primer is labeled, a monitor procedure comprising a spin column and a measurement (e.g., fluorescence or radioactivity) can be performed in less than one minute.

Another alternative for separating elongated primers from unelongated primers involve the use of PAGE. For example, the elongated primer may be separated from the unelongated primer by gel electrophoresis in less than 5 minutes.

Yet another alternative for separating elongated primers involves the use of immobilized oligonucleotides. For example oligonucleotides homologous to sequences found uniquely within the amplified DNA sequence can be used to capture nucleic acids produced by primer elongation specifically. These capturing oligonucleotides can be immobilized on a chip, or other substrate. Capture of the elongated oligonucleotides by the capturing oligonucleotides can be performed by RecA protein mediated methods, or by traditional solution hybridizations if necessary.

The use of fluorescent probes is most commonly used and preferred for the detection of RPA amplification products and have the advantage of providing for real-time detection.

These probes are labelled with a fluorophore, such as fluorescein (FAM) and a quencher, such as a Black Hole Quencher, in close proximity to the fluorophore. The probes have a blocking group at the 3' end to prevent extension from the probe by polymerase. A fluorescent signal is detected when the probe is cleaved and when the quencher and fluorophore are separated, allowing for real-time detection. The probe contains an abasic site, typically tetrahydrofuran (THF) or dR group, and cleavage occurs at the abasic site, typically by *E. coli* Exonuclease III (cleaving at THF) or *E. coli* fpg (glycolyase/lyase) (cleaving at the dR group).

Kits Comprising RPA Reaction Components

The invention also provides a kit for performing an RPA reaction.

The kit may comprise any of the reagents described herein for RPA in any one of the concentrations described above.

The kit may comprise any of the IDR-tagged macromolecules and/or IDR-tagged polypeptides described and defined herein. Preferably the kit further comprises additional RPA components selected from an RPA recombinase agent, and/or an RPA recombinase loading protein, and/or polymerase, and/or first and second nucleic acid primers, and/or an exonuclease, and/or a buffer, and/or a source of multivalent metal ions, preferably divalent metal cations such as $Mg^{2+}$, $Mn^{2+}$, $Ca^{2+}$, $Co^{2+}$ or $Ni^{2+}$.

The reagents of the kit may be freeze dried, in which case the reagents may be provided in any suitable amount such that when reconstituted the appropriate reagent concentration is achieved.

Polymerase

As discussed above, any of the IDR amino acid sequences as described and defined herein may be tagged to any protein component required for the performance of a nucleic acid synthesis reaction.

Any of the IDR amino acid sequences as described and defined herein may be tagged to any protein component required for the performance of a nucleic acid synthesis reaction wherein a polymerase is used to synthesize a new nucleic acid molecule by extending a primer nucleic acid molecule.

Accordingly, any suitable polymerase may be tagged with an IDR amino acid sequence as described and defined herein. The polymerase may be one which is compatible with and may be used in any reaction used to synthesize a new nucleic acid molecule by extending a primer nucleic acid molecule.

The polymerase may be one which is compatible with and may be used in any nucleic acid amplification reaction. The nucleic acid amplification reaction may be a reaction which involves thermal cycling. The nucleic acid amplification reaction may be an isothermal amplification reaction. The nucleic acid amplification reaction may be polymerase chain reaction (PCR), polymerase spiral reaction (PSR), loop mediated isothermal amplification (LAMP), nucleic acid sequence based amplification (NASBA), self-sustained sequence replication (3SR), rolling circle amplification (RCA), strand displacement amplification (SDA), multiple displacement amplification (MDA), ligase chain reaction (LCR), helicase dependent amplification (HDA), ramification amplification method (RAM), recombinase polymerase amplification (RPA), transcription-mediated amplification (TMA) or nicking enzyme amplification reaction (NEAR).

Sequence Tags

Any of the IDR-macromolecules or any of the IDR-polypeptides involved in biochemical reactions as described herein, including those involved in RPA reactions, may comprise one or more sequence tags. If used, any such sequence tags are preferably attached to a polypeptide as a fusion protein, as described herein. Sequence tags and means for attaching sequence tags to polypeptides are well known in the art.

Sequence tags may be short amino acid sequences or larger polypeptides including proteins.

Sequence tags may be attached to the C-terminus of a polypeptide, to the N-terminus of a polypeptide tag, to both the C- and N-terminus of a polypeptide or at any amino acid position along the length of a polypeptide in any combination.

Non-limiting examples of suitable amino acid sequence tags include 6-histidine (6×-His; HHHHHH; SEQ ID NO:89), c-myc epitope (EQKLISEEDL; SEQ ID NO:90), FLAG® octapeptide (DYKDDDDK; SEQ ID NO:91), Protein C (EDQVDPRLIDGK; SEQ ID NO:92), Tag-100 (EETARFQPGYRS; SEQ ID NO:93), V5 epitope (GKPIPNPLLGLDST; SEQ ID NO:94), VSV-G (YTDIEMNRLGK; SEQ ID NO:95), Xpress (DLYDDDDK; SEQ ID NO:96), and hemagglutinin (YPY-DVPDYA; SEQ ID NO:97).

Non-limiting examples of suitable protein tags include β-galactosidase, thioredoxin, His-patch thioredoxin, IgG-binding domain, inteinchitin binding domain, T7 gene 10, glutathione-S-transferase (GST), green fluorescent protein (GFP), and maltose binding protein (MBP).

It will be understood by those in the art that sequence tags and protein tags can be used interchangeably, e.g., for purification and/or identification purposes.

Solid Phase Biochemical Reactions

Biochemical reactions performed in processes according to the invention may be performed using solid phase or reversible solid phase techniques. Solid phase reaction systems suitable for performing the processes, uses and methods described herein may comprise a surface. Any suitable surface may be used.

Data described herein demonstrate that biochemical reactions may be performed with IDR-based reagents according to the invention using solid phase techniques in the absence of a crowding agent. One particular example is recombinase polymerase amplification of nucleic acids wherein primers are attached to a solid surface. Any suitable biochemical reaction amenable to performance using solid phase methods may be performed using such methods using processes according to the invention involving any of the IDR-based reagents described and defined herein.

A variety of such solid phase techniques are known in the art and may be used.

Macromolecules, such as polynucleotides, including nucleic acid amplification primers, peptides, haptens, hormones, drugs, etc. may be immobilized to a surface.

Any suitable macromolecular component of a biochemical reaction may be immobilized to a surface, including the IDR-based reagents described and defined herein.

Macromolecules, such as polynucleotides, e.g. primers for use in amplification reactions, may be immobilized to surfaces directly or indirectly. For example they may be attached directly to surfaces by chemical bonding. They may be indirectly attached to surfaces via an intermediate surface.

A surface may be e.g. a planar surface such as glass, a gel-based material, or the surface of a microparticle such as a bead or functionalised quantum dot. The material comprising the surface may itself be bound to a substrate. The substrate may be comprise any suitable material such as glass, plastics or polymeric material.

Macromolecules involved in biochemical reactions according to processes of the invention may be immobilized to a gel-based material such as e.g. polyacrylamide or a hydrogel, and wherein the gel-based material is itself bound to a supporting substrate such as glass or a plastics or polymeric material.

Pre-formed polynucleotides, for example, can be immobilized to surfaces by methods commonly employed to create nucleic acid microarrays. For example, polynucleotides may be synthesized and then spotted or printed onto a surface, typically a planar surface. Polynucleotides may be deposited onto surfaces using contact printing techniques. For example, solid or hollow tips or pins may be dipped into solutions comprising pre-formed polynucleotides and contacted with the surface. Alternatively, polynucleotides may be adsorbed onto micro-stamps and then transferred to a surface by physical contact. Non-contact printing techniques include thermic printing or piezoelectric printing wherein sub-nanolitre size microdroplets comprising pre-formed polynucleotides may be ejected from a printing tip using methods similar to those used in inkjet and bubblejet printing.

Polynucleotides may be synthesised directly on surfaces such as using so-called "on-chip" methods employed to create nucleic acid microarrays. On-chip techniques for generating polynucleotides include photolithography which involves the use of UV light directed through a photolithographic mask to selectively activate a protected nucleotide allowing for the subsequent incorporation of a new protected nucleotide. Cycles of UV-mediated deprotection and coupling of pre-determined nucleotides allows the in situ generation of a polynucleotide having a desired sequence. As an alternative to the use of a photolithographic mask, polynucleotides may be created on surfaces by the sequential deposition of nucleobases using inkjet printing technology and the use of cycles of coupling, oxidation and deprotection to generate an oligonucleotide having a desired sequence (for a review see Kosuri and Church, Nature Methods, 2014, 11, 499-507).

Surfaces for the attachment of macromolecules, including polynucleotides, peptides, haptens, hormones, drugs, etc. can be made of any suitable material. Typically a surface may comprise silicon, glass or any suitable polymeric material, such as polystyrene. A surface may comprise a gel surface, such as a polyacrylamide surface or a hydrogel surface. The gel surface may in turn be coupled to or bound to a solid support or a substrate, said support or substrate may comprise any suitable material such as silicon, glass or any suitable polymeric material. A surface may comprise a hydrogel material coupled to a polystyrene material.

A surface may be the surface of a microparticle, often referred to as a microsphere or microbead, or simply a bead.

A surface may comprise a hydrogel material coupled to a polystyrene material in the form of a microbead.

A variety of surface attachment methods and chemistries are available for the immobilization of macromolecules, such as polynucleotides, to surfaces such as microbeads. Surfaces may be functionalised or derivatized to facilitate attachment.

Such functionalisations are known in the art. For example, a surface may be functionalised with a polyhistidine-tag (hexa histidine-tag, 6×His-tag, His6 tag or His-tag®), Ni-NTA, streptavidin, biotin, an oligonucleotide, a polynucleotide (such as DNA, RNA, PNA, GNA, TNA or LNA), carboxyl groups, quaternary amine groups, thiol groups, azide groups, alkyne groups, DIBO, lipid, FLAG-tag (FLAG octapeptide), polynucleotide binding proteins, peptides, proteins, antibodies or antibody fragments. The surface may be functionalised with a molecule or group which specifically binds to the macromolecule to be immobilized or to another moiety attached to the macromolecule to be immobilized. Covalent immobilization of macromolecules to surfaces is commonly employed. Purely by way of example, a carboxylate-modified polystyrene latex surface is suitable for the covalent attachment of e.g. amine-terminated proteins, DNA, or other molecules for example via EDAC-mediated coupling. Other techniques are available. Although macromolecules will typically be attached chemically, they may also be attached to surfaces by indirect means such as via affinity interactions. For example, macromolecules to be immobilized may be functionalised with biotin and bound to surfaces coated with avidin or streptavidin, or vice-versa.

In any of the processes, uses and methods described and defined herein, a macromolecule may be attached to a surface via one or more covalent bonds. The one or more covalent bonds may be formed between a functional group on the surface and a functional group on the marcomolecule. The functional group on the macromolecule may be e.g. an amine group, a thiol group, a thiophosphate group or a thioamide group.

The functional group on the surface may be e.g. a bromoacetyl group, optionally wherein the bromoacetyl group is provided on a polyacrylamide surface derived using N-(5-bromoacetamidylpentyl) acrylamide (BRAPA).

In any of the processes, uses and methods described and defined herein a macromolecule may be attached to a surface, either directly or indirectly, via a linker. Any suitable linker which is biocompatible in nature may be used.

A linker may be a linear linker or a branched linker.

A linker may comprise a hydrocarbon chain. A hydrocarbon chain may comprise from 2 to about 2000 or more carbon atoms. The hydrocarbon chain may comprise an alkylene group, e.g. C2 to about 2000 or more alkylene groups. The hydrocarbon chain may have a general formula of —$(CH_2)_n$— wherein n is from 2 to about 2000 or more. The hydrocarbon chain may be optionally interrupted by one or more ester groups (i.e. —C(O)—O—) or one or more amide groups (i.e. —C(O)—N(H)—).

Any linker may be selected from the group comprising polyacrylamide, poly(2-hydroxyethyl methacrylate), Poly-2-methyl-2-oxazoline (PMOXA), zwitterionic polymers, e.g. poly(carboxybetaine methacrylate) (PCBMA), poly[N-(3-sulfopropyl)-N-methacryloxyethyl-N, N dimethyl ammonium betaine] (PSBMA), glycopolymers, and polypeptides.

A linker may comprise oligoethylene glycol-phosphate units having a general formula of —$[(CH_2—CH_2—O)_n—PO_2^-—O]_m$— where n is from 1 to about 600 or more and m could be 1-200 or more.

Any of the above-described linkers may be attached at one end of the linker to a macromolecule described herein, and at the other end of the linker to a first functional group wherein the first functional group may provide a covalent attachment to a surface. The first functional group may be e.g. an amine group, a thiol group, a thiophosphate group or a thioamide group as further described herein. The surface may be functionalised with a further functional group to provide a covalent bond with the first functional group. The further functional group may be e.g. a 2-bromoacetamido group as further described herein. Optionally a bromoacetyl group is provided on a polyacrylamide surface derived using N-(5-bromoacetamidylpentyl) acrylamide (BRAPA). The further functional group on the surface may be a bromoacetyl group, optionally wherein the bromoacetyl group is provided on a polyacrylamide surface derived using N-(5-bromoacetamidylpentyl) acrylamide (BRAPA) and the first functional group may be e.g. an amine group, a thiol group, a thiophosphate group or a thioamide group as appropriate. The surface to which polynucleotides are attached may comprise a gel. The surface may comprise a polyacrylamide surface, such as about 2% polyacrylamide, preferably the polyacrylamide surface is coupled to a solid support such as glass.

Microparticles and beads which facilitate reversible immobilization may be used. Solid phase reversible immobilization (SPRI) methods or modified methods are known in the art and may be employed (e.g. see DeAngelis M. M. et al. (1995) Solid-Phase Reversible Immobilization for the Isolation of PCR Products, Nucleic Acids Research, 23(22): 4742-4743.).

Surfaces can be provided in the form of e.g. paramagnetic beads. Paramagnetic beads can agglomerate under the influence of a magnetic field. For example, paramagnetic surfaces can be provided with chemical groups, e.g. carboxyl groups, which in appropriate attachment conditions will act as binding moieties for macromolecules including nucleic acids. Macromolecules can be eluted from such surfaces in appropriate elution conditions. Surfaces of microparticles and beads can be provided with UV-sensitive polycarbonate. Nucleic acids, for example, can be bound to the activated surface in the presence of a suitable immobilization buffer.

Microparticles and beads may be allowed to move freely within a reaction solution and then reversibly immobilized, e.g. by holding the bead within a microwell or pit etched into a surface. A bead can be localised as part of an array e.g. by the use of a unique nucleic acid "barcode" attached to the bead or by the use of colour-coding.

The surface may be part of an electrowetting-on-dielectric system (EWOD). EWOD systems provide a dielectric-coated surface which facilitates microfluidic manipulation of very small liquid volumes in the form of microdroplets (e.g. see Chou, W-L., et al. (2015) Recent Advances in Applications of Droplet Microfluidics, Micromachines, 6: 1249-1271.). Droplet volumes can programmably be created, moved, partitioned and combined on-chip by electrowetting techniques. Thus electrowetting systems provide alternative means to reversibly immobilize macromolecules to surfaces and/or to manipulate macromolecules immobilized to surfaces.

Accordingly, in any one of the processes or uses according to the invention as described or defined herein, the biochemical reaction may be performed in a solid phase reaction system which comprises a surface.

In any one of the processes or uses according to the invention as described or defined herein wherein the biochemical reaction is performed in a solid phase reaction system which comprises a surface, any macromolecule required for the performance of the reaction may be attached to the surface. For example, in one such process wherein the biochemical reaction is a process of amplifying a single stranded target nucleic acid molecule or a double stranded target nucleic acid molecule in the in vitro reaction system as described herein, the at least one nucleic acid primer, and/or the reaction macromolecule, and/or the IDR-macromolecule and/or the one or more polypeptide co-factors may be attached to the surface.

In any one of the processes or uses according to the invention as described or defined herein wherein the biochemical reaction is performed in a solid phase reaction system which comprises a surface, the IDR-macromolecule which is required for the performance of the reaction may be attached to the surface.

In any one of the processes or uses according to the invention as described or defined herein wherein the biochemical reaction is a recombinase polymerase amplification process of amplifying a double stranded target nucleic acid molecule in the in vitro reaction system, wherein the reaction is performed in a solid phase reaction system which comprises a surface, and wherein the recombinase agent and/or the recombinase loading protein and/or the single strand stabilizing agent and/or the polymerase and/or the exonuclease and/or the first nucleic acid primer and/or the second nucleic acid primer may be attached to the surface. In one such process or use, the first nucleic acid primer or the second nucleic acid primer may be attached to the surface. Alternatively, in other such processes or uses, both the first nucleic acid primer and the second nucleic acid primer may be attached to the surface.

In any one of the processes or uses according to the invention as described or defined herein wherein the biochemical reaction is performed in a solid phase reaction system, the surface to which a macromolecule is attached may be a microbead, preferably wherein the microbead comprises a silicon, glass, gel or a polymeric material, such as polystyrene, or any combination thereof.

In any one of the processes or uses described herein wherein the biochemical reaction is performed in a solid phase reaction system which comprises a surface and/or a substrate, the surface and/or the substrate may be provided as a flow-cell. Any suitable flow-cell compatible with the biochemical reaction being performed may be used. A suitable flow-cell may comprise a plurality of fluidic channels through which reagents used to perform the biochemical reaction may flow. Any one or more macromolecules used to perform the biochemical reaction may be attached to a surface lining a fluidic channel. A suitable flow-cell may be used to perform a biochemical reaction for amplification of a single stranded or a double stranded target nucleic acid molecule. Sequencing reactions performed using the processes, uses and methods described herein may also be performed using a suitable flow-cell.

EXAMPLES

The following Examples are provided to illustrate the invention but not to limit the invention.

Example 1. Recombinase Polymerase Amplification of *Listeria monocytogenes* Gene Hly Using Gp32 Having an IDR Tag Derived from Human Otx1

Purpose and Summary of Experiment

This experiment was performed to assess the performance of a Gp32 fusion protein preparation containing a tag comprising a histidine-rich amino acid domain sequence found in the intrinsically disordered region (IDR) of the human homeobox protein Otx1.

The example demonstrates recombinase polymerase amplification (RPA) of the *Listeria monocytogenes* gene hly across a range of template concentrations using Gp32 C-terminally tagged with the histidine rich intrinsically disordered region (IDR) domain (Otx1) in the absence of a crowding agent.

Materials and Methods

The specific amino acid sequence of the IDR domain tag used was AGHHHHHPHAHHPLSQSSGHHHHHHHHHHQGYGG SG (SEQ ID NO:24). This was attached to the C-terminus of phage vB EcoM NBG1 Gp32. The recombinant fusion protein was purified using standard 1-step immobilised metal (nickel) affinity chromatography relying on the histidines naturally present in the IDR domain tag of the fusion protein under test. The fusion protein was designated Gp32-HIS2. The full amino acid sequence of the fusion protein is presented as SEQ ID NO: 82 (Table 23).

The recombinant phage vB EcoM NBG1 Gp32 fusion protein was then tested in PEG-free amplification, i.e. in the absence of a crowding agent, using the indicated copies of a DNA template derived from *Listeria monocytogenes* genomic DNA. The test template was titrated in copy number as indicated in FIG. 1.

Reactions were set up by mixing 25 mM Tris HCl pH 8.3, 7.5 mM KOAc, 1 mM DTT, 2.5 mM ATP, 20 mM phosphocreatine, 1 µM creatine kinase, 1 mM dNTPs, 0.4 µM forward primer, 0.4 µM reverse primer, 0.12 µM probe, 20 µM Gp32 fusion, 4.8 µM UvsX, 8.6 µM UvsY, 0.135 µM *S. aureus* DNA polymerase, and 0.27 µM Exonuclease III. Reactions were initiated by the addition of template at the given concentration and with 33 mM MgOAc.

The relevant primers and probe are indicated below.

Forward primer: CGCCTGCAAGTCCTAAGACGC-CAATCGAAAAGAAAC (SEQ ID NO:98).

Reverse primer: CTGCATCTCCGTGGTATACTAATA-CATTGTTTTTA (SEQ ID NO:99).

Probe: CGAAAAGAAACACGCGGATGAAATCGA-TAAG[FAM][THF][BHQ-1]ATACAAGGATTGGA (SEQ ID NO:100), where FAM is fluorescein, THF is tetrahydrofuran and BHQ is Black Hole Quencher.

Reactions were then incubated at 39° C. and placed in a fluorometer with magnetic mixing using a bearing ball.

Results and Conclusion

As shown in FIG. 1 the test template was readily detected at high sensitivity within 7 minutes of initiation of the RPA reaction. Amplicons were detected with as little as 10 copies of target.

It was therefore found that amplification in the absence of a crowding agent, such as PEG, occurred efficiently using this Gp32 IDR-tagged fusion protein.

Example 2. Recombinase Polymerase Amplification of the *Listeria monocytogenes* Gene Hly Using Gp32 Having an IDR Tag Derived from Human MafA Purpose and Summary of Experiment This experiment was performed to assess the performance of a Gp32 fusion protein preparation containing a tag comprising a histidine-rich domain sequence found in the intrinsically disordered region (IDR) of the human transcription factor MafA.

The example demonstrates recombinase polymerase amplification (RPA) of the *Listeria monocytogenes* gene hly across a range of template concentrations using Gp32 C-terminally tagged with the histidine-rich intrinsically disordered region (IDR) domain (MafA) in the absence of a crowding agent.

Materials and Methods

The specific amino acid sequence of the IDR domain tag used was SGHHGAHHGAHHPAAAAAYEAFRGPGF-AGGGGADDMGAGHHHGAHHAAHH HHAAHHHHHHHHHGGAGHGGGAGHH (SEQ ID NO:27). This was attached to the C-terminus of phage vB EcoM NBG1 Gp32. The recombinant fusion protein was purified using standard 1-step immobilised metal (nickel) affinity chromatography relying on the histidines naturally present in the IDR domain tag of the fusion protein under test. The fusion protein was designated Gp32-HIS5. The full amino acid sequence of the fusion protein is presented as SEQ ID NO: 85 (Table 23).

Figure 2:
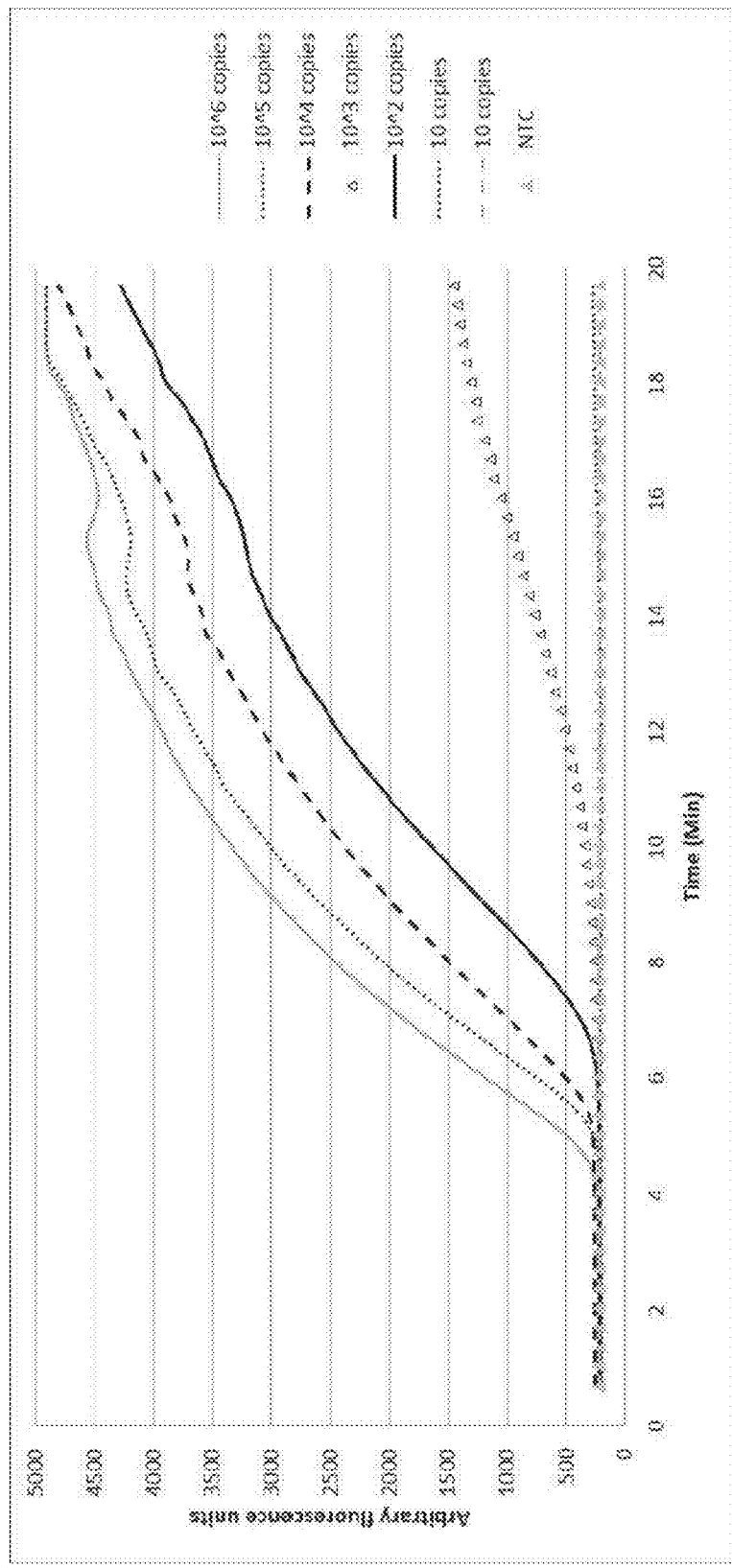
FIG. 2 shows real-time recombinase polymerase amplification traces using an IDR-tagged Gp32 fusion protein (Gp32-HIS5) at varying template nucleic acid concentrations.

The recombinant phage vB EcoM NBG1 Gp32 fusion protein was then tested in PEG-free amplification, i.e. in the absence of a crowding agent, using the indicated copies of a DNA template derived from *Listeria monocytogenes* genomic DNA. The test template was titrated in copy number as indicated in FIG. 2.

Reactions were set up by mixing 25 mM Tris HCl pH 8.3, 7.5 mM KOAc, 1 mM DTT, 2.5 mM ATP, 20 mM phosphocreatine, 1 µM creatine kinase, 1 mM dNTPs, 0.4 µM forward primer, 0.4 µM reverse primer, 0.12 µM probe, 20 µM Gp32 fusion, 4.8 µM UvsX, 8.6 µM UvsY, 0.135 µM *S. aureus* DNA polymerase, and 0.27 µM Exonuclease III. Reactions were initiated by the addition of template at the given concentration and with 33 mM MgOAc.

The relevant primers and probe are indicated below.

Forward primer: CGCCTGCAAGTCCTAAGACGC-CAATCGAAAAGAAAC (SEQ ID NO:98).

Reverse primer: CTGCATCTCCGTGGTATACTAATA-CATTGTTTTA (SEQ ID NO:99).

Probe: CGAAAAGAAACACGCGGATGAAATCGA-TAAG[FAM][THF][BHQ-1]ATACAAGGATTGGA (SEQ ID NO:100), where FAM is fluorescein, THF is tetrahydrofuran and BHQ is Black Hole Quencher.

Reactions were then incubated at 39° C. and placed in a fluorometer with magnetic mixing using a bearing ball.

Results and Conclusion

As shown in FIG. 2 the test template was readily detected at high sensitivity within 10 minutes of initiation of the RPA reaction. Amplicons were detected with as little as 10 copies of target.

It was therefore found that amplification in the absence of a crowding agent, such as PEG, occurred efficiently using this Gp32 IDR-tagged fusion protein.

Example 3. Recombinase Polymerase Amplification of the *Listeria* Monocytogenes Gene Hly Using Gp32 Having an IDR Tag Derived from *Saccharomyces cerevisiae* Hrp1

Purpose and Summary of Experiment

This experiment was performed to assess the performance of a Gp32 fusion protein preparation containing a tag comprising an intrinsically disordered region (IDR) of the *Saccharomyces cerevisiae* Hrp1 protein.

The example demonstrates recombinase polymerase amplification (RPA) of the *Listeria monocytogenes* gene hly across a range of template concentrations using Gp32 C-terminally tagged with the sequence comprising an intrinsically disordered region (IDR) of the yeast Hrp1 protein in the absence of a crowding agent.

Materials and Methods

The specific amino acid sequence of the IDR domain tag used was GGNNGGNNMNRRGG-NFGNQGDFNQMYQNPMMGGY-NPMMNPQAMTDYYQ KMQEYYQQMQ (SEQ ID NO:9). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR tag at the C-terminus of the fusion protein. The fusion protein was designated Gp32-HRP1. The full amino acid sequence of the fusion protein is presented as SEQ ID NO: 79 (Table 23).

Figure 3:
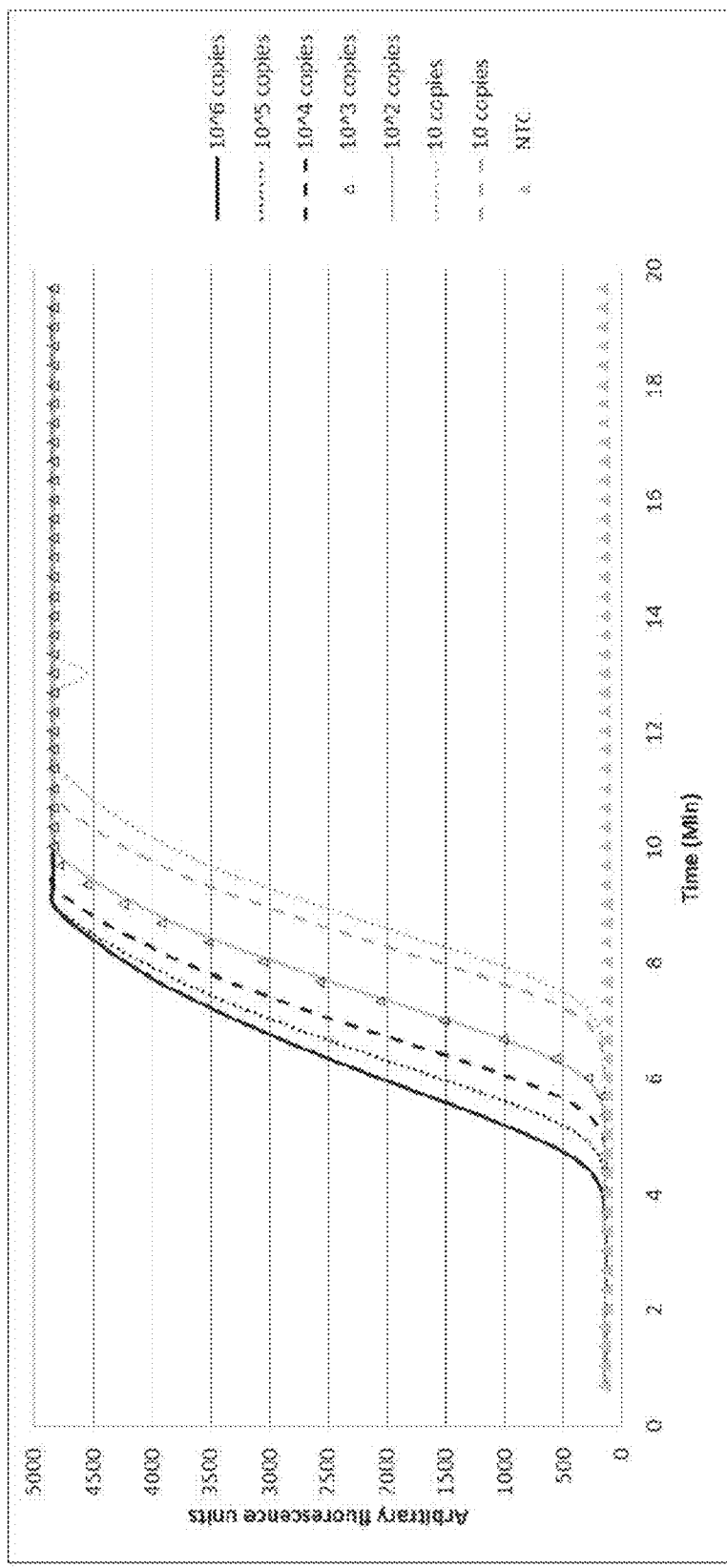
FIG. 3 shows real-time recombinase polymerase amplification traces using an IDR-tagged Gp32 fusion protein (Gp32-HRP1) at varying template nucleic acid concentrations.

The recombinant phage vB EcoM NBG1 Gp32 fusion protein was then tested in PEG-free amplification, i.e. in the absence of a crowding agent, using the indicated copies of a DNA template derived from *Listeria monocytogenes* genomic DNA. The test template was titrated in copy number as indicated in FIG. 3.

Reactions were set up by mixing 25 mM Tris HCl pH 8.3, 7.5 mM KOAc, 1 mM DTT, 2.5 mM ATP, 20 mM phosphocreatine, 1 µM creatine kinase, 1 mM dNTPs, 0.4 µM forward primer, 0.4 µM reverse primer, 0.12 µM probe, 20 µM Gp32 fusion, 4.8 µM UvsX, 8.6 µM UvsY, 0.135 µM *S. aureus* DNA polymerase, and 0.27 µM Exonuclease III. Reactions were initiated by the addition of template at the given concentration and with 33 mM MgOAc.

The relevant primers and probe are indicated below.

Forward primer: CGCCTGCAAGTCCTAAGACGC-CAATCGAAAAGAAAC (SEQ ID NO:98).

Reverse primer: CTGCATCTCCGTGGTATACTAATA-CATTGTTTTA (SEQ ID NO:99).

Probe: CGAAAAGAAACACGCGGATGAAATCGA-TAAG[FAM][THF][BHQ-1]ATACAAGGATTGGA (SEQ ID NO:100), where FAM is fluorescein, THF is tetrahydrofuran and BHQ is Black Hole Quencher.

Reactions were then incubated at 39° C. and placed in a fluorometer with magnetic mixing using a bearing ball.

Results and Conclusion

As shown in FIG. 3 the test template was readily detected at high sensitivity within 7 minutes of initiation of the RPA reaction. Amplicons were detected with as little as 10 copies of target.

It was therefore found that amplification in the absence of a crowding agent, such as PEG, occurred efficiently using this Gp32 IDR-tagged fusion protein.

Example 4. Recombinase Polymerase Amplification of the Listeria monocytogenes Gene Hly Using Gp32 Having an IDR Tag Derived from Saccharomyces cerevisiae Sup2

Purpose and Summary of Experiment

This experiment was performed to assess the performance of a Gp32 fusion protein preparation containing a tag comprising an intrinsically disordered region (IDR) domain of the Saccharomyces cerevisiae Sup2 protein.

The example demonstrates recombinase polymerase amplification (RPA) of the Listeria monocytogenes gene hly across a range of template concentrations using Gp32 C-terminally tagged with the sequence comprising an intrinsically disordered region (IDR) domain of the yeast Sup2 protein in the absence of a crowding agent.

Materials and Methods

The specific amino acid sequence of the IDR domain tag used was YNPQGGYQQ (SEQ ID NO:19). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR domain tag at the C-terminus of the fusion protein. The fusion protein was designated Gp32-Sup1. The full amino acid sequence of the fusion protein is presented as SEQ ID NO: 72 (Table 23).

The recombinant phage vB EcoM NBG1 Gp32 fusion protein was then tested in PEG-free amplification, i.e. in the absence of a crowding agent, using the indicated copies of a DNA template derived from Listeria monocytogenes genomic DNA. The test template was titrated in copy number as indicated in Figure C.

Reactions were set up by mixing 25 mM Tris HCl pH 8.3, 7.5 mM KOAc, 1 mM DTT, 2.5 mM ATP, 20 mM phosphocreatine, 1 µM creatine kinase, 1 mM dNTPs, 0.4 µM forward primer, 0.4 µM reverse primer, 0.12 µM probe, 20 µM Gp32 fusion, 4.8 µM UvsX, 8.6 µM UvsY, 0.135 µM S. aureus DNA polymerase, and 0.27 µM Exonuclease III. Reactions were initiated by the addition of template at the given concentration and with 33 mM MgOAc.

The relevant primers and probe are indicated below.

Forward primer: CGCCTGCAAGTCCTAAGACGC-CAATCGAAAAGAAAC (SEQ ID NO:98).

Reverse primer: CTGCATCTCCGTGGTATACTAATA-CATTGTTTTTA (SEQ ID NO:99).

Probe: CGAAAAGAAACACGCGGATGAAATCGA-TAAG[FAM][THF][BHQ-1]ATACAAGGATTGGA (SEQ ID NO:100), where FAM is fluorescein, THF is tetrahydrofuran and BHQ is Black Hole Quencher.

Reactions were then incubated at 39° C. and placed in a fluorometer with magnetic mixing using a bearing ball.

Results and Conclusion

Figure 4:
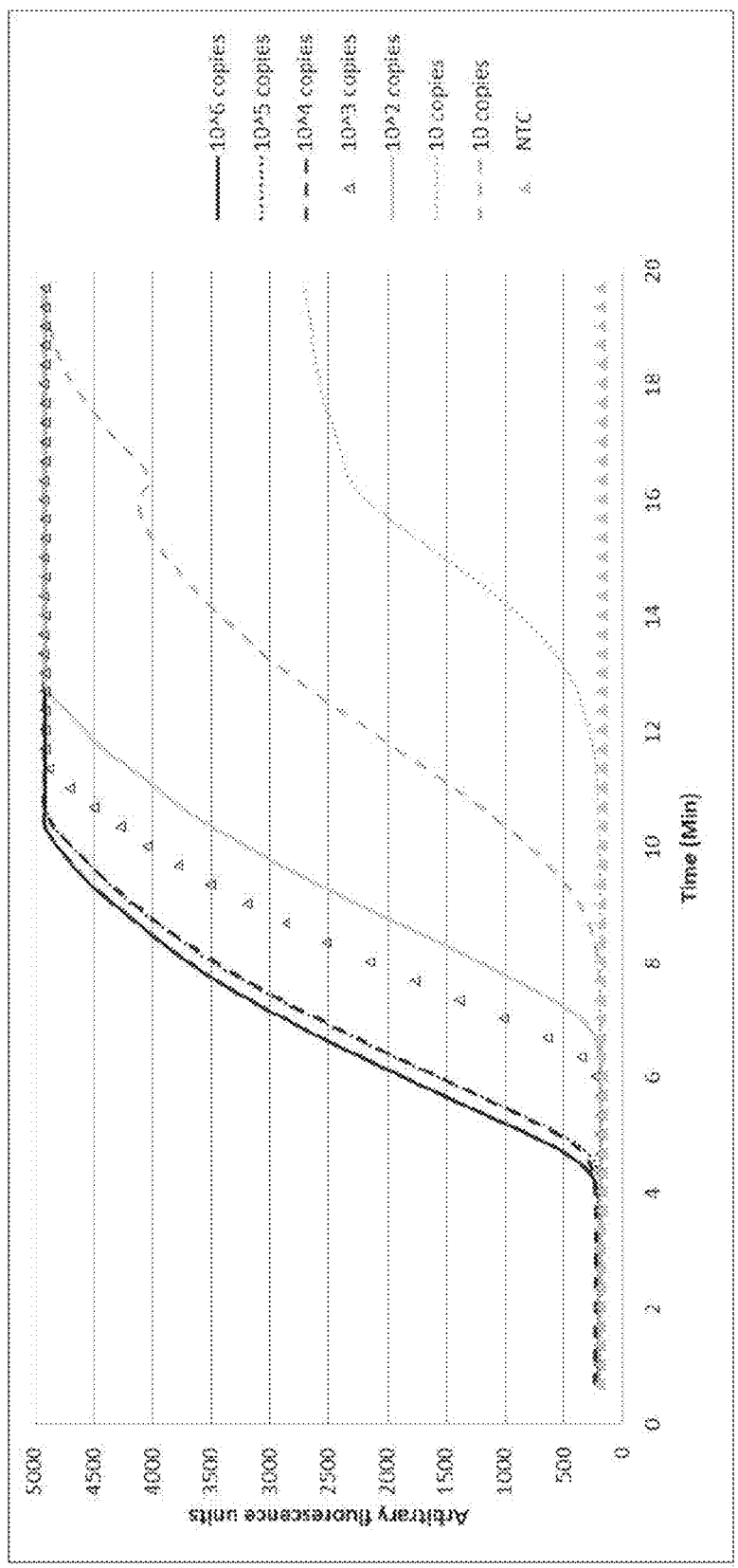
FIG. 4 shows real-time recombinase polymerase amplification traces using an IDR-tagged Gp32 fusion protein (Gp32-Sup1) at varying template nucleic acid concentrations.
Figure 5A:
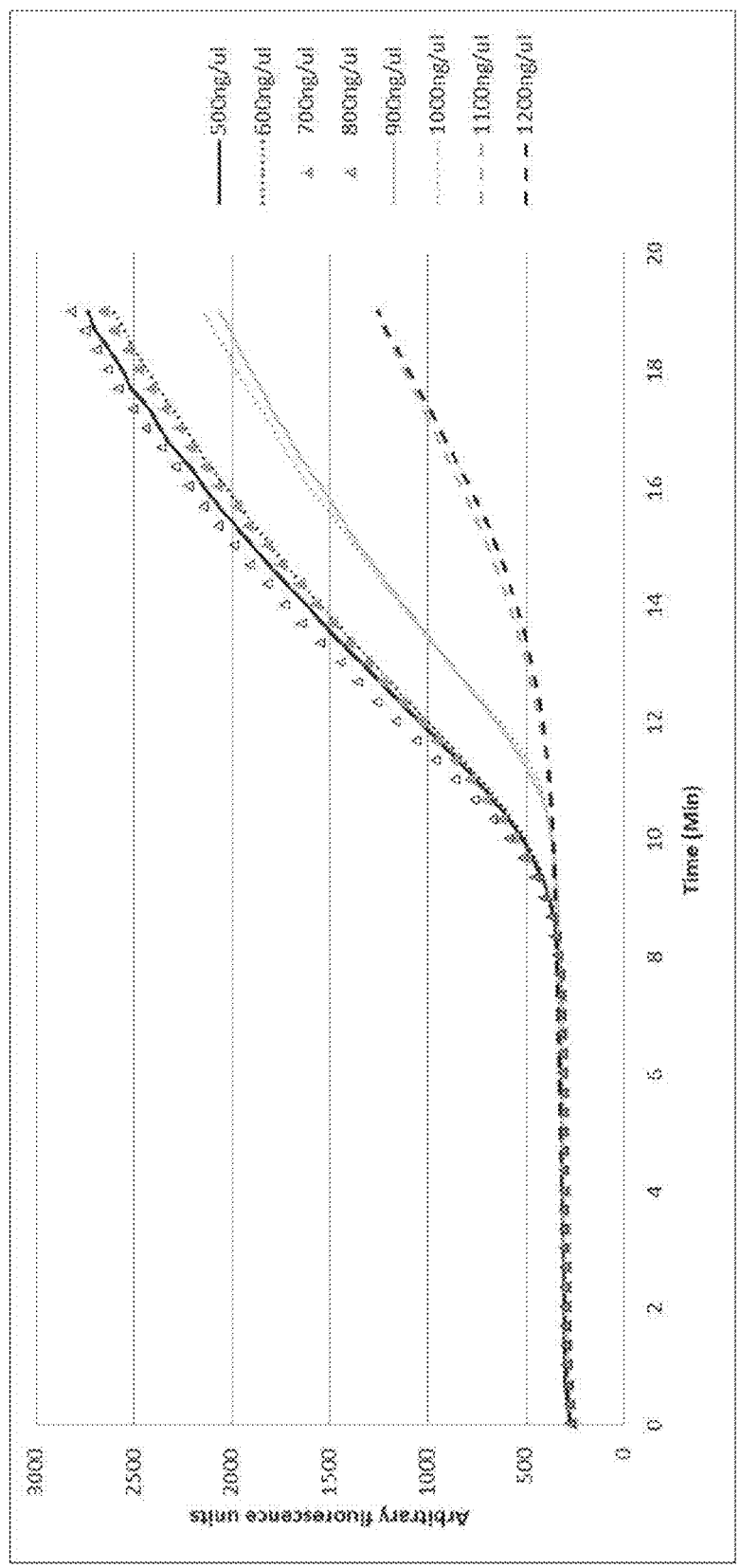
FIGS. 5A-5D show real-time recombinase polymerase amplification traces using an IDR-tagged Gp32 fusion protein (Gp32-Sup2) at varying template nucleic acid concentrations. The experiments shown in FIGS. 5A, B, C and D use respectively a Gp32 fusion protein with one, two, three and four Sup2 IDR repeats.
Figure 5B:
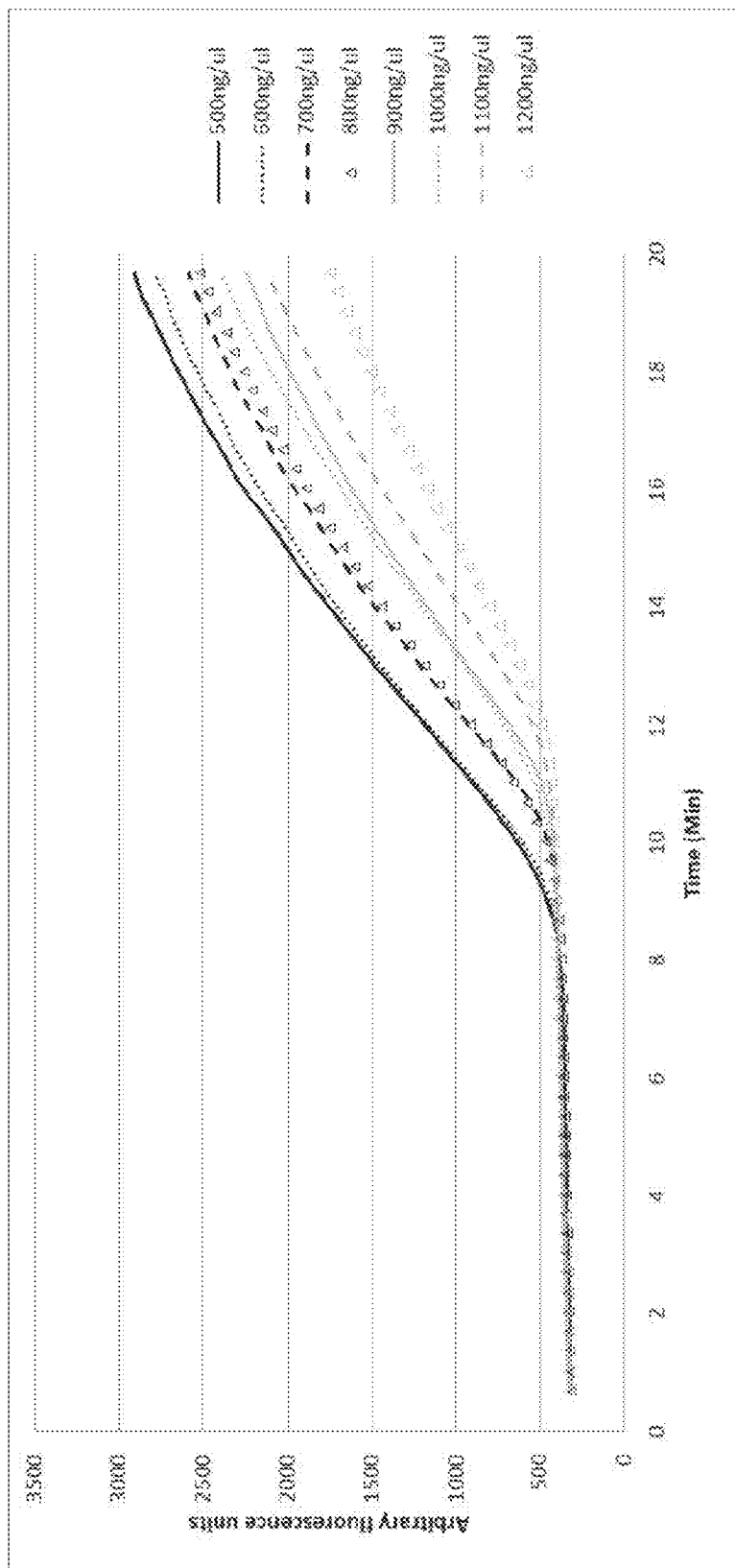
Figure 5C:
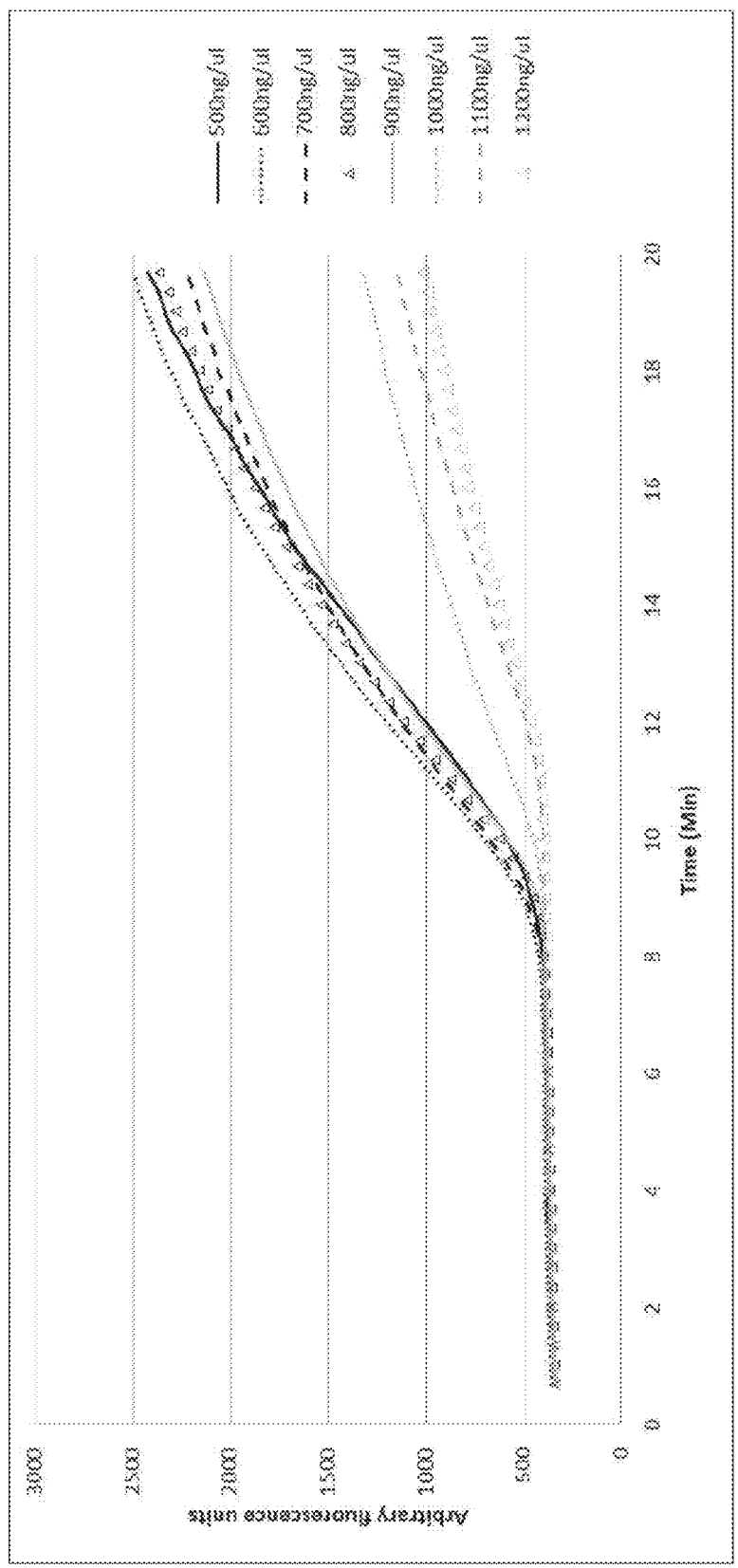
Figure 5D:
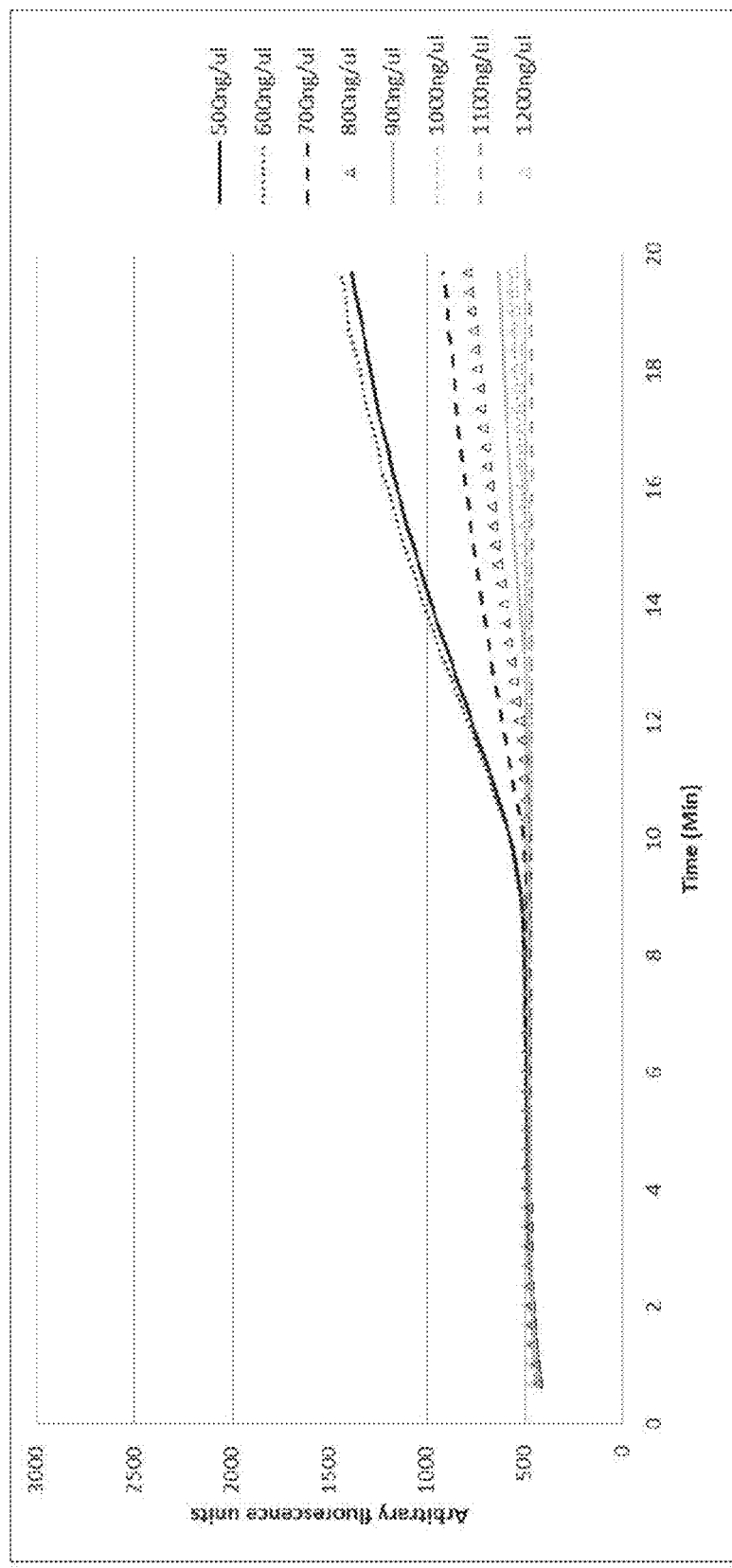

As shown in FIG. 4 the test template was readily detected at high sensitivity within 7 minutes of initiation of the RPA reaction. Amplicons were detected with as little as 10 copies of target.

It was therefore found that amplification in the absence of a crowding agent, such as PEG, occurred efficiently using this Gp32 IDR-tagged fusion protein.

Example 5. Recombinase Polymerase Amplification of the Human apoB Gene Using Gp32 Having IDR Tags Derived from Saccharomyces cerevisiae Sup2

Purpose and Summary of Experiment

This experiment was performed to assess the performances of a number of Gp32 fusion protein preparations containing tags comprising an intrinsically disordered region (IDR) domain amino acid sequence of the Saccharomyces cerevisiae Sup2 protein. Variable numbers of an IDR domain repeat unit were assessed and a range of concentrations of the fusion proteins were examined.

The example demonstrates recombinase polymerase amplification (RPA) of the human apolipoprotein B (apoB) gene using Gp32 C-terminally tagged with the sequence comprising an intrinsically disordered region (IDR) domain of the yeast Sup2 protein in the absence of a crowding agent.

Materials and Methods

The specific amino acid sequence of the IDR domain tag used was YNPQGGYQQ (SEQ ID NO:19). This was attached to the C-terminus of phage vB EcoM NBG1 Gp32. Either a single YNPQGGYQQ unit was attached, or two, three or four repeats were attached. The recombinant fusion protein was purified using standard 1-step immobilised metal (nickel) affinity chromatography relying on an additional heptahistidine tag placed at the very C-terminus of the fusion protein under test, i.e. placed after the IDR domain tag at the C-terminus of the fusion protein. The fusion proteins were designated Gp32-Sup2 (two repeats; SEQ ID NO:20), Gp32-Sup3 (three repeats; SEQ ID NO:21) and Gp32-Sup4 (four repeats; SEQ ID NO:22). The full amino acid sequences of the fusion proteins are presented respectively as SEQ ID NO: 73, SEQ ID NO: 74 and SEQ ID NO: 75 (Table 23).

The recombinant phage vB EcoM NBG1 Gp32 fusion proteins were then tested, along with Gp32-Sup1, in PEG-free amplification, i.e. in the absence of a crowding agent, using a DNA template derived from human genomic DNA.

Reactions were set up by mixing 25 mM Tris HCl pH 8.3, 7.5 mM KOAc, 1 mM DTT, 2.5 mM ATP, 20 mM phosphocreatine, 1 µM creatine kinase, 1 mM dNTPs, 0.4 µM forward primer, 0.4 µM reverse primer, 0.12 µM probe, Gp32 fusion protein at the concentrations indicated in FIGS. 5 A to D, 4.8 µM UvsX, 8.6 µM UvsY, 0.135 µM S. aureus DNA polymerase, and 0.27 µM Exonuclease III. Reactions were initiated by the addition of template and with 33 mM MgOAc. The test template copy number used in each case was 10,000.

The relevant primers and probe are indicated below.

Forward primer: GCAGCTGTATAGCAAATTCCTGTT-GAAAGCAG (SEQ ID NO:101).

Reverse primer: TCCTGGCTGTATTCATTGTTGT-TAAATTGG (SEQ ID NO:102).

Probe: CACTGATGCT TTTCCTAGACACGAGATGA [FAM-dT]G[THF]C[BHQ1-dT]TGTGGAGCCTTTGT (SEQ ID NO:103), where FAM is fluorescein, THF is tetrahydrofuran and BHQ is Black Hole Quencher.

Reactions were then incubated at 39° C. and placed in a fluorometer with magnetic mixing using a bearing ball.

Results and Conclusion

The results are shown in FIG. 5. FIG. 5A shows the results using a single IDR domain tag unit. FIGS. 5 B to D show the results using respectively two, three and four of the IDR domain tag unit repeats. The test template was detected after about 10 minutes of initiation of the RPA reaction.

It was found that amplification in the absence of a crowding agent, such as PEG, occurred efficiently using these Gp32-IDR tagged fusion proteins. The best performance was seen with a single IDR domain tag unit and with two IDR domain tag units. Three IDR domain tag units also gave good performance.

Example 6. Recombinase Polymerase Amplification of the *Listeria monocytogenes* Gene Hly Using Gp32 Having an IDR Tag Derived from Human MafA—Comparison of Magnesium Ion Concentrations Purpose of Experiment This experiment was performed to assess the performance of a Gp32 fusion protein preparation containing a tag comprising a histidine-rich domain sequence found in the intrinsically disordered region (IDR) of the human transcription factor MafA. The experiment assessed performance across a range of magnesium concentrations.

The example demonstrates recombinase polymerase amplification (RPA) of the *Listeria monocytogenes* gene hly across a range of magnesium concentrations using Gp32 C-terminally tagged with the histidine-rich intrinsically disordered region (IDR) domain (MafA) in the absence of a crowding agent.

Materials and Methods

The specific amino acid sequence of the IDR domain tag used was SGHHGAHHGAHHPAAAAAYEAFRGPGF-AGGGGADDMGAGHHHGAHHAAHH HHAAHHHHHHHHHHGGAGHGGGAGHH (SEQ ID NO:27). This was attached to the C-terminus of phage vB EcoM NBG1 Gp32. The recombinant fusion protein was purified using standard 1-step immobilised metal (nickel) affinity chromatography relying on the histidines naturally present in the IDR domain tag of the fusion protein under test. The fusion protein was designated Gp32-HIS5. The full amino acid sequence of the fusion protein is presented as SEQ ID NO: 85 (Table 23).

The recombinant phage vB EcoM NBG1 Gp32 fusion protein was then tested in PEG-free amplification, i.e. in the absence of a crowding agent, using the indicated copies of a DNA template derived from *Listeria monocytogenes* genomic DNA. The test template was provided at 10,000 copies per reaction and the magnesium ion concentration was varied from 5.6 mM up to 44.8 mM.

Reactions were set up by mixing 25 mM Tris HCl pH 8.3, 7.5 mM KOAc, 1 mM DTT, 2.5 mM ATP, 20 mM phosphocreatine, 1 µM creatine kinase, 1 mM dNTPs, 0.4 µM forward primer, 0.4 µM reverse primer, 0.12 µM probe, 20 µM Gp32 fusion, 4.8 µM UvsX, 8.6 µM UvsY, 0.135 µM *S. aureus* DNA polymerase, and 0.27 µM Exonuclease III. Reactions were initiated by the addition of template and the indicated concentration of MgOAc from 5.6 mM to 44.8 mM MgOAc.

The relevant primers and probe are indicated below.

Forward primer: CGCCTGCAAGTCCTAAGACGC-CAATCGAAAAGAAAC (SEQ ID NO:98).

Reverse primer: CTGCATCTCCGTGGTATACTAATA-CATTGTTTTA (SEQ ID NO:99).

Probe: CGAAAAGAAACACGCGGATGAAATCGA-TAAG[FAM][THF][BHQ-1]ATACAAGGATTGGA (SEQ ID NO:100), where FAM is fluorescein, THF is tetrahydrofuran and BHQ is Black Hole Quencher.

Reactions were then incubated at 39° C. and placed in a fluorometer with magnetic mixing using a bearing ball.

Results and Conclusion

It was found that amplification in the absence of a crowding agent such as PEG occurred efficiently using this Gp32 IDR-tagged fusion protein.

Figure 6:
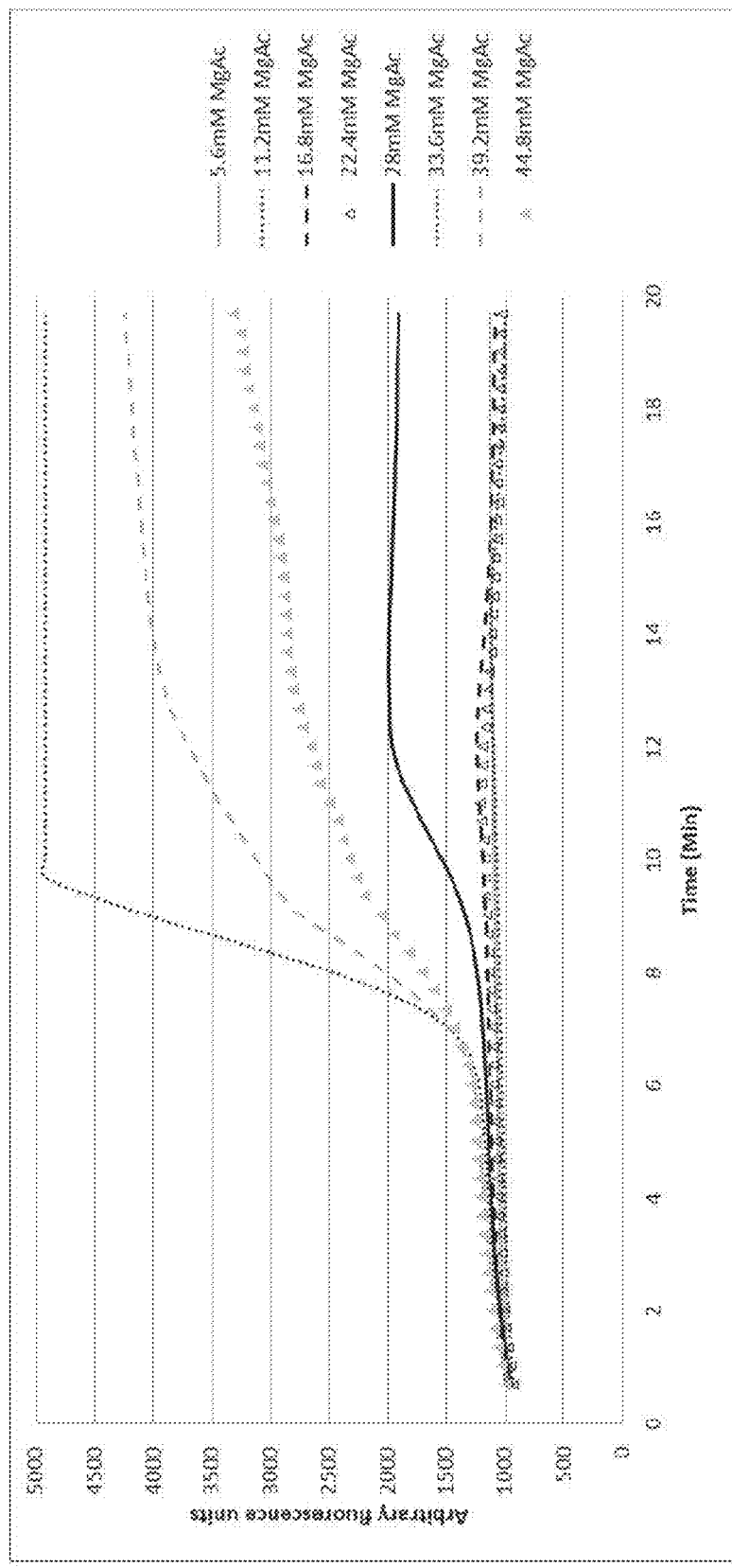
FIG. 6 shows real-time recombinase polymerase amplification traces using an IDR-tagged Gp32 fusion protein (Gp32-HIS5) at varying MgOAc concentrations.

As shown in FIG. 6, it was found that good amplification occurred using this Gp32 IDR-tagged fusion protein when 28 mM or more magnesium was present. The optimum concentration in this experiment appeared to be 33.6 mM, and further increases up to 44.8 mM yielded similar time to detection.

Example 7. Effects of Phosphocreatine Levels on Recombinase Polymerase Amplification of a Human ApoB Gene Fragment Purpose and Summary of Experiment This experiment was performed to assess the effects of varying the phosphocreatine levels on the performance of a Gp32 fusion protein preparation containing a tag comprising a histidine-rich domain sequence found in the intrinsically disordered region (IDR) of the human homeobox protein Otx1.

The example demonstrates recombinase polymerase amplification (RPA) of a fragment of the human apolipoprotein (apoB) gene using Gp32 C-terminally tagged with the histidine-rich intrinsically disordered region (IDR) domain (Otx1) in the absence of a crowding agent.

Materials and Methods

The specific amino acid sequence of the IDR domain tag used was AGHHHHHPHAHHPLSQSSGHHHHHHHHHHQGYGG SG (SEQ ID NO:24). This was attached to the C-terminus of phage vB EcoM NBG1 Gp32. The recombinant fusion protein was purified using standard 1-step immobilised metal (nickel) affinity chromatography relying on the histidines naturally present in the IDR domain tag of the fusion protein under test. The fusion protein was designated Gp32-HIS2. The full amino acid sequence of the fusion protein is presented as SEQ ID NO: 82 (Table 23).

The recombinant phage vB EcoM NBG1 Gp32 fusion protein was then tested in PEG-free amplification, i.e. in the absence of a crowding agent. A phosphocreatine titration was carried out using the human apoB assay. The test template was provided at a concentration of $10^4$ copies.

Reactions were set up by mixing 25 mM Tris HCl pH 8.3, 7.5 mM KOAc, 1 mM DTT, 2.5 mM ATP, levels of phosphocreatine indicated in the figures, 1 µM creatine kinase, 1 mM dNTPs, 0.4 µM forward primer, 0.4 µM reverse primer, 0.12 µM probe, 20 µM Gp32 fusion, 4.8 µM UvsX, 8.6 µM UvsY, 0.135 µM *S. aureus* DNA polymerase, and 0.27 µM Exonuclease III. Reactions were initiated by the addition of $10^4$ copies template per reaction and with 33 mM MgOAc.

Forward primer: GCAGCTGTATAGCAAATTCCTGTT-GAAAGCAG (SEQ ID NO:101).

Reverse primer: TCCTGGCTGTATTCATTGTTGT-TAAATTGG (SEQ ID NO:102).

Probe: CACTGATGCT TTTCCTAGACACGAGATGA [FAM-dT]G[THF]C[BHQ1-dT]TGTGGAGCCTTTGT (SEQ ID NO:103), where FAM is fluorescein, THF is tetrahydrofuran and BHQ is Black Hole Quencher.

Reactions were then incubated at 39° C. and placed in a fluorometer with magnetic mixing using a bearing ball.

Results and Conclusion

Figure 7A:
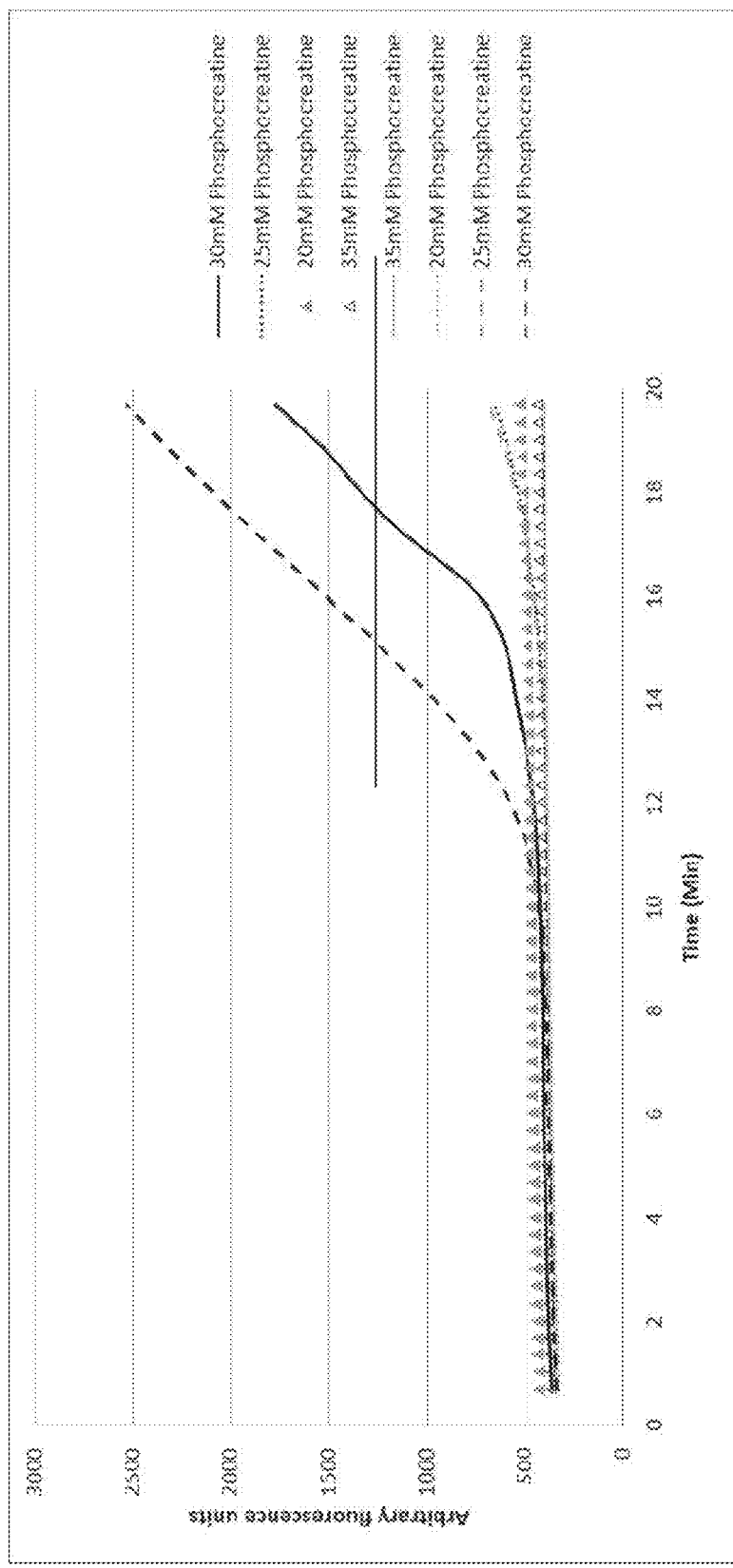
FIGS. 7A-7C show real-time recombinase polymerase amplification traces using an IDR-tagged Gp32 fusion protein (Gp32-HIS2) at varying phosphocreatine concentrations.
Figure 7B:
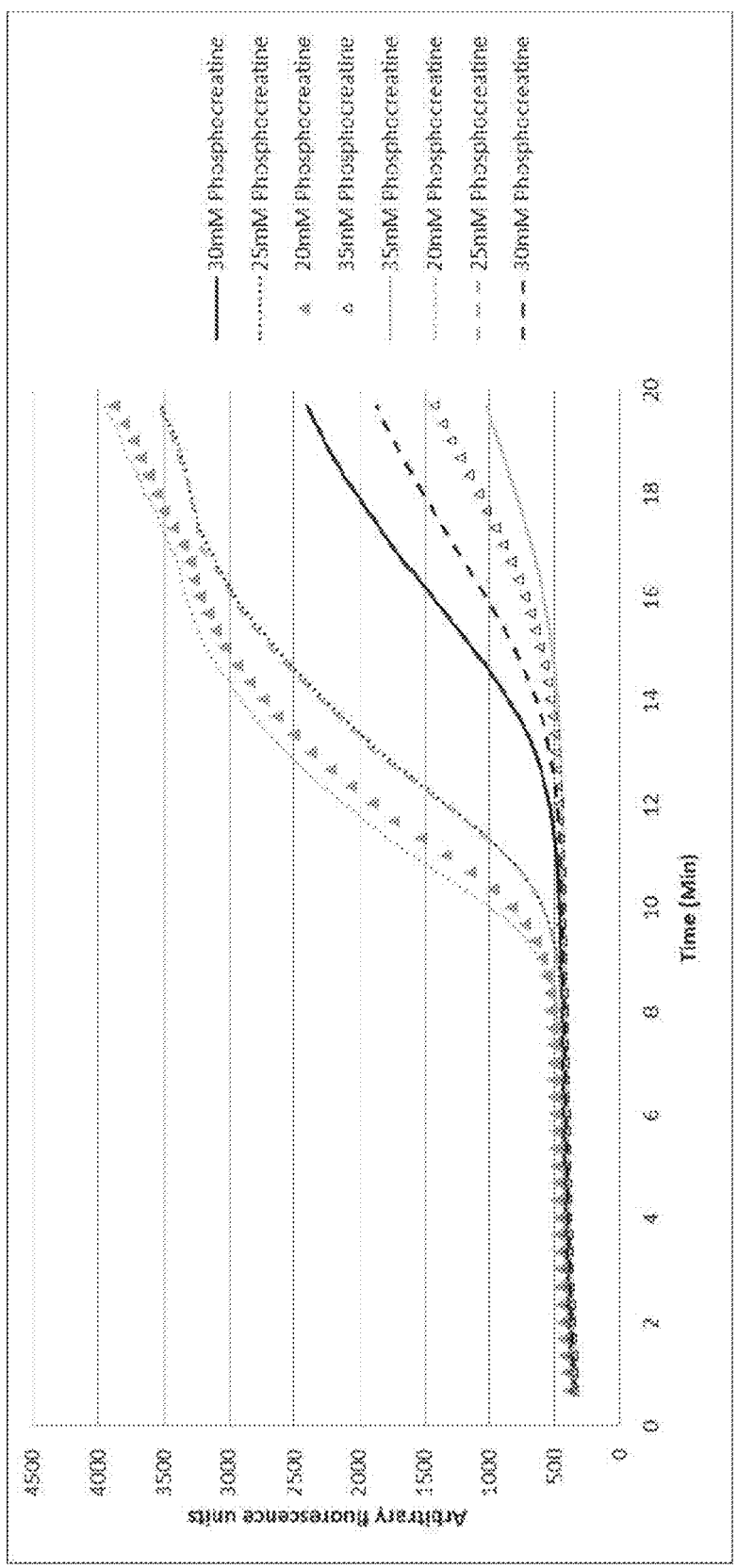
Figure 7C:
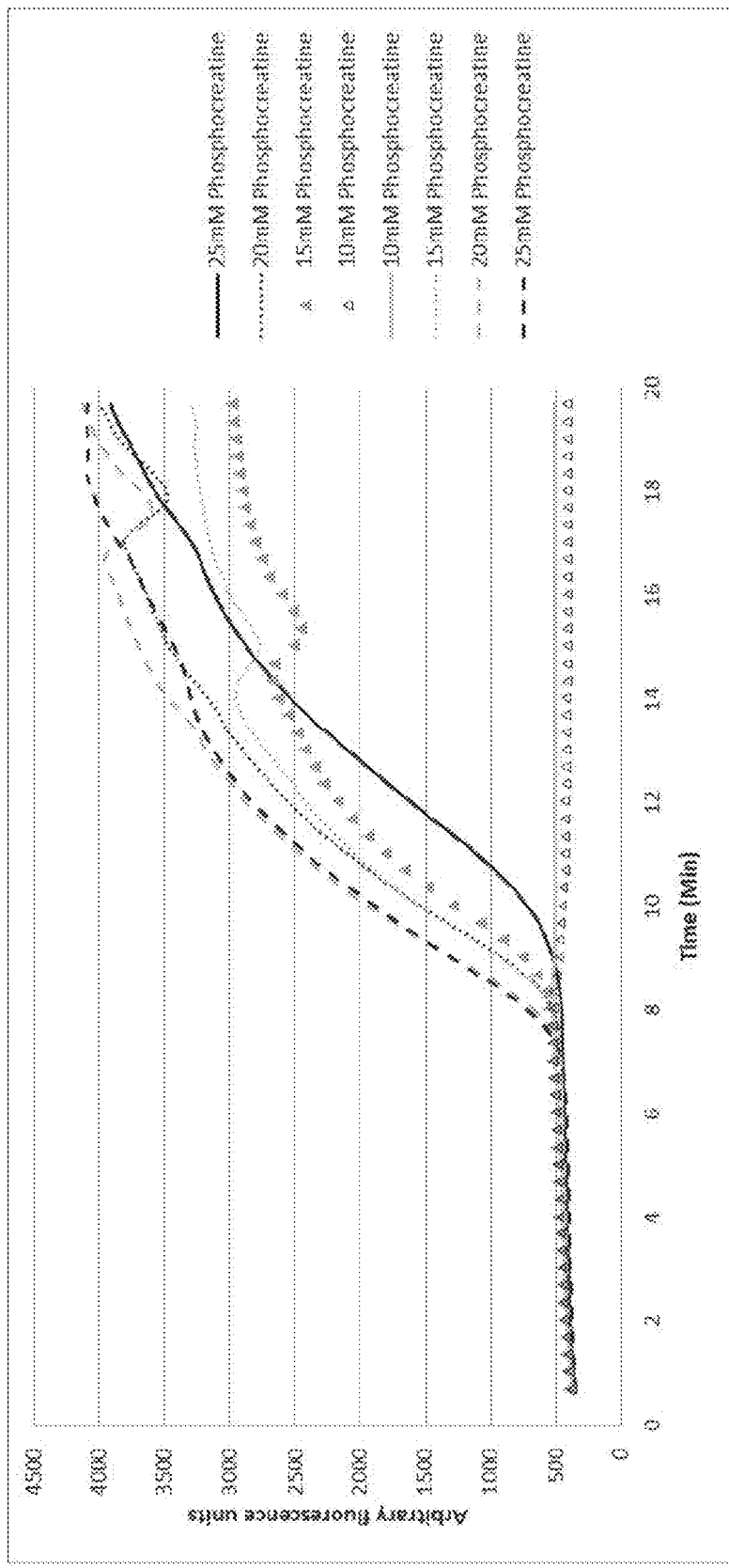

It was found that amplification occurred in the absence of a crowding agent such as PEG using this Gp32 IDR-tagged fusion protein. As shown in FIGS. 7 A, B and C, at the standard phosphocreatine concentration used in PEG based RPA (50 mM), little amplification activity was seen within 20 minutes. Reducing phosphocreatine to 20 mM resulted in optimum performance, but good performance was also observed between 15-25 mM, and lower levels of amplification within 20 minutes was also observed at 30-35 mM.

Example 8. Recombinase Polymerase Amplification of the *Listeria monocytogenes* Gene Hly Using Gp32 Having an IDR Tag Derived from *Saccharomyces cerevisiae* Hrp1—Comparison of Salt Concentrations Purpose and Summary of Experiment This experiment was performed to assess the performance of a Gp32 fusion protein preparation containing a tag comprising an intrinsically disordered region (IDR) of the *Saccharomyces cerevisiae* Hrp1 protein. The experiment assessed performance across a range of salt concentrations, in this case using potassium acetate.

The example demonstrates recombinase polymerase amplification (RPA) of the *Listeria monocytogenes* gene hly can be optimised across a range of salt concentrations using Gp32 C-terminally tagged with an intrinsically disordered region (IDR) of the *Saccharomyces cerevisiae* Hrp1 protein in the absence of a crowding agent.

Materials and Methods

The specific amino acid sequence of the IDR domain tag used was GGNNGGNNMNRRGG-NFGNQGDFNQMYQNPMMGGY-NPMMNPQAMTDYYQ KMQEYYQQMQ (SEQ ID NO:9). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR tag at the C-terminus of the fusion protein. The fusion protein was designated Gp32-HRP1. The full amino acid sequence of the fusion protein is presented as SEQ ID NO: 79 (Table 23).

The recombinant phage vB EcoM NBG1 Gp32 fusion protein was then tested in PEG-free amplification, i.e. in the absence of a crowding agent, using 100 copies of a DNA template derived from *Listeria monocytogenes* genomic DNA. The potassium acetate concentration was varied from 10 mM up to 100 mM.

Reactions were set up by mixing 25 mM Tris HCl pH 8.3, 7.5 mM KOAc, 1 mM DTT, 2.5 mM ATP, 20 mM phosphocreatine, 1 µM creatine kinase, 1 mM dNTPs, 0.4 µM forward primer, 0.4 µM reverse primer, 0.12 µM probe, 20 µM Gp32 fusion, 4.8 µM UvsX, 8.6 µM UvsY, 0.135 µM *S. aureus* DNA polymerase, and 0.27 µM Exonuclease III. Reactions were initiated by the addition of template and 33 mM MgOAc.

The relevant primers and probe are indicated below.

Forward primer: CGCCTGCAAGTCCTAAGACGC-CAATCGAAAAGAAAC (SEQ ID NO:98).

Reverse primer: CTGCATCTCCGTGGTATACTAATA-CATTGTTTTA (SEQ ID NO:99).

Probe: CGAAAAGAAACACGCGGATGAAATCGA-TAAG[FAM][THF][BHQ-1]ATACAAGGATTGGA (SEQ ID NO:100), where FAM is fluorescein, THF is tetrahydrofuran and BHQ is Black Hole Quencher.

Reactions were then incubated at 39° C. and placed in a fluorometer with magnetic mixing using a bearing ball.

Results and Conclusion

It was found that amplification in the absence of a crowding agent such as PEG occurred efficiently using this Gp32 IDR-tagged fusion protein.

It was also found that amplification in the absence of a crowding agent using this Gp32 IDR-tagged fusion protein can be optimised across a range of salt concentrations, of which potassium acetate is a representative example.

Figure 8:
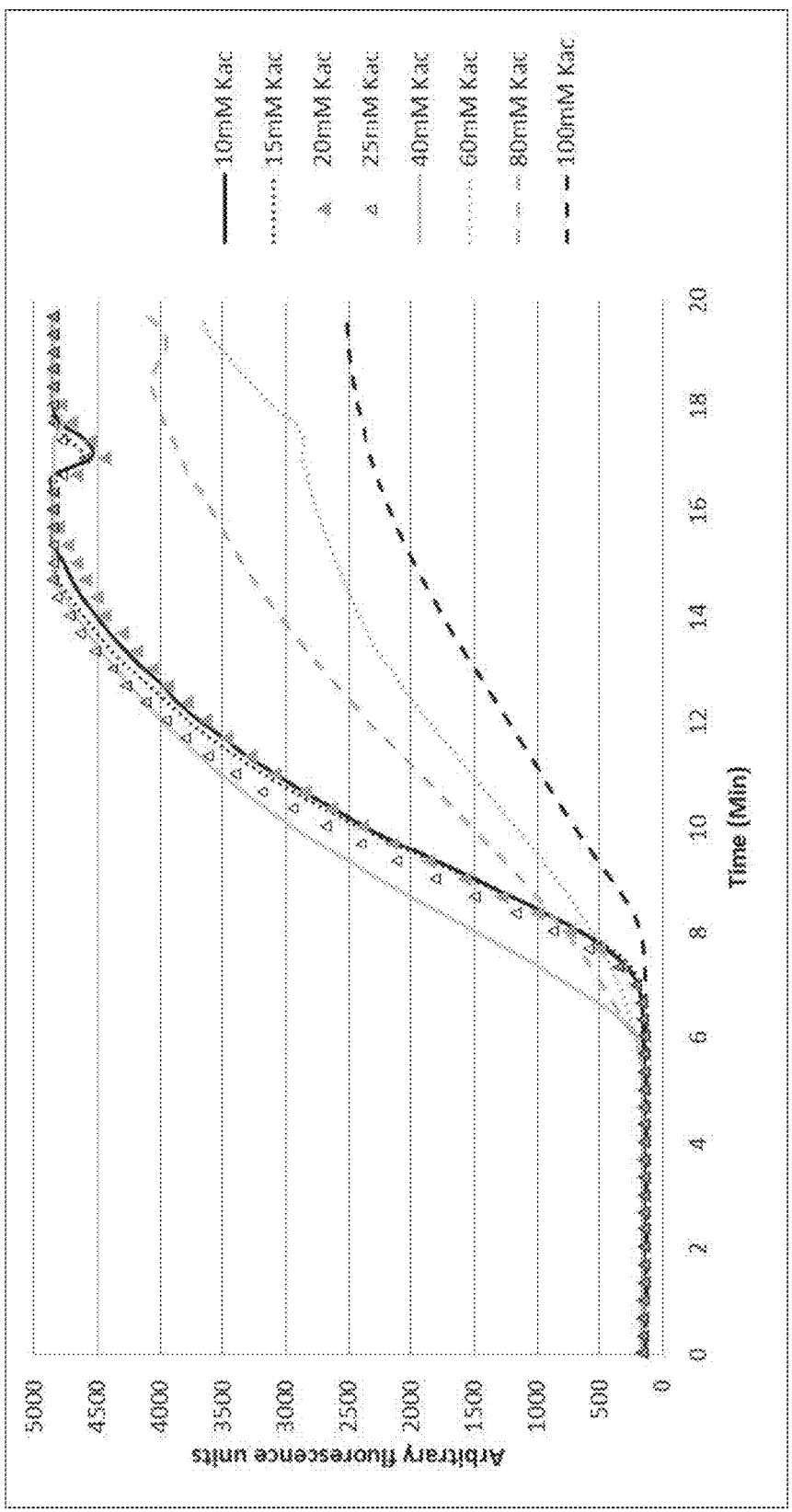
FIG. 8 shows real-time recombinase polymerase amplification traces using an IDR-tagged Gp32 fusion protein (Gp32-HRP1) at varying KOAc concentrations.

As shown in FIG. 8, it was found that good amplification occurred using this Gp32 IDR-tagged fusion protein when 10 mM or more potassium acetate was present. The optimum concentration range in this experiment appeared to be between 10 to 40 mM. At concentrations above 40 mM less efficient amplification was observed.

Example 9. Recombinase Polymerase Amplification of a Human ApoB Gene Fragment Using Gp32 Having an IDR Tag Derived from *Saccharomyces cerevisiae* Sup2—Synergistic Effect with Crowding Agent Purpose and Summary of Experiment This experiment was performed to assess the effect of low concentrations of a crowding agent, in this case PEG, on the reaction efficiency of a Gp32 fusion protein preparation containing a histidine-rich sequence found in the intrinsically disordered region of the yeast SUP2 gene, specifically the Sup1 sequence YNPQGGYQQ (SEQ ID NO:19), attached to the C-terminus of phage vB EcoM NBG1 Gp32. The performance of this fusion protein was compared to a Gp32 protein lacking the Sup1 IDR tag in recombinase polymerase amplification of a fragment of the human apolipoprotein (apoB) gene.

It was found that low concentrations of a crowing agent can enhance the reaction efficiency of the Sup1 IDR-tagged Gp32 and that conditions can be achieved where a synergistic effect can be observed.

Materials and Methods

Gp32-Sup1 The specific amino acid sequence of the IDR domain tag used was YNPQGGYQQ (SEQ ID NO:19). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR domain tag at the C-terminus of the fusion protein. The fusion protein was designated Gp32-Sup1. The full amino acid sequence of the fusion protein is presented as SEQ ID NO: 72 (Table 23).

Gp32 (7His)

Phage vB EcoM NBG1 Gp32 was purified using standard 1-step immobilised metal (nickel) affinity chromatography relying on a heptahistidine tag placed at the very C-terminus of the protein under test. The fusion protein was designated Gp32 (7His). The full amino acid sequence of the fusion protein is presented as SEQ ID NO: 65 (Table 23).

The recombinant phage vB EcoM NBG1 Gp32 fusion proteins were tested in RPA reactions, either in the presence or absence of a crowding agent using a DNA template comprising a fragment of the human apolipoprotein (apoB) gene.

Reactions were set up by mixing 25 mM Tris HCl pH 8.3, 7.5 mM KOAc, 1 mM DTT, 2.5 mM ATP, 50 mM phosphocreatine, 1 µM creatine kinase, 1 mM dNTPs, 0.4 µM forward primer, 0.4 µM reverse primer, 0.12 µM probe, 20 µM Gp32 fusion protein, 4.8 µM UvsX, 8.6 µM UvsY, 0.135 µM *S. aureus* DNA polymerase, and 0.27 µM Exonuclease III. Reactions were initiated by the addition of template and with 33 mM MgOAc. The test template copy number used in each case was 10,000. PEG was added to the final concentrations noted in the relevant figure. The species of PEG used was PEG molecular weight 35,000.

The relevant primers and probe are indicated below.

Forward primer: GCAGCTGTATAGCAAATTCCTGTT-GAAAGCAG (SEQ ID NO:101).

Reverse primer: TCCTGGCTGTATTCATTGTTGT-TAAATTGG (SEQ ID NO:102).

Probe: CACTGATGCT TTTCCTAGACACGAGATGA [FAM-dT]G[THF]C[BHQ1-dT]TGTGGAGCCTTTGT (SEQ ID NO:103), where FAM is fluorescein, THF is tetrahydrofuran and BHQ is Black Hole Quencher.

Reactions were then incubated at 39° C. and placed in a fluorometer with magnetic mixing using a bearing ball.

Results and Conclusion

Figure 9:
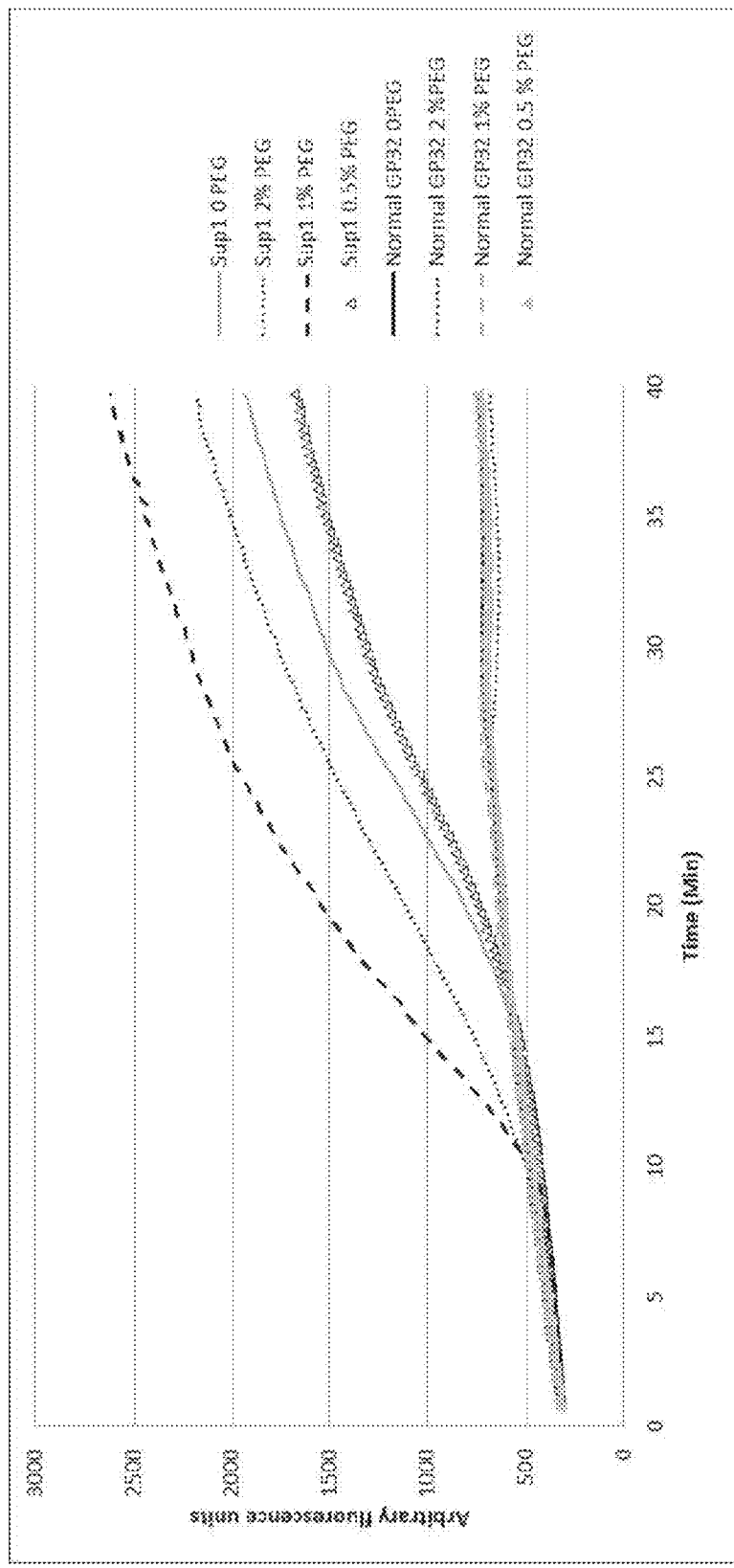
FIG. 9 shows real-time recombinase polymerase amplification traces using Gp32 tagged with seven histidine residues (for protein purification purpose, i.e. no IDR tag) compared with an IDR-tagged Gp32 fusion protein (Gp32-Sup1) either in the presence or absence of a crowding agent (PEG).

The results are shown in FIG. 9. FIG. 9 shows that when the Gp32-Sup1 IDR-tagged fusion protein was tested in the absence of the crowding agent PEG the test template was detected efficiently.

When the Gp32-7His fusion protein without the Sup1 IDR tag was tested in the presence of the crowding agent PEG, between 0.5% to 2%, a small but nevertheless detectable amount of amplified product was observed.

When the Gp32-Sup1 IDR-tagged fusion protein was tested in the presence of the crowding agent PEG the test template was detected efficiently. In this case a synergistic effect could be observed, with the amount of amplified product exceeding the combined amount when comparing the amount observed with: (i) the Gp32-Sup1 IDR-tagged fusion protein in the absence of PEG and (ii) the Gp32-7His fusion protein without the Sup1 IDR tag in the absence of PEG (see for example FIG. 9 and compare Sup1 1% PEG with Sup1 0% PEG+normal GP32 1% PEG).

These results demonstrate that an enhanced effect on the performance efficiency of a biochemical reaction can be observed when combining an IDR-tagged macromolecular component of the reaction with low concentrations of a crowding agent, and that conditions can be achieved that promote a synergistic effect on reaction efficiency when combining an IDR-tagged macromolecular component of the reaction with low concentrations of a crowding agent.

Example 10. Promotion of Phase Separation by IDR Tags in the Presence of Multivalent Metal Cations Purpose and Summary of Experiment This experiment was performed to assess, in an aqueous in vitro biochemical system, the effects of multivalent metal cations on the promotion of phase separation driven/caused by several Gp32 fusion proteins each having a tag comprising an intrinsically disordered region (IDR) domain amino acid sequence.

The example demonstrates that tags comprising IDR domain amino acid sequence are surprisingly capable of promoting phase separation, and more surprisingly that this effect is enhanced by the presence of multivalent metal cations.

Materials and Methods

Gp32-HIS2 Fusion Protein

The specific amino acid sequence of the IDR domain tag used was AGHHHHHPHAHHPLSQSSGHHHHHHHHHHHQGHG GSG (SEQ ID NO:24). This was attached to the C-terminus of phage vB EcoM NBG1 Gp32. The recombinant fusion protein was purified using standard 1-step immobilised metal (nickel) affinity chromatography relying on the histidines naturally present in the IDR domain tag of the fusion protein under test. The full amino acid sequence of the Gp32-HIS2 fusion protein is provided as SEQ ID NO:82 (Table 23).

Gp32-HRP1 Fusion Protein

The specific amino acid sequence of the IDR domain tag used was GGNNGGNNMNRRGG-NFGNQGDFNQMYQNPMMGGY-NPMMNPQAMTDYYQ KMQEYYQQMQ (SEQ ID NO:9). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR tag at the C-terminus of the fusion protein. The full amino acid sequence of the Gp32-HRP1 fusion protein is provided as SEQ ID NO:79 (Table 23).

Gp32-Sup1 Fusion Protein

The specific amino acid sequence of the IDR domain tag used was YNPQGGYQQ (SEQ ID NO:19). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR domain tag at the C-terminus of the fusion protein. The full amino acid sequence of the Gp32-Sup1 fusion protein is provided as SEQ ID NO:72 (Table 23).

Gp32-Fib Fusion Protein

The specific amino acid sequence of the IDR domain tag used was PGFSPRGGGFGGRGGFGDRGGRG-GRGGFGGGRGRGGGFRGRGR (SEQ ID NO:1). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR domain tag at the C-terminus of the fusion protein. The full amino acid sequence of the Gp32-Fib fusion protein is provided as SEQ ID NO:69 (Table 23).

Phase Separation Assay

The methods outlined below apply for all the fusion proteins tested. The volumes of the fusion protein solutions used depended upon the protein concentrations after purification.

A 50 µl solution was made up in each case, comprising the tagged fusion protein at a final concentration of 1000 ng/µl and metal ion, in either the acetate or the chloride form, at the target concentration indicated below and in the relevant figures presented herein.

For the Gp32-HIS2 fusion, protein concentration after purification was 48 mg/ml. 1.04 µl of this fusion protein was used in each 50 µl reaction to achieve a final concentration of 1000 ng/µl in solution. For the Gp32-HRP1 fusion, protein concentration after purification was 39 mg/ml. 1.28 µl of this fusion protein was used in each 50 µl reaction to achieve a final concentration of 1000 ng/µl in solution. For the Gp32-Sup1 fusion, protein concentration after purification was 36 mg/ml. 1.4 µl of this fusion protein was used in each 50 µl reaction to achieve a final concentration of 1000 ng/µl in solution. For the Gp32-Fib fusion, protein concentration after purification was 20.2 mg/ml. 2.48 µl of this fusion protein was used in each 50 µl reaction to achieve a final concentration of 1000 ng/µl in solution.

In these experiments the divalent metal cation concentration required for detectible phase separation enhancement to occur was tested with representative divalent metal cations: magnesium (MgOAc), manganese ($MgCl_2$) and calcium ($CaCl_2$). The acetate forms of manganese and calcium were not used simply due to their known instability in solution. Manganese will oxidise over time in the acetate solution, and calcium acetate seems to support the growth of some bacteria in solution whereas calcium chloride does not.

Following constitution of a mixture comprising water, the IDR-tagged protein and divalent metal cations, the mixture was vortexed, spun down and a 10 µl sample of the mixture was transferred to a DHC-B01 C-Chip haemocytometer slide. The slide was then imaged under a microscope at ×400 magnification. Detectible phase separation was assessed by the formation of spherical-like globular foci/particles which can be identified visually via magnification and counted using the haemocytometer. A globular foci count per unit volume can then be performed. Globular foci counts were performed by counting the number of globular foci which formed in a magnification area of 218 µm×175 µm at ×400 magnification. This was done by splitting the magnified image into 20 square segments (4×5 of the image), counting the globular foci in one of these segments and then multiplying this number by 20.

Results and Conclusions

It was observed that the transition that occurs between just below the minimum detectible phase separating concentration (MPSC) in this assay and just above the MPSC occurred very suddenly in all of the reactions performed. At just below the MPSC no detectible phase-separated aqueous particles were observed at all, and the solution was found to be empty of visibly detectible particles (globular foci). Above the MPSC the transition was very apparent with hundreds of visibly detectible particles (globular foci) suddenly forming.

The size of the globular foci varied and was found to be correlated with the IDR tag and the divalent metal cation used. It was determined that the specific sizes of the globular foci was unimportant.

Globular foci were present as particle-like structures being broadly spherical in shape. For any given IDR tag and any given divalent metal ion combination an average diameter of a population of globular foci can readily be determined using standard methods.

Results using individual fusion proteins are outlined below.

Gp32-HIS2 Fusion Protein

The minimum concentration of magnesium required to enhance the formation of detectible phase-separated aqueous particles in these conditions was determined to be 10 mM—approximately 600 particles (globular foci) were counted within the field.

The minimum concentration of calcium ions required to enhance the formation of detectible phase-separated aqueous particles in these conditions was determined to be 12 mM—approximately 500 particles (globular foci) were counted within the field.

The minimum concentration of manganese ions required to enhance the formation of detectible phase-separated aqueous particles in these conditions was determined to be 2 mM—approximately 180 particles (globular foci) were counted within the field.

Figure 10A:
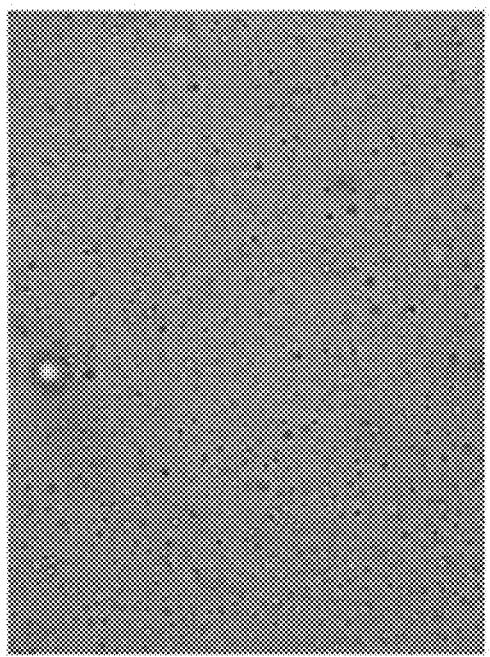
FIGS. 10A-10D show the effect of multivalent metal cations on the promotion of phase separation (particle formation) mediated by IDR amino acid sequence tags in the absence of a crowding agent. The IDR amino acid sequences were tagged to the Gp32 protein to create the Gp32-HIS2 fusion protein (FIG. 10A), the Gp32-HRP1 fusion protein (FIG. 10B), the Gp32-Sup1 fusion protein (FIG. 10C) and the Gp32-Fib fusion protein (FIG. 10D). In each case the effect of representative concentrations of divalent metal cations, i.e. magnesium (MgOAc), manganese ($MgCl_2$) and calcium ($CaCl_2$)) was tested.
Figure 10A:
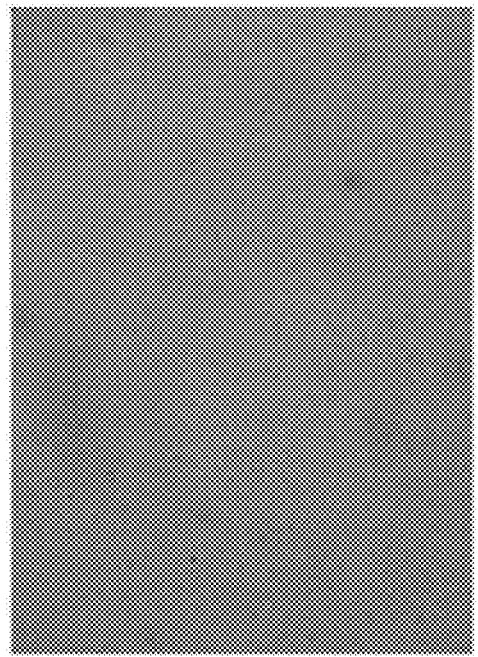
Figure 10A:
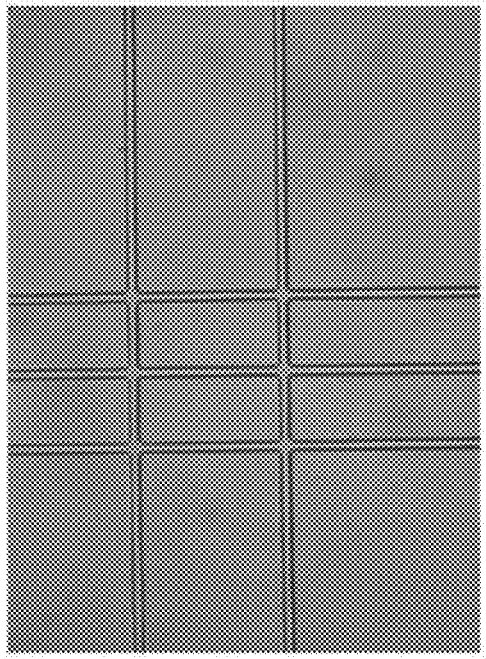
Figure 10A:
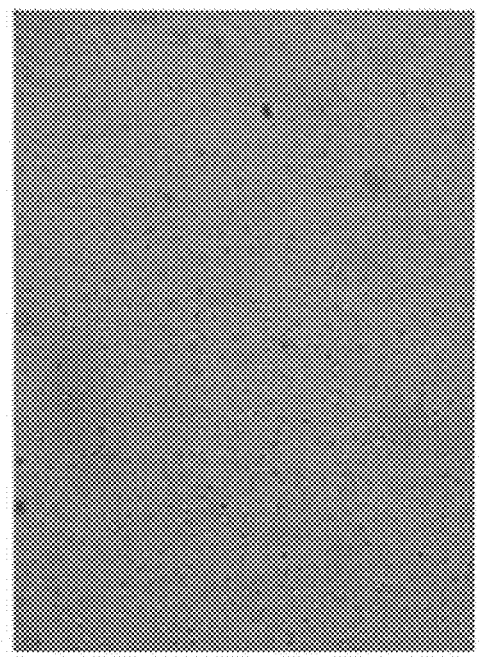

Representative magnified images are shown in FIG. 10A.

Gp32-HRP1 Fusion Protein

The minimum concentration of magnesium ions required to enhance the formation of detectible phase-separated aqueous particles in these conditions was determined to be 16 mM. At this concentration approximately 580 particles (globular foci) were counted within the field.

The minimum concentration of calcium ions required to enhance the formation of detectible phase-separated aqueous particles in these conditions was determined to be 24 mM. At this concentration approximately 240 particles (globular foci) were counted within the field.

The minimum concentration of manganese ions required to enhance the formation of detectible phase-separated aqueous particles in these conditions was determined to be 6 mM. At this concentration approximately 260 particles (globular foci) were counted within the field.

Figure 10B:
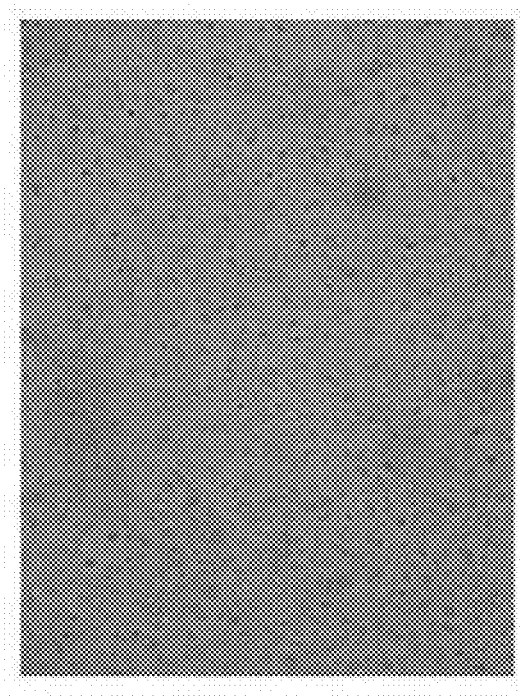
Figure 10B:
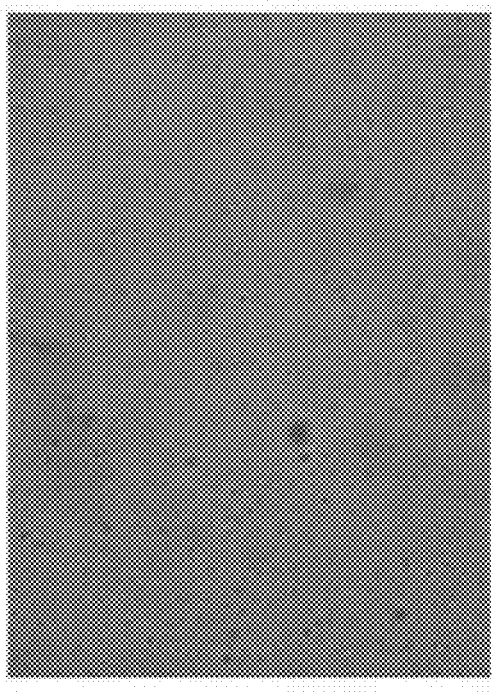
Figure 10B:
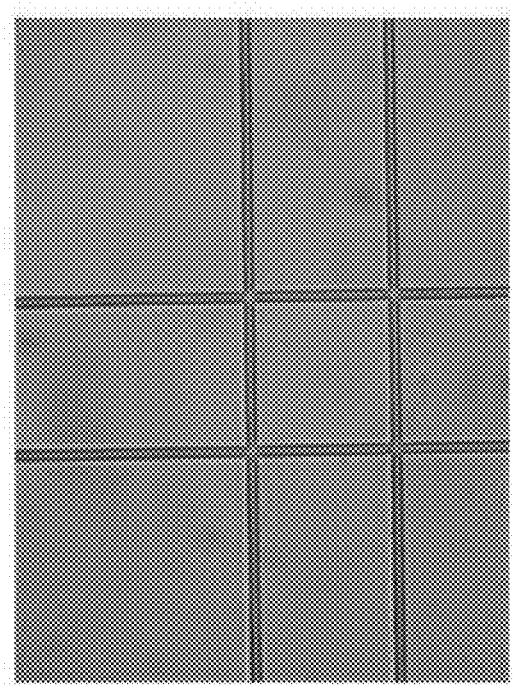
Figure 10B:
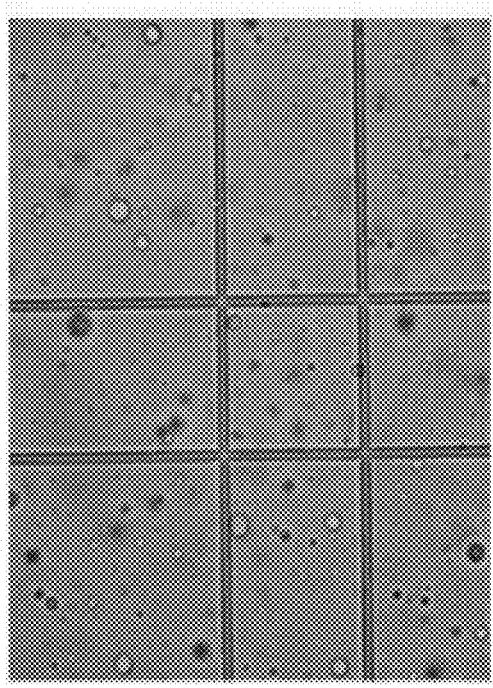

Representative magnified images are shown in FIG. 10B.

Gp32-Sup1 Fusion Protein

The minimum concentration of magnesium ions required to enhance the formation of detectible phase-separated aqueous particles in these conditions was determined to be 24 mM. At this concentration approximately 280 particles (globular foci) were counted within the field.

The minimum concentration of calcium ions required to enhance the formation of detectible phase-separated aqueous particles in these conditions was determined to be 32 mM. At this concentration approximately 460 particles (globular foci) were counted within the field.

The minimum concentration of manganese ions required to enhance the formation of detectible phase-separated aqueous particles in these conditions was determined to be 4 mM. At this concentration approximately 220 particles (globular foci) were counted within the field.

Figure 10C:
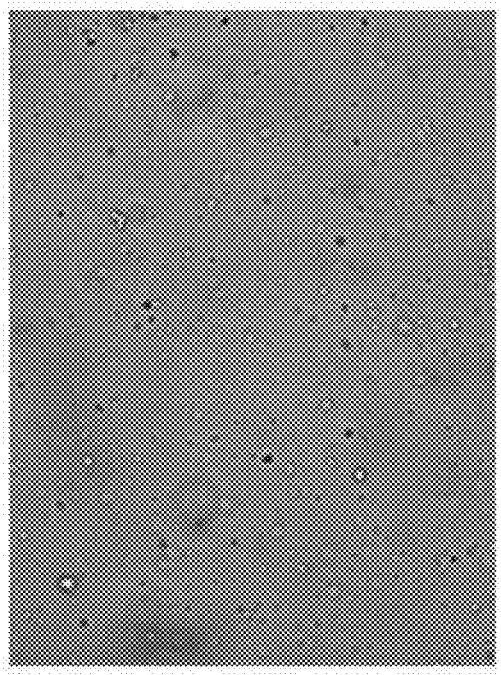
Figure 10C:
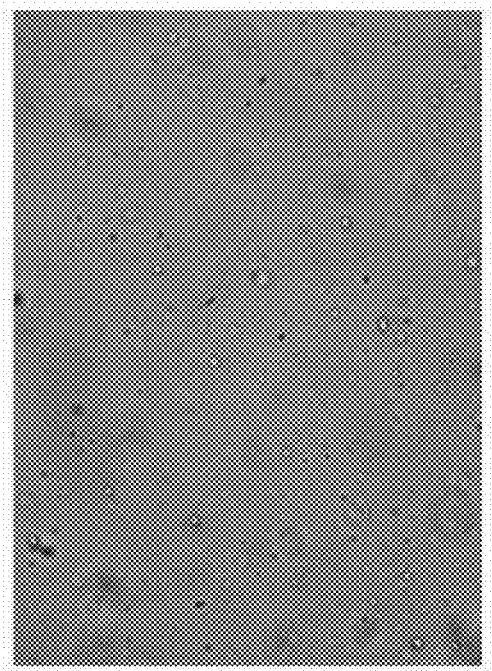
Figure 10C:
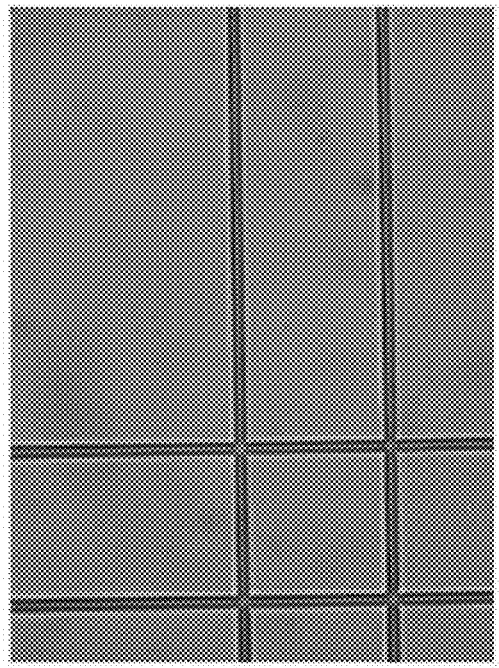
Figure 10C:
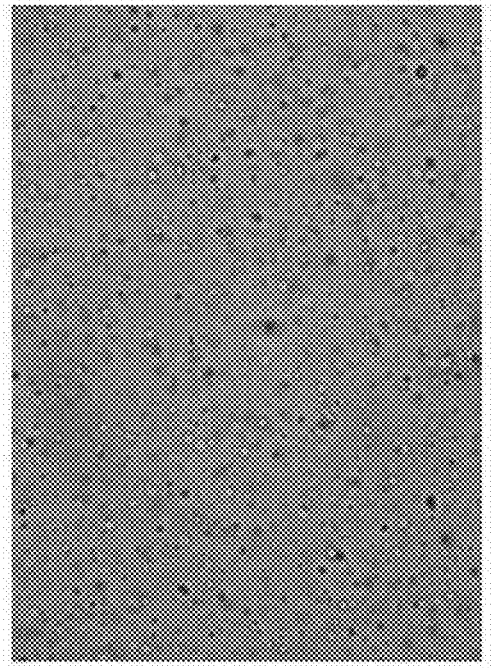

Representative magnified images are shown in FIG. 10C.

Gp32-Fib Fusion Protein

The minimum concentration of magnesium ions required to enhance the formation of detectible phase-separated aqueous particles in these conditions was determined to be 500 µM. At this concentration approximately 340 particles (globular foci) were counted within the field.

The minimum concentration of calcium ions required to enhance the formation of detectible phase-separated aqueous particles in these conditions was determined to be 1 mM. At this concentration approximately 500 particles (globular foci) were counted within the field.

The minimum concentration of manganese ions required to enhance the formation of detectible phase-separated aqueous particles in these conditions was determined to be 500 µM. At this concentration approximately 360 particles (globular foci) were counted within the field.

Figure 10D:
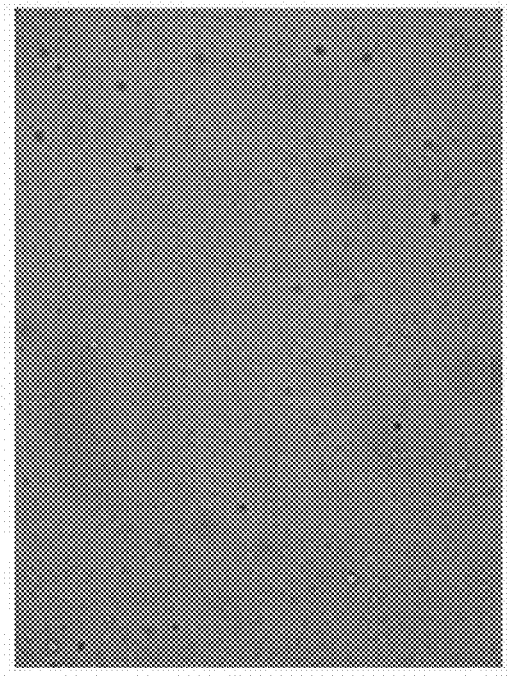
Figure 10D:
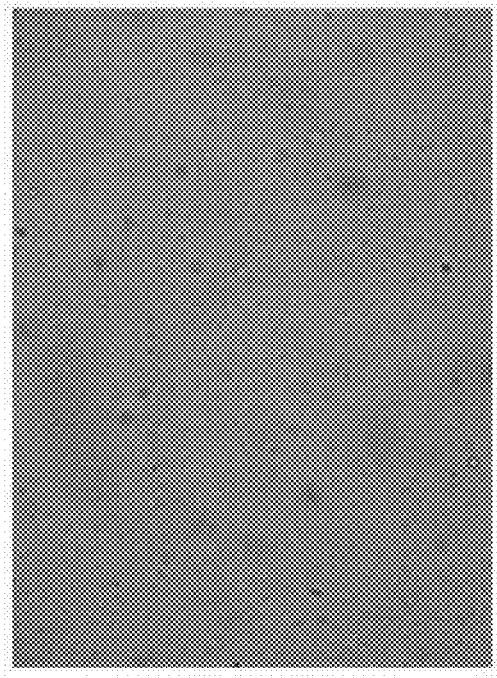
Figure 10D:
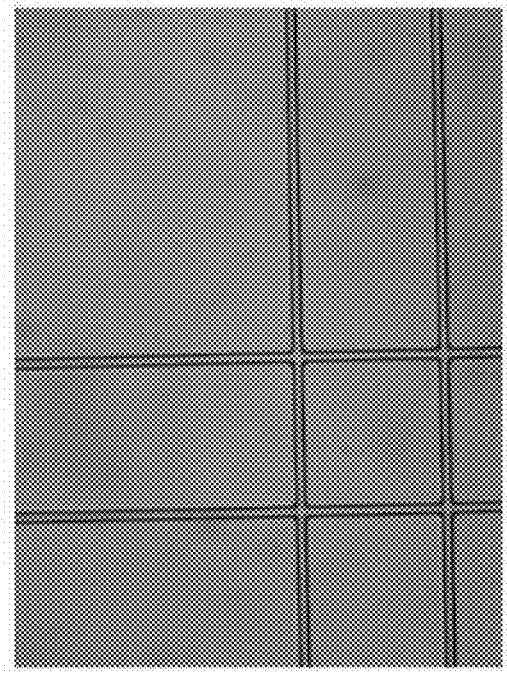
Figure 10D:
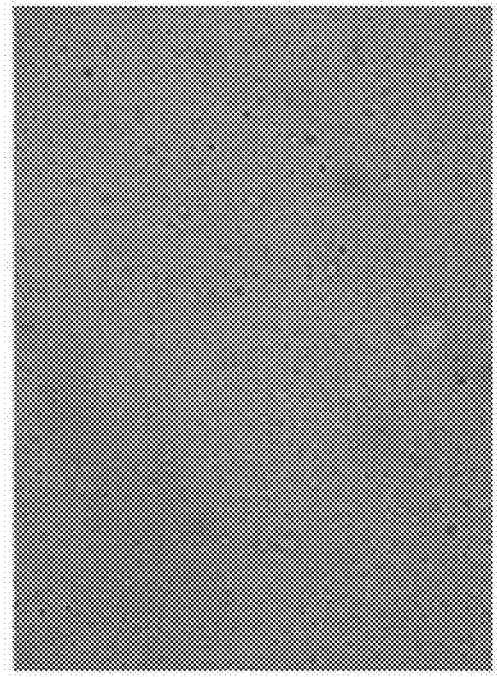
Figure 11A:
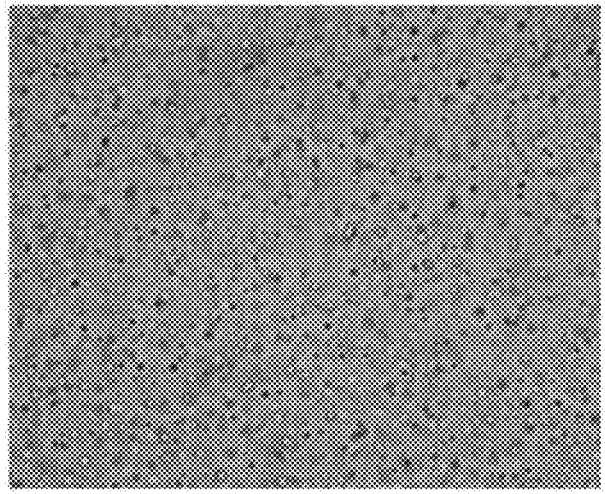
FIGS. 11A-11E show the effect of multivalent metal cations on the promotion of phase separation (particle formation) mediated by IDR amino acid sequence tags in the absence of a crowding agent. The IDR amino acid sequences were tagged to the Gp32 protein to create the Gp32-Fib fusion protein (FIG. 11A), the Gp32-Sup1 fusion protein (FIG. 11B), the Gp32-HIS2 fusion protein (FIG. 11C), the Gp32-HRP1 fusion protein (FIG. 11D), the Gp32-HIS5 fusion protein (FIG. 11E). In each case the effect of representative concentrations of divalent metal cations, i.e. magnesium (MgOAc), manganese ($MgCl_2$) and calcium ($CaCl_2$) was tested.
Figure 11A:
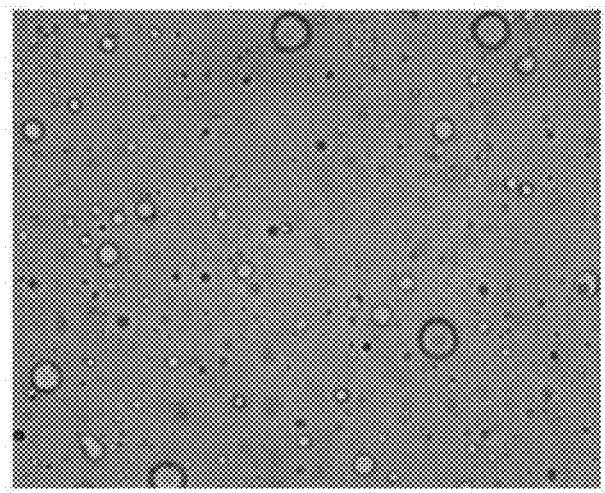
Figure 11A:
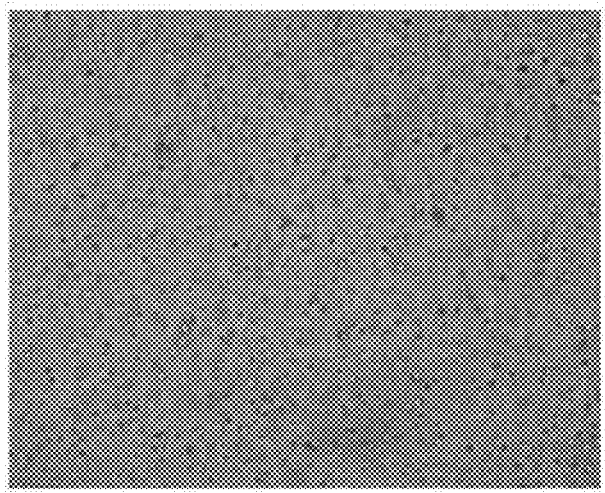
Figure 11B:
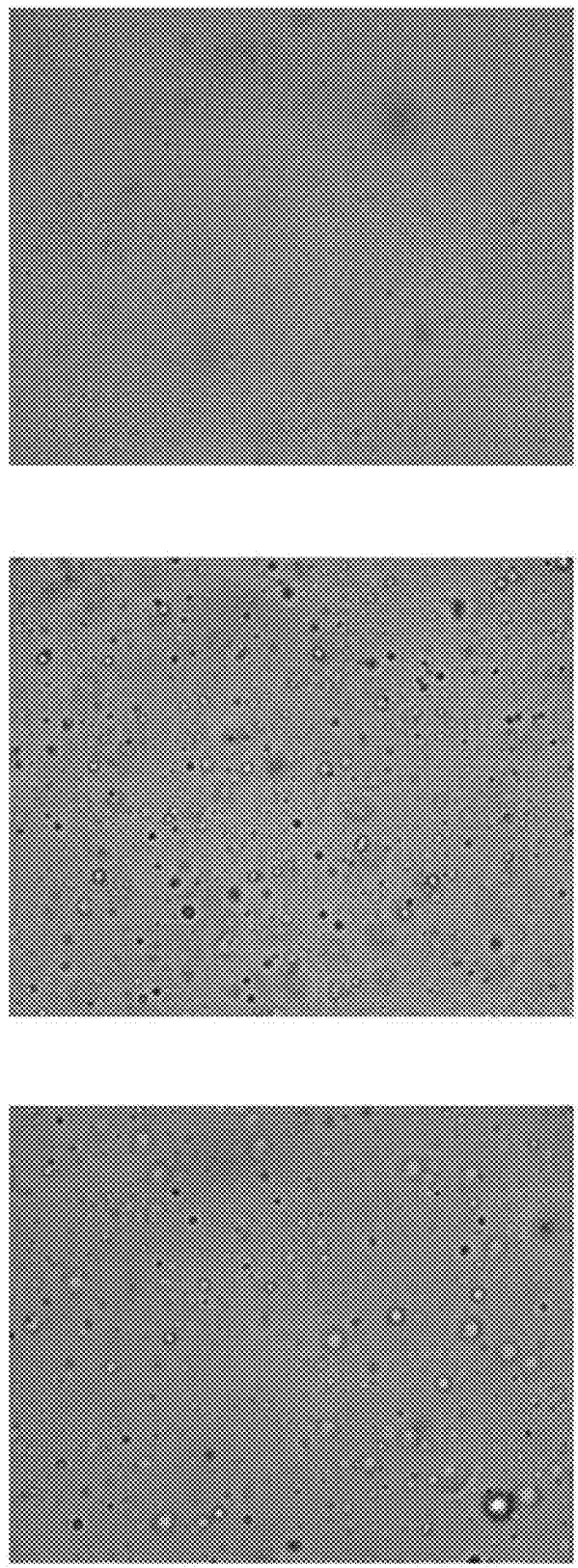
Figure 11C:
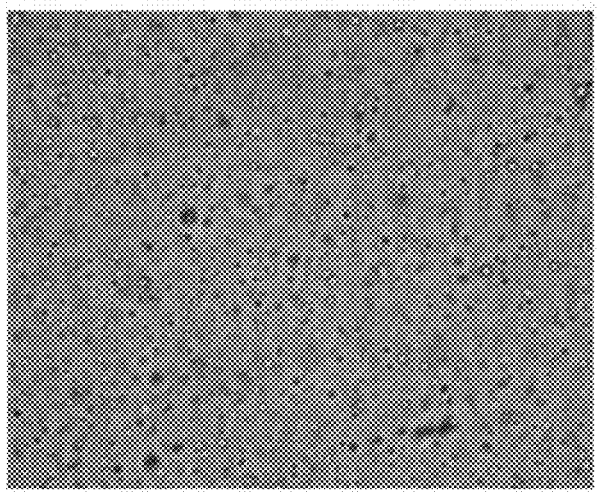
Figure 11C:
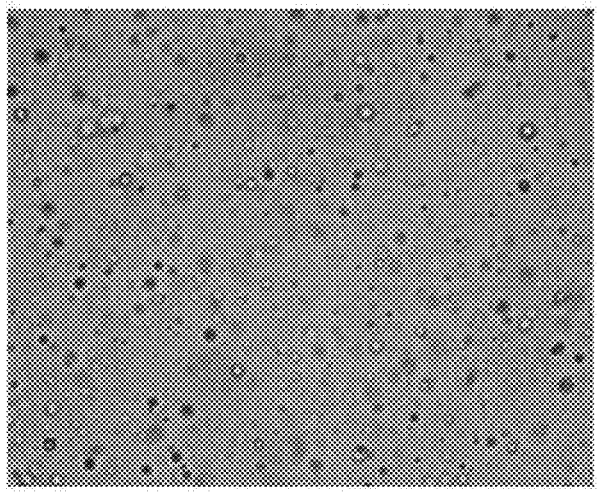
Figure 11C:
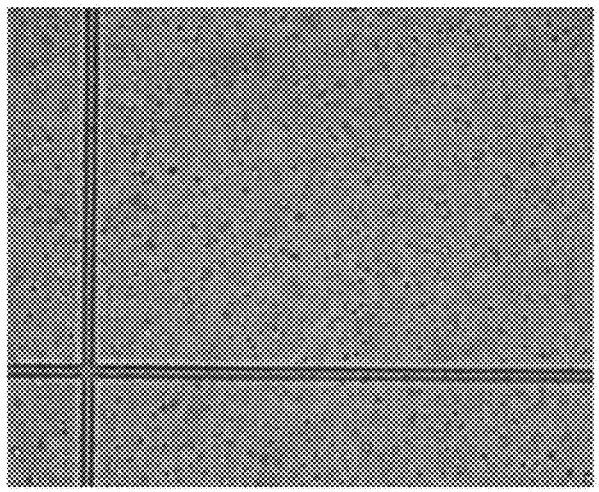
Figure 11D:
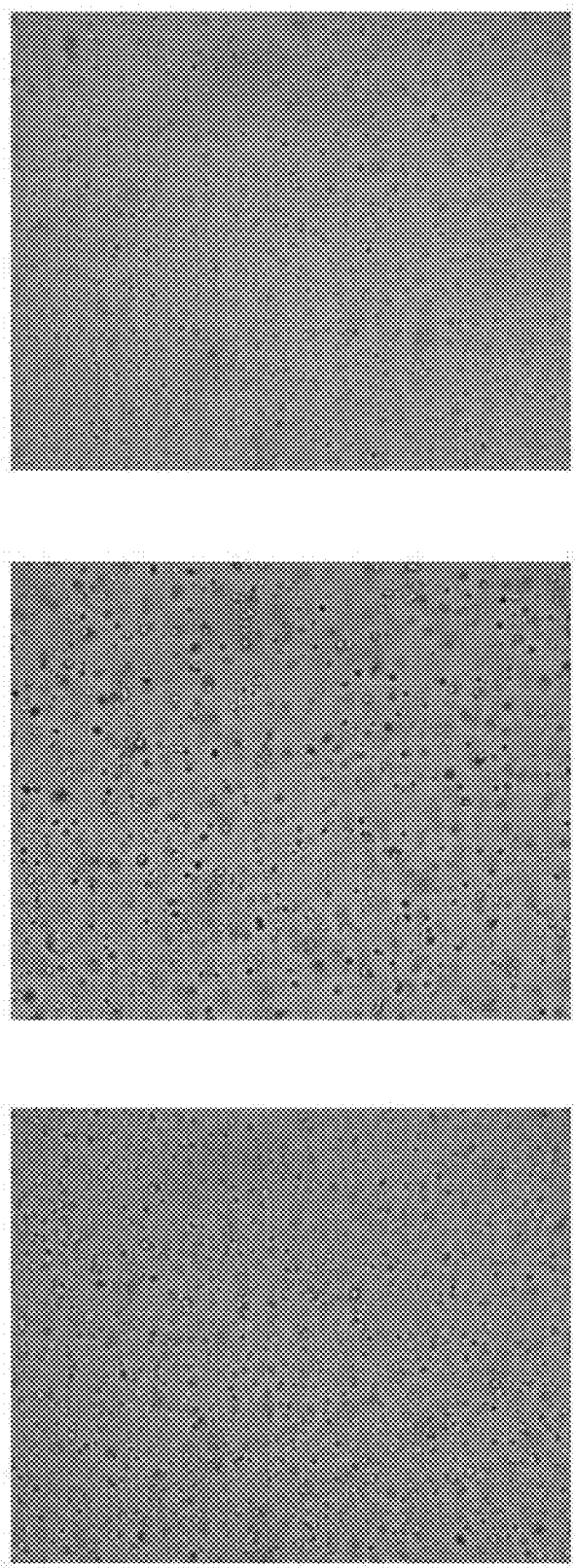
Figure 11E:
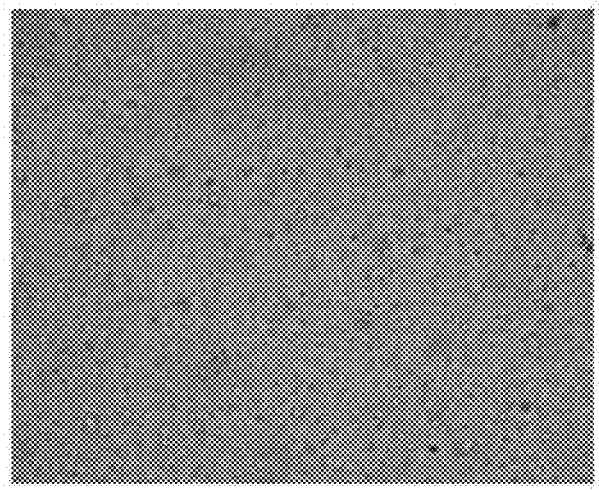
Figure 11E:
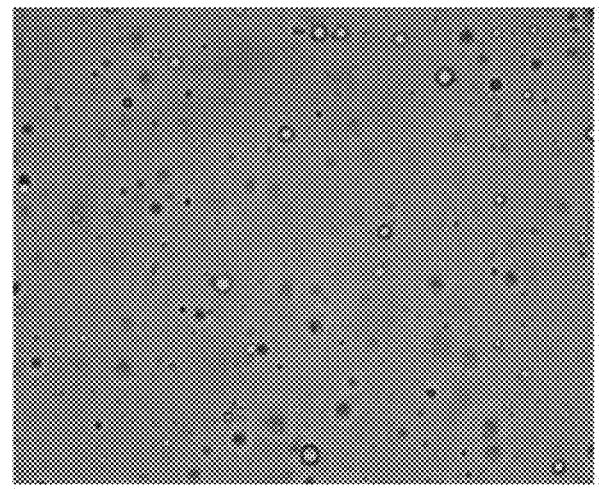
Figure 11E:
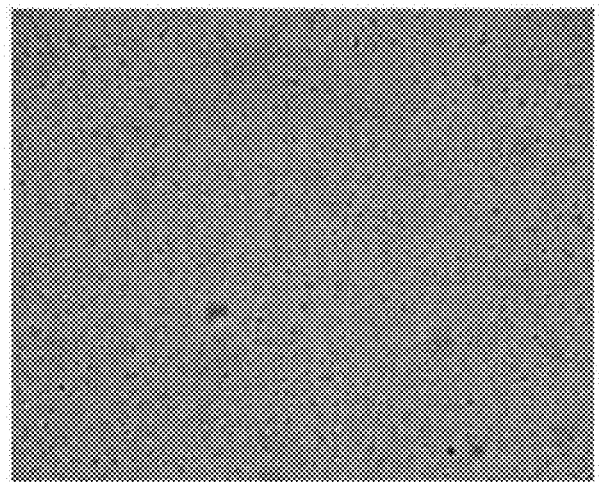

Representative magnified images are shown in FIG. 10D.

Using these assays it was determined that the functional capability of an IDR or IDR domain to enhance the formation of detectible phase-separated aqueous particles in an in vitro biochemical environment when tagged to a protein can be established when 10 or more particles (globular foci) were are formed in a magnification area of 218 µm×175 µm at ×400 magnification. The functional capability of an IDR or IDR domain to induce phase separation in an in vitro biochemical environment when tagged to a protein can be established when preferably 50 or more particles (globular foci) were are formed in a magnification area of 218 µm×175 µm at ×400 magnification, more preferably when 100 or more particles (globular foci) were are formed.

The term "globular foci" as used herein is synonymous with "globule", "particle" or "globular particle" and these terms can be used interchangeably.

Example 11. Formation of Globular Foci by IDR Tags in the Presence of Multivalent Metal Cations Purpose and Summary of Experiment This experiment was performed to assess, in an in vitro biochemical reaction system, the effects of multivalent metal cations on the promotion of phase separation driven/caused by several Gp32 fusion proteins each having a tag comprising an intrinsically disordered region (IDR) domain amino acid sequence.

The example demonstrates that tags comprising IDR domain amino acid sequences are capable of promoting/enhancing phase separation, and that this effect occurs in the presence of various multivalent metal cations.

Materials and Methods

Gp32-Fib Fusion Protein

The specific amino acid sequence of the IDR domain tag used was PGFSPRGGGFGGRGGFGDRGGRG-GRGGFGGGRGRGGGFRGRGR (SEQ ID NO:1). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR domain tag at the C-terminus of the fusion protein. The full amino acid sequence of the Gp32-Fib fusion protein is provided as SEQ ID NO:69 (Table 23).

Gp32-Sup1 Fusion Protein

The specific amino acid sequence of the IDR domain tag used was YNPQGGYQQ (SEQ ID NO:19). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR domain tag at the C-terminus of the fusion protein. The full amino acid sequence of the Gp32-Sup1 fusion protein is provided as SEQ ID NO:72 (Table 23).

Gp32-HIS2 Fusion Protein

The specific amino acid sequence of the IDR domain tag used was AGHHHHHPHAHHPLSQSSGHHHHHHHHHHQGYG GSG (SEQ ID NO:24). This was attached to the C-terminus of phage vB EcoM NBG1 Gp32. The recombinant fusion protein was purified using standard 1-step immobilised metal (nickel) affinity chromatography relying on the histidines naturally present in the IDR domain tag of the fusion protein under test. The full amino acid sequence of the Gp32-HIS2 fusion protein is provided as SEQ ID NO:82 (Table 23).

Gp32-HRP1 Fusion Protein

The specific amino acid sequence of the IDR domain tag used was GGNNGGNNMNRRGG-NFGNQGDFNQMYQNPMMGGY-NPMMNPQAMTDYYQ KMQEYYQQMQ (SEQ ID NO:9). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR tag at the C-terminus of the fusion protein. The full amino acid sequence of the Gp32-HRP1 fusion protein is provided as SEQ ID NO:79 (Table 23).

Gp32-HIS5 Fusion Protein

The specific amino acid sequence of the IDR domain tag used was SGHHGAHHGAHHPAAAAAYEAFRGPGF-AGGGGADDMGAGHHHGAHHAAHH HHAAHHHHHHHHHHGGAGHGGGAGHH (SEQ ID NO:27). This was attached to the C-terminus of phage vB EcoM NBG1 Gp32. The recombinant fusion protein was purified using standard 1-step immobilised metal (nickel) affinity chromatography relying on the histidines naturally present in the IDR domain tag of the fusion protein under test. The full amino acid sequence of the Gp32-HIS5 fusion protein is presented as SEQ ID NO: 85.

Phase Separation Assay

The methods outlined below apply for all the fusion proteins tested. The volumes of the fusion protein solutions used depended upon the protein concentrations after purification.

A 50 µl solution was made up in each case comprising the tagged fusion protein at a final concentration of 1000 ng/µl (29.4 µM) and divalent metal cation. The metal ions tested were $Mg^{2+}$ (MgOAc), $Mn^{2+}$ ($MnCl_2$) and $Ca^{2+}$ ($CaCl_2$)) and in each case these were used at a final concentration of 20 mM.

Following constitution of a mixture comprising water, the IDR-tagged protein and multivalent metal cations, the mixture was vortexed, spun down and a 10 µl sample of the mixture was transferred to a DHC-B01 C-Chip haemocytometer slide. The slide was then imaged using bright field microscopy at ×400 magnification. Phase separation was assessed by the formation of spherical-like globular foci (particles) which can be identified visually via magnification and counted using the haemocytometer.

Results and Conclusions

Representative magnified images are shown in FIGS. 11 A to E.

For each of the IDR-tagged Gp32 fusion proteins tested, detectible phase separation was observed as determined by the formation of detectible spherical-like phase-separated particles (globular foci). In each case the effect was observed in the presence of $Mg^{2+}$, $Mn^{2+}$ and $Ca^{2+}$ divalent metal ions.

Thus the ability of multivalent metal ions to induce/enhance phase separation appears to be a general property applicable to a broad range of different IDR tags having quite different amino acid sequences.

Example 12. Formation of Globular Foci by Gp32 Having an IDR Tag Derived from *Saccharomyces cerevisiae* Hrp1

Purpose and Summary of Experiment

This experiment was performed to assess the capability of a Gp32 fusion protein preparation containing a tag comprising an intrinsically disordered region (IDR) of the *Saccharomyces cerevisiae* Hrp1 protein in forming globular foci in an exemplary in vitro biochemical reaction environment in the absence of a crowding agent.

The example demonstrates that the tag comprising the IDR domain amino acid sequences was capable of promoting/enhancing phase separation, as determined by the formation of detectible phase-separated aqueous particles, in the exemplary in vitro biochemical reaction environment and in the absence of a crowding agent.

Materials and Methods

The specific amino acid sequence of the IDR domain tag used was GGNNGGNNMNRRGG-NFGNQGDFNQMYQNPMMGGY-NPMMNPQAMTDYYQ KMQEYYQQMQ (SEQ ID NO:9). This was attached to the C-terminus of phage vB EcoM NBG1 Gp32. The recombinant fusion protein was purified using standard 1-step immobilised metal (nickel)

affinity chromatography relying on an additional heptahistidine tag placed at the very C-terminus of the fusion protein under test, i.e. placed after the IDR tag at the C-terminus of the fusion protein. The fusion protein was designated Gp32-HRP1. The full amino acid sequence of the fusion protein is presented as SEQ ID NO: 79 (Table 23).

An exemplary in vitro biochemical reaction environment was created to test the effects of the IDR domain sequence tag. In this case, the environment was one which characterises recombinase polymerase amplification reactions.

Reactions were set up according to the following protocol. A reaction mixture was created with the following components: 25 mM Tris HCl pH 8.3, 7.5 mM KOAc, 1 mM DTT, 2.5 mM ATP, 20 mM phosphocreatine, 1 µM creatine kinase, 1 mM dNTPs, 0.2 µM forward primer, 0.2 µM reverse primer, 0.516 µM probe, 22.6 µM Gp32-HRP fusion, 8.4 µM UvsX, 15.3 µM UvsY, 0.135 µM S. aureus DNA polymerase (large subunit), and 0.27 µM Exonuclease III. Gp32, UvsX, UvsY, polymerase and Exonuclease III were prepared as a premix before being added in one step to the mixture of primer, buffer, nucleotides and creatine kinase. The total volume was 44 µl. Once combined, 6 µl of 280 mM MgOAc was added to the mixture to achieve a final concentration of 33 mM. 10 µl of the reaction mix was then transferred to a C-Chip haemocytometer slide which was placed on a heated stage set to 39° C. before being observed under the microscope where images were taken under bright field light conditions and fluorescence conditions.

The relevant primers and probe are indicated below.

```
Forward primer:
                              (SEQ ID NO: 98)
CGCCTGCAAGTCCTAAGACGCCAATCGAAAAGAAAC.

Reverse primer:
                              (SEQ ID NO: 99)
CTGCATCTCCGTGGTATACTAATACATTGTTTTA.

Probe:
                              (SEQ ID NO: 104)
CCGCAATGGTGCACTCTCAGTACAATCTGCTCTGATG labelled with FAM (fluorescein).
```

Results and Conclusion

Figure 12:
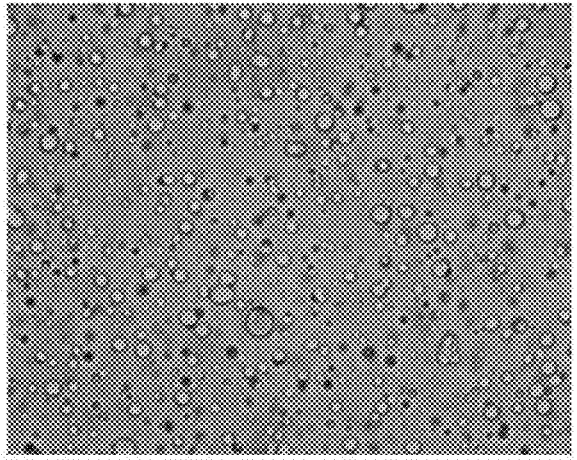
FIG. 12 shows the effect of a divalent metal cation, i.e. magnesium (MgOAc), on the capability of an IDR-tagged Gp32 fusion protein (Gp32-HRP1) to promote phase separation (particle formation) in an exemplary in vitro biochemical reaction environment in the absence of a crowding agent.
Figure 12:
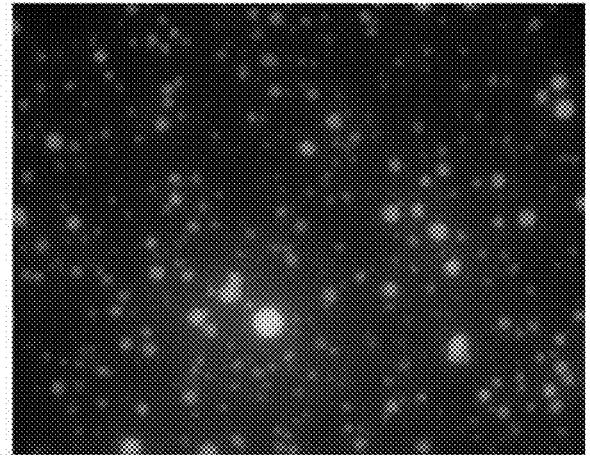
Figure 12:
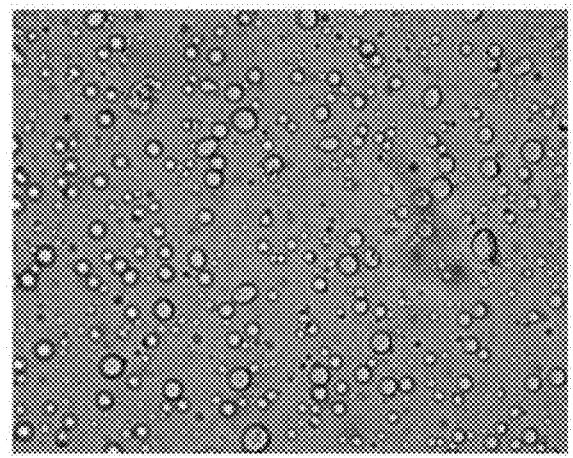
Figure 12:
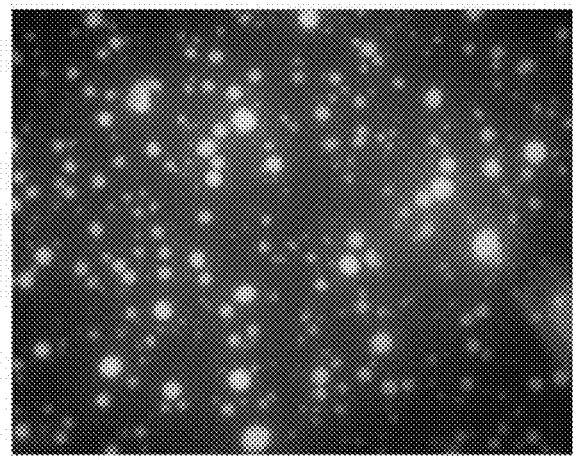

As shown in FIG. 12, the HRP tag attached to Gp32 promoted the formation of many detectible phase-separated aqueous particles (globular foci) which were seen to be dense in oligonucleotide (as detected by the fluorescent labelled probe).

A separate experiment was conducted with identical materials and conditions except that the Gp32 protein was tagged only with the heptahistidine sequence and not with the HRP IDR tag. In these experiments globular foci did not form (data not shown) indicating that the formation of globular foci was driven specifically by the IDR tag, and also that consequently the heptahistidine sequence is not a functional IDR as defined herein.

The results demonstrate the functional capability of an IDR domain tag, in this case represented by the *Saccharomyces cerevisiae* HRP1 amino acid sequence tag indicated above, of promoting detectable phase separation in an in vitro biochemical reaction environment, in this case represented by the reaction mixture environment which characterises recombinase polymerase amplification reactions, and in the absence of a crowding agent.

Example 13. Formation of Globular Foci by Gp32 Having an IDR Tag Derived from Human Otx1

Purpose and Summary of Experiment

This experiment was performed to assess the capability of a Gp32 fusion protein preparation containing a tag comprising an intrinsically disordered region (IDR) of the human Otx1 protein in forming globular foci in an exemplary in vitro biochemical reaction environment in the absence of a crowding agent.

The example demonstrates that the tag comprising the IDR domain amino acid sequences was capable of promoting detectable phase separation in the exemplary in vitro biochemical reaction environment and in the absence of a crowding agent.

Materials and Methods

The specific amino acid sequence of the IDR domain tag used was AGHHHHHPHAHHPLSQSSGHHHHHHHHHHQGYGGSG (SEQ ID NO:24). This was attached to the C-terminus of phage vB EcoM NBG1 Gp32. The recombinant fusion protein was purified using standard 1-step immobilised metal (nickel) affinity chromatography relying on the histidines naturally present in the IDR domain tag of the fusion protein under test. The fusion protein was designated Gp32-HIS2. The full amino acid sequence of the fusion protein is presented as SEQ ID NO: 82 (Table 23).

An exemplary in vitro biochemical reaction environment was created to test the effects of the IDR domain sequence tag. In this case the environment was one which characterises recombinase polymerase amplification reactions.

Reactions were set up according to the following protocol. A reaction mixture was created with the following components: 25 mM Tris HCl pH 8.3, 7.5 mM KOAc, 1 mM DTT, 2.5 mM ATP, 20 mM phosphocreatine, 1 µM creatine kinase, 1 mM dNTPs, 0.2 µM forward primer, 0.2 µM reverse primer, 0.516 µM probe, 22.6 µM Gp32-HIS2 fusion, 8.4 µM UvsX, 15.3 µM UvsY, 0.135 µM S. aureus DNA polymerase (large subunit), and 0.27 µM Exonuclease III. Gp32-His2, UvsX, UvsY, polymerase and Exonuclease III were prepared as a premix before being added in one step to the mixture of primer, buffer, nucleotides and creatine kinase. The total volume was 44 µl. Once combined, 6 µl of 280 mM MgOAc was added to the mixture to achieve a final concentration of 33 mM. 10 µl of the reaction mix was then transferred to a C-Chip haemocytometer slide which was placed on a heated stage set to 39° C. before being observed under the microscope where images were taken under bright field light conditions and fluorescence conditions.

The relevant primers and probe are indicated below.

```
Forward primer:
                              (SEQ ID NO: 98)
CGCCTGCAAGTCCTAAGACGCCAATCGAAAAGAAAC.

Reverse primer:
                              (SEQ ID NO: 99)
CTGCATCTCCGTGGTATACTAATACATTGTTTTA.

Probe:
                              (SEQ ID NO: 104)
CCGCAATGGTGCACTCTCAGTACAATCTGCTCTGATG labelled with FAM (fluorescein).
```

Results and Conclusion

Figure 13:
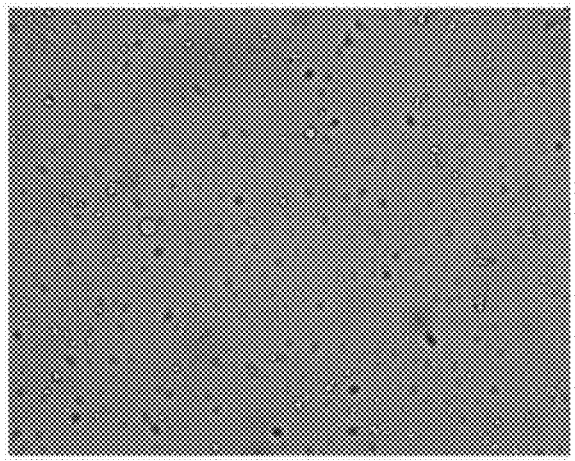
FIG. 13 shows the effect of a divalent metal cation, i.e. magnesium (MgOAc), on the capability of an IDR-tagged Gp32 fusion protein (Gp32-HIS2) to promote phase separation (particle formation) in an exemplary in vitro biochemical reaction environment in the absence of a crowding agent.
Figure 13:
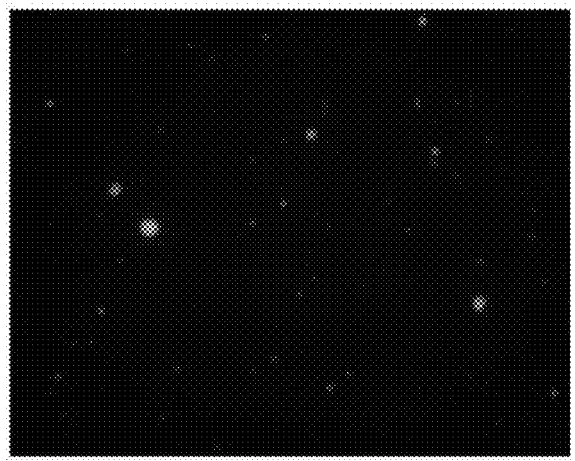
Figure 13:
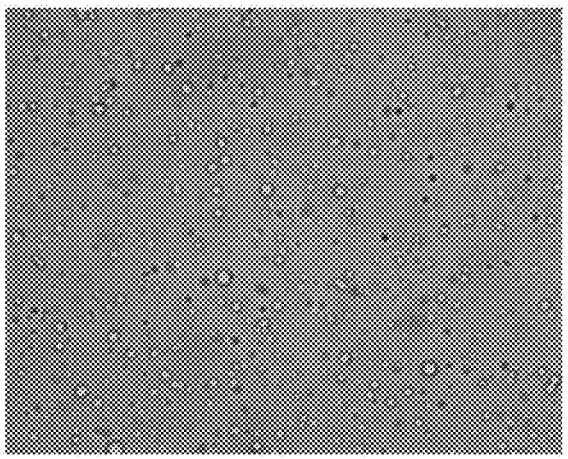
Figure 13:
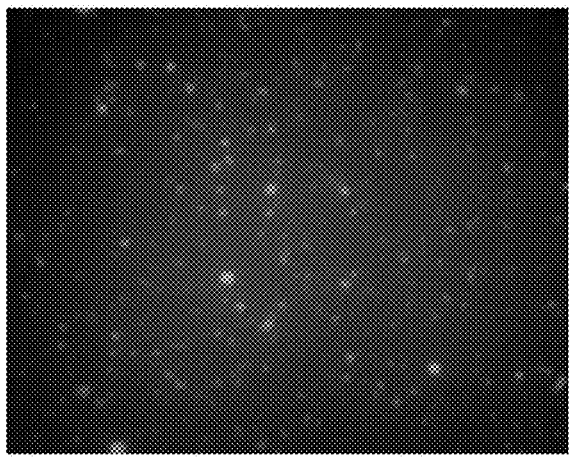

As shown in FIG. 13, the HIS2 IDR tag attached to Gp32 promoted the formation of many detectible phase-separated aqueous particles (globular foci) which were seen to be dense in oligonucleotide (as detected by the fluorescent labelled probe). It was noted that the globules appeared smaller in size compared to those which formed when the HRP IDR tag was attached to Gp32 as described further herein.

The results demonstrate the functional capability of an IDR domain tag, in this case represented by the HIS2 amino acid sequence tag indicated above, of promoting detectable phase separation in an in vitro biochemical reaction environment, in this case represented by the reaction mixture environment which characterises recombinase polymerase amplification reactions, and in the absence of a crowding agent.

Example 14. Effect of Multivalent Metal Cations on the Formation of Globular Foci by Gp32 Having an IDR Tag Derived from *Saccharomyces cerevisiae* Hrp1

Purpose and Summary of Experiment

This experiment was performed to assess the effects of multivalent metal cations on the ability of a Gp32 fusion protein preparation containing a tag comprising an intrinsically disordered region (IDR) of the *Saccharomyces cerevisiae* Hrp1 protein in forming globular foci in an exemplary in vitro biochemical reaction environment in the absence of a crowding agent.

The example demonstrates that the tag comprising the IDR domain amino acid sequences was capable of promoting/enhancing phase separation, as determined by the formation of detectible phase-separated aqueous particles, in the absence of a crowding agent, that phase separation is enhanced upon the presence of multivalent metal cations and optimised concentrations for promoting phase separation can be determined.

Materials and Methods

The specific amino acid sequence of the IDR domain tag used was GGNNGGNNMNRRGG-NFGNQGDFNQMYQNPMMGGY-NPMMNPQAMTDYYQ KMQEYYQQMQ (SEQ ID NO:9). This was attached to the C-terminus of phage vB EcoM NBG1 Gp32. The recombinant fusion protein was purified using standard 1-step immobilised metal (Nickel) affinity chromatography relying on an additional heptahistidine tag placed at the very C-terminus of the fusion protein under test, i.e. placed after the IDR tag at the C-terminus of the fusion protein. The fusion protein was designated Gp32-HRP1. The full amino acid sequence of the fusion protein is presented as SEQ ID NO: 79 (Table 23).

An exemplary in vitro biochemical reaction environment was created to test the effects of the IDR domain sequence tag in the presence of varying concentrations of divalent metal cation. In this case, the environment was one which characterises recombinase polymerase amplification reactions.

Reactions were set up according to the following protocol. A reaction mixture was created with the following components: 25 mM Tris HCl pH 8.3, 7.5 mM KOAc, 1 mM DTT, 2.5 mM ATP, 20 mM phosphocreatine, 1 µM creatine kinase, 1 mM dNTPs, 0.26 µM forward primer, 0.26 µM reverse primer, 0.4 µM probe, 22.6 µM Gp32-HRP fusion, 8.4 µM UvsX and 15.3 µM UvsY. Gp32, UvsX and UvsY were prepared as a premix before being added in one step to the mixture of primer, buffer, nucleotides and creatine kinase. MgOAc was added to the mixture to achieve the final concentrations as shown in the relevant figures. 10 µl of the reaction mix was then transferred to a C-Chip haemocytometer slide which was placed on a heated stage set to 39° C. before being observed under the microscope where images were taken under bright field light conditions and fluorescence conditions.

The relevant primers and probe are indicated below.

```
Forward primer:
                              (SEQ ID NO: 98)
CGCCTGCAAGTCCTAAGACGCCAATCGAAAAGAAAC.

Reverse primer:
                              (SEQ ID NO: 99)
CTGCATCTCCGTGGTATACTAATACATTGTTTTTA.

Probe:
                              (SEQ ID NO: 104)
CCGCAATGGTGCACTCTCAGTACAATCTGCTCTGATG labelled with FAM (fluorescein).
```

Results and Conclusion

Figure 14A:
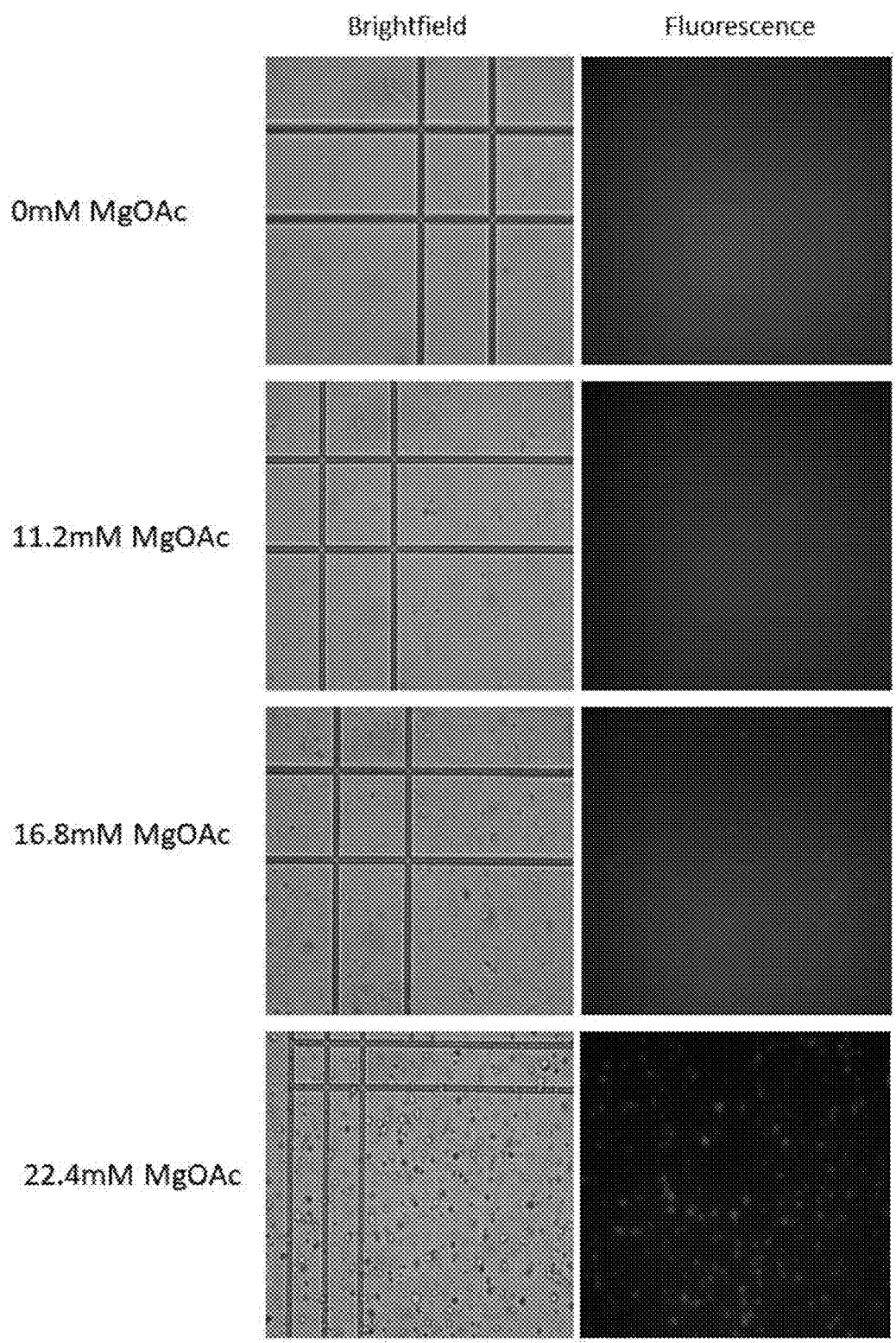
FIGS. 14A and 14B show the effect of varying concentrations of a divalent metal cation, i.e. magnesium (MgOAc), on the capability of an IDR-tagged Gp32 fusion protein (Gp32-HRP1) to promote phase separation (particle formation) in an exemplary in vitro biochemical reaction environment in the absence of a crowding agent.
Figure 14B:
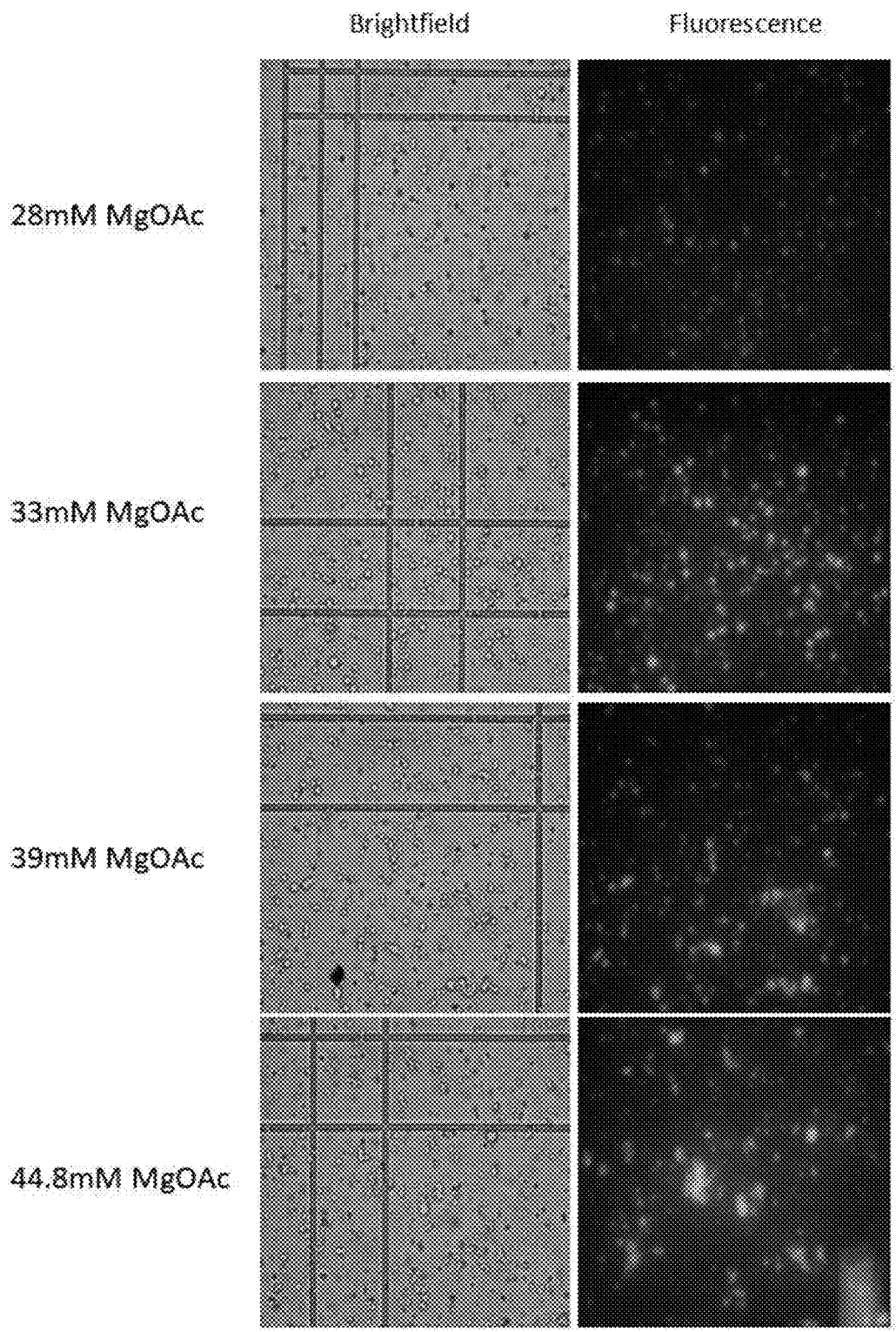

As shown in FIGS. 14 A & B, the HRP IDR tag attached to Gp32 promoted the formation of many detectible phase-separated aqueous particles (globular foci) which were seen to be dense in oligonucleotide (as detected by the fluorescent labelled probe).

Globular foci were clearly visible at 22.4 mM MgOAc. Optimum formation of globular foci occurred at 33 mM MgOAc. Some clumping of globules began to be observed at concentrations above 33 mM.

Remarkably, 33 mM MgOAc is the concentration of magnesium at which optimum amplification efficiency is observed in recombinase polymerase amplification (RPA) reactions using IDR-tagged Gp32 in the absence of a crowding agent, as described herein. Thus the efficiency of IDR tag-mediated formation of globular foci surprisingly correlates with the efficiency of an exemplary biochemical reaction in an in vitro system in the absence of a crowding agent, in this case amplification in RPA reactions using an IDR-tagged protein as an example test biochemical system.

The results support the surprising conclusion that the performance of an IDR domain sequence tag in driving/increasing the efficiency of a biochemical reaction in the absence of a crowding agent can correlate with the efficiency of phase separation, and this in turn appears to be enhanced by the concentration of multivalent metal cations, or a functional equivalent thereof, included in the system to affect the function of the intrinsically disordered region or domain.

Example 15. Effect of Multivalent Metal Cations on the Formation of Globular Foci by Gp32 Having an IDR Tag Derived from Human Otx1

Purpose and Summary of Experiment

This experiment was performed to assess the effects of multivalent metal cations on the ability of a Gp32 fusion protein having a tag comprising an intrinsically disordered region (IDR) of the human Otx1 protein in forming particles/globular foci in an exemplary in vitro biochemical reaction environment in the absence of a crowding agent.

The example demonstrates that the tag comprising the IDR domain amino acid sequences was capable of promoting detectible phase separation in the exemplary in vitro biochemical reaction environment and in the absence of a crowding agent, that detectible phase separation is enhanced by the presence of multivalent metal cations and optimised concentrations for promoting detectible phase separation can be determined.

Materials and Methods

The specific amino acid sequence of the IDR domain tag used was AGHHHHHPHAHHPLSQSSGHHHHHHHHHHQGYG GSG (SEQ ID NO:24). This was attached to the C-terminus of phage vB EcoM NBG1 Gp32. The recombinant fusion protein was purified using standard 1-step immobilised metal (nickel) affinity chromatography relying on the histidines naturally present in the IDR domain tag of the fusion protein under test. The fusion protein was designated Gp32-HIS2. The full amino acid sequence of the fusion protein is presented as SEQ ID NO: 82 (Table 23).

An exemplary in vitro biochemical reaction environment was created to test the effects of the IDR domain sequence tag in the presence of varying concentrations of divalent metal cation. In this case, the environment was one which characterises recombinase polymerase amplification reactions.

Reactions were set up according to the following protocol. A reaction mixture was created with the following components: 25 mM Tris HCl pH 8.3, 7.5 mM KOAc, 1 mM DTT, 2.5 mM ATP, 20 mM phosphocreatine, 1 µM creatine kinase, 1 mM dNTPs, 0.26 µM forward primer, 0.26 µM reverse primer, 0.4 µM probe, 20 µM Gp32-HIS2 fusion, 8.4 µM UvsX and 8.6 µM UvsY. Gp32, UvsX and UvsY, were prepared as a premix before being added in one step to the mixture of primer, buffer, nucleotides and creatine kinase. MgOAc was added to the mixture to achieve the final concentrations as shown in the relevant figures. 10 µl of the reaction mix was then transferred to a C-Chip haemocytometer slide which was placed on a heated stage set to 39° C. before being observed under the microscope where images were taken under bright field light conditions and fluorescence conditions.

The relevant primers and probe are indicated below.

```
Forward primer:
                              (SEQ ID NO: 98)
CGCCTGCAAGTCCTAAGACGCCAATCGAAAAGAAAC.

Reverse primer:
                              (SEQ ID NO: 99)
CTGCATCTCCGTGGTATACTAATACATTGTTTTTA.

Probe:
                              (SEQ ID NO: 104)
CCGCAATGGTGCACTCTCAGTACAATCTGCTCTGATG labelled with FAM (fluorescein).
```

Results and Conclusion

Figure 15A:
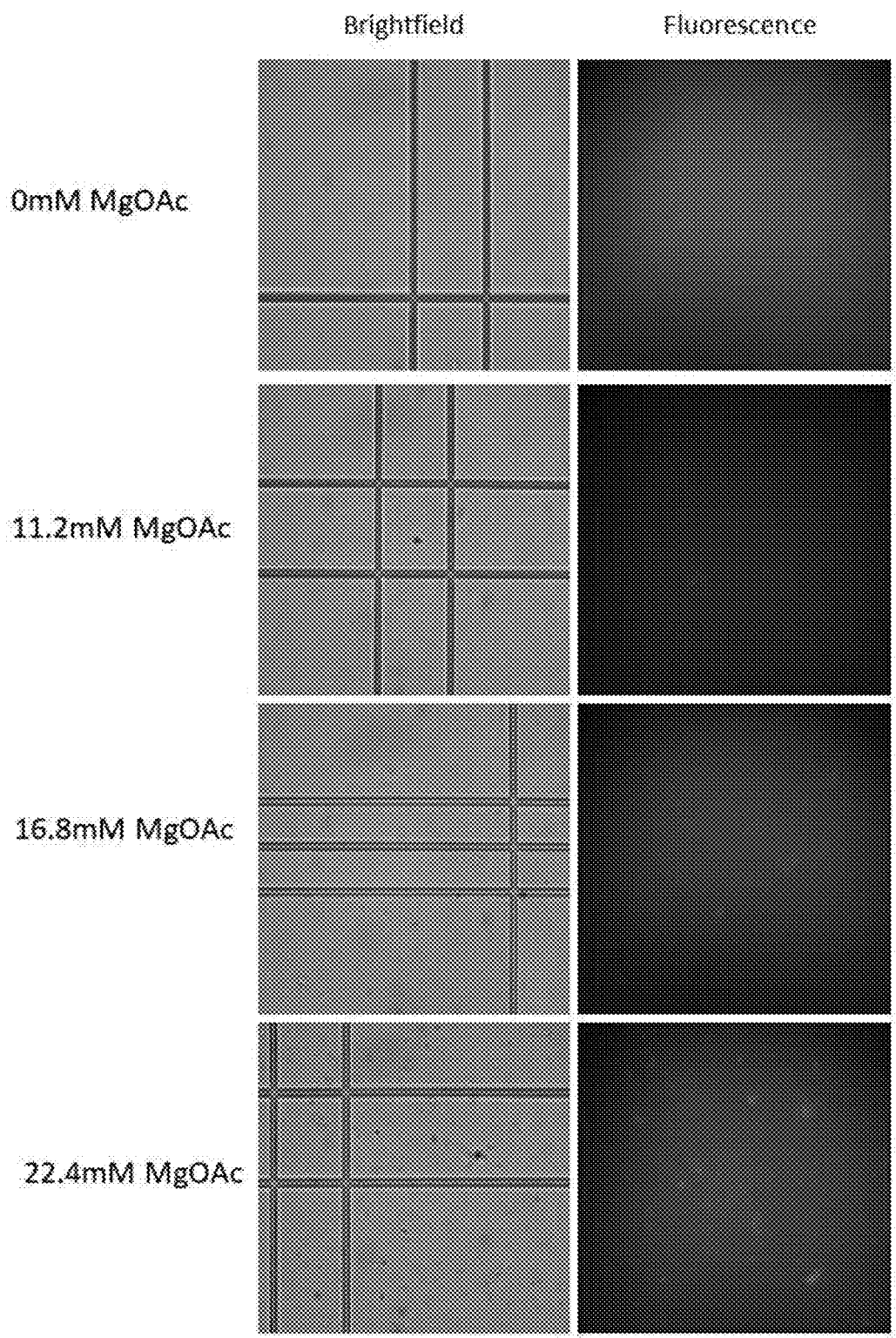
FIGS. 15A and 15B show the effect of varying concentrations of a divalent metal cation, i.e. magnesium (MgOAc), on the capability of an IDR-tagged Gp32 fusion protein (Gp32-HIS2) to promote phase separation (particle formation) in an exemplary in vitro biochemical reaction environment in the absence of a crowding agent.
Figure 15B:
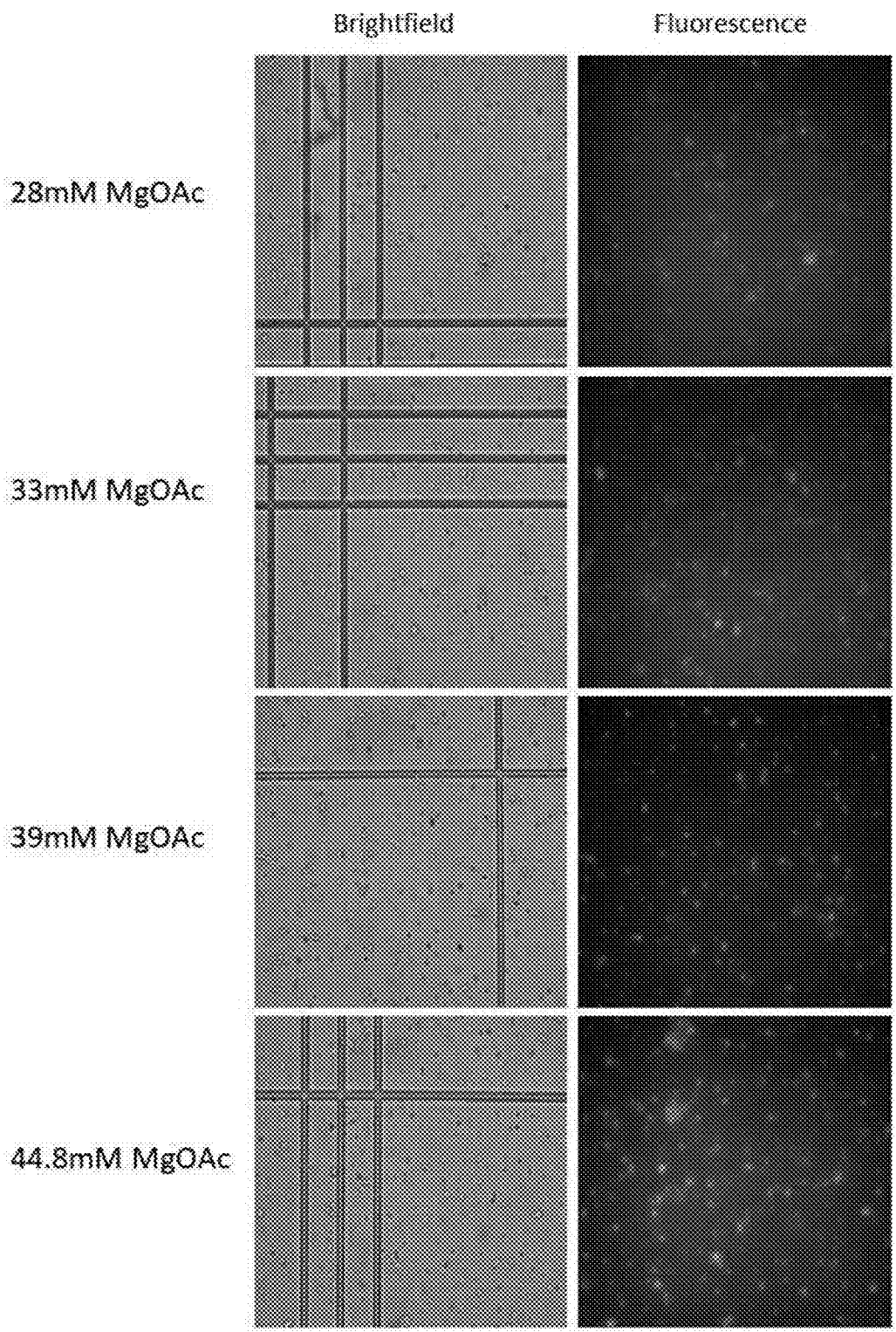

As shown in FIGS. 15 A and B, the HIS2 tag attached to Gp32 promoted the formation of many globular foci which were seen to be dense in oligonucleotide (as detected by the fluorescent labelled probe).

Globular foci were clearly visible at 22.4 mM MgOAc. Optimum formation of globular foci occurred between 33 and 39 mM MgOAc. Some clumping of globules began to be observed at concentrations above 39 mM.

Remarkably, 33 mM to 39 mM MgOAc is the concentration of magnesium at which optimum amplification efficiency is observed in recombinase polymerase amplification (RPA) reactions using IDR-tagged Gp32 in the absence of a crowding agent, as described herein. Thus the efficiency of IDR tag-mediated formation of globular foci surprisingly correlates with the efficiency of an exemplary biochemical reaction in an in vitro system in the absence of a crowding agent, in this case amplification in RPA reactions using an IDR-tagged protein as an example test biochemical system.

The results support the surprising conclusion that the performance of an IDR domain sequence tag in driving/increasing the efficiency of a biochemical reaction in the absence of a crowding agent can correlate with the efficiency of phase separation, and this in turn appears to be enhanced by the concentration of multivalent metal cations, or a functional equivalent thereof, included in the system to affect the function of the intrinsically disordered region or domain.

Example 16. Effect of Magnesium Concentration on the Formation of Globular Foci by Gp32 Having an IDR Tag Derived from *Saccharomyces cerevisiae* Hrp1

Purpose and Summary of Experiment

This experiment was performed to assess the effects of magnesium ions on the ability of a Gp32 fusion protein preparation containing a tag comprising an intrinsically disordered region (IDR) of the *Saccharomyces cerevisiae* Hrp1 protein in forming globular foci in an exemplary in vitro biochemical reaction environment in the absence of a crowding agent.

The example demonstrates that the tag comprising the IDR domain amino acid sequences was capable of promoting/enhancing phase separation, as determined by the formation of detectable phase-separated aqueous particles, in the exemplary in vitro biochemical reaction environment and in the absence of a crowding agent, that phase separation is dependent upon the presence of magnesium ions and that all protein components of the reaction mixture were found to be associated with the phase-separated particles and not with the bulk phase.

Materials and Methods

The specific amino acid sequence of the IDR domain tag used was GGNNGGNNMNRRGG-NFGNQGDFNQMYQNPMMGGY-NPMMNPQAMTDYYQ KMQEYYQQMQ (SEQ ID NO:9). This was attached to the C-terminus of phage vB EcoM NBG1 Gp32. The recombinant fusion protein was purified using standard 1-step immobilised metal (nickel) affinity chromatography relying on an additional heptahistidine tag placed at the very C-terminus of the fusion protein under test, i.e. placed after the IDR tag at the C-terminus of the fusion protein. The fusion protein was designated Gp32-HRP1. The full amino acid sequence of the fusion protein is presented as SEQ ID NO: 79 (Table 23).

An exemplary in vitro biochemical reaction environment was created to test the effects of the IDR domain sequence tag either in the presence or absence of magnesium ions.

Reactions were set up according to the following protocol. A 1 ml reaction mixture was created with the following components: 25 mM Tris HCl pH 8.3, 7.5 mM KOAc, 1 mM DTT, 2.5 mM ATP, 20 mM phosphocreatine, 1 µM creatine kinase, 0.4 µM forward primer, 0.4 µM reverse primer, 0.4 µM probe, 20.26 µM Gp32-HRP fusion, 5 µM UvsX, 8.67 µM UvsY, 0.127 µM *S. aureus* DNA polymerase (large subunit) and either 0 mM or 33.6 mM MgOAc.

The relevant primers and probe are indicated below.

```
Forward primer:
                              (SEQ ID NO: 98)
CGCCTGCAAGTCCTAAGACGCCAATCGAAAAGAAAC.
```

-continued

```
Reverse primer:
                                    (SEQ ID NO: 99)
CTGCATCTCCGTGGTATACTAATACATTGTTTTTA.

Probe:
                                   (SEQ ID NO: 104)
CCGCAATGGTGCACTCTCAGTACAATCTGCTCTGATG labelled with FAM (fluorescein).
```

Photographs were taken of the completed mixtures.

Mixtures were spun at 2,000 rcf for 1 minute. Supernatants were removed from the MgOAc mixture. In the mixture with 33.6 mM MgOAc a small pellet was left behind which was assumed to be composed of phase-separated globules/particles. No similar pellet was seen in mixtures without MgOAc. 10 µl of 1% SDS solution was added to the pellet for solubilisation. The pellet was estimated to be 4.5 µl in volume making an estimated total volume of 14.5 µl. 1 µl of each sample was analysed by SDS-PAGE.

Results and Conclusion

Figure 16A:
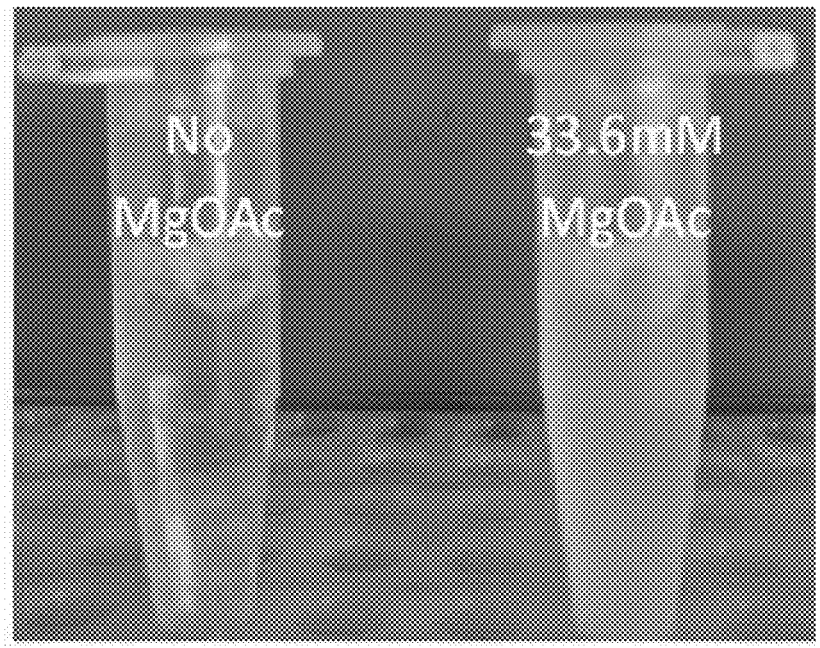
FIGS. 16A-16C show the effect of addition of a divalent metal cation, i.e. magnesium (MgOAc), on the capability of an IDR-tagged Gp32 fusion protein (Gp32-HRP1) to promote phase separation in an exemplary in vitro biochemical reaction environment in the absence of a crowding agent. Phase separation is demonstrated by the formation of an opaque solution following the addition of MgOAc due to particle formation (FIG. 16A) and particle formation is further demonstrated by pelleting of the particles (FIG. 16B). RPA protein components are demonstrated to associate with particles as revealed by SDS-PAGE analysis of pelleted material.
Figure 16B:
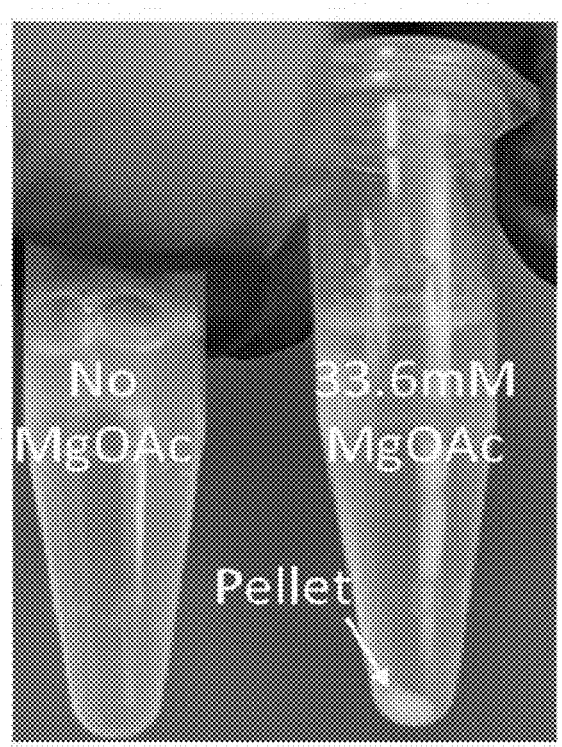

As shown in FIG. 16A, addition of magnesium acetate to the 1 ml of RPA mixture caused the mixture to become opaque. This was not observed in the absence of magnesium acetate. This opaque effect was the same effect as seen in equivalent smaller reactions, and when globular foci/phase-separated particles had been observed to form with typical diameters estimated to be in the range of 2-3 microns by microscopy, and typically at about 200-400 particles per nanolitre. When subject to centrifugation these opaque mixtures cleared and a pellet or lower phase was seen to form at the bottom of the tube which was assumed to be a mass of particles forced together into a single volume (FIG. 16B). The estimated volume of this pelleted fraction was approximately 4 µl, which is roughly the predicted total volume of particles anticipated to form assuming an average particle diameter of 3 µm (hence a volume of approximately 13 femtoliters) and an abundance of about 400 particles per nanolitre, 400,000 particles per microliter based on haemocytometer/microscope field calculations, which generates an estimated volume of around 5 nl of particles per microliter of mixture, and thus about 5 microliters per ml of mixture.

Figure 16C:
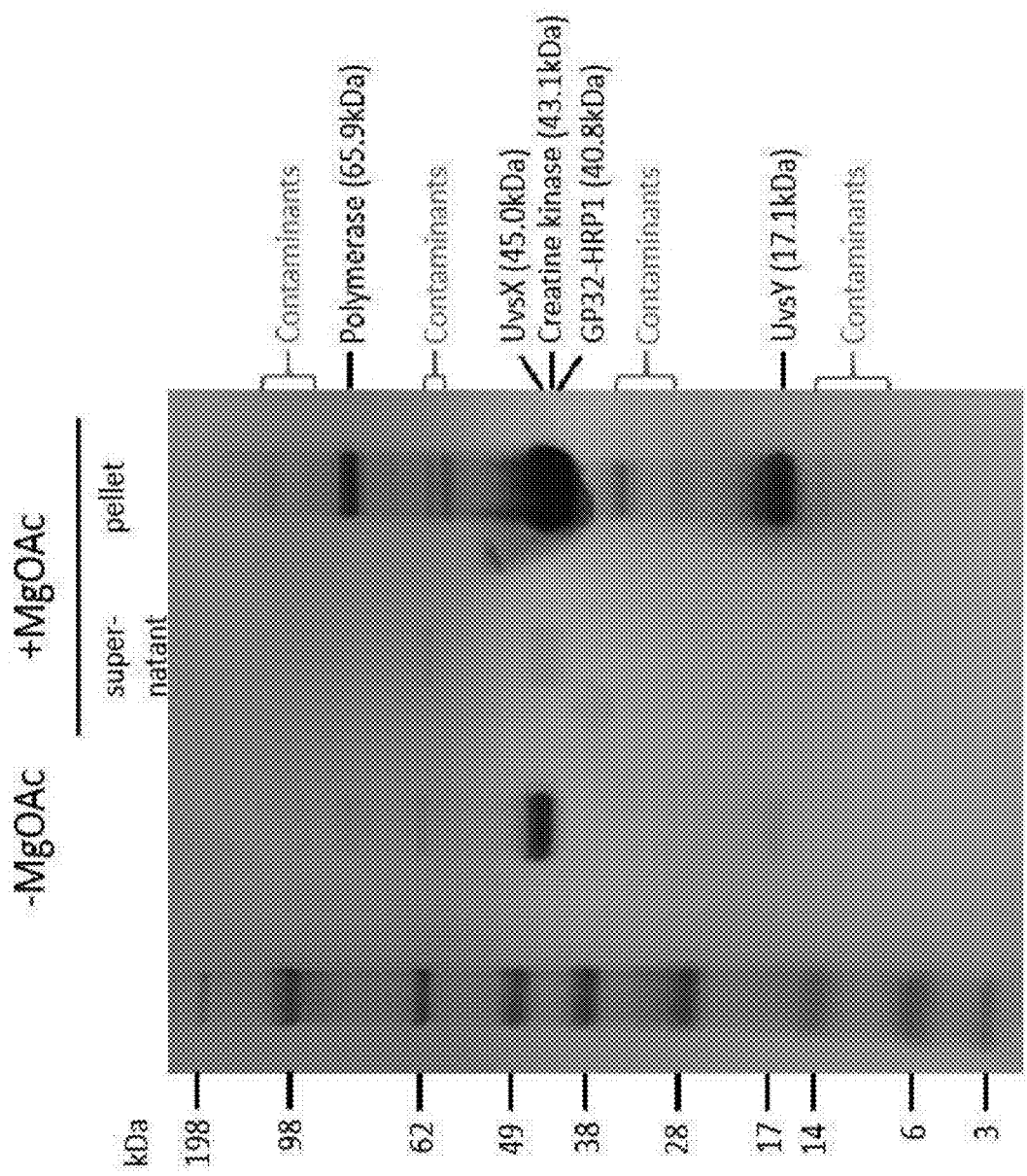

Analysis of one microliter of the bulk mixture (or cleared phase) before and after the addition of magnesium acetate shows that before addition the various proteins can be identified as expected in the clear liquid—Gp32 being the most prominent protein by mass. Following condensation and clearing only trace amounts of protein can be found in the supernatant, while the pellet is vastly enriched in all proteins added to the RPA mixture (FIG. 16C). By deduction it can be assumed that roughly a 200-fold concentration of reactants had been achieved and that total protein was at a concentration of approximately 200 µg/µl.

The results demonstrate that all protein components of the RPA reaction mixture, i.e. creatine kinase, Gp32-HRP fusion, UvsX, UvsY and polymerase are associated with the phase-separated particles and not with the bulk phase.

Example 17. Demonstration of the Essential Nature of an Amino Acid Sequence Comprising an Intrinsically Disordered Region in Increasing the Efficiency of a Biochemical Reaction Purpose and Summary of Experiment This experiment was performed to assess the performance of a Gp32 protein lacking a tag comprising an amino acid sequence comprising an intrinsically disordered region (IDR) in an exemplary in vitro biochemical reaction environment either in the presence or absence of a crowding agent.

The example demonstrates that in the absence of a tag comprising the IDR domain amino acid sequences, Gp32 was unable in the absence of a crowding agent to mediate recombinase polymerase amplification efficiently and to a point at which detection was made in this assay system within the period of analysis. By comparison with other Examples described above, such as Examples 1 to 5, these data establish that the tag comprising the IDR domain amino acid sequences is essential in increasing the efficiency of the biochemical reaction in the absence of a crowding agent.

Materials and Methods

The phage vB EcoM NBG1 Gp32 protein was purified in its native form lacking any form of exogenous IDR tag or histidine tag. The protein was purified using heparin resin and eluted with a NaCl step gradient. Native Gp32 protein from the 400 mM NaCl fraction was subjected to testing.

An exemplary in vitro biochemical reaction environment was created to test the effects of the Native Gp32 protein either in the presence or absence of crowding agent.

Reactions were set up according to the following protocols.

PEG-free reaction mixtures were created with the following components: 25 mM Tris HCl pH 8.3, 7.5 mM KOAc, 1 mM DTT, 2.5 mM ATP, 20 mM phosphocreatine, 1 µM creatine kinase, 1 mM dNTPs, 0.4 µM forward primer, 0.4 µM reverse primer, 0.12 µM probe, 20 µM native Gp32 protein, 4.8 µM UvsX, 8.6 µM UvsY, 0.135 µM S. aureus DNA polymerase (large subunit) and 0.27 µM Exonuclease III.

PEG-based reaction mixtures were created with the following components: 50 mM Tris HCl pH 8.3, 100 mM KOAc, 1 mM DTT, 2.5 mM ATP, 50 mM phosphocreatine, 1 µM creatine kinase, 1 mM dNTPs, 0.4 µM forward primer, 0.4 µM reverse primer, 0.12 µM probe, 20 µM native Gp32 protein, 4.8 µM UvsX, 8.6 µM UvsY, 0.27 µM S. aureus DNA polymerase (large subunit), 0.27 µM Exonuclease III and PEG at a final concentration as shown in the relevant figure. The species of PEG used was PEG molecular weight 35,000.

In all reactions the relevant primers and probe are indicated below.

Forward primer: CGCCTGCAAGTCCTAAGACGC-CAATCGAAAAGAAAC (SEQ ID NO:98).

Reverse primer: CTGCATCTCCGTGGTATACTAATA-CATTGTTTTTA (SEQ ID NO:99).

Probe: CGAAAAGAAACACGCGGATGAAATCGA-TAAG[FAM][THF][BHQ-1]ATACAAGGATTGGA (SEQ ID NO:100), where FAM is fluorescein, THF is tetrahydrofuran and BHQ is Black Hole Quencher.

All reactions were initiated by the addition of 33 mM MgOAc and 100 copies of a DNA template derived from Listeria genomic DNA. Reactions were then incubated at 39° C. and placed in a fluorometer with magnetic mixing using a bearing ball.

Results and Conclusion

Figure 17:
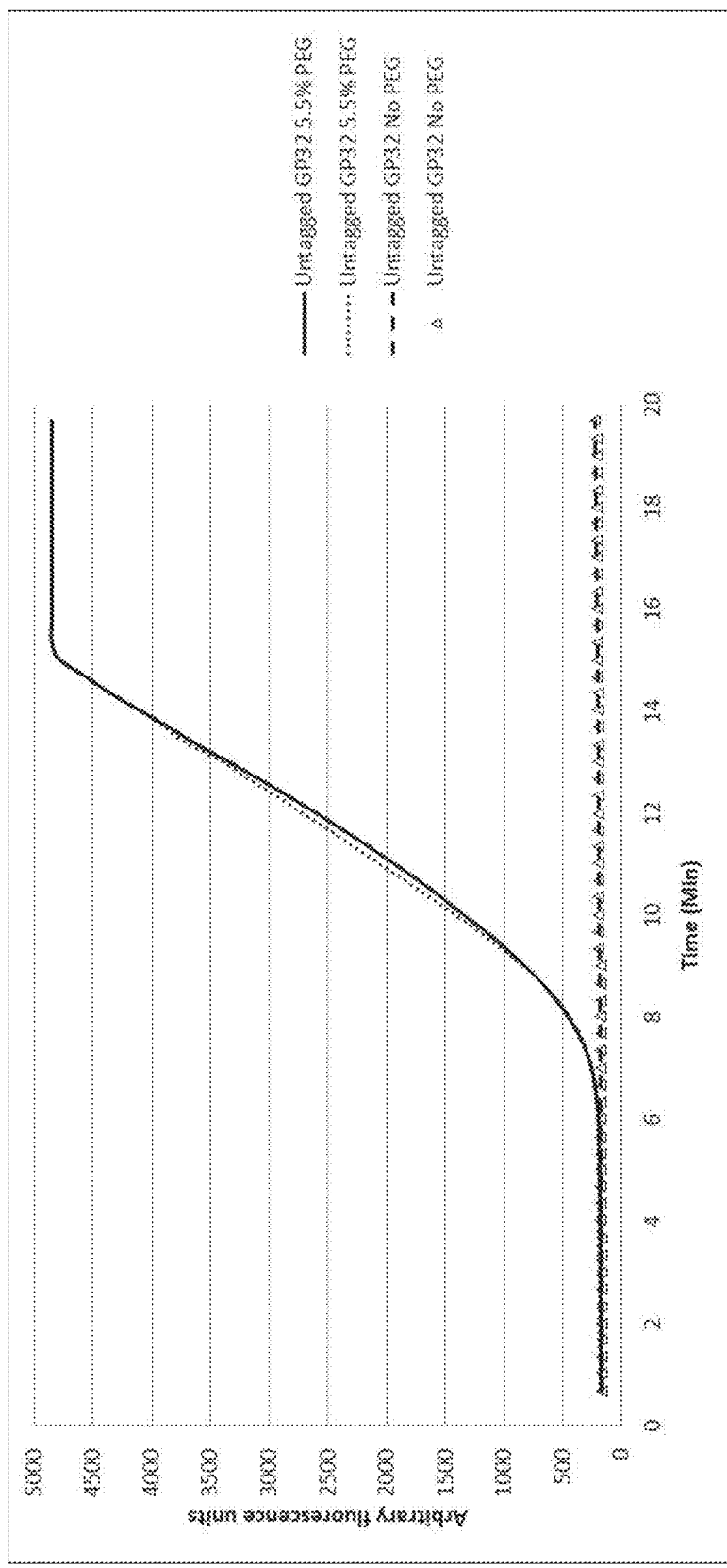
FIG. 17 shows real-time recombinase polymerase amplification traces using a native Gp32 fusion protein either in the presence of absence of crowding agent. The experiment reveals that Gp32 which is not tagged with an amino acid sequence comprising an intrinsically disordered region (IDR) is unable to mediate amplification in the absence of a crowding agent.

As shown in FIG. 17, rapid amplification with native Gp32 protein was observed in the presence of 5.5% PEG. However, no amplification was observed with native Gp32 protein in the absence of PEG.

In other Examples described above, such as Examples 1 to 5, Gp32-mediated amplification was observed in the absence of PEG only when the Gp32 protein was tagged with an amino acid sequence comprising an intrinsically disordered region (IDR).

Accordingly, and taken together with data presented in other Examples described herein, these data establish that the tag comprising the amino acid sequence comprising the intrinsically disordered region (IDR) applied to a protein component essential for the function of an in vitro biochemical reaction is able to bypass the requirement for a crowding agent in the reaction and increases the efficiency of the biochemical reaction compared to the efficiency observed in the absence of the IDR tag sequence.

Example 18. Recombinase Polymerase Amplification on a Solid Surface Using Gp32 Having an IDR Tag Derived from Human Otx1

Purpose and Summary of Experiment

This experiment was performed to assess the performance of a Gp32 fusion protein preparation containing a tag comprising a histidine-rich amino acid domain sequence found in the intrinsically disordered region (IDR) of the human homeobox protein Otx1.

The example demonstrates recombinase polymerase amplification (RPA) of an artificial nucleic acid template on a solid surface using Gp32 C-terminally tagged with the histidine rich intrinsically disordered region (IDR) domain (Otx1) in the absence of a crowding agent both in real-time and end-point assays.

Materials and Methods

The specific amino acid sequence of the IDR domain tag used was AGHHHHHPHAHHPLSQSSGHHHHHHHHHHQGYGG SG (SEQ ID NO:24). This was attached to the C-terminus of phage vB EcoM NBG1 Gp32. The recombinant fusion protein was purified using standard 1-step immobilised metal (nickel) affinity chromatography relying on the histidines naturally present in the IDR domain tag of the fusion protein under test. The fusion protein was designated Gp32-HIS2. The full amino acid sequence of the fusion protein is presented as SEQ ID NO: 82 (Table 23).

The recombinant phage vB EcoM NBG1 Gp32 fusion protein was then tested in PEG-free amplification, i.e. in the absence of a crowding agent, on a solid surface. The tests were performed using two oligonucleotide primers attached to the surface of beads in differing proportions. Amplification was detected by fluorescence, either in real-time using a cleavable quenched fluorescent probe or by end-point detection of annealed fluorescent probes. In both real-time and end-point RPA reactions the beads were the same. Beads were sourced from Bangs Laboratories, Inc. (bangslabs.com) and had a polystyrene core that was carboxylated and had a hydrogel grown on it to which oligonucleotides were covalently attached.

Real-Time RPA Reactions

Reactions were set up by mixing 25 mM Tris HCl pH 8.3, 7.5 mM KOAc, 1 mM DTT, 2.5 mM ATP, 20 mM phosphocreatine, 1 µM creatine kinase, 1 mM dNTPs, 120 nM probe, 20 µM Gp32 fusion, 4.9 µM UvsX, 7.6 µM UvsY, 0.146 µM S. aureus DNA polymerase and 0.34 µM Exonuclease III. The reaction mixture also included 800,000 beads/µl, each bead having approximately 750,000 oligonucleotide primers per bead consisting of a mix of PA30 forward primer and PB30 reverse primer.

Reactions were initiated by the addition of 33.6 mM MgOAc and an artificial DNA template called TF1L at a final concentration of 800,000 template copies per µl reaction mixture.

The relevant primers, probe and template are indicated below.

PA30 forward primer: CCATCTCATCCCTGCGTGTCTCCGACTCAG (SEQ ID NO:105).

PB30 reverse primer: CCTATCCCCTGTGTGCCTTGGCAGTCTCAG (SEQ ID NO:106).

Probe: AGCAGAAGCAATACCGCCAGCAATAGCA[dT-FAM]G[THF]G[dT-Quencher]AGAGCGAGCTGCC (SEQ ID NO:107), where FAM is fluorescein, THF is tetrahydrofuran and Quencher is Black Hole Quencher.

TF1L template sequence:

(SEQ ID NO: 108)
CCATCTCATCCCTGCGTGTCTCCGACTCAGTGTTTTAGGGTCCCCGGGGT

TAAAAGGTTTCGAACTCAACAGCTGTCTGGCAGCTCGCTCTACGCATGCT

ATTGCTGGCGGTATTGCTTCTGCTCTTGCTGGTGGCGCCATGTCTAAATT

GTTTGGAGCTGAGACTGCCAAGGCACACAGGGGATAGG.

Reactions were then incubated for 30 minutes at 39° C. in a T8 fluorometer and fluorescence in the FAM channel recorded.

Figure 18A:
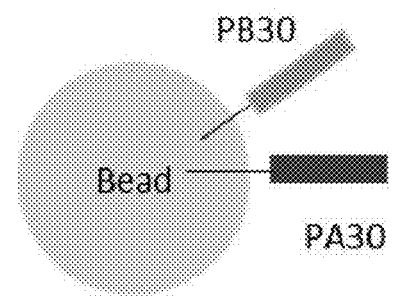
FIG. 18A is a cartoon depicting a reaction mixture set up for real-time amplification using dual-primer beads.
Figure 18B:
FIG. 18B is a cartoon depicting amplified products in the real-time reaction.
Figure 18B:
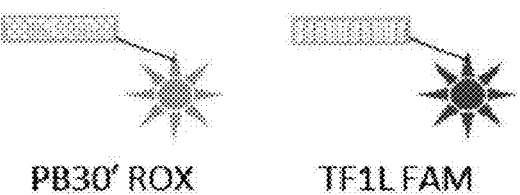
Figure 18B:
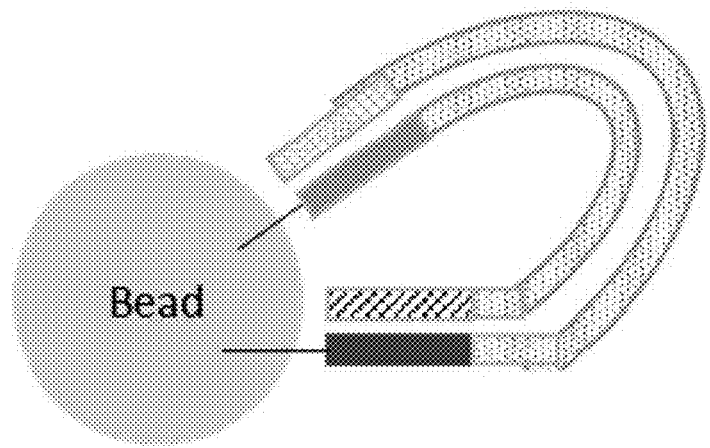

FIG. 18A is a cartoon depicting a reaction mixture set up for real-time amplification using dual-primer beads. FIG. 18B is a cartoon depicting amplified products in the real-time reaction.

End-Point RPA Reactions

Reactions were set up by mixing 25 mM Tris HCl pH 8.3, 7.5 mM KOAc, 1 mM DTT, 2.5 mM ATP, 20 mM phosphocreatine, 1 µM creatine kinase, 1 mM dNTPs, 20 µM Gp32 fusion, 4.9 µM UvsX, 7.6 µM UvsY and 0.146 µM S. aureus DNA polymerase. The reaction mixture also included 800,000 beads/µl, each bead having approximately 750,000 oligonucleotide primers per bead consisting of a mix of PA30 forward primer and PB30 reverse primer.

Reactions were initiated by the addition of 33.6 mM MgOAc and an artificial DNA template called TF1L at a final concentration of 800,000 template copies per µl reaction mixture.

The relevant primers and template are indicated below.

```
PA30 forward primer:
                                    (SEQ ID NO: 105)
CCATCTCATCCCTGCGTGTCTCCGACTCAG.

PB30 reverse primer:
                                    (SEQ ID NO: 106)
CCTATCCCCTGTGTGCCTTGGCAGTCTCAG.

TF1L template sequence:
                                    (SEQ ID NO: 108)
CCATCTCATCCCTGCGTGTCTCCGACTCAGTGTTTTAGGGTCCCCGGGGT

TAAAAGGTTTCGAACTCAACAGCTGTCTGGCAGCTCGCTCTACGCATGCT

ATTGCTGGCGGTATTGCTTCTGCTCTTGCTGGTGGCGCCATGTCTAAATT

GTTTGGAGCTGAGACTGCCAAGGCACACAGGGGATAGG.
```

Reactions were then incubated for 30 minutes at 39° C. and then stopped by the addition of Sodium Dodecyl Sulfate (SDS) to 1% final concentration and heating to 65° C. for 10 minutes to denature the proteins.

SDS was removed by diluting tenfold with water, vortexing, centrifuging for 15 minutes at ~18,000 g and then removing the supernatant. Beads were resuspended in TE pH 8.0, 0.05% Triton X-100 buffer to give approximately 800,000 beads/µl.

Two fluorescent oligonucleotide probes (PB30' probe (ROX-5'-CTGAGACTGCCAAGGCACACAGGGGA-TAGG; SEQ ID NO:109) and TF1L probe (FAM-5'-GGTTTCGAACTCAACAGCTG; SEQ ID NO:110), where ROX is carboxyrhodamine and FAM is fluorescein) were hybridised to beads in TE pH 8.0, 0.05% Triton X-100, 100 mM NaCl buffer, with both probes at a final concentration of 1 µM and 80,000 beads/µl. Hybridisation was performed by heating to 95° C. for 2 minutes, then cooling to 25° C. at 0.1° C./second. A positive control was run using beads that already had TF1L amplicon attached. Beads were then cleaned to remove unhybridized probes by diluting the hybridisation mixture sixfold in TE pH 8.0, 0.05% Triton X-100 buffer and centrifuging for 15 minutes at approximately 18,000 g and then as much supernatant as possible was removed. Beads were resuspended in TE pH 8.0, 0.05% Triton X-100 buffer. Reactions were then incubated for 5 minutes at 39° C. in a T8 fluorometer (FAM level set to 17%, ROX level set to 8%) and fluorescence in the FAM and ROX channels were recorded.

Figure 18C:
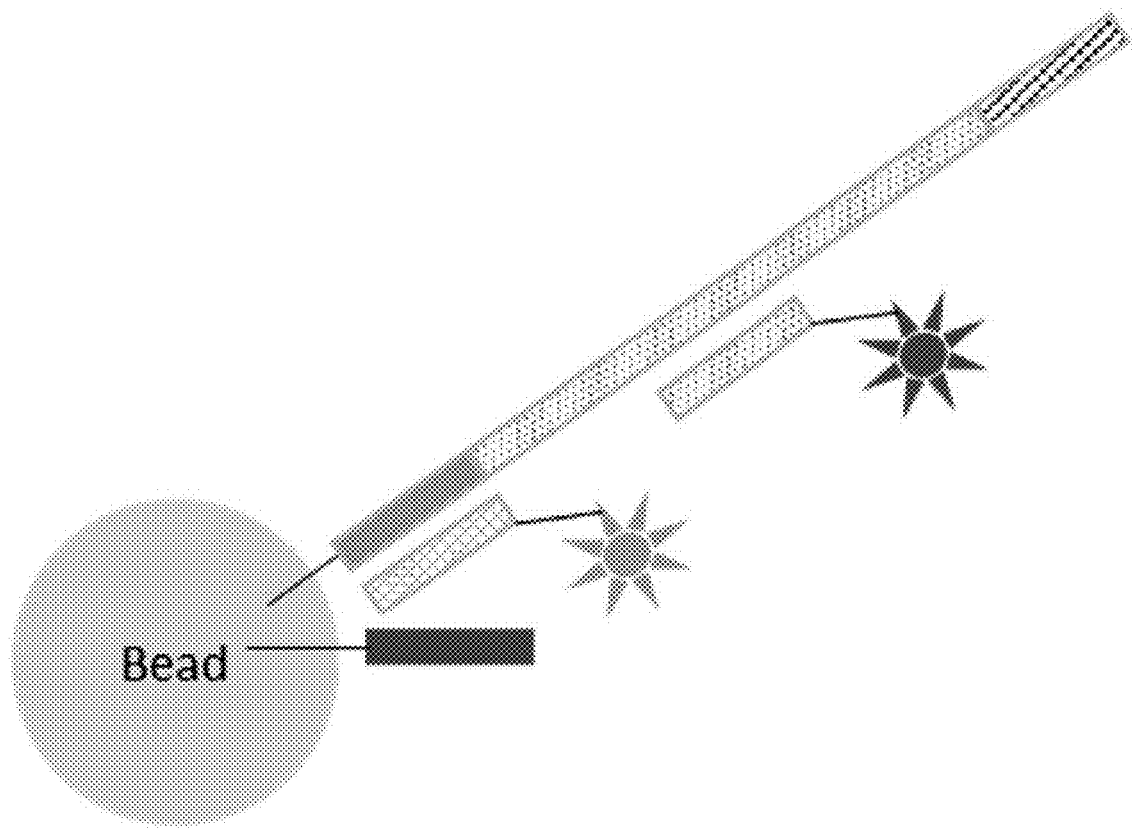
FIG. 18C is a cartoon depicting amplification characterisation in the end-point reaction.

FIG. 18C is a cartoon depicting amplification characterisation in the end-point reaction.

Results

Real-Time RPA Reactions

Figure 18D:
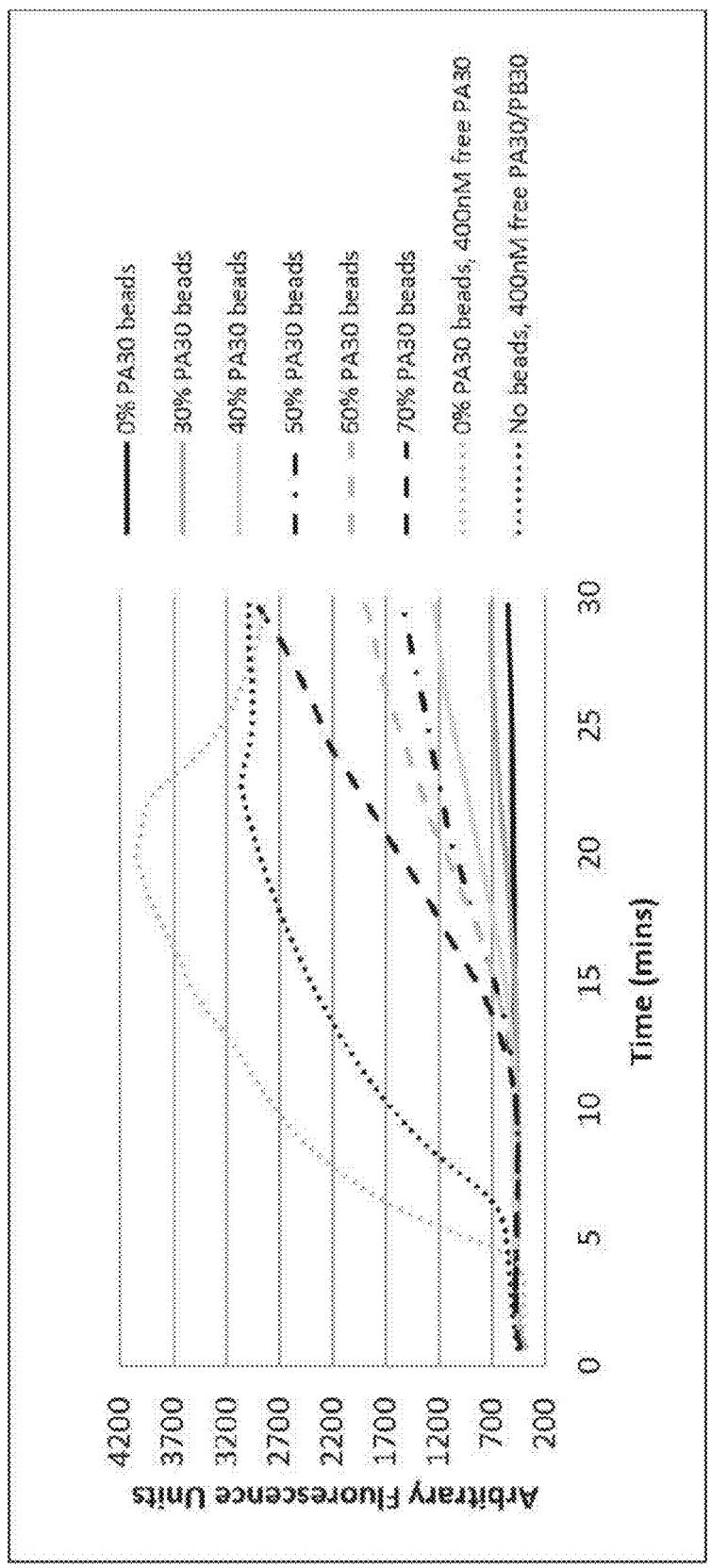
FIG. 18D shows real-time recombinase polymerase amplification traces using an IDR-tagged Gp32 fusion protein (Gp32-HIS2) using primers attached to a solid surface or using primers free in solution.

FIG. 18D shows real-time fluorescence detection of TF1L amplicon using the specific exonuclease cleaved probe. PA30 primer percentages specified in the figure denote the percentage of bead-bound oligonucleotide that are PA30 oligonucleotide, with the remainder of the bead-bound oligonucleotide being PB30 oligonucleotide. Amplification is detected when all PA30 and PB30 oligonucleotide primers are bead-bound, as well as when PA30 and PB30 oligonucleotide primers are in liquid phase or when PB30 is bead-bound and PA30 is in liquid phase. No amplification was detected when only PB30 was present on the beads and when there was no PA30.

End-Point RPA Reactions

Figure 18E:
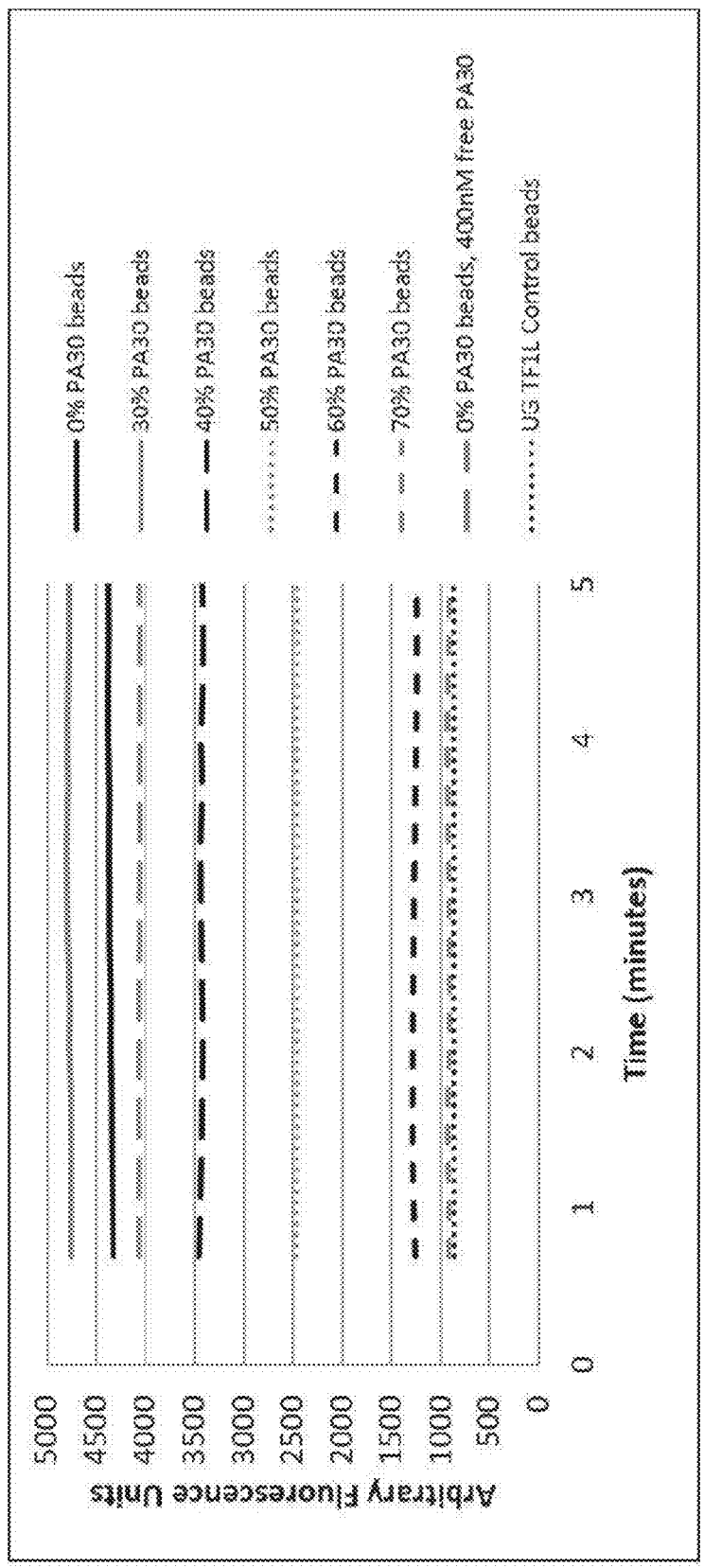
FIGS. 18E and 18F show end-point recombinase polymerase amplification traces using an IDR-tagged Gp32 fusion protein (Gp32-HIS2) using primers attached to a solid surface.
Figure 18F:
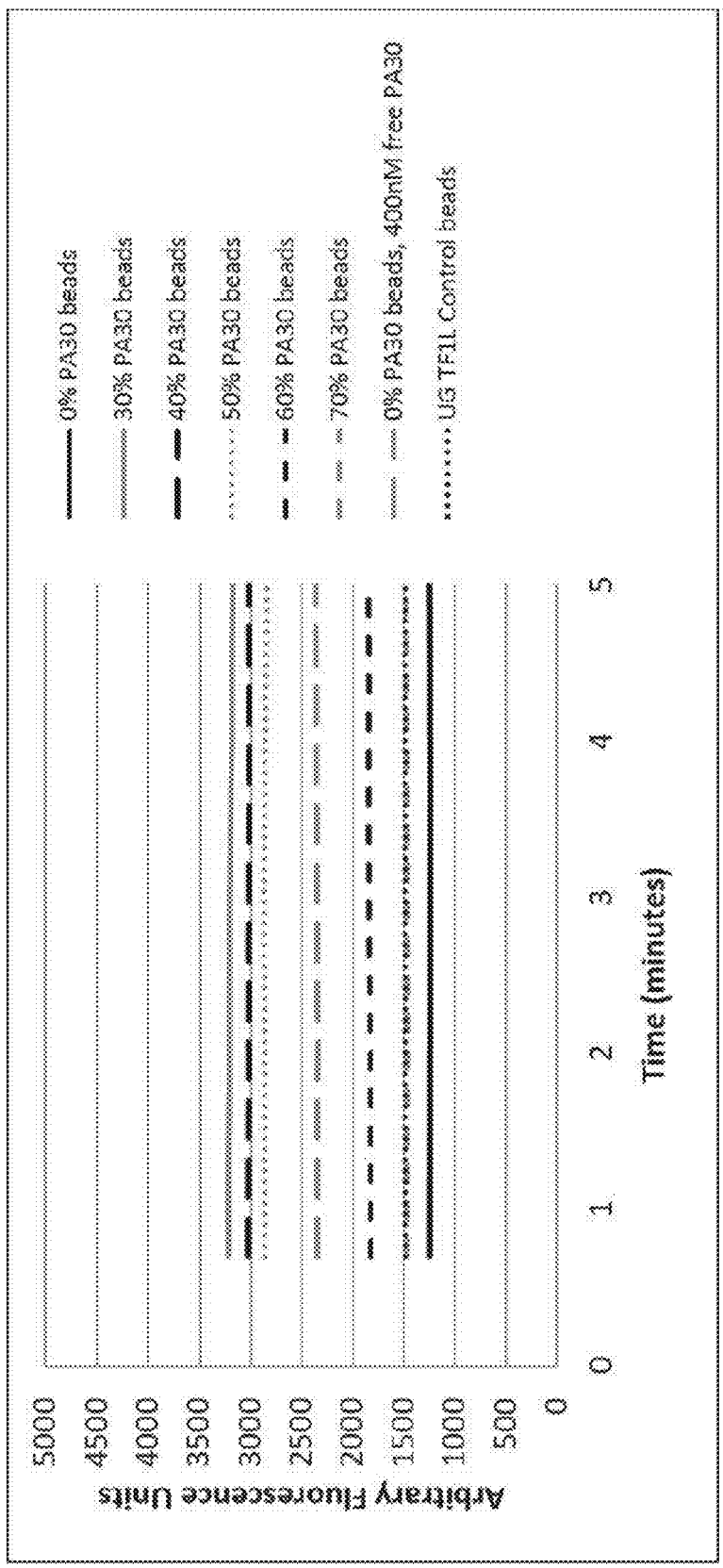

End-point fluorescence detection of TF1L amplicon was observed using probes specific to the PB30 oligonucleotide primer (ROX-labelled, FIG. 18E) and TF1L amplicon (FAM-labelled, FIG. 18F). Percentages specified in the figure denote the percentage of bead-bound oligonucleotide that are PA30 oligonucleotide, with the remainder of the bead-bound oligonucleotide being PB30 oligonucleotide. The table below shows the levels of fluorescence for each bead type, the ratio of TF1L probe fluorescence to PB30' probe fluorescence and the same ratio normalised to unamplified control beads with TF1L amplicon attached directly to account for background fluorescence caused by imperfect washing.

| Beads | TF1L fluorescence | PB30' fluorescence | TF1L: PB30 | Normalised ratio |
|---|---|---|---|---|
| 0% PA30 beads | 1249.75 | 4372 | 0.29 | 0.17 |
| 30% PA30 beads | 3194.8125 | 4773.9375 | 0.67 | 0.39 |
| 40% PA30 beads | 3017.1875 | 3424.625 | 0.88 | 0.52 |
| 50% PA30 beads | 2857.1875 | 2456.6875 | 1.16 | 0.68 |
| 60% PA30 beads | 1838.75 | 1264.75 | 1.45 | 0.85 |
| 70% PA30 beads | 1471.1875 | 923.5 | 1.59 | 0.93 |
| 0% PA30 beads, 400 nM free PA30 | 2355.8125 | 4060.9375 | 0.58 | 0.34 |
| TF1L Control beads | 1484.6875 | 868.8125 | 1.71 | 1 |

Conclusion

It was found that nucleic acid amplification in the absence of a crowding agent, such as PEG, occurred efficiently using the Gp32-HIS2 fusion protein both in real-time and end-point assays.

Example 19. Identification of Amino Acid Sequences Comprising Intrinsically Disordered Regions The amino acid sequences of phage vB EcoM NBG1 Gp32, T4 UvsY and T4 UvsX were examined via the MetaDisorder software program (MetaDisorder: a meta-server for the prediction of intrinsic disorder in proteins. Kozlowshi, L. P., et al., BMC Bioinformatics, 2012, 13(1): 111).

Figure 19A:
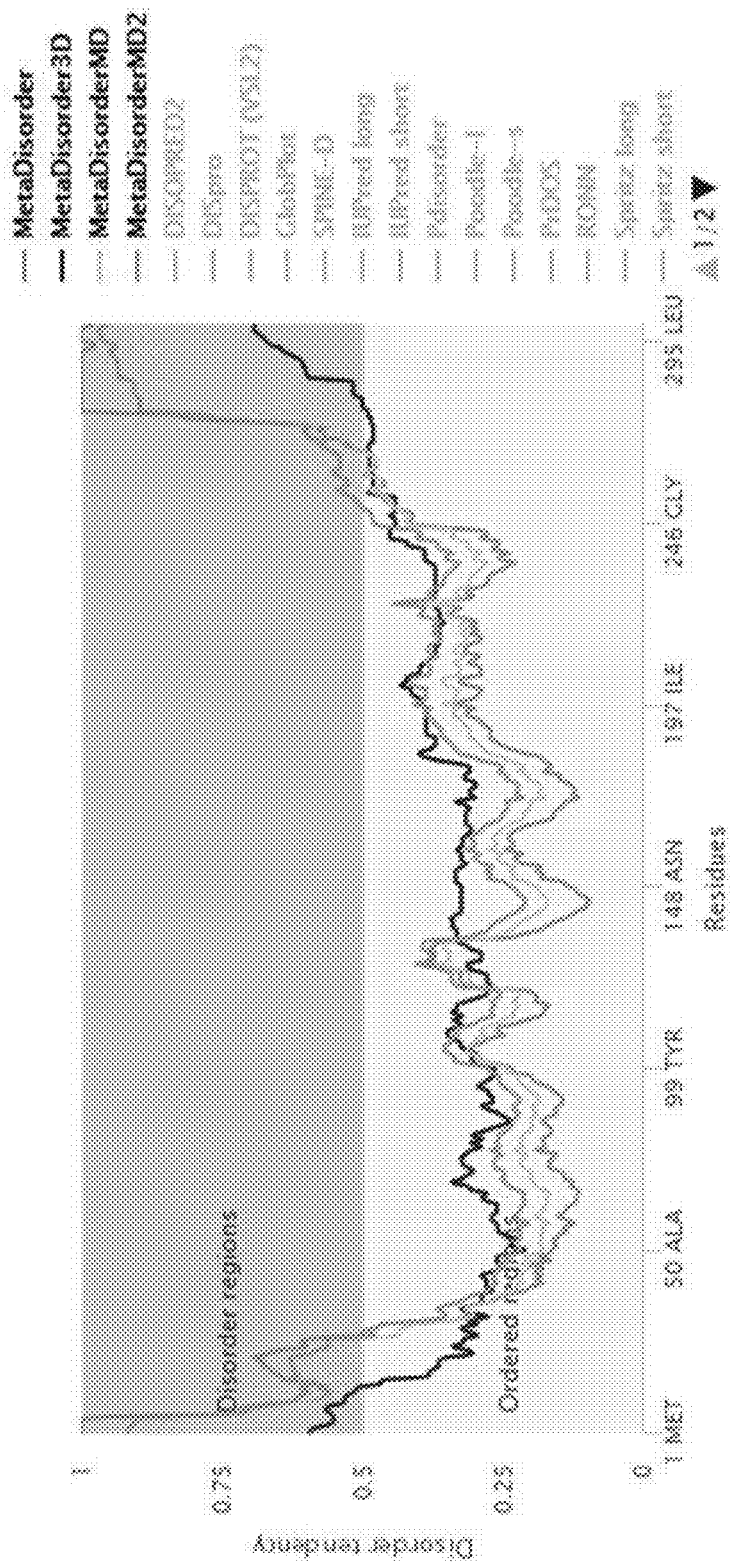
FIG. 19A-19C show disorder profiles generated using the MetaDisorder software program for Gp32 (FIG. 19A), UvsY (FIG. 19B) and UvsX (FIG. 19C).
Figure 19B:
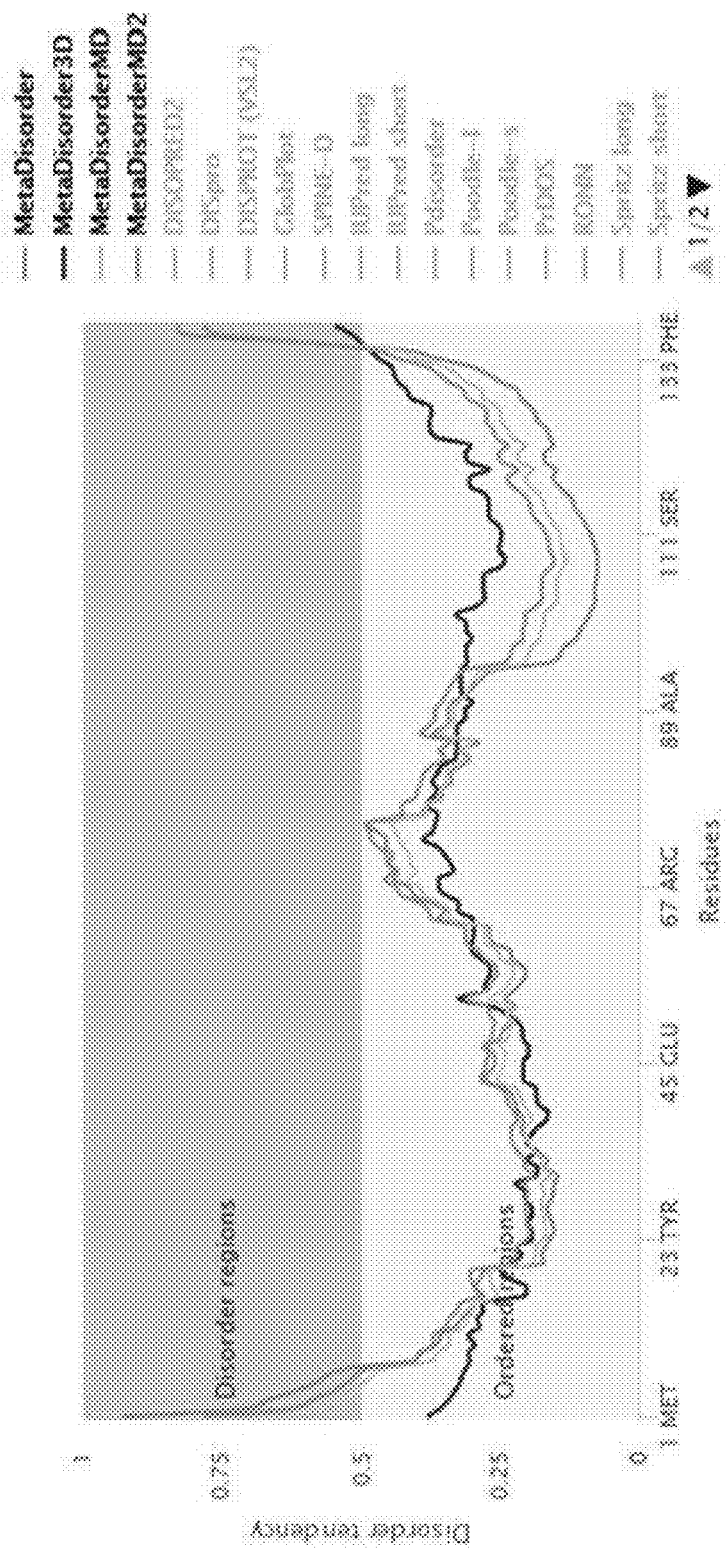
Figure 19C:
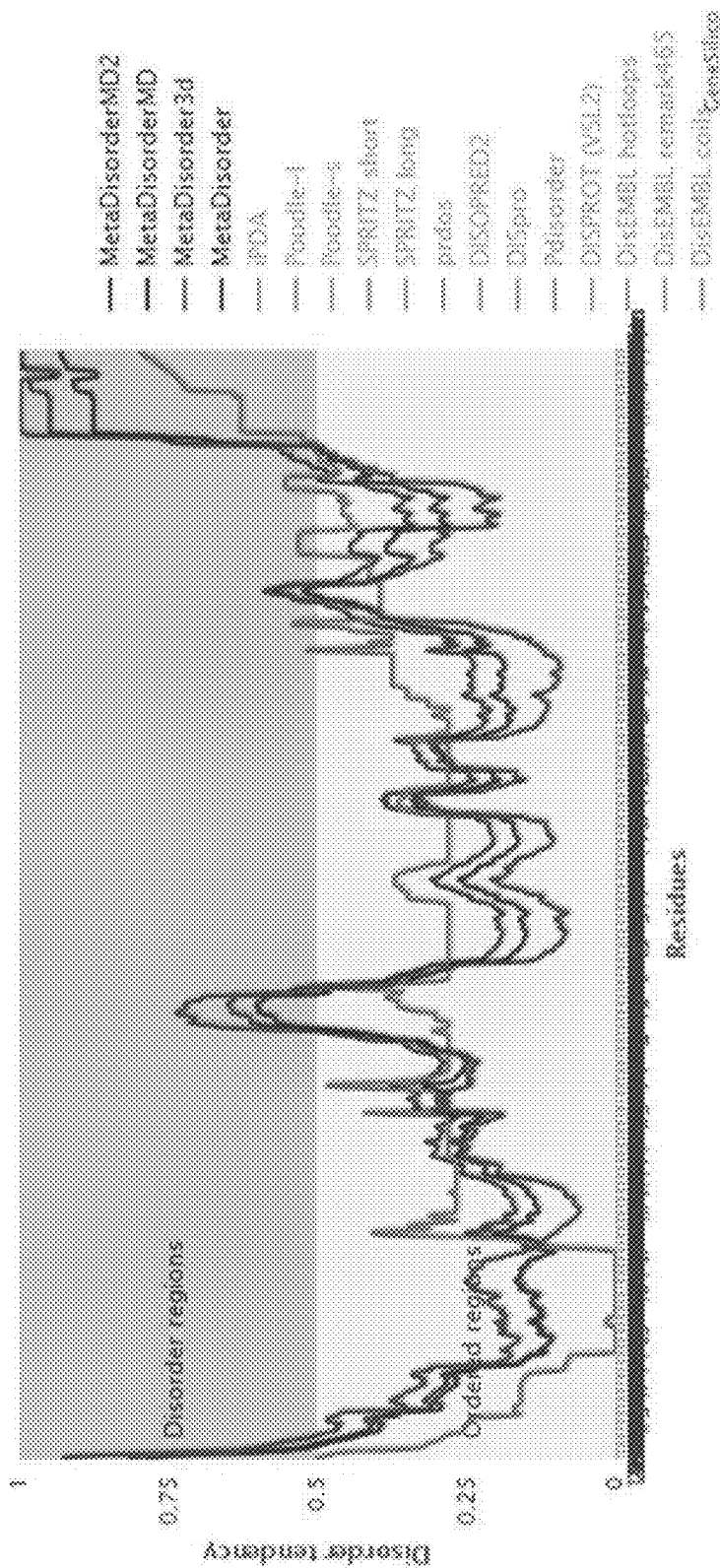
Figure 20A:
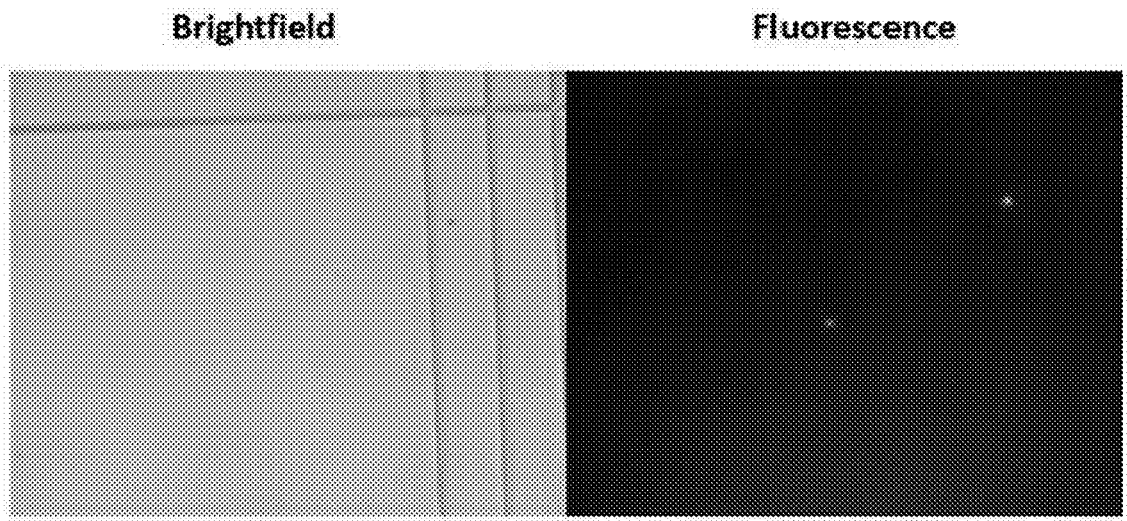
FIG. 20A-20D show the effect of varying concentrations of a divalent metal cation, i.e. magnesium ($MgCl_2$), on the capability of an IDR-tagged RB69 ligase fusion protein (RB69 ligase-HIS2) to promote phase separation (particle formation) in an exemplary in vitro biochemical reaction environment in the absence of a crowding agent.
Figure 20A:
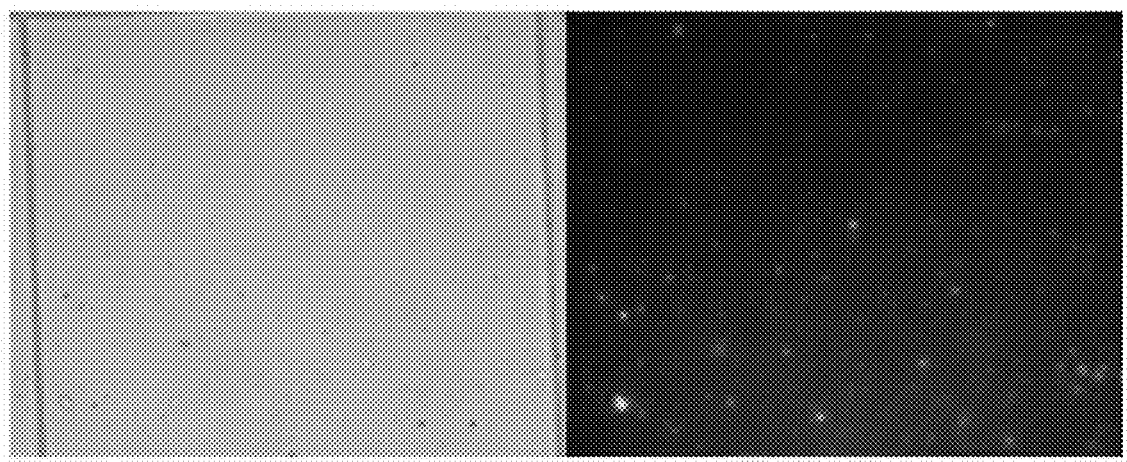
Figure 20B:
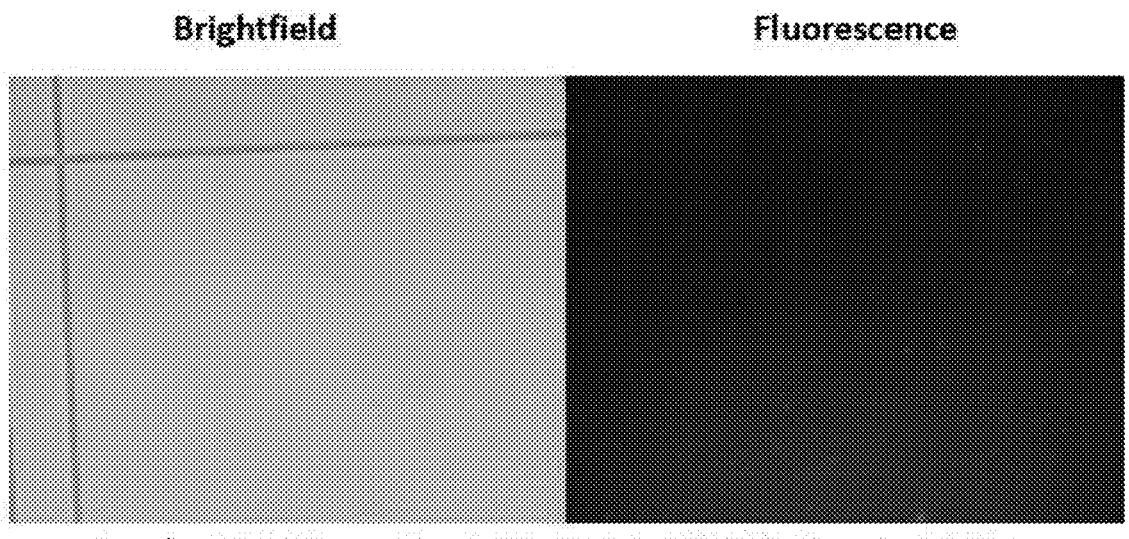
Figure 20B:
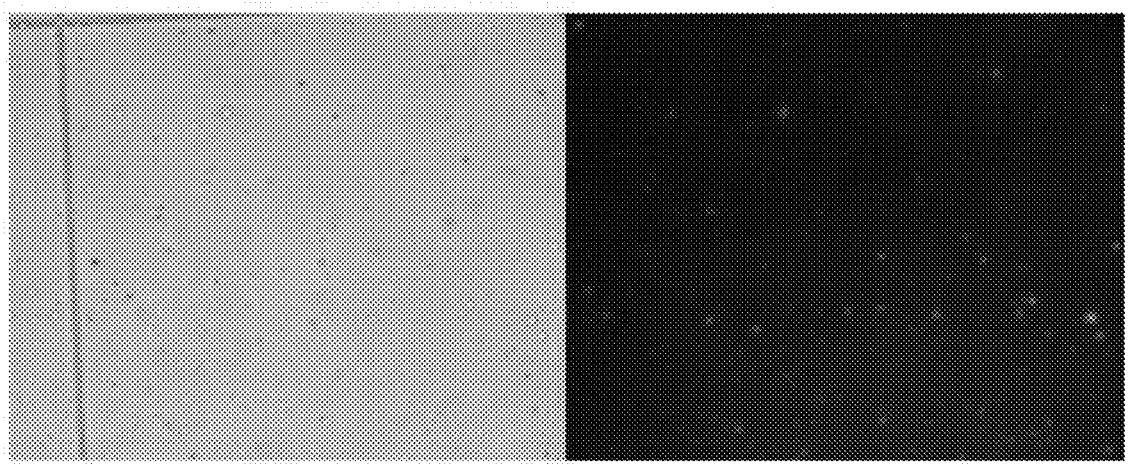
Figure 20C:
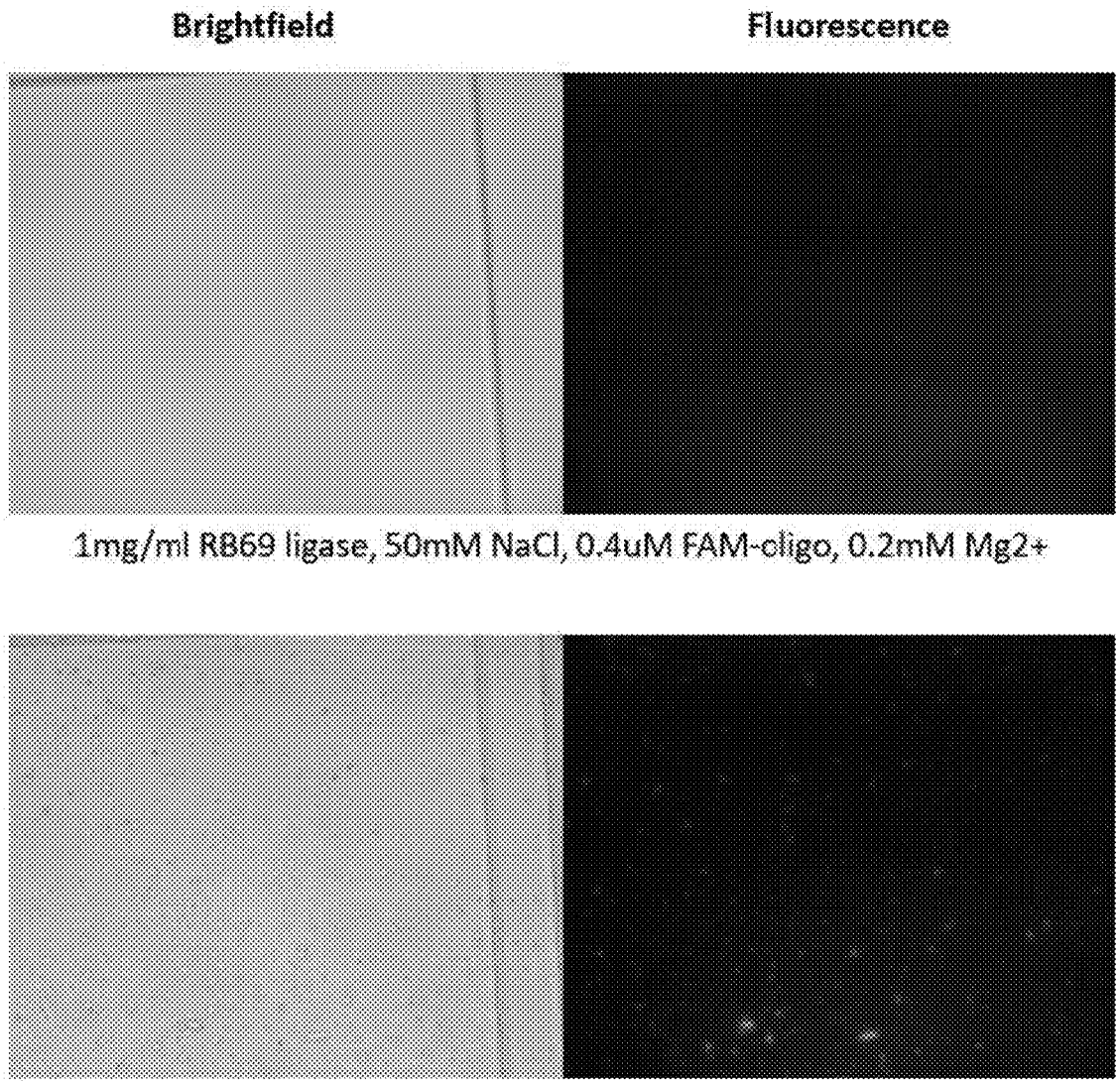
Figure 20D:
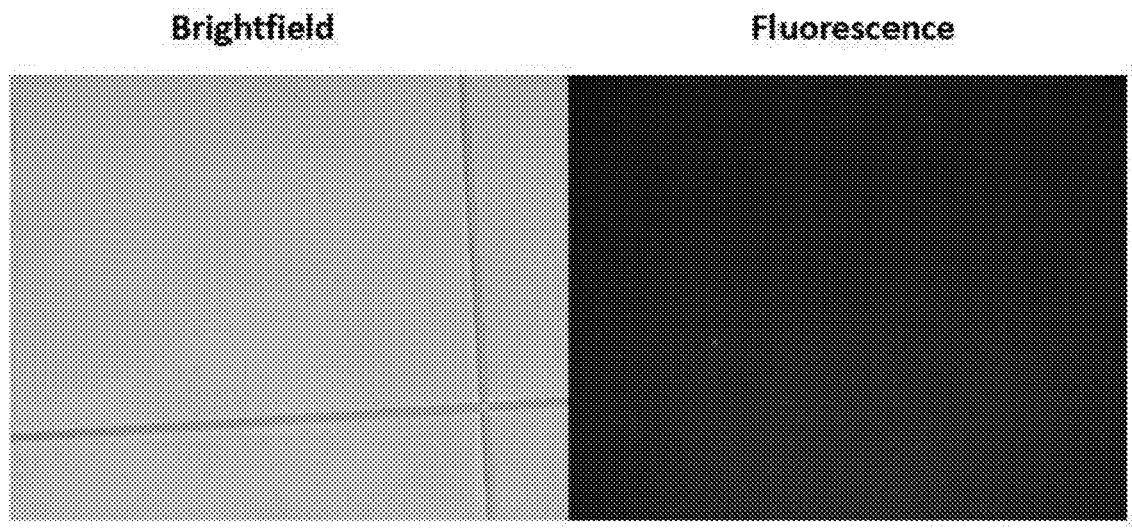
Figure 20D:
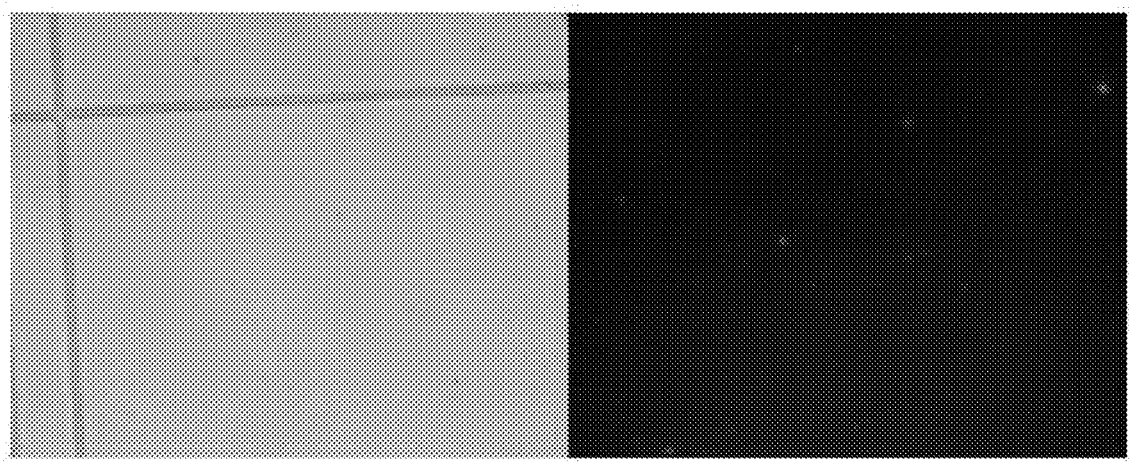

As shown in FIGS. 19 A, B and C respectively, the full length amino acid sequences of phage vB EcoM NBG1 Gp32, T4 UvsY and T4 UvsX contain amino acid sequence stretches which score greater than 0.5 when analysed by the algorithm, and thus comprise intrinsically disordered region sequences.

The example demonstrates that intrinsically disordered region sequences or domains thereof can readily be identified using standard analytical methods.

Example 20. Comparison of the Phase Separation Promoting Activity of RB69 Ligase and RB69 Ligase Having an IDR Tag Derived from Human Otx1

Purpose and Summary of Experiment

This experiment was performed to assess the phase separation promoting activity of a ligase enzyme fusion protein preparation containing a tag comprising a histidine-rich amino acid domain sequence found in the intrinsically disordered region (IDR) of the human homeobox protein Otx1 (His2 tag).

The experiment demonstrated that the formation of phase-separated aqueous particles (globular foci) by RB69 ligase-His2 in the absence of a crowding agent was enhanced by $Mg^{2+}$ concentration, whereas the formation of globular foci by RB69 ligase correlated poorly or not at all with $Mg^{2+}$ concentration.

Materials and Methods

The specific amino acid sequence of the IDR domain tag used was AGHHHHHPHAHHPLSQSSGHHHHHHHHHHQGYGGSG (SEQ ID NO:24; Table 1). This was attached to the C-terminus of RB69 DNA ligase. The recombinant fusion protein and IDR-free protein were purified using standard 1-step immobilised metal (nickel) affinity chromatography relying on the histidines naturally present in the IDR domain tag of the fusion protein under test and a poly-histidine tag at the C-terminus of IDR-free protein. The fusion protein was designated RB69 ligase-His2 and the IDR-free protein was designated RB69 ligase. The full amino acid sequence of the proteins are presented as SEQ ID NO: 111 and SEQ ID NO: 112 respectively in Table 24 below.

TABLE 24

| Name of protein | SEQ ID NO. | Amino acid sequence |
|---|---|---|
| RB69 ligase | 111 | MILDILNQIAAIGSTKTKQEILKKNKDNKLLERVYRLTYARGIQY YIKKWPGPGERSQAYGLLELDDMLDFIEFTLATRKLTGNAAIKEL MGYIADGKPDDVEVLRRVMMRDLEVGASVSIANKVWPGLIQLQ PQMLASAYDEKLITKNIKWPAFAQLKADGARCFAEVRDDGVQF FSRAGNEYHGLTLLADELMEMTKEARERHPNGVLIDGELVYHSF DIKKAVSSGNDLSFLFGDNEESEEVQVADRSTSNGLANKSLQGTI SPKEAEGMVLQAWDYVPLDEVYSDGKIKGQKYDVRFAALENM AEGFKRIEPIENQLVRNLDEAKVVYKKYVDQGLEGIILKNRDSY WENKRSKNLIKFKEVIDIALEVVGYYEHSKDPNKLGGVELVSRC RRITTDCGSGFKDTTHKTVDGVKVLIPLDERHDLDRERLMSEAR EGKLIGRIADCECNGWVHSKGREGTVGIFLPIIKGFRFDKTEADSF EDVFGSWDQTGVSGHHHHH |
| RB69 ligase-His2 | 112 | MILDILNQIAAIGSTKTKQEILKKNKDNKLLERVYRLTYARGIQY YIKKWPGPGERSQAYGLLELDDMLDFIEFTLATRKLTGNAAIKEL MGYIADGKPDDVEVLRRVMMRDLEVGASVSIANKVWPGLIQLQ PQMLASAYDEKLITKNIKWPAFAQLKADGARCFAEVRDDGVQF FSRAGNEYHGLTLLADELMEMTKEARERHPNGVLIDGELVYHSF DIKKAVSSGNDLSFLFGDNEESEEVQVADRSTSNGLANKSLQGTI SPKEAEGMVLQAWDYVPLDEVYSDGKIKGQKYDVRFAALENM AEGFKRIEPIENQLVRNLDEAKVVYKKYVDQGLEGIILKNRDSY WENKRSKNLIKFKEVIDIALEVVGYYEHSKDPNKLGGVELVSRC RRITTDCGSGFKDTTHKTVDGVKVLIPLDERHDLDRERLMSEAR EGKLIGRIADCECNGWVHSKGREGTVGIFLPIIKGFRFDKTEADSF EDVFGSWDQTGVSGHHHHHPHAHHPLSQSSGHHHHHHHHHQ GYGGSG |

The probe oligo used in the experiments was:

(SEQ ID NO: 104)
CCGCAATGGTGCACTCTCAGTACAATCTGCTCTGATG labelled with FAM (fluorescein).

A 50 µl solution was made up comprising the ligase at a final concentration of 1 mg/ml, 50 mM NaCl, 0.4 µM FAM-oligo and $MgCl_2$ at the target concentration indicated in the relevant figures. 10p of the reaction mix was then transferred to a C-Chip haemocytometer slide and images were taken under bright field light conditions and fluorescence conditions.

Results and Conclusion

As shown in FIG. 20, RB69 ligase-His2 enhanced the formation of many phase-separated aqueous particles (globular foci) which were seen to be dense in the oligonucleotide probe (as detected by the fluorescent label) in the presence of $Mg^{2+}$. Untagged RB69 ligase had very little effect in enhancing globular foci formation, even at 20 mM $Mg^{2+}$.

Example 21. Assessment of Ligase Activity Performance of RB69 Ligase Having an IDR Tag Derived from Human Otx1

Purpose and Summary of Experiment

This experiment was performed to assess the ligase activity performance of a ligase enzyme fusion protein preparation containing a tag comprising a histidine-rich amino acid domain sequence found in the intrinsically disordered region (IDR) of the human homeobox protein Otx1 (His2 tag).

The experiment demonstrated that double-ligated products increased when the concentration of RB69 ligase-His2 was increased.

Materials and Methods

The specific amino acid sequence of the IDR domain tag used was AGHHHHHPHAHHPLSQSSGHHHHHHHHHQGYGGSG (SEQ ID NO:24; Table 1). This was attached to the C-terminus of RB69 DNA ligase. The recombinant IDR fusion protein was purified using standard 1-step immobilised metal (nickel) affinity chromatography relying on the histidines naturally present in the IDR domain tag of the fusion protein under test. The fusion protein was designated RB69 ligase-His2. The full amino acid sequence of the protein is presented in Table 24 above.

The ligation template was a 170 bp fragment (Lig170) amplified from a pUC19 vector (New England Biolabs). A 50 µl amplification reaction was set up by mixing 25 µl DreamTaq Green Master Mix (Thermo Fisher Scientific), 0.2 µM Lig170_FW primer, 0.2 µM Lig170_RV primer, 1 pg pUC19. PCR reactions were performed as follows: 95° C. for 2 minutes; 35 cycles of 95° C. for 30 seconds, 55° C. for 30 seconds and 72° C. for 1 minute; followed by a final extension for 5 minutes at 72° C. Amplification product was run in a 2% agarose gel. The band of the target DNA was excised and purified by a Monarch DNA Gel Extraction Kit (New England Biolabs). DNA was further phosphorylated at the 5' end by T4 polynucleotide kinase (T4 PNK, Thermo Fisher Scientific). A 50 µl phosphorylation reaction was set up by mixing 1× reaction buffer A, 1 mM ATP, 1 U T4 PNK and DNA from the previous step. The phosphorylation reaction was incubated at 37° C. for 30 minutes. 5'-phosphorylated double-stranded DNA was purified by a Monarch PCR & DNA Cleanup Kit (New England Biolabs) and quantified by a Qubit dsDNA HS assay kit (Thermo Fisher Scientific).

The relevant primers and template sequences are indicated below.

Lig170_FW primer:

(SEQ ID NO: 113)
5'-GAGCGCAACGCAATTAA-3'.

```
-continued
Lig170_RV primer:
                                      (SEQ ID NO: 114)
5'-ATCCGCTCACAATTCCACAC-3'.

Lig170 template:
                                      (SEQ ID NO: 115)
5'-GAGCGCAACGCAATTAATGTGAGTTAGCTCACTCATT

AGGCACCCCAGGCTTTACACTTTATGCTTCCGGCTCGTATGTTGTGTG

GAATTGTGAGCGGAT-3'.
```

Illumina adaptor was prepared by slow annealing two oligos, 1.5 µM ILMN_AD_P5 and 1.5 µM ILMN_AD_P7rc_IDX01. The annealing process was heating the oligo mixture to 95° C. and cooled to 14° C. at a rate of 0.1° C./min.

```
ILMN_AD_P5:
                                      (SEQ ID NO: 116)
5'-AATGATACGGCGACCACCGAGATCTACACTCTTTCCCTACACGACGC

TCTTCCGATCT-3'.

ILMN_AD_P7rc_IDX01:
                                      (SEQ ID NO: 117)
5'-PO4-GATCGGAAGAGCACACGTCTGAACTCCAGTCACATCACGATCT

CGTATGCCGTCTTCTGCTTG-3'.
```

RB69 ligase-His2 was 35 mg/ml and it was diluted to 1 mg/ml as a working stock. A 20 µl solution was made up comprising T4 PNK treated Lig170 at a final concentration of 1 ng/µl, 187.5 nM Illumina adaptor, 5% PEG 35000, 1×T4 DNA Ligase Reaction Buffer (New England Biolabs), and RB69 ligase-His2 at a final concentration of 0.1/0.2/0.3/0.4 mg/ml. Ligation reactions were performed at 16° C. for 20 minutes and 65° C. for 15 minutes. To be visualised on an agarose gel, 8 parallel reactions were set up for each reaction condition and combined before loading to a 2% agarose gel. Gel image was analysed by ImageJ (National Institutes of Health) and optical densities of bands were plotted by Excel (Microsoft).

Results and Conclusion

Figure 21:
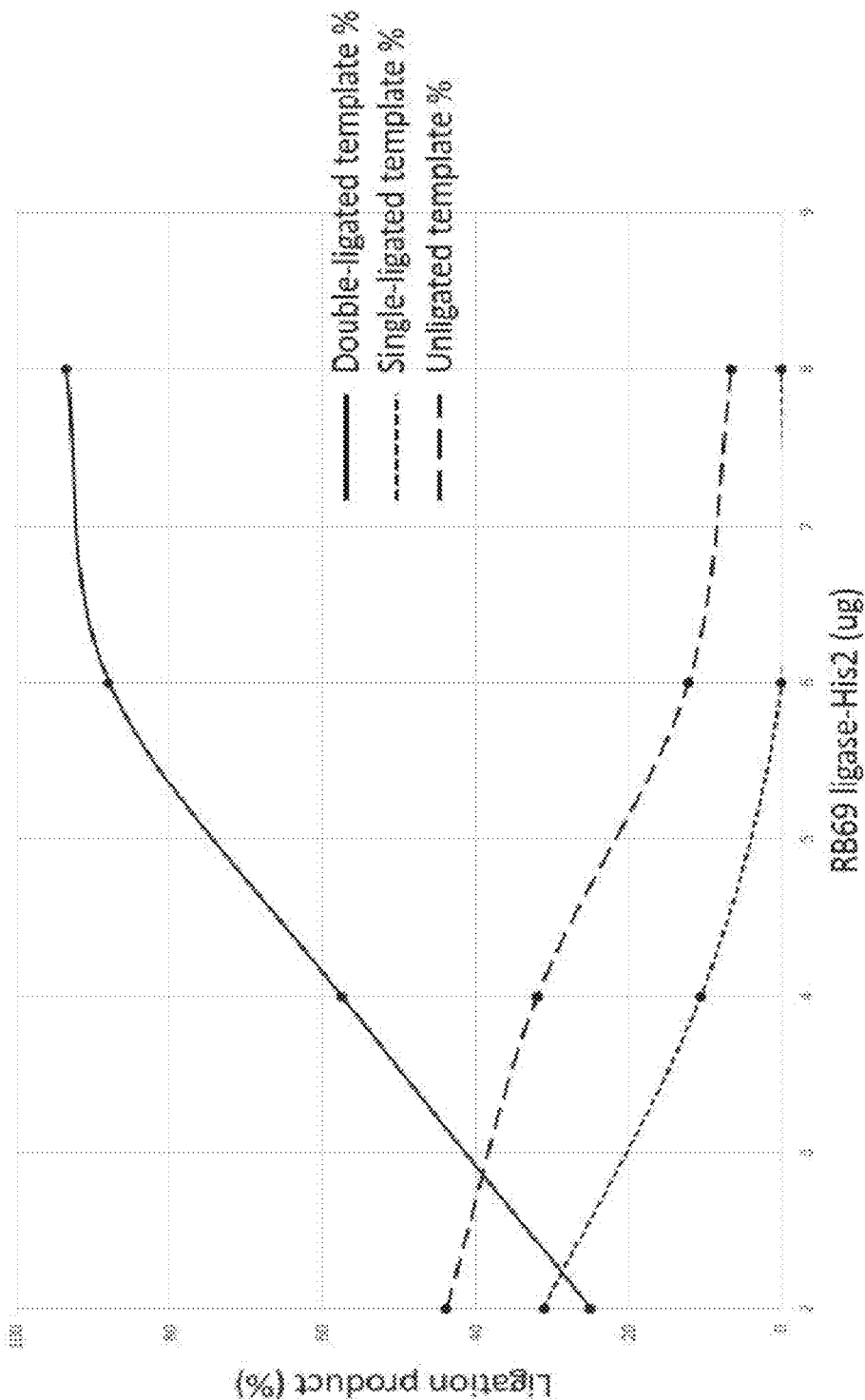
FIG. 21 shows the ligase activity performance of an IDR-tagged RB69 ligase fusion protein (RB69 ligase-HIS2) in an exemplary in vitro biochemical reaction environment in the absence of a crowding agent.

As shown in FIG. 21, double-ligated products increased when concentrations of RB69 ligase-His2 increased. When 0.4 mg/ml of RB69 ligase-His2 was used in a 20 µl reaction (0.8 µg in the figure), 93.5% of template could be ligated at both ends by Illumina adaptors.

Example 22. Comparison of the Ligase Activity Performance of RB69 Ligase and RB69 Ligase Having an IDR Tag Derived from Human Otx1

Purpose and Summary of Experiment

This experiment was performed to assess the activity performance of a ligase enzyme fusion protein preparation containing a tag comprising a histidine-rich amino acid domain sequence found in the intrinsically disordered region (IDR) of the human homeobox protein Otx1 (His2 tag).

The experiment demonstrated that the His2 tag could significantly increase the TA ligation efficiency of RB69 ligase compared to the efficiency of untagged RB69 ligase.

Materials and Methods

The specific amino acid sequence of the IDR domain tag used was AGHHHHHPHAHHPLSQSSGHHHHHHHHHHQGYG GSG (SEQ ID NO:24; Table 1). This was attached to the C-terminus of RB69 DNA ligase. The recombinant fusion protein and IDR-free protein were purified using standard 1-step immobilised metal (nickel) affinity chromatography relying on the histidines naturally present in the IDR domain tag of the fusion protein under test and a poly-histidine tag at the C-terminus of the IDR-free protein. The fusion protein was designated RB69 ligase-His2 and the IDR-free protein was designated RB69 ligase. The full amino acid sequence of proteins are presented in Table 24 above.

The ligation template was a 170 bp fragment (Lig170) amplified from a pUC19 vector (New England Biolabs). A 50p amplification reaction was set up by mixing 25 µl DreamTaq Green Master Mix (Thermo Fisher Scientific), 0.2 µM Lig170_FW primer, 0.2 µM Lig170_RV primer, 1 pg pUC19. PCR reaction was performed as follows: 95° C. for 2 minutes; 35 cycles of 95° C. for 30 seconds, 55° C. for 30 seconds and 72° C. for 1 minute; followed by a final extension for 5 minutes at 72° C. Amplification product was run in a 2% agarose gel. The band of the target DNA was excised and purified by a Monarch DNA Gel Extraction Kit (New England Biolabs). DNA was further phosphorylated at the 5' end by T4 polynucleotide kinase (T4 PNK, Thermo Fisher Scientific). A 50 µl phosphorylation reaction was set up by mixing 1× reaction buffer A, 1 mM ATP, 1 U T4 PNK and DNA from the previous step. The phosphorylation reaction was incubated at 37° C. for 30 minutes. 5'-phosphorated double-stranded DNA was purified by a Monarch PCR & DNA Cleanup Kit (New England Biolabs) and quantified by a Qubit dsDNA HS assay kit (Thermo Fisher Scientific).

The relevant primers and template sequences are indicated below.

```
Lig170_FW primer:
                                      (SEQ ID NO: 113)
5'-GAGCGCAACGCAATTAA-3'.

Lig170_RV primer:
                                      (SEQ ID NO: 114)
5'-ATCCGCTCACAATTCCACAC-3'.

Lig170 template:
                                      (SEQ ID NO: 115)
5'-GAGCGCAACGCAATTAATGTGAGTTAGCTCACTCATT

AGGCACCCCAGGCTTTACACTTTATGCTTCCGGCTCGTATGTTGTGTG

GAATTGTGAGCGGAT-3'.
```

Illumina adaptor was prepared by slow annealing two oligos, 1.5 µM ILMN_AD_P5 and 1.5 µM ILMN_AD_P7rc_IDX01. The annealing process was heating the oligo mixture to 95° C. and cooled to 14° C. at a rate of 0.1° C./min.

```
ILMN_AD_P5:
                                      (SEQ ID NO: 116)
5'-AATGATACGGCGACCACCGAGATCTACACTCTTTCCCTACACGACGC

TCTTCCGATCT-3'.

ILMN_AD_P7rc_IDX01:
                                      (SEQ ID NO: 117)
5'-PO4-GATCGGAAGAGCACACGTCTGAACTCCAGTCACATCACGATCT

CGTATGCCGTCTTCTGCTTG-3'.
```

RB69 ligase-His2 was 35 mg/ml and RB69 ligase was 27.75 mg/ml. They were diluted to 1 mg/ml as working stocks. T4 DNA ligase was quantified by Pierce BCA protein assay kit (Thermo Fisher Scientific) and diluted to 1 mg/ml as a working stock. A 20 µl solution was made up comprising T4 PNK treated Lig170 at a final concentration of 1 ng/ul, 187.5 nM Illumina adaptor, 5% PEG 35000, 1×T4 DNA Ligase Reaction Buffer (New England Biolabs), and T4 DNA ligase/RB69 ligase/RB69 ligase-His2 at a final concentration of 0.075 mg/ml. Ligation reactions were performed at 16° C. for 20 minutes and 65° C. for 15 minutes. DNA was purified by 0.8× AMPure XP for PCR beads (Beckman Coulter) according to the manufacturer's instructions. Purified DNA was mixed with 25 µl DreamTaq Green Master Mix (Thermo Fisher Scientific), 0.2 µM ILMN_P5 primer, 0.2 µM ILMN_P7 primer. PCR reactions were performed as follows: 95° C. for 2 minutes; 10 cycles of 95° C. for 30 seconds, 55° C. for 30 seconds and 72° C. for 1 minute; followed by a final extension for 5 minutes at 72° C. Amplification product was purified by 1×AMPure XP for PCR beads. Purified DNA was quantified by Qubit dsDNA HS assay kit and amount of DNA was plotted by Excel (Microsoft).

```
ILMN_P5:
                                    (SEQ ID NO: 118)
5'-AATGATACGGCGACCACCGA-3'

ILMN_P7:
                                    (SEQ ID NO: 119)
5'-CAAGCAGAAGACGGCATACG-3'
```

Results and Conclusion

Figure 22:
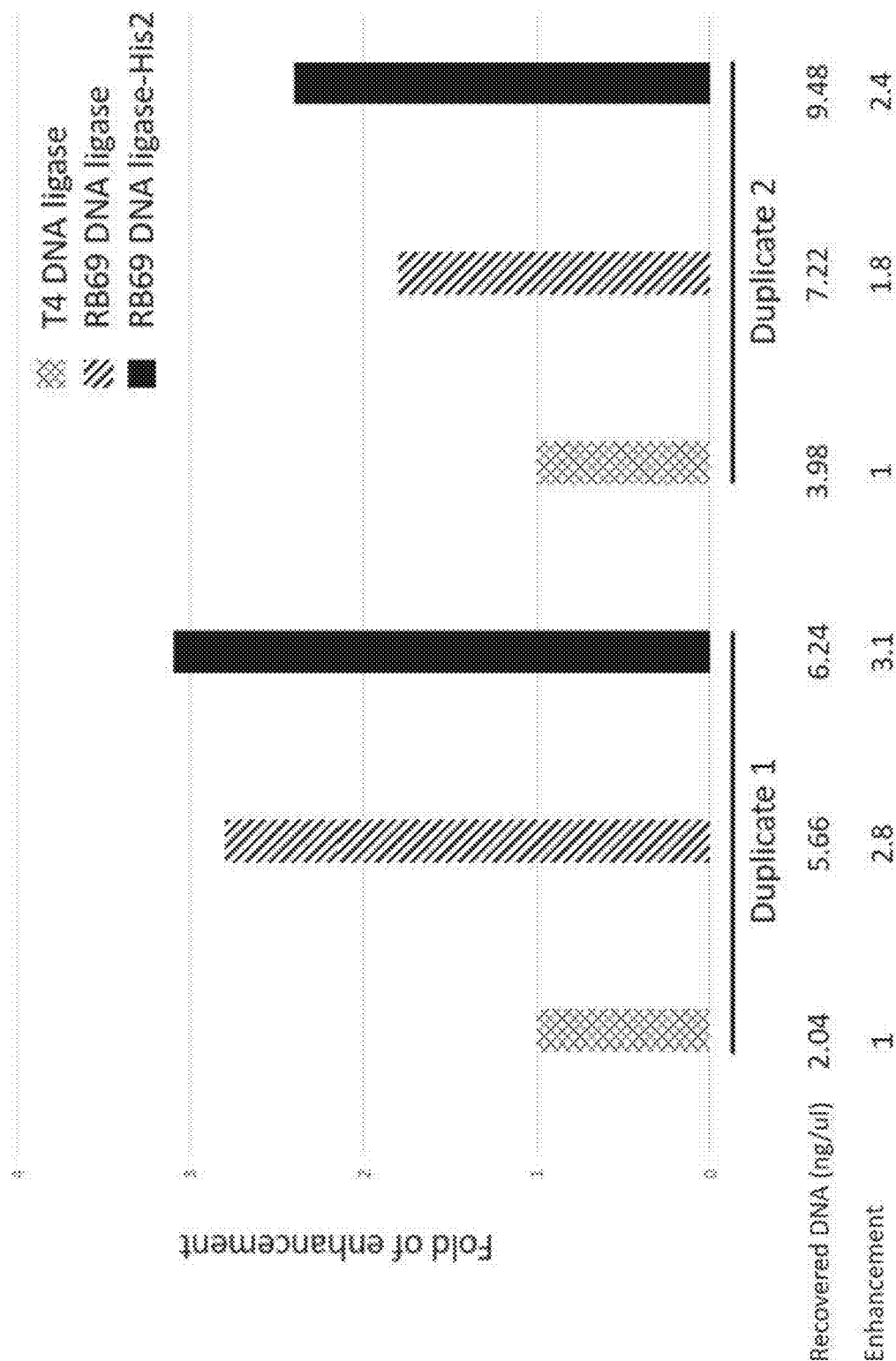
FIG. 22 shows the ligase activity performance of an IDR-tagged RB69 ligase fusion protein (RB69 ligase-HIS2) in an exemplary in vitro biochemical reaction environment in the absence of a crowding agent compared with untagged RB69 ligase and T4 DNA ligase.

As shown in FIG. 22, only double-ligated products could be amplified. Both RB69 ligase and RB69 ligase-His2 demonstrated significantly increased ligation efficiencies. Especially RB69 ligase-His2 could have up to 3.1 fold enhancement of ligation efficiency.

Example 23. Comparison of the Ligase Activity Performance of NEBNext Ultra II Ligase and RB69 Ligase Having an IDR Tag Derived from Human Otx1

Purpose and Summary of Experiment

This experiment was performed to assess the activity performance of NEBNext Ultra II Ligation Master Mix compared with a ligase enzyme fusion protein preparation containing a tag comprising a histidine-rich amino acid domain sequence found in the intrinsically disordered region (IDR) of the human homeobox protein Otx1 (His2 tag).

The experiment demonstrated that RB69 ligase-His2 had a significantly enhanced ligation efficiency compared to NEBNext Ultra II Ligation Master Mix.

Materials and Methods

The specific amino acid sequence of the IDR domain tag used was AGHHHHHPHAHHPLSQSSGHHHHHHHHHHQGYGG SG (SEQ ID NO:24). This was attached to the C-terminus of RB69 DNA ligase. The recombinant fusion protein was purified using standard 1-step immobilised metal (nickel) affinity chromatography relying on the histidines naturally present in the IDR domain tag of the fusion protein under test. The fusion protein was designated RB69 ligase-His2. The full amino acid sequence of the protein is presented in Table 24 above.

The ligation template was a 170 bp fragment (Lig170) amplified from a pUC19 vector (New England Biolabs). A 50 µl amplification reaction was set up by mixing 25 µl DreamTaq Green Master Mix (Thermo Fisher Scientific), 0.2 µM Lig170_FW primer, 0.2 µM Lig170_RV primer, 1 pg pUC19. PCR reaction was performed as follows: 95° C. for 2 minutes; 35 cycles of 95° C. for 30 seconds, 55° C. for 30 seconds and 72° C. for 1 minute; followed by a final extension for 5 minutes at 72° C. Amplification product was run in a 2% agarose gel. The band of the target DNA was excised and purified by a Monarch DNA Gel Extraction Kit (New England Biolabs). DNA was further phosphorylated at the 5' end by T4 polynucleotide kinase (T4 PNK, Thermo Fisher Scientific). A 50 µl phosphorylation reaction was set up by mixing 1× reaction buffer A, 1 mM ATP, 1 U T4 PNK and DNA from the previous step. The phosphorylation reaction was incubated at 37° C. for 30 minutes. 5'-phosphorated double-stranded DNA was purified by a Monarch PCR & DNA Cleanup Kit (New England Biolabs) and quantified by a Qubit dsDNA HS assay kit (Thermo Fisher Scientific).

The relevant primers and template sequences are indicated below.

```
Lig170_FW primer:
                                    (SEQ ID NO: 113)
5'-GAGCGCAACGCAATTAA-3'.

Lig170_RV primer:
                                    (SEQ ID NO: 114)
5'-ATCCGCTCACAATTCCACAC-3'.

Lig170 template:
                                    (SEQ ID NO: 115)
5'-GAGCGCAACGCAATTAATGTGAGTTAGCTCACTCATT

AGGCACCCCAGGCTTTACACTTTATGCTTCCGGCTCGTATGTTGTGTG

GAATTGTGAGCGGAT-3'.
```

Illumina adaptor was prepared by slow annealing two oligos, 1.5 µM ILMN_AD_P5 and 1.5 µM ILMN_AD_P7rc_IDX01. The annealing process was heating the oligo mixture to 95° C. and cooled to 14° C. at a rate of 0.1° C./min.

```
ILMN_AD_P5:
                                    (SEQ ID NO: 116)
5'-AATGATACGGCGACCACCGAGATCTACACTCTTTCCCTACACGACGC

TCTTCCGATCT-3'.

ILMN_AD_P7rc_IDX01:
                                    (SEQ ID NO: 117)
5'-PO4-GATCGGAAGAGCACACGTCTGAACTCCAGTCACATCACGATCT

CGTATGCCGTCTTCTGCTTG-3'.
```

RB69 ligase-His2 was 35 mg/ml and was diluted to 1 mg/ml as a working stock.

A 93.5 µl solution was made up comprising 10 ng T4 PNK treated Lig170, 187.5 nM Illumina adaptor, 30 µl NEBNext Ultra II Ligation Master Mix, and 1 µl NEBNext Ligation Enhancer. Ligation reactions were performed at 20° C. for 15 minutes. Ligation reactions were terminated by adding 6.5 µl of 0.5M EDTA and DNA was purified by 0.8×AMPure XP for PCR beads (Beckman Coulter) according to the manufacturer's instructions. A 93.5 µl solution was made up comprising 10 ng T4 PNK treated Lig170, 187.5 nM Illumina adaptor, 5%/7% PEG 35000, 1×T4 DNA Ligase Reaction Buffer (New England Biolabs), and RB69 ligase-His2 at a final concentration of 0.2/0.3/0.4 mg/ml. Ligation reactions were performed at 16° C. for 20 minutes. Ligation reactions were terminated by adding 4.5 µl of 0.5M EDTA and 2 ul Protease K (New England Biolabs) and incubated at 40° C. for 30 minutes. DNA was purified by 0.8×AMPure XP for PCR beads (Beckman Coulter) according to the manufacturer's instructions. Purified DNA was mixed with 25 µl DreamTaq Green Master Mix (Thermo Fisher Scientific), 0.2 µM ILMN_P5 primer, 0.2 µM ILMN_P7 primer. PCR reactions were performed as follows: 95° C. for 2 minutes; 10 cycles of 95° C. for 30 seconds, 55° C. for 30 seconds and 72° C. for 1 minute; followed by a final extension for 5 minutes at 72° C. Amplification product was purified by 1×AMPure XP for PCR beads. Purified DNA was quantified by Qubit dsDNA HS assay kit and amount of DNA were plotted by Excel (Microsoft). DNA was also analysed by a 2% agarose gel.

```
ILMN_P5:
                                        (SEQ ID NO: 118)
5'-AATGATACGGCGACCACCGA-3'.

ILMN_P7:
                                        (SEQ ID NO: 119)
5'-CAAGCAGAAGACGGCATACG-3'.
```

Results and Conclusion

Figure 23:
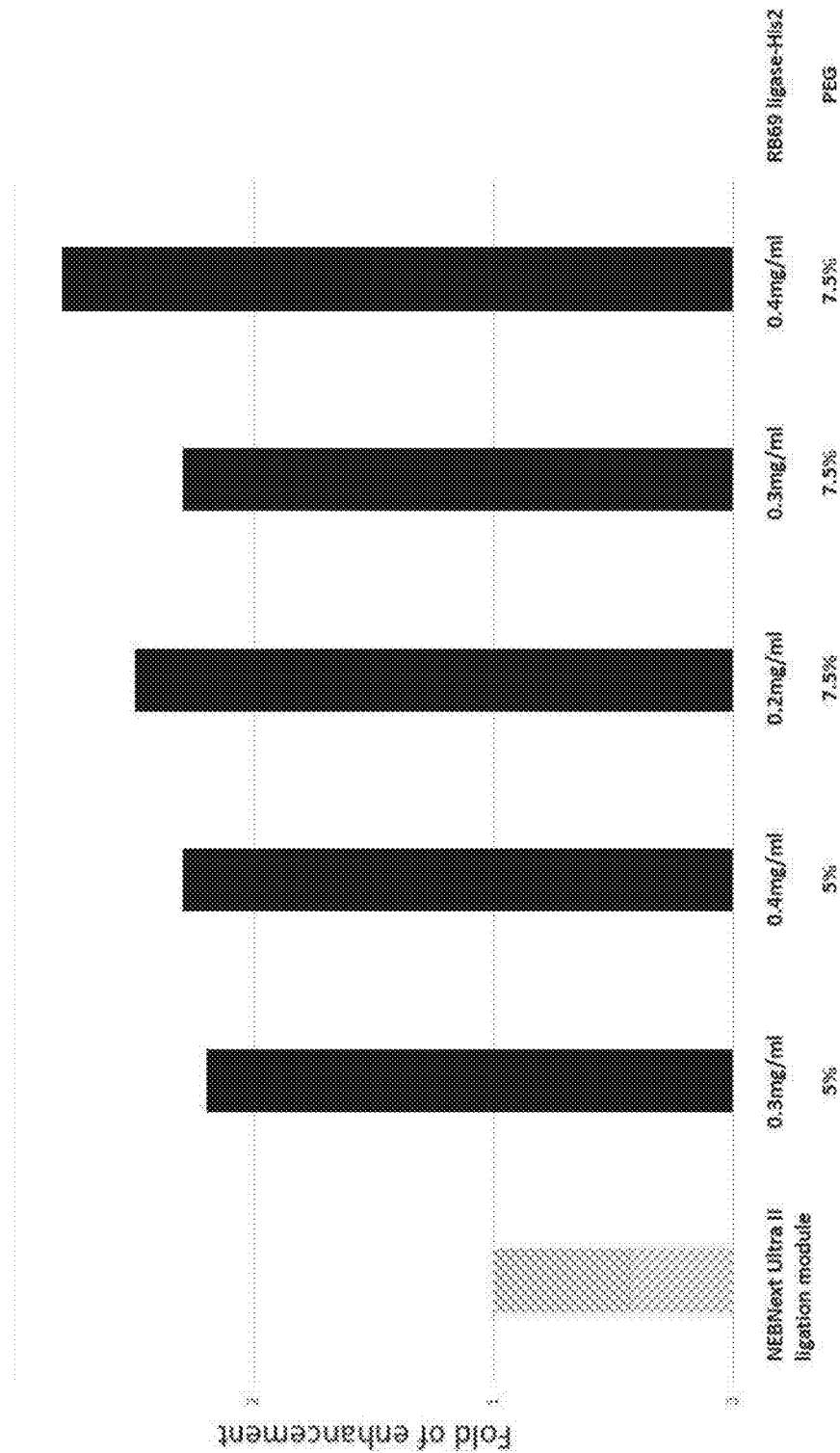
FIG. 23 shows the ligase activity performance of an IDR-tagged RB69 ligase fusion protein (RB69 ligase-HIS2) in an exemplary in vitro biochemical reaction environment in the absence of a crowding agent compared with NEBNext Ultra II ligation master mix.

Only double-ligated products could be amplified. As shown in FIG. 23, RB69 ligase-His2 could have up to 2.8 fold enhancement of ligation efficiency compared to NEBNext Ultra II Ligation Master Mix.

Example 24. Analysis of the Effect of ATP on the Phase Separation Performance of RB69 Ligase Having an IDR Tag Derived from Human Otx1

Purpose and Summary of Experiment

The purpose of this experiment was to analyse the effect of ATP on the ability of a ligase enzyme fusion protein preparation to cause phase separation. The ligase enzyme fusion protein has a tag comprising a histidine-rich amino acid domain sequence found in the intrinsically disordered region (IDR) of the human homeobox protein Otx1 (His2 tag).

The experiment demonstrated that ATP significantly enhanced phase separation mediated by the His2 tag.

Materials and Methods

The specific amino acid sequence of the IDR domain tag used was AGHHHHHPHAHHPLSQSSGHHHHHHHHHHQGYG GSG (SEQ ID NO:24). This was attached to the C-terminus of RB69 DNA ligase. The recombinant IDR fusion protein and IDR-free protein were purified using standard 1-step immobilised metal (nickel) affinity chromatography relying on the histidines naturally present in the IDR domain tag of the fusion protein under test and a poly-histidine tag at the C-terminus of IDR-free protein. The fusion protein was designated RB69 ligase-His2 and the IDR free protein was designated RB69 ligase. The full amino acid sequences of the proteins are presented in Table 24 above. FAM-oligo is CCGCAATGGTGCACTCTCAGTACAATCTGCTCT-GATG (SEQ ID NO:104) labelled with FAM (fluorescein).

A 50 µl solution was made up comprising the ligase at a final concentration of 1 mg/ml, 0.4 µM FAM-oligo and 0/20 mM $MgCl_2$ and 0/1 mM ATP. 10p of the reaction mix was then transferred to a C-Chip haemocytometer slide and images were taken under bright field light conditions and fluorescence conditions.

Results and Conclusion

Figure 24:
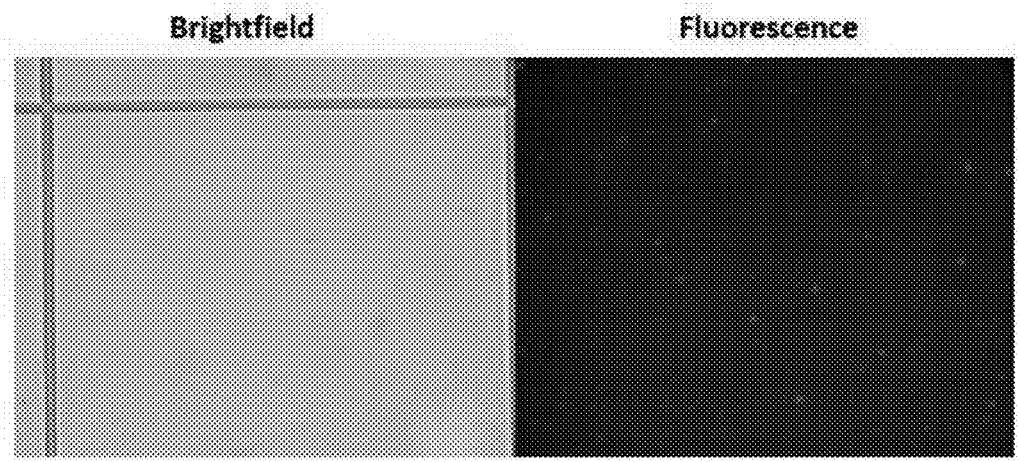
FIG. 24 shows the effect of ATP on the capability of an IDR-tagged RB69 ligase fusion protein (RB69 ligase-HIS2) to promote phase separation (particle formation) in an exemplary in vitro biochemical reaction environment in the absence of a crowding agent.
Figure 24:
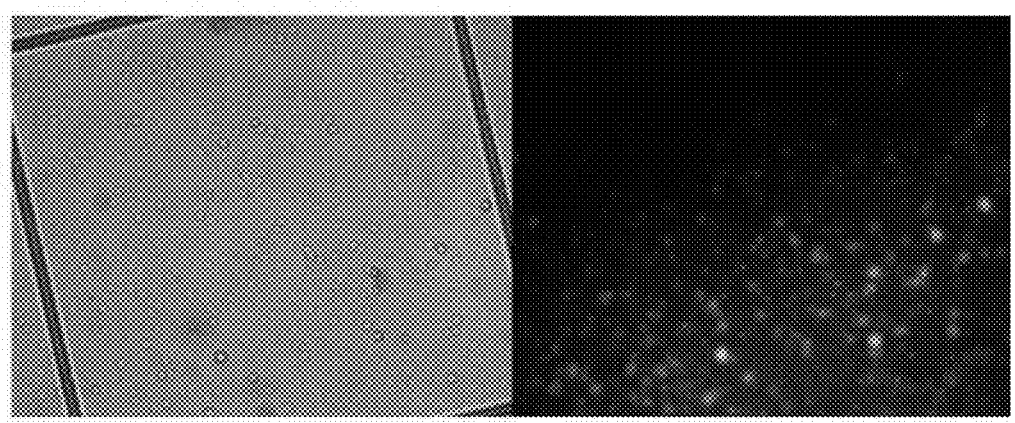
Figure 24:
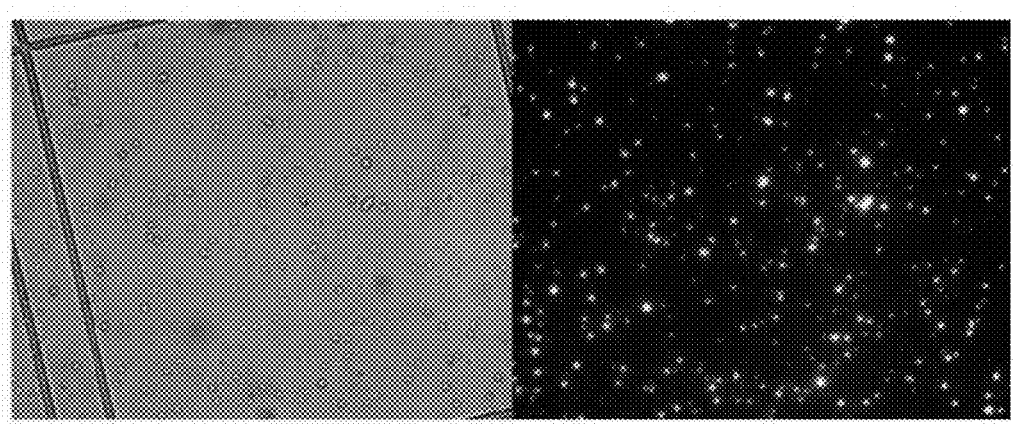

As shown in FIG. 24, very few phase-separated aqueous particles (globular foci) were observed using the IDR-free RB69 ligase. RB69 ligase-His2 significantly promoted the formation of many globular foci in the presence of 1 mM ATP. After addition of 20 mM $Mg^{2+}$, brighter fluorescence of globular foci was observed indicating a further enhancement of globular foci formation and/or that more DNA was forced to co-localise in the globular foci.

Example 25. Recombinase Polymerase Amplification on a Solid Surface Using Gp32 Having an IDR Tag Derived from Saccharomyces cerevisiae Hrp1

Purpose and Summary of Experiment

This experiment was performed to assess the capability of a Gp32 fusion protein preparation containing a tag comprising an intrinsically disordered region (IDR) of the Saccharomyces cerevisiae Hrp1 protein in amplification on a solid surface.

The example demonstrates recombinase polymerase amplification (RPA) of an artificial nucleic acid template on a solid surface using Gp32 C-terminally tagged with the intrinsically disordered region (IDR) of the Saccharomyces cerevisiae Hrp1 protein in the absence of a crowding agent both in real-time and end-point assays.

Materials and Methods

The specific amino acid sequence of the IDR domain tag used was GGNNGGNNMNRRGG-NFGNQGDFNQMYQNPMMGGY-NPMMNPQAMTDYYQ KMQEYYQQMQ (SEQ ID NO:9). This was attached to the C-terminus of T4 phage Gp32. The recombinant fusion protein was purified using standard 1-step immobilised metal (nickel) affinity chromatography relying on an additional heptahistidine tag placed at the very C-terminus of the fusion protein under test, i.e. placed after the IDR tag at the C-terminus of the fusion protein. The fusion protein was designated T4-Gp32-HRP1. The full amino acid sequence of the fusion protein is presented as SEQ ID NO: 120 below

```
                                        (SEQ ID NO: 120)
MFKRKSTAELAAQMAKLNGNKGFSSEDKGEWKLKLDNAGNGQAVIRFLPS

KNDEQAPFAILVNHGFKKNGKWYIETCSSTHGDYDSCPVCQYISKNDLYN

TDNKEYSLVKRKTSYWANILVVKDPAAPENEGKVFKYRFGKKIWDKINAM

IAVDVEMGETPVDVTCPWEGANFVLKVKQVSGFSNYDESKFLNQSAIPNI

DDESFQKELFEQMVDLSEMTSKDKFKSFEELNTKFGQVMGTAVMGGAAAT

AAKKADKVADDLDAFNVDDFNTKTEDDFMSSSSGSSSSADDTDLDDLLND

LGGNNGGNNMNRRGGNFGNQGDFNQMYQNPMMGGYNPMMNPQAMTDYYQK

MQEYYQQMQHHHHHHH
```

The recombinant T4 phage Gp32 fusion protein was then tested in PEG-free amplification, i.e. in the absence of a crowding agent, on a solid surface. The tests were performed using two oligonucleotide primers attached to the surface of beads. Amplification was detected by the incorporation of a fluorescent nucleotide at a nickase site found in the amplicon using an end-point reaction. Beads were sourced from Bangs Laboratories, Inc. (bangslabs.com) and had a polystyrene core that was carboxylated and was grafted with a copolymer to which oligonucleotides were covalently attached. Beads were deposited onto a glass substrate that was patterned into discrete regions using standard microfabrication technologies like photolithography, soft lithography, etching, etc. The resulting regions have characteristics such as being hydrophobic or hydrophilic and can attract or repel samples to be analyzed. Grace BioLabs Flex Well™ removable incubation chambers were used to divide a single piece of patterned glass into eight reaction chambers measuring 6.5 mm×6.5 mm each estimated to contain 12.25 million beads in an ordered array on the surface. Differing amounts of amplification template were added to different reaction chambers such that if all template hybridised to primers on beads a reaction chamber would have 0, 5, 10, 20, 40 or 80 copies of template per bead, with the assumption that hybridisation would be much less than 100% efficient. Single stranded DNA template (UP1-UP2'_TF1L template sequence: AATGATACGGCGACCACCGTGATCTA-CACTGTTTTACAACCTCAGCATGGA AAAAGGTTTCGAACT-CAACAGCTGTCTGGCAGCTCGCTCTACGCATGCT-ATT GCTGGCGGTAT-TGCTTCTGCTCTTGCTGGTGGCGCCATGTCTAAAT TGTCGA TACATCTCGTATGCCGTCTTCTGCTTG (SEQ ID NO: 121) was added to reaction chambers in 50 µl buffer (10 mM Tris HCl pH 8.0.1 mM EDTA, 0.05% Triton X-100, 100 mM NaCl), covered with Flex Well™ Seal-Strips™ and heated to 50° C. for 1 hour to allow template to anneal to complementary oligonucleotides on the beads. Excess buffer was then removed and the beads washed twice with TTM buffer (1 0 mM Tris HCl pH 8.0, 10 mM MgCh, 0.05% Triton X-100) and then twice with reaction buffer (25 mM Tris HCl pH 8.3, 7.5 mM KOAc, 1 mM DTT) to remove any template that had not annealed.

Reactions were set up by mixing 25 mM Tris HCl pH 8.3, 7.5 mM KOAc, 1 mM DTT, 2.5 mM ATP, 20 mM phosphocreatine, 1.7 µM creatine kinase, 1 mM dNTPs, 6.6 µM Gp32 fusion, 2.7 µM UvsX, 2.7 µM UvsY, 0.22 µM S. aureus DNA polymerase and 23 mM MgOAc. The reaction mixture also included 290,000 beads/mm$^2$, with 0.59 µl reaction mix/mm$^2$ each bead having approximately 600,000 oligonucleotide primers per bead consisting of a mix of UP1 forward primer and UP2-18 reverse primer having the sequences below:

```
UP1 forward primer:
                            (SEQ ID NO: 122)
AATGATACGGCGACCACCGAGATCTACAC.

UP2-18 reverse primer:
                            (SEQ ID NO: 123)
CAAGCAGAAGACGGCATA.
```

Reactions were then incubated for 60 minutes at 43° C. and then stopped by washing (adding/removing) twice with ST™ buffer (10 mM Tris HCl pH 8.0, 10 mM MgCl$_2$, 0.05% Triton X-100 and Sodium Dodecyl Sulfate (SDS) to 1% final concentration) to denature the proteins. The beads were then washed twice by adding/removing TTM buffer (10 mM Tris HCl pH 8.0, 1 mM EDTA, 0.05% Triton X-100) to remove the SDS.

The beads were then covered in 25 µl 1× CutSmart buffer (NEB—50 mM KOAc, 20 mM Tris-acetate, 10 mM MgOAc, 100 µg/ml BSA, pH 7.9) with 2.5 U nickase Nt. BbvCI. The UP1-UP2'_TF1L template includes a single copy of the recognition site of Nt. BbvCI (CC/TCAGC) which introduces a nick in one strand of the DNA. Beads were heated to 37° C. for 45 minutes to ensure any amplicons were nicked. Nicking was stopped by washing (adding/removing) twice with ST™ buffer (10 mM Tris HCl pH 8.0, 1 mM EDTA, 0.05% Triton X-100 and Sodium Dodecyl Sulfate (SDS) to 1% final concentration) to denature the nickase. The beads were then washed twice by adding/removing TTM buffer (10 mM Tris HCl pH 8.0, 1 mM EDTA, 0.05% Triton X-100) to remove the SDS and twice with reaction buffer (25 mM Tris HCl pH 8.3, 7.5 mM KOAc, 1 mM DTT).

The final step in the protocol was to incorporate fluorescently labelled dUTP into amplicons. This was done by submerging the beads in reaction buffer (25 mM Tris HCl pH 8.3, 7.5 mM KOAc, 1 mM DTT) with 0.11 µM S. aureus DNA polymerase, 160 µM Aminoallyl-dUTP-XX-ATTO-594 (Jena Bioscience) and 23 mM MgOAc and heating to 43° C. for 45 minutes. Extension was stopped by washing (adding/removing) twice with ST™ buffer (10 mM Tris HCl pH 8.0, 1 mM EDTA, 0.05% Triton X-100 and Sodium Dodecyl Sulfate (SDS) to 1% final concentration) to denature the nickase. The beads were then washed twice by adding/removing TTM buffer (10 mM Tris HCl pH 8.0, 1 mM EDTA, 0.05% Triton X-100) to remove the SDS. The Flexwells were then removed and a glass coverslip and small volume of TTM buffer were placed on the glass wafer. The wafer was examined using a fluorescent microscope, with brightfield and fluorescent pictures taken of the same locations.

Results

Figure 25A:
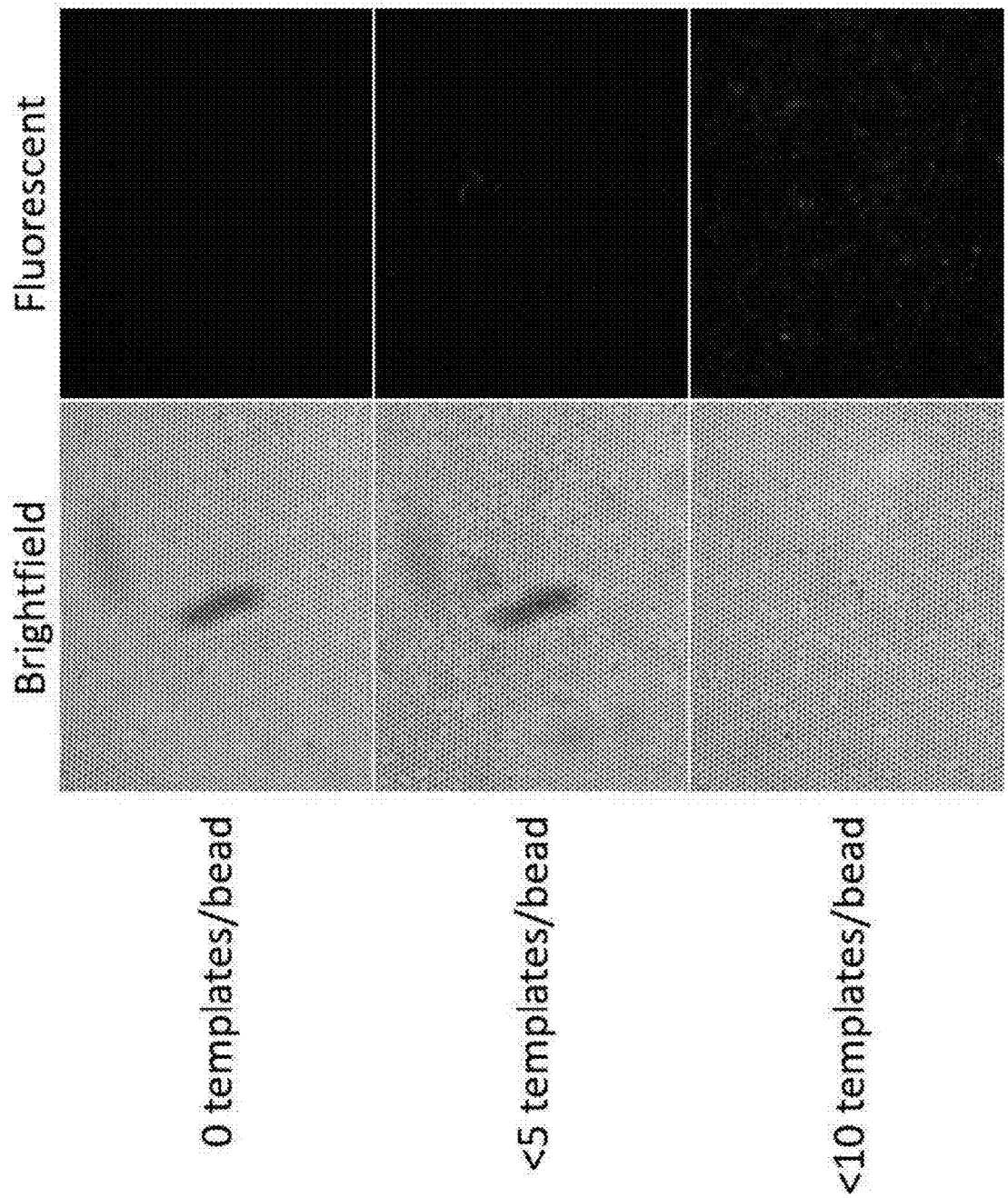
FIGS. 25A and 25B show brightfield and fluorescent images of representative sections of FlexWell™ chambers that had 0, 5, 10, 20, 40 or 80 copies of single stranded UP1-UP2'-TF1L template per bead annealed at 50° C. for 1 hour and then amplified by recombinase polymerase amplification using an IDR-tagged Gp32 fusion protein (Gp32-Hrp1) using primers attached to a solid surface in the absence of a crowding agent such as PEG. Amplification was detected by nicking amplicons with Nt. BbvCI and extending the nick with Aminoallyl-dUTP-XX-ATTO-594. No fluorescence was observed on beads where template had not been added and an increasing amount of fluorescence was observed on beads where increasing amounts of template had been annealed. This shows that amplification occurred on the solid surface of the beads in the absence of a crowding agent.
Figure 25B:
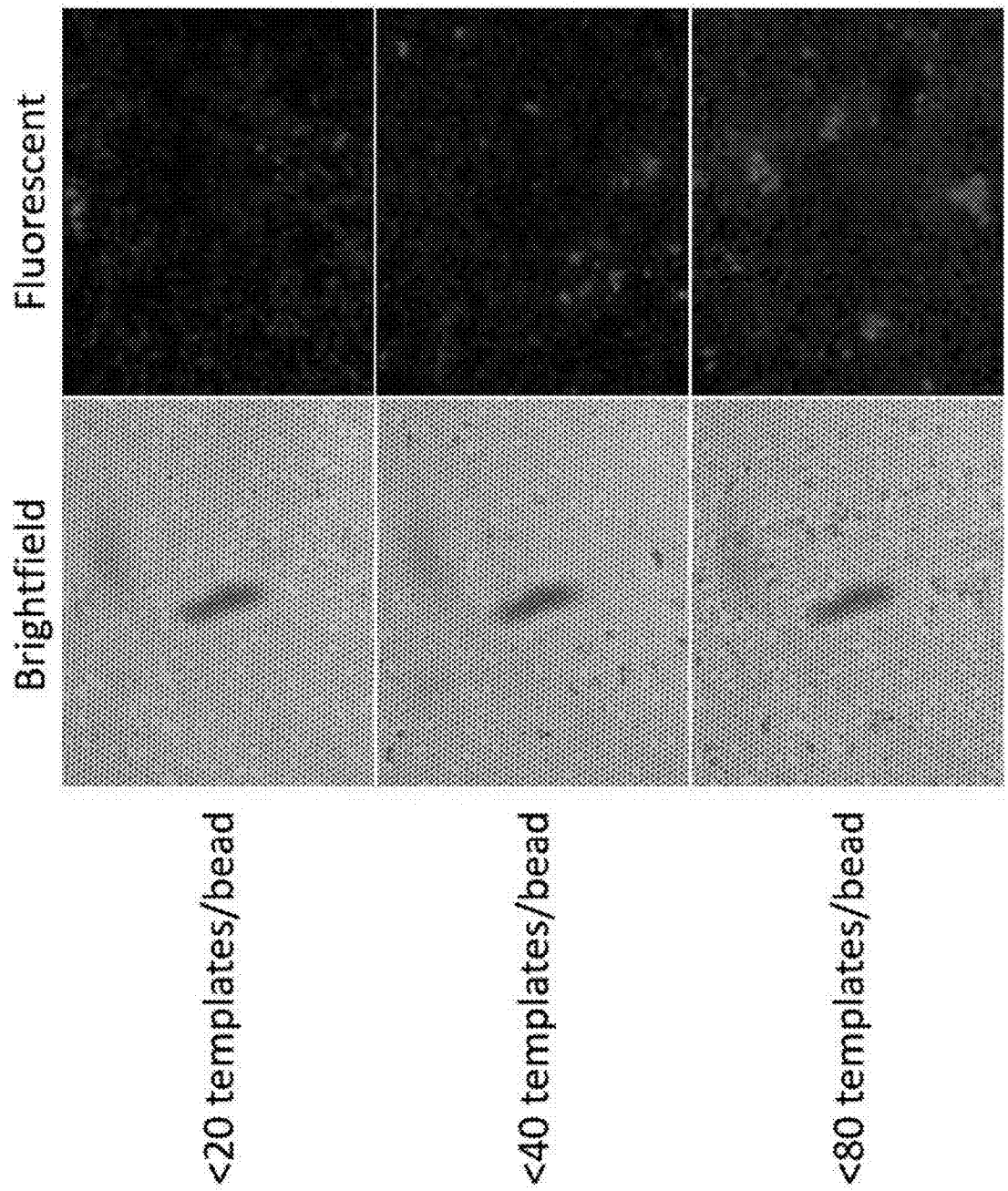

End-point fluorescence detection of UP1-UP2'-TF1L amplicon was observed using the incorporation of ATTO-594 labelled dUTP into the Nt. Bbv CI nicking site of the amplicon. FIG. 25 shows that when no template was added, beads remained dark, but as template increased an increasing proportion of beads were fluorescent and the level of fluorescence increased.

Conclusion

It was found that nucleic acid amplification in the absence of a crowding agent, such as PEG, occurred efficiently using the T4 Gp32-Hrp1 fusion protein on surfaces.

Example 26. Analysis of the Effect of Gp32-HRP1 ssDNA Binding Protein with Associated Phase Separation on Cas12a Protein Performance Purpose and Summary of Experiment The purpose of this experiment was to analyse the effect of an IDR-tagged Gp32 ssDNA binding protein in the presence of Polyethylene Glycol (PEG) 35K under conditions that promote phase separation on the activity of the Cas12a nuclease protein, in association with a guide RNA, to bind and cut a double-stranded DNA target monitored by fluorescence readout. The Gp32 ssDNA binding protein used has a tag comprising an amino acid domain sequence found in the intrinsically disordered region (IDR) of the yeast HRP protein (Gp32-HRP1). In the presence of this tag and PEG, phase separation occurs substantially in the absence of other factors even at low concentrations of the protein.

The duplex nucleic acid target for Cas12a in this case has a 6-FAM/BHQ1 pairing which when cleaved generates a nucleotide fragment containing the 6-FAM label which should melt essentially immediately from the annealed hybrid leading to lead to a measurable fluorescence increase. This template was additionally engineered to interact with Gp32-HRP1 by virtue of an additional single-stranded region to hook.

The experiment demonstrates that using Gp32-HRP1 ssDNA binding protein in the presence of PEG35K leads to the formation of phase-separated aqueous particles (globules or globular foci) and concomitantly significantly enhanced the rate that Cas12a cuts its DNA target in an in vitro system.

Materials and Methods

The specific amino acid sequence of the IDR domain tag used was GGNNGGNNMNRRGGN FGNQGDFNQMYQNPMMGGYNPMMNPQAMTD YYQKMQEYYQQMQ (SEQ ID NO: 9). This was attached to the C-terminus of T4 Gp32 ssDNA binding protein. The recombinant IDR fusion protein was purified using standard 1-step immobilised metal (nickel) affinity chromatography relying on 7 additional histidines appended to the C-terminus of the IDR tag. The fusion protein was designated T4 GP32-HRP1. The full amino acid sequence of the protein is presented as SEQ ID NO: 120.

```
The guide-RNA sequence is
5'-UAAUUUCUACUGUUGUAGAUAAAGUGCUCAUCAUUGGAAAACG-3'

(SEQ ID NO: 134).
```

The double-stranded/single-stranded DNA target was prepared by annealing two oligos, top oligo 5'-GAACGTTTTCCAATGATGAGCACTTTTAAAGTTC-TATGTATCAAAGCGGCCA TTTGCGG-3' labelled with FAM (fluorescein) at 5' end (SEQ ID NO: 135) and bottom oligo 5'-AGAACTTTAAAAGTGCTCATCATTG-GAAAACGTTC-3' labelled with BHQ-1 (quencher) at 3' end (SEQ ID NO: 136). The annealing process was heating the 1 μM oligo mixture to 95° C. and cooled to 14° C. at a rate of 0.1° C./min. This provides a duplex target site for the cas12a nuclease with the supplied guide RNA but also an additional 24 single-stranded residues which may interact with Gp32-HRP1 with an anticipated binding of about 3 monomers of protein. In this fashion it was anticipated that much of the annealed target will be forced to locate in phase-separated Gp32-HRP1 globules should they arise. Furthermore the presence of a fluorophore and quencher on either strand which should be in close proximity when annealed, but disperse following a cut (as the resulting hybrid is only a few nucleotides long) provides a convenient mechanism to assess the rate of cutting. As expected, in a Cas12a-dependent fashion fluorescence changes from generally low levels and increases over time.

EnGen Lba Cas12a protein was purchased from New England Biolabs.

Solutions were made up which did or did not include Cas12a protein, PEG35K or T4 GP32 HRP1 protein. The solutions were comprised of: 30 mM NaCl, 10 mM Tris Acetate pH8.3, 20 mM Mg Acetate, 0.1 mg/ml BSA, 33.3 nM guide RNA, 50 nM dsDNA, 5% PEG35K. When included in the reactions, the following components were present at the following concentrations: 33.3 nM Cas12a protein, 333 ng/μl T4 GP32 HRP1 protein. To assess reaction rate behavior, 30 μl of reaction solution was transferred to 0.2 ml tubes and assayed using an Axxin T16 fluorescence reader, using a run temperature of 42° C. Independently, 20 μl of reaction solution was warmed at 42° C. for approximately 1 minute and then transferred to a C-Chip haemocytometer slide and images were taken under bright field light conditions and fluorescence conditions. These images therefore represented a snapshot of the microscopic state of the system within the first few minutes of the reaction.

Results and Conclusion

Figure 26A:
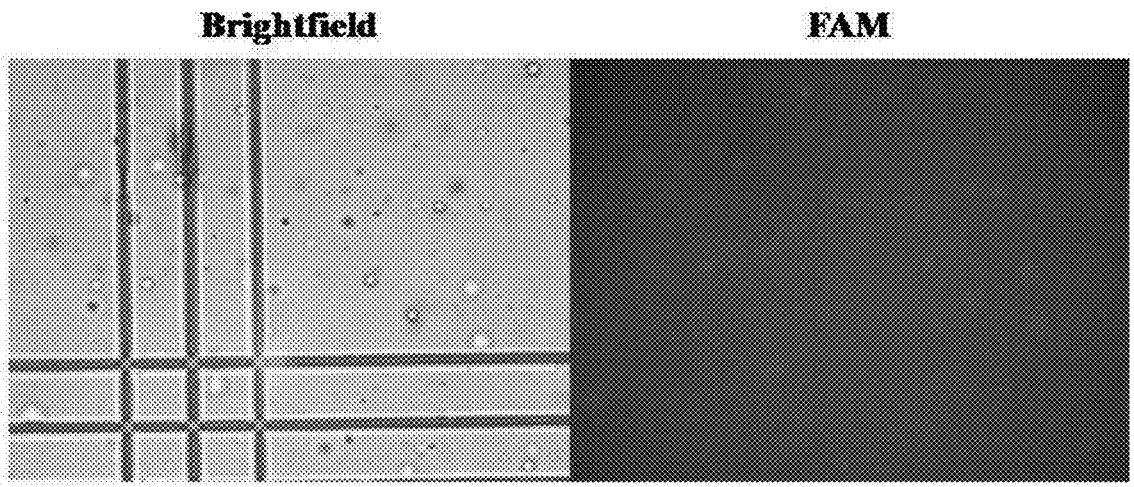
FIG. 26A shows brightfield and fluorescent images demonstrating the formation of phase-separated aqueous particles mediated by an IDR-tagged Gp32 fusion protein (Gp32-Hrp1).
Figure 26A:
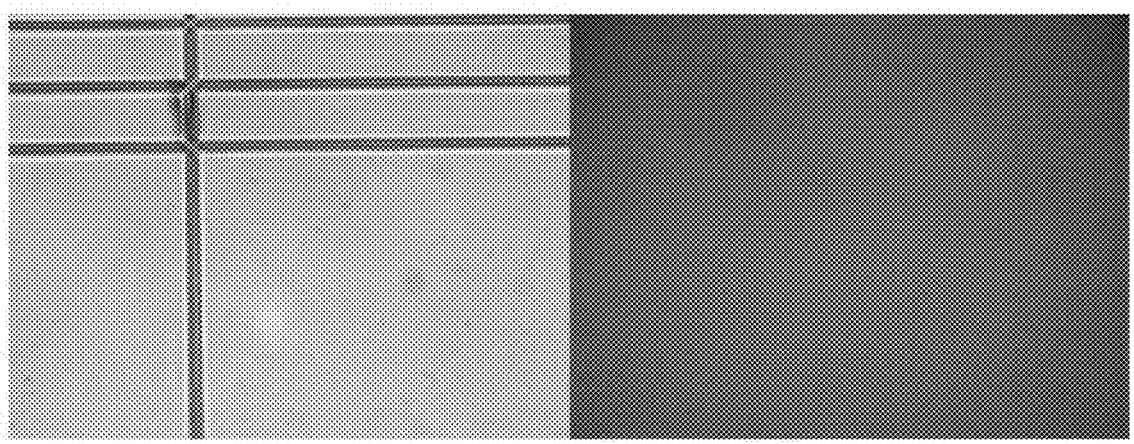
Figure 26A:
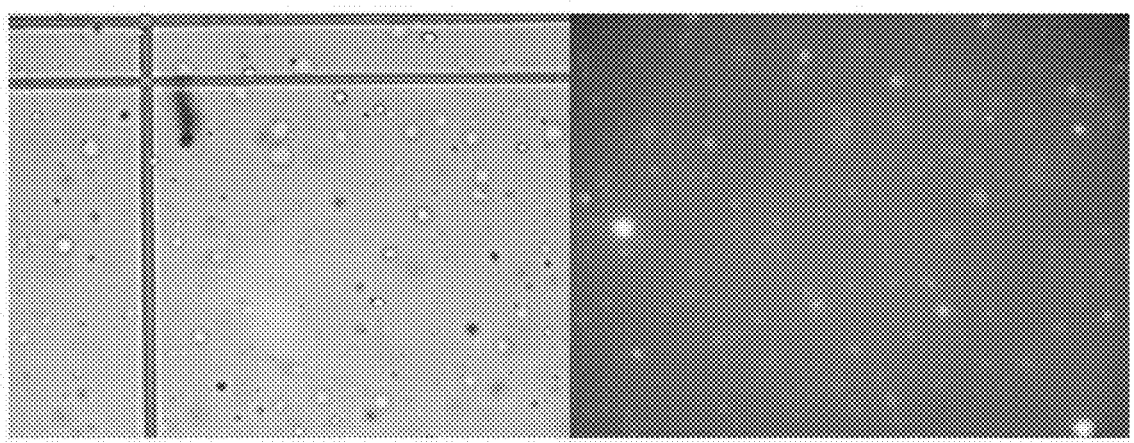
Figure 26B:
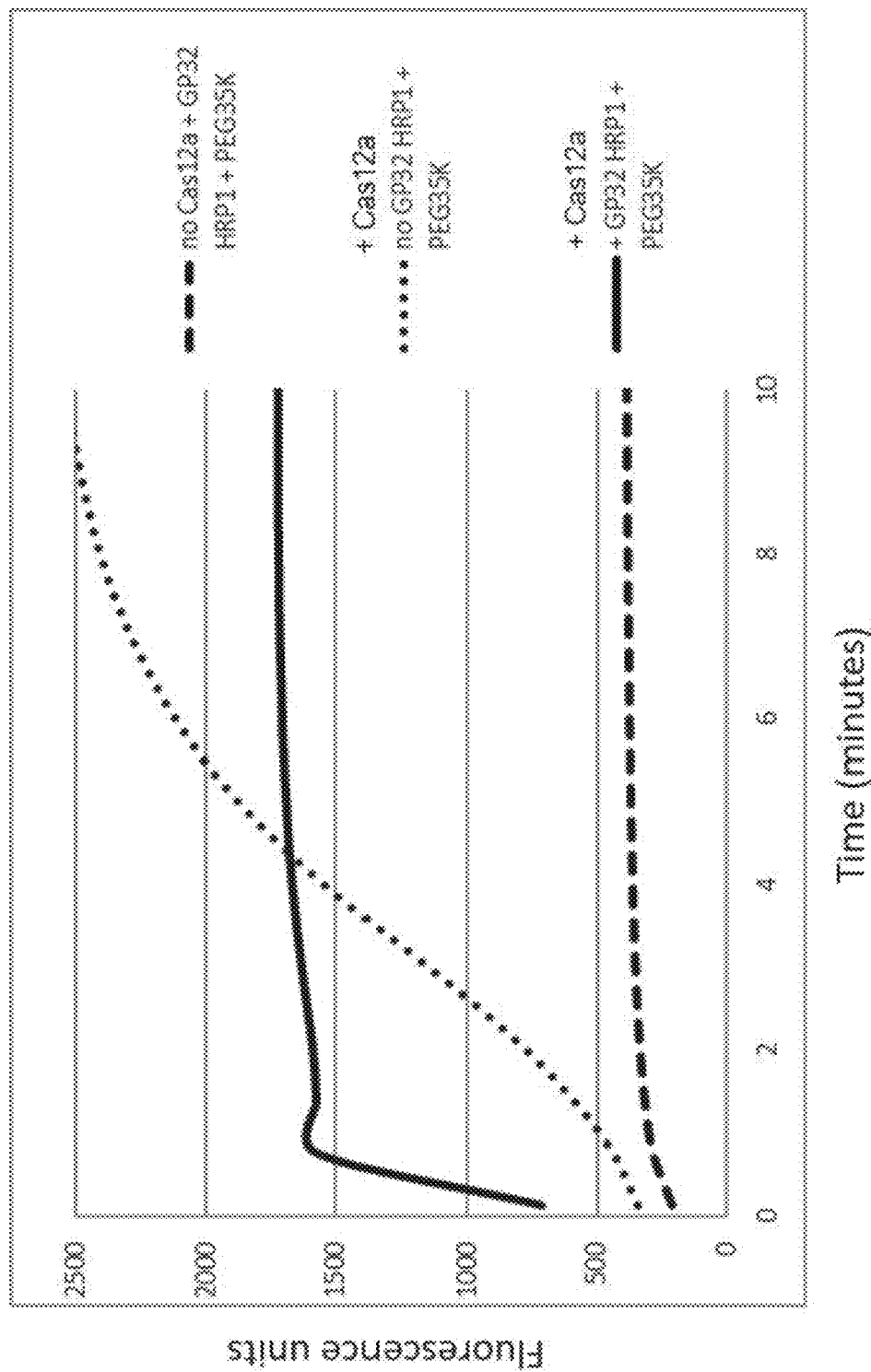
FIG. 26B shows a plot demonstrating increased efficiency of a reaction (rate of nucleic acid cutting by Cas12a) upon the formation of phase-separated aqueous particles mediated by Gp32-Hrp1.

As shown in FIG. 26A, without Cas12a protein but in the presence of Gp32-HRP1 and PEG, phase-separated aqueous particles (globular foci) were observed but demonstrated only weak fluorescence when the labelled, but largely quenched, target DNA was present in the presence of Gp32-HRP1 and PEG (at the early timepoint at which the reaction was analysed microscopically). Naturally, no cutting is anticipated absent Cas12a protein as supported by minimal change in fluorescence change over time as shown in the flat character of the fluorescence plot (FIG. 26B) albeit some fluorescence is observed, possibly due to incomplete annealing of the fluorophore/quencher probe and consequent background.

When Cas12a protein was present, but in the absence of T4 Gp32 HRP1, no globular foci were observed, indicating the as-expected requirement for T4 Gp32 HRP1 to enable globule formation. The kinetic analysis indicated that target cutting increased steadily over time as assessed up to 10 minutes. Microscopically the overall fluorescence appeared slightly higher than in the Cas12a-minus sample indicating that within a few minutes some annealed probe had been processed consistent with the kinetic study.

However in stark and remarkable contrast, in the presence of Cas12a and T4 Gp32-HRP1 (and PEG), many globular foci were observed and generally much stronger fluorescence was observed throughout the microscope image, suggesting both the need for T4 Gp32-HRP1 for globule formation, but in addition that this lead to more processing (note once processed the small released products would not necessarily be expected to localize any longer to the globules). The kinetic graph was markedly and stunningly different under these conditions as well, and showed very rapid fluorescence accumulation to a peak, around, or before 1 minute (just after the sample was placed into the reader), and then a plateau for the remainder of the analysis time. This significant enhancement in DNA cutting rate observed in the presence of T4 Gp32-HRP1 is we propose consistent with the notion that the phase-separated particles markedly promoted specific cutting, presumably caused by a co-localisation of the Cas12a protein and its dsDNA target inside the globular foci enabling a greatly increased rate of reaction. In a fashion similar to the amplification system demonstrated herein this indicates that even when only a single system component acts to drive phase separation, other participants may be drawn to that phase leading local high concentrations and massively accelerated kinetics.

It is to be understood that different applications of the disclosed IDR-based methods, processes, macromolecules, polypeptides and uses may be tailored to the specific needs in the art. It is also to be understood that the terminology used herein is for the purpose of describing particular embodiments of the invention only, and is not intended to be limiting.

As used in this specification and the appended claims, the singular forms "a", "an", and "the" include plural referents unless the content clearly dictates otherwise. Thus, for example, references to an entity such as "a macromolecule", "a polypeptide", "a polynucleotide", "a cell", "a host cell" and so on, includes two or more such entities.

Terms such as "about" and "approximately" are to be understood as encompassing the relevant figure+/−10% of the value of the figure, or +/−5% of the value of the figure unless the content clearly dictates otherwise.

Where a range of numbers is presented as being "between" a lower value and an upper value, the range is to be interpreted as including the upper and lower values. For example, a range of between 22 mM to 50 mM, or between about 22 mM to about 50 mM, should be interpreted as including the values of 22 mM and 50 mM or the values of about 22 mM and about 50 mM.

All publications, patents and patent applications cited herein are hereby incorporated by reference in their entirety.

The invention claimed is:

1. A method for performing an in-vitro nucleic acid amplification reaction, the method comprising:
   performing a recombinase polymerase amplification (RPA) reaction in presence of at least one fusion protein, wherein the at least one fusion protein comprises an RPA component fused to a polypeptide comprising at least one functional intrinsically-disordered region (IDR),
   wherein the at least one fusion protein causes liquid-liquid demixing and formation of a plurality of phase-separated aqueous compartments.

2. The method of claim 1, wherein the RPA component of the fusion protein is selected from the group consisting of: a recombinase agent, a single-strand stabilizing agent, a polymerase, and a recombinase loading protein.

3. The method of claim 2, wherein said RPA reaction is performed in the presence of at least one further fusion protein, wherein that at least one further fusion protein comprises a different RPA component fused to a polypeptide comprising at least one functional IDR, wherein the different RPA component is selected from the group consisting of: a recombinase agent, a single-strand stabilizing agent, a polymerase, and a recombinase loading protein.

4. The method of claim 1, wherein said RPA component comprises a recombinase agent that is selected from the group consisting of: T4 UvsX, T6 UvsX, RB18 UvsX, E. coli phage wV7 UvsX, Shigella phage CB8 UvsX, Shigella phage Shfl2 UvsX, E. coli phage AR1 UvsX, phage vB_E-coM_G4507 UvsX, Shigella phage SHFML-11 UvsX, Escherichia phage vB_EcoM_DalCa UvsX, E. coli RecA, E. coli RadA, E. coli RadB, E. coli Rad 51, and any functional analog, homolog, or derivative thereof.

5. The method of claim 1, wherein the RPA component comprises a recombinase agent that is a UvsX polypeptide.

6. The method of claim 1, wherein said RPA component comprises a single strand stabilizing agent that is a Gp32 protein.

7. The method of claim 6, wherein said Gp32 protein is selected from the group consisting of: phage T4 Gp32 protein, phage Rb69 Gp32, phage vB_EcoM_NBG1 Gp32, and any functional analog, homolog, or derivative thereof.

8. The method of claim 6, wherein said Gp32 protein is T4-Gp32 and the at least one functional IDR comprises an intrinsically disordered region of *Saccharomyces cerevisiae* Hrp1 protein and said at least one fusion protein comprises the amino acid sequence of SEQ ID NO:120.

9. The method of claim 1, wherein said RPA component comprises a polymerase that is selected from the group consisting of: pol-α, pol-β, pol-δ, pol-ε, *Bacillus stearothermophilus* polymerase I large fragment, *Bacillus subtilis* Pol I large fragment (Bsu polymerase), *Listeria monocytogenes* DNA polymerase I, *S. aureus* DNA polymerase I (Sau polymerase), *E. coli* DNA polymerase I Klenow fragment, *E. coli* DNA polymerase I, *E. coli* DNA polymerase II, *E. coli* DNA polymerase III, *E. coli* DNA polymerase IV, *E. coli* DNA polymerase V, bacteriophage T4 gp43 DNA polymerase, T7 DNA polymerase, Phi-29 DNA polymerase, and any functional analog, homolog, or derivative thereof; or any combination thereof.

10. The method of claim 1, wherein said RPA component comprises a recombinase loading protein the is selected from the group consisting of: UvsY, *E. coli* RecO, *E. coli* RecR, and any functional analog, homolog, or derivative thereof.

11. The method of claim 1, wherein the RPA component comprises a recombinase loading protein that is a UvsY polypeptide.

12. The method of claim 1, wherein said polypeptide is fused to the N-terminus of the RPA component, the C-terminus of the RPA component, or any amino acid position along a length of the RPA component.

13. The method of claim 1, wherein said at least one functional IDR comprises any of the following amino acid sequences:
    (i) (YNPQGGYQQ)$_n$ (SEQ ID NO: 19), wherein n is a positive integer between 1 and 10;
    (ii) (YSPTSPS)$_n$ (SEQ ID NO: 124), wherein n is a positive integer between 1 and 10;
    (iii) (FSPTSPT)$_n$ (SEQ ID NO: 125), wherein n is a positive integer between 1 and 10;
    (iv) (YSPTSP-A/N/G)$_n$ (SEQ ID NO: 126), wherein n is a positive integer between 1 and 10; and
    (v) (YSPGSPA)$_n$ (SEQ ID NO: 127), wherein n is a positive integer between 1 and 10.

14. The method of claim 13, wherein n=1, 2, or 3 in any of the amino acid sequences.

15. The method of claim 1, wherein said at least one functional IDR comprises an amino acid sequence having at least 80% sequence identity to any one of SEQ ID NOs: 1-43.

16. The method of claim 1, wherein said at least one functional IDR comprises an amino acid sequence of any of SEQ ID NOs: 1-43.

17. The method of claim 1, wherein said at least one functional IDR comprises an amino acid sequence having any of at least 4, at least 5, at least 6, at least 7, at least 8, at least 9, and at least 10 consecutive glutamine residues.

18. The method of claim 1, wherein said at least one functional IDR comprises an amino acid sequence comprising at least one aromatic tyrosine residue and at least one phenylalanine residue.

19. The method of claim 1, wherein said at least one functional IDR increases by at least 5% the efficiency of the RPA reaction as compared to an RPA reaction performed under the same conditions without using the at least one functional IDR.

20. The method of claim 1, wherein said at least one fusion protein is a single fusion protein.

21. The method of claim 1, wherein said RPA reaction is performed in presence of at least one multivalent metal ion.

22. The method of claim 21, wherein said at least one multivalent metal ion is present at a concentration of at least 22 mM.

23. The method of claim 21, wherein said at least one multivalent metal ion comprises any of $Mg^{2+}$, $Mn^{2+}$, $Ca^{2+}$, $Co^{2+}$ or $Ni^{2+}$.

24. The method of claim 1, wherein said RPA reaction is performed in presence of ATP.

25. The method of claim 24, wherein the ATP is provided at a concentration of 1 mM to 3.5 mM.

26. A method of performing a nucleic acid amplification reaction, the method comprising:
    contacting first and second nucleoprotein primers each comprising a recombinase agent, a single-strand stabilizing agent, a nucleic acid primer, and a recombinase loading protein with a double-stranded target nucleic acid molecule under conditions such that the first and second nucleoprotein primers bind to first and second strands of the double-stranded target nucleic acid; and
    extending 3' ends of the first and second nucleoprotein primers with a polymerase and dNTPs to generate first and second amplified nucleic acid strands,
    wherein at least one of the recombinase agent, the single-strand stabilizing agent, the polymerase, and the recombinase loading protein is fused to a polypeptide including at least one functional intrinsically disordered region (IDR) such that said at least one functional IDR causes liquid-liquid demixing and formation of a plurality of phase-separated aqueous compartments.

* * * * *